(12) United States Patent
Gunderson et al.

(10) Patent No.: US 11,169,157 B2
(45) Date of Patent: Nov. 9, 2021

(54) METHODS FOR STABLE COMPLEX FORMATION AND RELATED KITS

(71) Applicant: Encodia, Inc., San Diego, CA (US)

(72) Inventors: Kevin L. Gunderson, San Diego, CA (US); Norihito Muranaka, San Diego, CA (US)

(73) Assignee: ENCODIA, INC., San Diego, CA (US)

( * ) Notice: Subject to any disclaimer, the term of this patent is extended or adjusted under 35 U.S.C. 154(b) by 0 days.

(21) Appl. No.: 17/149,324

(22) Filed: Jan. 14, 2021

(65) Prior Publication Data

US 2021/0208150 A1 Jul. 8, 2021

Related U.S. Application Data

(63) Continuation of application No. PCT/US2021/012224, filed on Jan. 5, 2021.

(60) Provisional application No. 62/958,176, filed on Jan. 7, 2020.

(51) Int. Cl.
*G01N 33/68* (2006.01)
*G01N 33/58* (2006.01)
*G01N 33/53* (2006.01)

(52) U.S. Cl.
CPC ....... *G01N 33/582* (2013.01); *G01N 33/5308* (2013.01); *G01N 33/68* (2013.01)

(58) Field of Classification Search
CPC ... G01N 33/582; G01N 33/5308; G01N 33/68
See application file for complete search history.

(56) References Cited

U.S. PATENT DOCUMENTS

| | | | |
|---|---|---|---|
| 6,787,325 | B1 | 9/2004 | Sugiyama et al. |
| 8,642,744 | B2 | 2/2014 | Smart et al. |
| 2008/0305957 | A1 | 12/2008 | Thisted et al. |
| 2009/0264300 | A1 | 10/2009 | Franch et al. |
| 2019/0112626 | A1 | 4/2019 | Lee et al. |
| 2019/0145982 | A1 | 5/2019 | Chee et al. |

(Continued)

FOREIGN PATENT DOCUMENTS

| | | |
|---|---|---|
| WO | 2000/057183 A1 | 9/2000 |
| WO | 2016/164530 A1 | 10/2016 |

(Continued)

OTHER PUBLICATIONS

Mannik et al. Covalently cross-linked immune complexes prepared with multivalent cross-linking antigens. J. Immunology 1981, vol. 127, No. 5, pp. 1999-2006. (Year: 1981).*

(Continued)

*Primary Examiner* — Shafiqul Haq
(74) *Attorney, Agent, or Firm* — Rimon, P.C.

(57) ABSTRACT

The present disclosure relates to methods and kits for forming a stable complex comprising a binding agent and a target (e.g., a macromolecule). In some embodiments, the target comprises a peptide, a polypeptide, or a protein to be analyzed. In some embodiments, the present disclosure relates to formation of a stable complex comprising a binding agent and a target (e.g., a macromolecule) to be analyzed in a method which employs barcoding and nucleic acid encoding of molecular recognition events, and/or detectable labels. Provided herein is also a programmable system for information transfer comprising one or more adaptor molecules.

21 Claims, 15 Drawing Sheets

Specification includes a Sequence Listing.

(56) References Cited

U.S. PATENT DOCUMENTS

| | | |
|---|---|---|
| 2020/0348307 A1 | 11/2020 | Beierle et al. |
| 2020/0348308 A1 | 11/2020 | Chee et al. |

FOREIGN PATENT DOCUMENTS

| | | | | |
|---|---|---|---|---|
| WO | WO-2017192633 A9 | * | 12/2017 | ......... G01N 33/6824 |
| WO | 2019/089836 A1 | | 5/2019 | |
| WO | 2019/089851 A1 | | 5/2019 | |
| WO | 2019/133892 A1 | | 7/2019 | |

OTHER PUBLICATIONS

International Search Report for international patent application PCT/US2021/012224, dated Mar. 25, 2021, 3 pages.

Written Opinion of the International Searching Authority for international patent application PCT/US2021/012224, dated Mar. 25, 2021, 11 pages.

Daniel N Frank, "BARCRAWL and BARTAB: software tools for the design and Implementation of barcoded primers for highly multiplexed DNA sequencing," BMC Bioinformatics, Oct. 29, 2009 (Oct. 29, 2009), vol. 10,362. p. 1-13 https://doi.org/10.1186/1471-2105-10-362.

Hirsch et al., "Easily reversible desthiobiotin binding to streptavidin, avidin, and other biotin-binding proteins: uses for protein labeling, detection, and isolation," Analytical Biochemistry 308 (2002) 343-357.

Asanuma H et al., "Synthesis of azobenzene-tethered DNA for reversible photo-regulation of DNA functions: hybridization and transcription," Nat Protoc. 2007;2(1):203-212 doi:10.1038/nprot.2006.465.

Engelen W et al., "Antibody-controlled actuation of DNA-based molecular circuits," Nat Commun. Feb. 17, 2017;8:14473, 8 pages doi:10.1038/ncomms14473.

Gerry NP et al., "Universal DNA microarray method for multiplex detection of low abundance point mutations," J Mol Biol. Sep. 17, 1999;292(2):251-262.

Han D et al., "Nucleic acid based logical systems," Chemistry. May 12, 2014;20(20):5866-5873 doi:10.1002/chem.201304891.

Harroun SG et al., "Programmable DNA switches and their applications," Nanoscale. Mar. 8, 2018;10(10):4607-4641 doi:10.1039/c7nr07348h.

Huang F et al., "DNA branch migration reactions through photocontrollable toehold formation," J Am Chem Soc. May 29, 2013;135(21):7967-7973 (13 pages) doi: 10.1021/ja4018495.

Ladner DP et al., "Multiplex detection of hotspot mutations by rolling circle-enabled universal microarrays," Lab Invest. Aug. 2001;81(8):1079-1086.

Liu W et al., "Synthetic mimics of biotin/(strept)avidin," Chem Soc Rev. May 9, 2017;46(9):2391-2403 doi;10.1039/c7cs00011a.

MacCulloch T et al., "Emerging applications of peptide-oligonucleotide conjugates: bioactive scaffolds, self-assembling systems, and hybrid nanomaterials," Org Biomol Chem. Feb. 13, 2019;17(7):1668-1682 doi:10.1039/c8ob02436g.

Mantooth SM et al., "Dynamic Hydrogels from Host-Guest Supramolecular Interactions," Macromol Biosci. Jan. 2019;19(1):e1800281, 12 pages doi:10.1002/mabi.201800281.

Menge C, Heckel A. "Coumarin-caged dG for improved wavelength-selective uncaging of DNA," Org Lett. Sep. 2, 2011;13(17):4620-4623 doi:10.1002/smll.201100182.

Nakamura T et al., "A metal-ion-responsive adhesive material via switching of molecular recognition properties," Nat Commun. Aug. 7, 2014;5:4622, 9 pages doi:10.1038/ncomms5622.

O'Reilly FJ et al., "Cross-linking mass spectrometry: methods and applications in structural," molecular and systems biology. Nat Struct Mol Biol. Nov. 2018;25(11):1000-1008.

Ruble BK et al., "Caged oligonucleotides for studying biological systems," J Inorg Biochem. Sep. 2015;150:182-188 doi:10.1016/j.jinorgbio.2015.03.010.

Smits AH et al., "Characterizing Protein-Protein Interactions Using Mass Spectrometry: Challenges and Opportunities," Trends Biotechnol. Oct. 2016;34(10):825-834 http://dx.doi.org/10.1016/j.tibtech.2016.02.04.

Stephanopoulos N. "Peptide-Oligonucleotide Hybrid Molecules for Bioactive Nanomaterials," Bioconjug Chem. Jul. 17, 2019;30(7):1915-1922 doi:10.1021/acs.bioconjchem.9b00259.

Szymański W et al., "Reversible photocontrol of biological systems by the incorporation of molecular photoswitches," Chem Rev. Aug. 14, 2013;113(8):6114-6178 dx.doi.org/10.1021/cr300179f.

Terai T et al., "Rational development of caged-biotin protein-labeling agents and some applications in live cells," Chem Biol. Oct. 28, 2011;18(10):1261-1272 doi:10.1016/j.chembiol.2011.09.007.

Xing S et al., "Techniques for the Analysis of Protein-Protein Interactions in Vivo," Plant Physiol. Jun. 2016;171(2):727-758 www.plantphysiol.org/cgi/doi/10.1104/pp.16.00470.

Yan Y et al., "Photoswitchable oligonucleotide-modified gold nanoparticles: controlling hybridization stringency with photon dose," Nano Lett. May 9, 2012;12(5):2530-2536 dx.doi.org/10.1021/nl300739n.

Yan et al., "Photocontrolled DNA hybridization stringency with fluorescence detection in heterogeneous assays," ACS Sens. 2016, 1, 566-571 doi:10.1021/acssensors.5b00233.

Wu YP et al., "Target-activated streptavidin-biotin controlled binding probe," Chem Sci. Nov. 17, 2017;9(3):770-776 doi:10.1039/c7sc04014h.

* cited by examiner

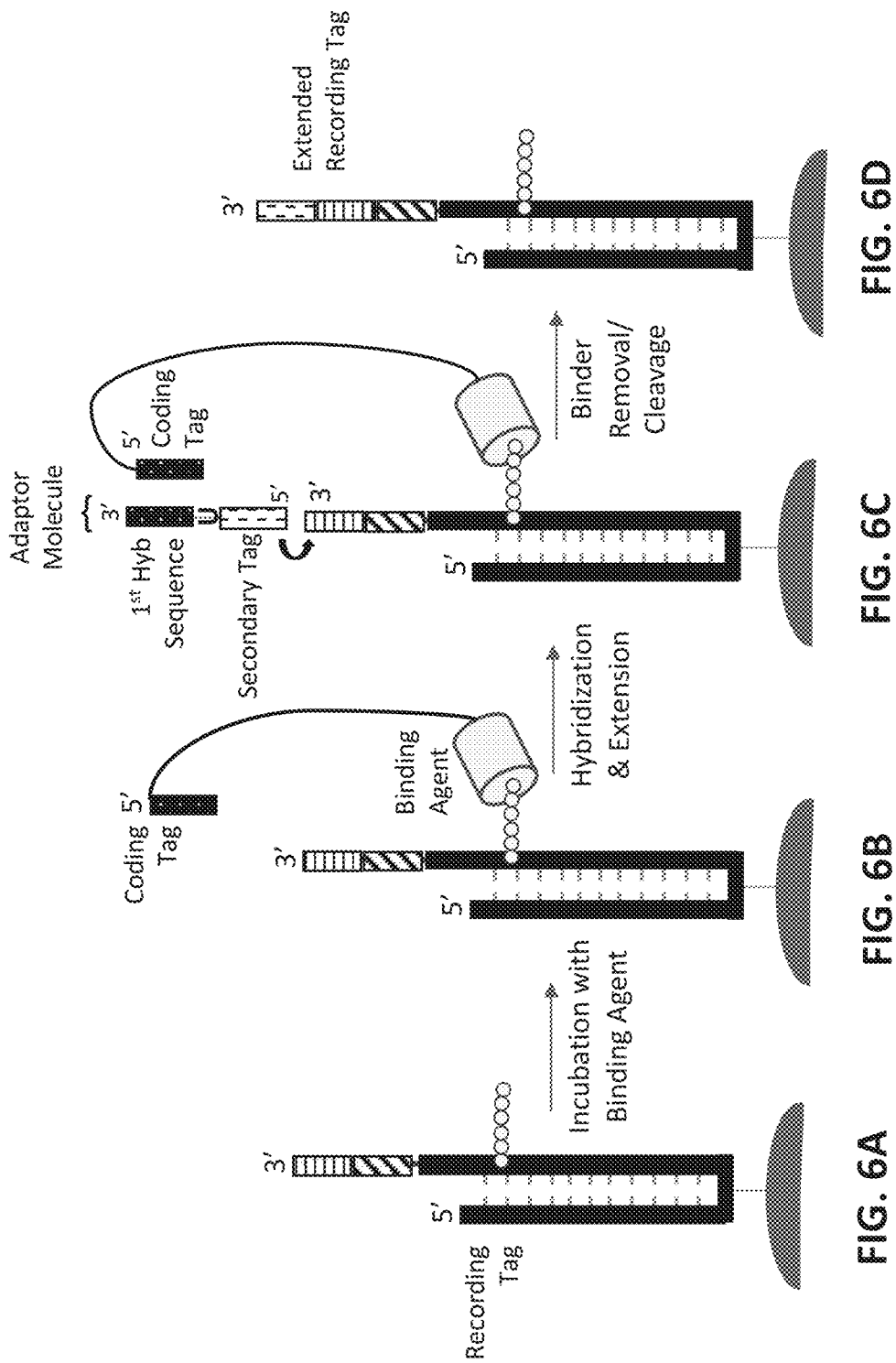

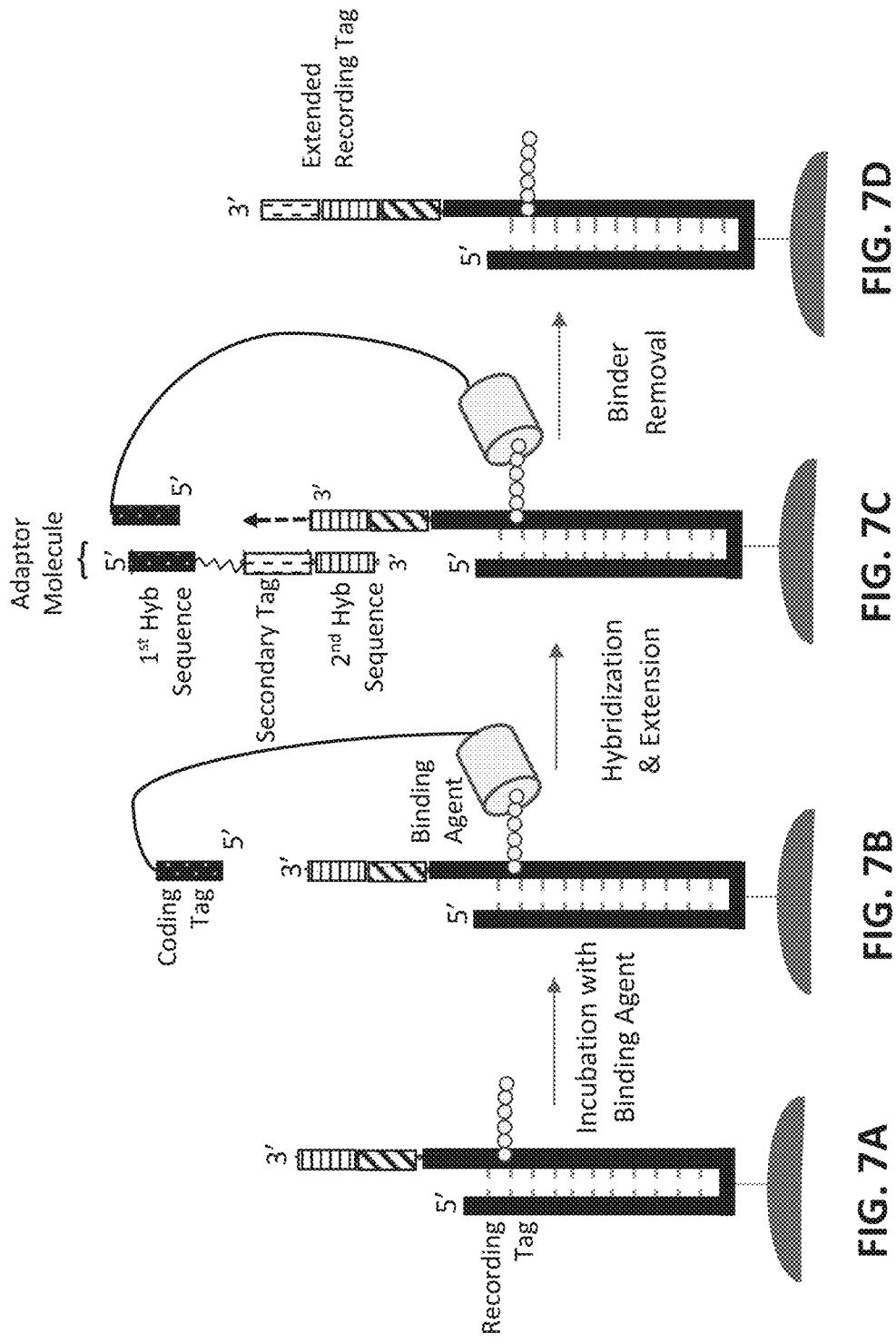

METHODS FOR STABLE COMPLEX FORMATION AND RELATED KITS

RELATED APPLICATION

The present application is a continuation application of International Patent Application Serial No. PCT/US2021/012224, filed on Jan. 5, 2021, entitled "METHODS FOR STABLE COMPLEX FORMATION AND RELATED KITS," which claims priority to U.S. provisional patent application No. 62/958,176, filed on Jan. 7, 2020. The disclosures and contents of the above-referenced applications are incorporated herein by reference in their entireties for all purposes.

STATEMENT REGARDING FEDERALLY SPONSORED RESEARCH

This invention was made with government support awarded by the National Cancer Institute of the National Institutes of Health under Grant No. R44CA203629. The United States Government has certain rights in this invention pursuant to this grant.

SEQUENCE LISTING ON ASCII TEXT

This patent application file contains a Sequence Listing submitted in computer readable ASCII text format (file name: 4614-2002130_ST25.txt, recorded: 12 Jan. 2021, size: 16,635 bytes). The content of the Sequence Listing file is incorporated herein by reference in its entirety.

TECHNICAL FIELD

The present disclosure relates to methods and kits for analyzing a macromolecule including information transfer between molecules, such as transfer of identifying information between nucleic acid molecules. Also, methods and kits for forming a stable complex comprising a binding agent and a target (e.g., a macromolecule, a polypeptide) to be analyzed are disclosed. Such methods employs barcoding and nucleic acid encoding of molecular recognition events, and/or detectable labels. Also provided herein is a programmable system for information transfer comprising, using or involving one or more adaptor molecules.

BACKGROUND

Recognition and binding of molecular targets using binding agents can be useful for characterization and/or detection of target biomolecules. Some analysis methods involve non-covalently associated complexes of proteins or proteins with other molecules (see e.g., Xing et al., Plant Physiol. (2016) 171(2): 727-758). For example, molecular recognition and characterization of a protein or peptide macromolecule can be performed using an immunoassay. There are various immunoassay formats including ELISA, multiplex ELISA (e.g., spotted antibody arrays, liquid particle ELISA arrays), digital ELISA, reverse phase protein arrays (RPPA), and others. However, these different immunoassay platforms share similar challenges including the development of high affinity and highly-specific (or selective) antibodies (binding agents), limited ability to multiplex at both the sample and analyte level, limited sensitivity and dynamic range, and cross-reactivity and background signals. Other methods for characterizing proteins include the use of mass spectrometry (e.g., Smits et al., Trends Biotechnol. (2016) 34(10):825-834; O'Reilly et al., Nat Struct Mol Biol. (2018) 25(11): 1000-1008). It may be desirable in performing some assays that a binding agent binds to the target and forms a stable complex for downstream steps in the assay or analysis to take place. In some cases, crosslinking reagents and methods exist for applications involving binding agents for targets. It may be preferred that binding agents and detection assays are performed in a manner that allows specificity and stability in a controllable manner that allows processing of a plurality of binding agents and targets. Additionally, speed and reversibility may also be a desired feature for the binding reaction. However, current reagents and techniques are somewhat limited in some of these aspects.

Accordingly, there remains a need for improved techniques relating to performing binding reactions, as well as to products, methods and kits for accomplishing the same. The present invention provides novel methods and compositions which may be utilized in a wide variety of nucleic acid-based and/or protein (e.g., binding agent)-based procedures, and further provides other related advantages. In some cases, the provided methods for performing a binding reaction are compatible with information transfer, such as between nucleic acids associated with the binding agent and the target, with applications to macromolecule sequencing and/or analysis (e.g., protein sequencing and/or analysis). In some examples, the information transfer is between a nucleic acid tag associated with the binding agent and a nucleic acid tag associated with the target (e.g., by extension or ligation).

These and other aspects of the invention will be apparent upon reference to the following detailed description. To this end, various references are set forth herein which describe in more detail certain background information, procedures, compounds and/or compositions, and are each hereby incorporated by reference in their entireties.

BRIEF SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

Provided herein are methods for performing a binding reaction comprising contacting a binding agent with a target, wherein the binding agent and the target each comprises or is associated with a stabilizing component; allowing the binding agent to interact with a binding site located on the target; and linking the stabilizing components to form a stable complex comprising the binding agent, the target and the stabilizing components.

Provided herein is also a method for analyzing a macromolecule comprising the steps of: (a) providing a macromolecule joined to a support, wherein the macromolecule comprises or is associated with a first stabilizing component; (b) contacting the macromolecule with a binding agent capable of binding to the macromolecule, wherein the binding agent comprises or is associated with a second stabilizing component; (c) after binding of the binding agent to the macromolecule, linking the first and second stabilizing components together to form a stable complex comprising the binding agent, the macromolecule and the stabilizing components; (d) analyzing the macromolecule by obtaining information about the binding agent bound to the macromolecule.

In some embodiments, the stabilizing components are linked upon introduction of a linking agent, and no covalent bonds are formed during formation of the stable complex. In other embodiments, the stabilizing components are linked upon introduction to light.

In some embodiments, the linking agent comprises a polypeptide.

In some embodiments, the first or second stabilizing component comprises a polynucleotide, and the linking agent comprises a linking polynucleotide that hybridizes to the polynucleotide of one of the stabilizing components.

In some embodiments, the first stabilizing component is the same as the second stabilizing component. In some other embodiments, the first stabilizing component has a lower affinity to the linking agent in comparison to an affinity of the second stabilizing component to the linking agent.

In some embodiments, the method comprises contacting a plurality of binding agents with a single macromolecule, or contacting a plurality of binding agents with a plurality of macromolecules, and wherein at least one binding agent of the plurality of binding agents is capable of binding to the macromolecule and each binding agent of the plurality of binding agents comprises or is associated with the second stabilizing component.

In some embodiments, the binding agent is fluorescently labeled to enable detection of the contact between the macromolecule and the binding agent; and analyzing the macromolecule comprises detecting fluorescence from the binding agent after contacting the macromolecule.

In some embodiments, the macromolecule comprises a polypeptide and the binding agent or a binding agent from the plurality of binding agents is capable of binding to a N-terminal amino acid (NTAA) of the polypeptide or to a modified NTAA of the polypeptide.

In some embodiments, analyzing the macromolecule comprises identifying at least one amino acid residue of the polypeptide.

In some embodiments, providing a macromolecule comprises providing the polypeptide associated with a recording tag; the binding agent or each binding agent from the plurality of binding agents comprises or is associated with a coding tag with identifying information regarding the binding agent; obtaining an information about the binding agent comprises transferring an information from the coding tag to the recording tag after binding of the binding agent to the macromolecule to generate an extended recording tag; and identifying at least one amino acid residue of the polypeptide comprises analyzing the extended recording tag.

In some embodiments, the method further comprises: providing an adaptor molecule comprising a first hybridization sequence and a secondary tag, wherein the first hybridization sequence is substantially complementary to at least a portion of the coding tag, to allow hybridization between the first hybridization sequence and the coding tag; and transferring information of the secondary tag to the recording tag to generate an extended recording tag, wherein the information of the secondary tag is transferred from the adaptor molecule to the recording tag after the coding tag associated with the binding agent hybridizes with the first hybridization sequence on the adaptor molecule.

In some embodiments, transferring information of the coding tag to the recording tag is performed after the stabilizing components are linked together.

In some embodiments, transferring information comprises contacting the coding tag with a reagent for transferring the identifying information, the reagent comprising a reagent for primer extension reaction, a chemical ligation reagent or a biological ligation reagent.

In some embodiments, the stable complex is disrupted after the transfer of information from the coding tag to the recording tag by removing the linking agent from the stable complex or by introducing a destabilizing agent.

In some embodiments, the method further comprises contacting the polypeptide with a N-terminal modifier agent prior to binding of the binding agent to the polypeptide to form the modified NTAA of the polypeptide.

In some embodiments, the method further comprises removing the modified NTAA of the polypeptide after transferring the information from the coding tag to the recording tag to expose a new NTAA of the polypeptide. In some instances, the method includes treating the protein or peptide with a reagent for modifying a terminal amino acid of the protein or peptide.

In some embodiments, the method further comprises repeating at least one more time prior to analyzing the extended recording tag steps of: contacting the polypeptide with a N-terminal modifier agent to form the modified NTAA of the polypeptide; contacting the polypeptide with a binding agent capable of binding to the modified NTAA of the polypeptide or with a plurality of binding agents wherein at least one binding agent of the plurality of binding agents is capable of binding to the modified NTAA of the polypeptide, wherein each binding agent of the plurality of binding agents comprises or is associated with the second stabilizing component; linking the first and second stabilizing components together to form a stable complex comprising the binding agent, the macromolecule and the stabilizing components; optionally, removing the modified NTAA of the polypeptide.

In some embodiments, the extended recording tag is analyzed using a nucleic acid sequencing method. In some embodiments, the stabilizing components are attached to or associated with the binding agent and the target, respectively, at a site different from the binding site between the binding agent and the target. In some embodiments, the method further includes adding a universal priming site to the extended recording tag. In some embodiments, the method includes repeating some of the provided steps one or more times in a cyclic manner.

Provided herein are also methods for analyzing a macromolecule comprising the steps of: providing a macromolecule and an associated recording tag joined to a support; contacting the macromolecule with a binding agent capable of binding to the macromolecule, wherein the binding agent comprises a coding tag with identifying information regarding the binding agent, to allow binding between the macromolecule and the binding agent; providing an adaptor molecule comprising a first hybridization sequence substantially complementary to at least a portion of the coding tag (or portion thereof), and a secondary tag, to allow hybridization between the adaptor molecule (or the first hybridization sequence) and the coding tag (or the portion of the coding tag); transferring the information of the secondary tag to the recording tag to generate an extended recording tag; and analyzing the extended recording tag.

Provided herein is a kit for analyzing a macromolecule comprising: a binding agent comprising a coding tag, which comprises identifying information regarding the binding agent, wherein the binding agent is configured to bind a macromolecule associated with a first stabilizing component and with a recording tag joined to a support, and wherein the binding agent is associated with a second stabilizing component; the recording tag associated with the first stabilizing component; a linking agent configured to linking the first and second stabilizing components together after binding of the binding agent to the macromolecule to form a stable complex comprising the binding agent, the macromolecule and the stabilizing components.

In some embodiments, the kit comprises a plurality of binding agents and wherein at least one binding agent of the plurality of binding agents is capable of binding to the macromolecule and each binding agent of the plurality of binding agents comprises or is associated with the second stabilizing component. In some embodiments, the macromolecule comprises a polypeptide. In some embodiments, the kit further comprises: an adaptor molecule comprising a first hybridization sequence substantially complementary to at least a portion of the coding tag, and a secondary tag, wherein an information of the secondary tag is configured for transfer from the adaptor molecule to the recording tag to generate an extended recording tag after the coding tag associated with the binding agent hybridizes with the first hybridization sequence on the adaptor molecule. In some embodiments, the coding tag and/or the recording tag comprises a unique molecular identifier (UMI) or a barcode sequence.

Provided herein are also kits for analyzing a macromolecule comprising: a binding agent comprising a coding tag, which comprises identifying information regarding the binding agent; an adaptor molecule comprising a first hybridization sequence substantially complementary to at least a portion of the coding tag, and a secondary tag; wherein the binding agent is configured to bind a macromolecule associated with a recording tag; and wherein information from the secondary tag is configured for transfer from the adaptor molecule to the recording tag. In some embodiments, the kit comprises a plurality of binding agents and a plurality of adaptor molecules. The plurality of adaptor molecules includes at least one adaptor molecule capable of hybridizing to at least one coding tag associated with the binding agent. In some cases, multiple coding tags associated with the binding agent are configured to hybridize to adaptor molecules comprising the same secondary tag. In some embodiments, the adaptor molecule further comprises a second hybridization sequence substantially complementary to a portion of the recording tag.

BRIEF DESCRIPTION OF THE DRAWINGS

Non-limiting embodiments of the present invention will be described by way of example with reference to the accompanying figures, which are schematic and are not intended to be drawn to scale. For purposes of illustration, not every component is labeled in every figure, nor is every component of each embodiment of the invention shown where illustration is not necessary to allow those of ordinary skill in the art to understand the invention.

In FIG. 1A, a target joined to a recording tag is associated with a first stabilizing component. In FIG. 1B, the target is contacted with a binding agent associated with a second stabilizing component and the binding agent interacts with the target. In FIG. 1C, a linking agent is introduced and the two stabilizing components are linked and a stable complex containing the binding agent and the target is formed. In FIG. 1D, information is transferred from the coding tag to the recording tag (e.g. by extension). While the schematic depicts a stabilizing component and linking agent each as one molecule, it is within the scope of the invention that each stabilizing component or the linking agent may contain sub-components or comprise two or more molecules.

FIG. 2A shows a target joined to a recording tag. In FIG. 2B, the target is associated with a first stabilizing component containing a nucleic acid that hybridizes to a portion of the recording tag, and the target is contacted with a binding agent associated with a second stabilizing component via hybridization of the joined nucleic acid. In FIG. 2C, a linking agent is introduced and the stabilizing components are linked, forming a stable complex containing the binding agent and the target. In FIG. 2D, information is transferred from the coding tag to the recording tag (e.g. by extension).

FIG. 3A shows a peptide target joined to a recording tag with a biotin molecule attached at the 5' end and a binding agent configured to bind an N-terminal phenylalanine ("F" binding agent) and associated nucleic acid components (including a coding tag). In FIG. 3B, the peptide is contacted with the binding agent associated with a second biotin via hybridization of the joined nucleic acid. In FIG. 3C, streptavidin or neutravidin is introduced and interacts with the biotin molecules, forming a stable complex containing the binding agent and the peptide-recording tag conjugate, and information transfer by extension occurs. FIG. 3D depicts the extended recording tag containing information transferred from the coding tag.

FIG. 6A-FIG. 6D depicts an exemplary macromolecule analysis assay involving information transfer using an adaptor molecule with a first hybridization sequence and a secondary tag. In FIG. 6A, a peptide to be analyzed is joined to a recording tag immobilized on a support. In FIG. 6B, the peptide is contacted with a binding agent associated with a coding tag and the binding agent interacts with the peptide to be analyzed. In FIG. 6C, an adaptor molecule comprising a first hybridization sequence ($1^{st}$ hyb sequence) and secondary tag is introduced. The first hybridization sequence contains a sequence complementary to the coding tag associated with the binding agent. Once the adaptor molecule is in place (via hybridization to the coding tag), information from the secondary tag on the adaptor molecule containing identifying information regarding the binding agent is transferred from the adaptor molecule to the recording tag via ligation, thereby generating an extended recording tag. After information transfer, the adaptor molecule (portion besides the secondary tag) may be released by digestion, such as by treating with USER Enzyme. After information transfer, the binding agent may be optionally removed, as shown in FIG. 6D. A cycle of steps shown in FIG. 6B-6D may be repeated one or more times to further extend the recording tag.

FIG. 7A-FIG. 7D depicts an exemplary macromolecule analysis assay involving information transfer using an adaptor molecule with a first hybridization sequence, a secondary tag, and a second hybridization sequence. In FIG. 7A, a peptide to be analyzed is joined to a recording tag immobilized on a support. In FIG. 7B, the peptide is contacted with a binding agent associated with a coding tag and the binding agent interacts with the peptide to be analyzed. In FIG. 7C, an adaptor molecule comprising a first hybridization sequence ($1^{st}$ hyb sequence), secondary tag, and second hybridization sequence ($2^{nd}$ hyb sequence) is introduced. The first hybridization sequence contains a sequence complementary to the coding tag associated with the binding agent. The second hybridization sequence contains a sequence complementary to a portion of the recording tag. Once the adaptor molecule is in place (via hybridization to the coding tag and recording tag), information from the secondary tag on the adaptor molecule containing identifying information regarding the binding agent is transferred from the adaptor molecule to the recording tag (e.g. via extension). The adaptor molecule contains a linker between the first hybridization sequence and the secondary tag, which is used to stop polymerase extension. After information transfer, the binding agent may be optionally removed, as shown in FIG. 7D. A cycle of steps shown in FIG. 7B-7D may be repeated one or more times to further extend the recording tag.

FIG. 9A shows a splint adaptor molecule containing a first hybridization sequence (Payload seq 1, PL1) complementary to a region on the coding tag (PL1'), followed by a PEG-based linker, a spacer sequence (Sp'), a barcode sequence (BC') and another spacer sequence (Sp') complementary to a region on the recording tag (Sp). FIG. 9B shows encoding yield in the information transfer assay utilizing an engineered F-binder. The encoding assay was performed with the F-binder conjugated with two different coding tags that contain oligonucleotides complementary to hybridization sequences Payload seq 1 (PL1) and Payload seq 1 (PL2); splint adaptor molecules as shown in FIG. 9A containing from 5' end to 3' end a first hybridization sequence (either PL1 or PL2), a secondary tag (Sp' and BC') and a second hybridization sequence (Sp') were added to allow hybridization between the splint adaptor molecule, the coding tag and the recording tag. Coding tags were fused to 3 peptides (AA-PA, AFA-PA or FA-PA, SEQ ID NOs: 3-5) or used without peptide. Encoding yield on each peptide was obtained by evaluating encoded recoding tag corresponding to the attached peptide by a NGS readout. High encoding yield was observed only for the target peptide FA-PA having F as the N-terminal amino acid.

FIG. 10A. A binder (shown as cylinder) fused with a coding tag binds to the target peptide (shown as several circles connected together). This interaction is stabilized with Clamp oligo having terminal sequences complementary to portions of the coding tag and recording tag and serving as stabilizing components (stabilization through hybridization). After that, Encoding oligo (adaptor molecule) is annealed to the portion of the coding tag. Encoding oligo can then be directly ligated to the recording tag, or can be first ligated to Clamp oligo and then ligated to the recording tag. FIG. 10B. Encoding oligo from FIG. 10A is shown ligated to Clamp oligo and is ready for ligation to the recording tag. After ligation to the recording tag and removal of the binder, USER enzyme can be used to cleave the U residue and remove the extra sequence from the ligated product. The encoding cycle can be repeated with a new binder and a new Encoding oligo to produce a further extended recording tag. FIG. 10C. The extended recording tag produced from several cycles of encoding using the spacer-less ligation approach (ssDNA ligase is used for ligation). FIG. 10D. After final cycle of encoding, Capping oligonucleotide is introduced to add a priming site to the extended recording tag for further analysis by NGS.

In FIG. 12A no SA was added (no stabilization), whereas in FIG. 12B 50 nM of streptavidin (SA) was added to connect DSB on the recording tag and biotin associated with the binding agent (stabilization). The samples were then exposed either to a stringent wash (encoding efficiencies indicated by left bars), or directly proceeded to the encoding without the wash (encoding efficiencies indicated by right bars).

In FIG. 13A encoding efficiencies measured at two temperatures (25° C. and 37° C.) are shown for the setup where recording tags did not contain a DSB molecule at its 5' end (no stabilization during encoding), whereas in FIG. 13B DSB was attached to the recording tags (stabilization during encoding).

FIG. 14A shows a binder (shown as cylinder) fused with a coding tag that binds to the target peptide (shown as several circles connected together) immobilized on a support with a recording tag. S1 and S2 are two complementary polynucleotides that serve as the first and second stabilizing components (protected from hybridization before binding). After binding, introduction of light or a linking agent can trigger hybridization or association of the stabilizing components by a variety of ways shown in the FIG. 14B. Light or a linking agent can trigger isomerization, uncaging or structural transformation of one of the components.

DETAILED DESCRIPTION

Figure 1:
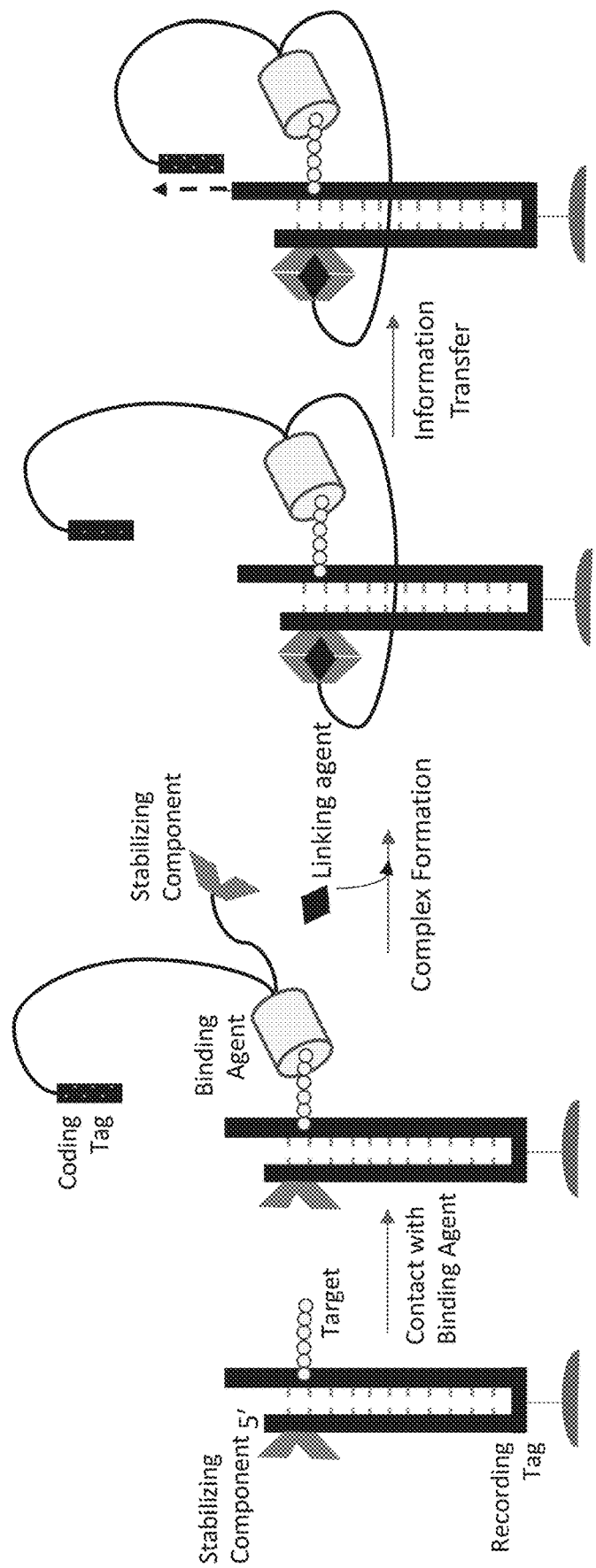
FIG. 1A-1D depicts an exemplary binding reaction and formation of a stable complex for information transfer.
Figure 2:
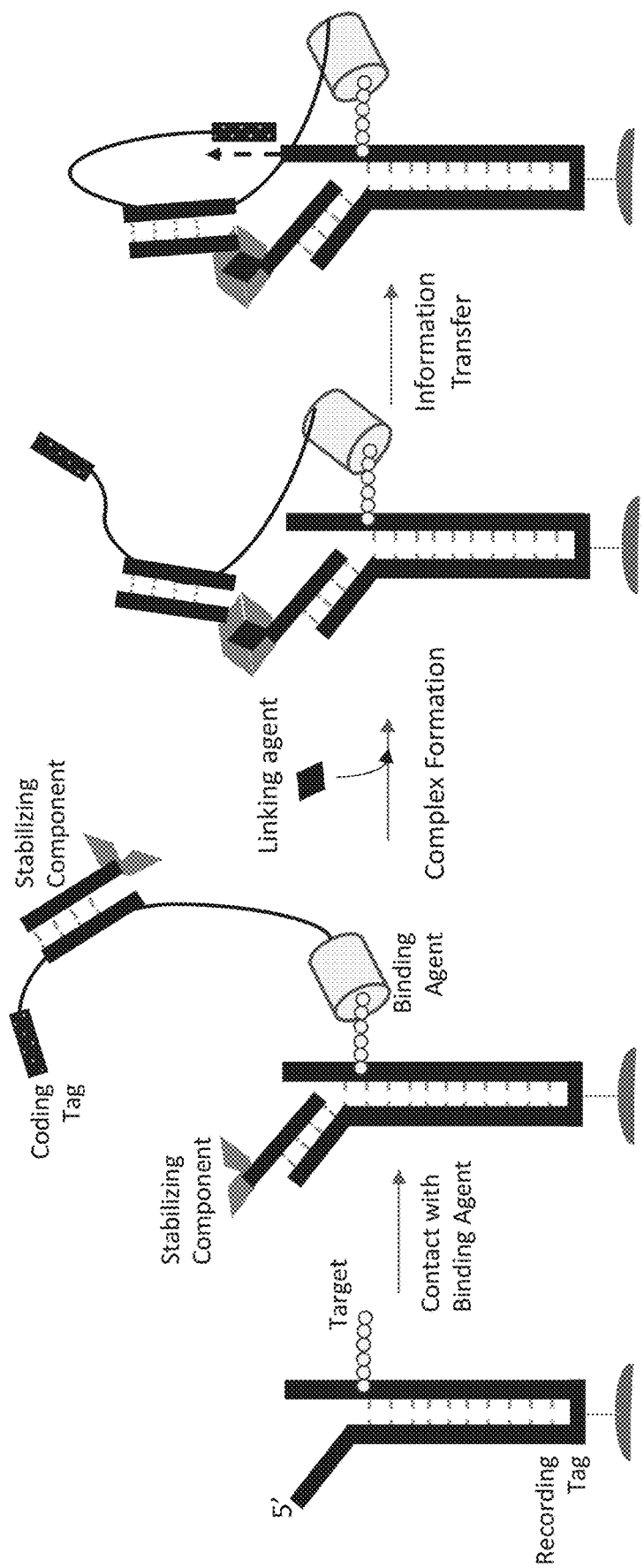
FIG. 2A-2D depicts an exemplary binding reaction and formation of a stable complex for information transfer with stabilizing components associated with nucleic acids.

Provided herein are methods and kits for performing a binding reaction comprising contacting a binding agent with a target, wherein the binding agent and the target each comprises or is associated with a stabilizing component; allowing the binding agent to interact with a binding site located on the target; and linking the stabilizing components to form a stable complex. In some embodiments, each of the stabilizing components is attached to or associated with the binding agent and the target, respectively, at a site different from the binding site between the binding agent and the target. In some aspects, the target in the binding reaction is a macromolecule, e.g., a polypeptide. In some aspects, the binding reaction is performed with a plurality of binding agents and a plurality of macromolecules, e.g., polypeptides. In some embodiments, the provided methods for performing a binding reaction is performed in an assay for sequencing or analysis of the polypeptides. In some embodiments, the analysis employs barcoding and nucleic acid encoding of molecular recognition events, and/or detectable labels. In some aspects, the stable complex formed comprising the binding agent and target is compatible with steps in the analysis including transferring information between nucleic acid tags (e.g., a DNA tag or a DNA recording tag). In some embodiments, the target macromolecules are digested prior to performing the binding reaction. Also provided are kits containing components and/or reagents for performing the provided binding reactions. In some embodiments, the kits also include instructions for performing any of the methods provided for performing the binding reaction and for macromolecule sequencing and/or analysis.

Recognition and binding of molecular targets using binding agents can be useful for characterization and/or detection of target biomolecules. It may be desired for performing some assays that a binding agent binds to the target and forms a stable complex for downstream steps in the assay or analysis to take place. There remains a need for improved techniques relating to performing binding reactions, as well as to products, methods and kits for accomplishing the same. The present invention provides novel methods and compositions which may be utilized in a wide variety of nucleic acid-based and/or protein (e.g., binding agent)-based procedures, and further provides other related advantages. In some embodiments, the provided methods for performing a binding reaction include providing components which form a "clamp" that stabilizes a binding reaction or stabilizes a complex containing a binding agent and a target (e.g., a polypeptide). The provided methods are useful for performing a binding reaction and maintaining interaction between a binding agent and a target. In the absence of the clamp, the complex may be less stable and/or the binding agent and target may not remain bound for a desired amount of time.

In some embodiments, the present disclosure provides, in part, methods for performing a binding reaction for use with or as part of a method for highly-parallel, high throughput digital macromolecule (e.g., polypeptide) characterization and quantitation, with direct applications to protein and peptide characterization and sequencing. In some embodiments, the provided methods are for forming a stable complex comprising a binding agent and a target including linking the associated stabilizing components, wherein the stabilizing components are linked directly or indirectly to the binding agent and the target, respectively. In some embodiments, the target comprises macromolecules, e.g., a plurality of macromolecules obtained from a sample. In some embodiments, the sample is obtained from a subject. In some cases, the provided methods for performing a binding reaction are compatible with information transfer, with applications to macromolecule sequencing and/or analysis (e.g., protein sequencing and/or analysis), such as between nucleic acids associated with the binding agent and the target. In some examples, the information transfer is between a nucleic acid tag associated with the binding agent and a nucleic acid tag associated with the target (e.g., by extension or ligation).

In some examples, the information transferred comprises identifying information regarding a binding agent that is configured to bind to the macromolecule. The information transfer can be achieved by any suitable means such as by extension or ligation, and can be between nucleic acid molecules, e.g., between a nucleic acid tag associated with the binding agent and a secondary tag on an adaptor molecule. In some embodiments, a method for analyzing a macromolecule is provided, comprising the steps of: (a) providing a macromolecule and an associated recording tag joined to a support; (b) contacting the macromolecule with a binding agent capable of binding to the macromolecule, wherein the binding agent comprises a coding tag with identifying information regarding the binding agent, to allow binding between the macromolecule and the binding agent; (c) transferring information of the coding tag to the recording tag to generate an extended recording tag, wherein the information of the coding tag is transferred to the recording tag after the binding agent is bound to the macromolecule; and (d) analyzing the extended recording tag. In some embodiments, a method for analyzing a macromolecule is provided, comprising the steps of: (a) providing a macromolecule and an associated recording tag joined to a support; (b) contacting the macromolecule with a binding agent capable of binding to the macromolecule, wherein the binding agent comprises a coding tag with identifying information regarding the binding agent, to allow binding between the macromolecule and the binding agent; (c) providing an adaptor molecule comprising a first hybridization sequence and a secondary tag, wherein the first hybridization sequence is substantially complementary to at least a portion of the coding tag, to allow hybridization between the first hybridization sequence and the coding tag, wherein step (c) is performed before, after or simultaneously with step (b); (d) transferring information of the secondary tag to the recording tag to generate an extended recording tag, wherein the information of the secondary tag is transferred from the adaptor molecule to the recording tag after the coding tag associated with the binding agent hybridizes with the first hybridization sequence on the adaptor molecule; and (e) analyzing the extended recording tag.

The challenge with encoding information about the binding agent bound to the macromolecule into the extended recording tag in the abovementioned examples is that after binding and washing, the binding agent can quickly dissociate before the information about the binding agent is recorded into the recording tag. The stabilization approach described herein enables higher temperature and longer time duration encoding, since linking the stabilizing components minimizes prolonged dissociation of binding agent from the target polypeptide. Higher temperatures and longer encoding times are beneficial for slower encoding methods (such as ligation), reduce non-specific primer-primer interactions, enable use of enzymes that have a higher operating temperature, such as CircLigase, and enable the use of stringent annealing conditions when using adaptor molecules for encoding. The combination of the described stabilization approach and ssDNA ligation can enable "spacerless" encoding paving the way for effective targeted enrichment.

Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

All publications, including patent documents, scientific articles and databases, referred to in this application are incorporated by reference in their entireties for all purposes to the same extent as if each individual publication were individually incorporated by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

DEFINITIONS

Unless defined otherwise, all technical and scientific terms used herein have the same meaning as is commonly understood by one of ordinary skill in the art to which the present disclosure belongs. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a," "an" and "the" include plural referents unless the context clearly dictates otherwise. Thus, for example, reference to "a peptide" includes one or more peptides, or mixtures of peptides. Also, and unless specifically stated or obvious from context, as used herein, the term "or" is understood to be inclusive and covers both "or" and "and".

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X.

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

An "individual" or "subject" includes a mammal. Mammals include, but are not limited to, domesticated animals (e.g., cows, sheep, cats, dogs, and horses), primates (e.g., humans and non-human primates such as monkeys), rabbits, and rodents (e.g., mice and rats). An "individual" or "subject" may include birds such as chickens, vertebrates such as fish and mammals such as mice, rats, rabbits, cats, dogs, pigs, cows, ox, sheep, goats, horses, monkeys and other non-human primates. In certain embodiments, the individual or subject is a human.

As used herein, the term "sample" refers to anything which may contain an analyte for which an analyte assay is desired. As used herein, a "sample" can be a solution, a suspension, liquid, powder, a paste, aqueous, non-aqueous or any combination thereof. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

In some embodiments, the sample is a biological sample. A biological sample of the present disclosure encompasses a sample in the form of a solution, a suspension, a liquid, a powder, a paste, an aqueous sample, or a non-aqueous sample. As used herein, a "biological sample" includes any sample obtained from a living or viral (or prion) source or other source of macromolecules and biomolecules, and includes any cell type or tissue of a subject from which nucleic acid, protein and/or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom. In some embodiments, the sample can be derived from a tissue or a body fluid, for example, a connective, epithelium, muscle or nerve tissue; a tissue selected from the group consisting of brain, lung, liver, spleen, bone marrow, thymus, heart, lymph, blood, bone, cartilage, pancreas, kidney, gall bladder, stomach, intestine, testis, ovary, uterus, rectum, nervous system, gland, and internal blood vessels; or a body fluid selected from the group consisting of blood, urine, saliva, bone marrow, sperm, an ascitic fluid, and subfractions thereof, e.g., serum or plasma.

The terms "level" or "levels" are used to refer to the presence and/or amount of a target, e.g., a substance or an organism that is part of the etiology of a disease or disorder, and can be determined qualitatively or quantitatively. A "qualitative" change in the target level refers to the appearance or disappearance of a target that is not detectable or is present in samples obtained from normal controls. A "quantitative" change in the levels of one or more targets refers to a measurable increase or decrease in the target levels when compared to a healthy control.

As used herein, the term "macromolecule" encompasses large molecules composed of smaller subunits. Examples of macromolecules include, but are not limited to peptides, polypeptides, proteins, nucleic acids, carbohydrates, lipids, macrocycles, or a combination or complex thereof. A macromolecule also includes a chimeric macromolecule composed of a combination of two or more types of macromolecules, covalently linked together (e.g., a peptide linked to a nucleic acid). A macromolecule may also include a "macromolecule assembly", which is composed of non-covalent complexes of two or more macromolecules. A macromolecule assembly may be composed of the same type of macromolecule (e.g., protein-protein) or of two or more different types of macromolecules (e.g., protein-DNA).

As used herein, the term "polypeptide" encompasses peptides and proteins, and refers to a molecule comprising a chain of two or more amino acids joined by peptide bonds. In some embodiments, a polypeptide comprises 2 to 50 amino acids, e.g., having more than 20-30 amino acids. In some embodiments, a peptide does not comprise a secondary, tertiary, or higher structure. In some embodiments, the polypeptide is a protein. In some embodiments, a protein comprises 30 or more amino acids, e.g. having more than 50 amino acids. In some embodiments, in addition to a primary structure, a protein comprises a secondary, tertiary, or higher structure. The amino acids of the polypeptides are most typically L-amino acids, but may also be D-amino acids, modified amino acids, amino acid analogs, amino acid mimetics, or any combination thereof. Polypeptides may be naturally occurring, synthetically produced, or recombinantly expressed. Polypeptides may be synthetically produced, isolated, recombinantly expressed, or be produced by a combination of methodologies as described above. Polypeptides may also comprise additional groups modifying the amino acid chain, for example, functional groups added via post-translational modification. The polymer may be linear or branched, it may comprise modified amino acids, and it may be interrupted by non-amino acids. The term also encompasses an amino acid polymer that has been modified naturally or by intervention; for example, disulfide bond formation, glycosylation, lipidation, acetylation, phosphorylation, or any other manipulation or modification, such as conjugation with a labeling component.

As used herein, the term "amino acid" refers to an organic compound comprising an amine group, a carboxylic acid group, and a side-chain specific to each amino acid, which serve as a monomeric subunit of a peptide. An amino acid includes the 20 standard, naturally occurring or canonical amino acids as well as non-standard amino acids. The standard, naturally-occurring amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr). An amino acid may be an L-amino acid or a D-amino acid. Non-standard amino acids may be modified amino acids, amino acid analogs, amino acid mimetics, non-standard proteinogenic amino acids, or non-proteinogenic amino acids that occur naturally or are chemically synthesized. Examples of non-standard amino acids include, but are not limited to, selenocysteine, pyrolysine, and N-formylmethionine, (β-amino acids, Homo-amino acids, Proline and Pyruvic acid derivatives, 3-substituted alanine derivatives, glycine derivatives, ring-substituted phenylalanine and tyrosine derivatives, linear core amino acids, N-methyl amino acids.

As used herein, the term "post-translational modification" refers to modifications that occur on a peptide after its translation, e.g., translation by ribosomes, is complete. A post-translational modification may be a covalent chemical modification or enzymatic modification. Examples of post-translation modifications include, but are not limited to, acylation, acetylation, alkylation (including methylation), biotinylation, butyrylation, carbamylation, carbonylation, deamidation, deiminiation, diphthamide formation, disulfide bridge formation, eliminylation, flavin attachment, formylation, gamma-carboxylation, glutamylation, glycylation, glycosylation, glypiation, heme C attachment, hydroxylation, hypusine formation, iodination, isoprenylation, lipidation, lipoylation, malonylation, methylation, myristoylation, oxidation, palmitoylation, pegylation, phosphopantetheinylation, phosphorylation, prenylation, propionylation, retinylidene Schiff base formation, S-glutathionylation, S-nitrosylation, S-sulfenylation, selenation, succinylation, sulfination, ubiquitination, and C-terminal amidation. A post-translational modification includes modifications of the amino terminus and/or the carboxyl terminus of a peptide. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl). A post-translational modification also includes modifications, such as but not limited to those described above, of amino acids falling between the amino and carboxy termini. The term post-translational modification can also include peptide modifications that include one or more detectable labels.

As used herein, the term "binding agent" or "binder" refers to a nucleic acid molecule, a peptide, a polypeptide, a protein, carbohydrate, or a small molecule that binds to, associates, unites with, recognizes, or combines with a binding target, e.g., a polypeptide or a component or feature of a polypeptide. A binding agent may form a covalent association or non-covalent association with the polypeptide or component or feature of a polypeptide. A binding agent may also be a chimeric binding agent, composed of two or more types of molecules, such as a nucleic acid molecule-peptide chimeric binding agent or a carbohydrate-peptide chimeric binding agent. A binding agent may be a naturally occurring, synthetically produced, or recombinantly expressed molecule. A binding agent may bind to a single monomer or subunit of a polypeptide (e.g., a single amino acid of a polypeptide) or bind to a plurality of linked subunits of a polypeptide (e.g., a di-peptide, tri-peptide, or higher order peptide of a longer peptide, polypeptide, or protein molecule). A binding agent may bind to a linear molecule or a molecule having a three-dimensional structure (also referred to as conformation). For example, an antibody binding agent may bind to linear peptide, polypeptide, or protein, or bind to a conformational peptide, polypeptide, or protein. A binding agent may bind to an N-terminal peptide, a C-terminal peptide, or an intervening peptide of a peptide, polypeptide, or protein molecule. A binding agent may bind to an N-terminal amino acid, C-terminal amino acid, or an intervening amino acid of a peptide molecule. A binding agent may preferably bind to a chemically modified or labeled amino acid (e.g., an amino acid that has been labeled by a chemical reagent) over a non-modified or unlabeled amino acid. For example, a binding agent may preferably bind to an amino acid that has been labeled or modified over an amino acid that is unlabeled or unmodified. A binding agent may bind to a post-translational modification of a peptide molecule. A binding agent may exhibit selective binding to a component or feature of a polypeptide (e.g., a binding agent may selectively bind to one of the 20 possible natural amino acid residues and bind with very low affinity or not at all to the other 19 natural amino acid residues). A binding agent may exhibit less selective binding, where the binding agent is capable of binding or configured to bind to a plurality of components or features of a polypeptide (e.g., a binding agent may bind with similar affinity to two or more different amino acid residues). A binding agent may comprise a coding tag, which may be joined to the binding agent by a linker.

As used herein, the term "linker" refers to one or more of a nucleotide, a nucleotide analog, an amino acid, a peptide, a polypeptide, a polymer, or a non-nucleotide chemical moiety that is used to join two molecules. A linker may be used to join a binding agent with a coding tag, a recording tag with a polypeptide, a polypeptide with a support, a recording tag with a solid support, etc. In certain embodiments, a linker joins two molecules via enzymatic reaction or chemistry reaction (e.g., click chemistry).

The term "ligand" as used herein refers to any molecule or moiety connected to the compounds described herein. "Ligand" may refer to one or more ligands attached to a compound. In some embodiments, the ligand is a pendant group or binding site (e.g., the site to which the binding agent binds).

As used herein, the term "proteome" can include the entire set of proteins, polypeptides, or peptides (including conjugates or complexes thereof) expressed by a genome, cell, tissue, or organism at a certain time, of any organism. In one aspect, it is the set of expressed proteins in a given type of cell or organism, at a given time, under defined conditions. Proteomics is the study of the proteome. For example, a "cellular proteome" may include the collection of proteins found in a particular cell type under a particular set of environmental conditions, such as exposure to hormone stimulation. An organism's complete proteome may include the complete set of proteins from all of the various cellular proteomes. A proteome may also include the collection of proteins in certain sub-cellular biological systems. For example, all of the proteins in a virus can be called a viral proteome. As used herein, the term "proteome" include subsets of a proteome, including but not limited to a kinome; a secretome; a receptome (e.g., GPCRome); an immunoproteome; a nutriproteome; a proteome subset defined by a post-translational modification (e.g., phosphorylation, ubiquitination, methylation, acetylation, glycosylation, oxidation, lipidation, and/or nitrosylation), such as a phosphoproteome (e.g., phosphotyrosine-proteome, tyrosine-kinome, and tyrosine-phosphatome), a glycoproteome, etc.; a proteome subset associated with a tissue or organ, a developmental stage, or a physiological or pathological condition; a proteome subset associated a cellular process, such as cell cycle, differentiation (or de-differentiation), cell death, senescence, cell migration, transformation, or metastasis; or any combination thereof. As used herein, the term "proteomics" refers to qualitative or quantitative analysis of the proteome within cells, tissues, and bodily fluids, and the corresponding spatial distribution of the proteome within the cell and within tissues. Additionally, proteomics studies include the dynamic state of the proteome, continually changing in time as a function of biology and defined biological or chemical stimuli.

The terminal amino acid at one end of a peptide or polypeptide chain that has a free amino group is referred to herein as the "N-terminal amino acid" (NTAA). The terminal amino acid at the other end of the chain that has a free carboxyl group is referred to herein as the "C-terminal amino acid" (CTAA). The amino acids making up a peptide may be numbered in order, with the peptide being "n" amino acids in length. As used herein, NTAA is considered the $n^{th}$ amino acid (also referred to herein as the "n NTAA"). Using this nomenclature, the next amino acid is the n–1 amino acid, then the n–2 amino acid, and so on down the length of the peptide from the N-terminal end to C-terminal end. In certain embodiments, an NTAA, CTAA, or both may be modified or labeled with a moiety or a chemical moiety.

As used herein, the term "barcode" refers to a nucleic acid molecule of about 2 to about 30 bases (e.g., 2, 3, 4, 5, 6, 7, 8, 9, 10, 11, 12, 13, 14, 15, 16, 17, 18, 19, 20, 21, 22, 23, 24, 25, 26, 27, 28, 29 or 30 bases) providing a unique identifier tag or origin information for a polypeptide, a binding agent, a set of binding agents from a binding cycle, a sample polypeptides, a set of samples, polypeptides within a compartment (e.g., droplet, bead, or separated location), polypeptides within a set of compartments, a fraction of polypeptides, a set of polypeptide fractions, a spatial region or set of spatial regions, a library of polypeptides, or a library of binding agents. A barcode can be an artificial sequence or a naturally occurring sequence. In certain embodiments, each barcode within a population of barcodes is different. In other embodiments, a portion of barcodes in a population of barcodes is different, e.g., at least about 10%, 15%, 20%, 25%, 30%, 35%, 40%, 45%, 50%, 55%, 60%, 65%, 70%, 75%, 80%, 85%, 90%, 95%, 97%, or 99% of the barcodes in a population of barcodes is different. A population of barcodes may be randomly generated or non-randomly generated. In certain embodiments, a population of barcodes are error-correcting or error-tolerant barcodes. Barcodes can be used to computationally deconvolute the multiplexed sequencing data and identify sequence reads derived from an individual polypeptide, sample, library, etc. A barcode can also be used for deconvolution of a collection of polypeptides that have been distributed into small compartments for enhanced mapping. For example, rather than mapping a peptide back to the proteome, the peptide is mapped back to its originating protein molecule or protein complex.

As used herein, the term "coding tag" refers to a polynucleotide with any suitable length, e.g., a nucleic acid molecule of about 2 bases to about 100 bases, including any integer including 2 and 100 and in between, that comprises identifying information for its associated binding agent. A "coding tag" may also be made from a "sequenceable polymer" (see, e.g., Niu et al., 2013, Nat. Chem. 5:282-292; Roy et al., 2015, Nat. Commun. 6:7237; Lutz, 2015, Macromolecules 48:4759-4767; each of which are incorporated by reference in its entirety). A coding tag may comprise an encoder sequence, which is optionally flanked by one spacer on one side or optionally flanked by a spacer on each side. A coding tag may also be comprised of an optional UMI and/or an optional binding cycle-specific barcode. A coding tag may be single stranded or double stranded. A double stranded coding tag may comprise blunt ends, overhanging ends, or both. A coding tag may refer to the coding tag that is directly attached to a binding agent, to a complementary sequence hybridized to the coding tag directly attached to a binding agent (e.g., for double stranded coding tags), or to coding tag information present in an extended recording tag. In certain embodiments, a coding tag may further comprise a binding cycle specific spacer or barcode, a unique molecular identifier, a universal priming site, or any combination thereof.

As used herein, the term "spacer" (Sp) refers to a nucleic acid molecule of about 1 base to about 20 bases (e.g., 1, 2, 3, 4, 5, 6, 7, 8, 9, 10, 11, 12, 13, 14, 15, 16, 17, 18, 19, or 20 bases) in length that is present on a terminus of a recording tag, coding tag or adaptor molecule. In certain embodiments, a spacer sequence flanks a secondary tag or an encoder sequence of a coding tag on one end or both ends. Following binding of a binding agent to a polypeptide, annealing between complementary spacer sequences on their associated coding tag (or adaptor molecule) and recording tag, respectively, allows transfer of binding information through a primer extension reaction or ligation to the recording tag, coding tag, or a di-tag construct. Sp' refers to spacer sequence complementary to Sp. Preferably, spacer sequences within a library of binding agents possess the same number of bases. A common (shared or identical) spacer may be used in a library of binding agents. A spacer sequence may have a "cycle specific" sequence in order to track binding agents used in a particular binding cycle. The spacer sequence (Sp) can be constant across all binding cycles, be specific for a particular class of polypeptides, or be binding cycle number specific. Polypeptide class-specific spacers permit annealing of a cognate binding agent's coding tag information present in an extended recording tag from a completed binding/extension cycle to the coding tag of another binding agent recognizing the same class of polypeptides in a subsequent binding cycle via the class-specific spacers. Only the sequential binding of correct cognate pairs results in interacting spacer elements and effective primer extension. A spacer sequence may comprise sufficient number of bases to anneal to a complementary spacer sequence in a recording tag to initiate a primer extension (also referred to as polymerase extension) reaction, or provide a "splint" for a ligation reaction, or mediate a "sticky end" ligation reaction. A spacer sequence may comprise a fewer number of bases than the encoder sequence within a coding tag.

As used herein, the term "recording tag" refers to a moiety, e.g., a chemical coupling moiety, a nucleic acid molecule, or a sequenceable polymer molecule (see, e.g., Niu et al., 2013, Nat. Chem. 5:282-292; Roy et al., 2015, Nat. Commun. 6:7237; Lutz, 2015, Macromolecules 48:4759-4767; each of which are incorporated by reference in its entirety) to which identifying information of a coding tag can be transferred, either directly or indirectly (e.g., via an adaptor molecule). For example, information from a secondary tag of an adaptor molecule (e.g., as a proxy, representation or correlation of the information of a coding tag) can be transferred to the recording tag. In some embodiments, identifying information about the macromolecule (e.g., UMI information) associated with the recording tag can be transferred to the coding tag. Identifying information can comprise any information characterizing a molecule such as information pertaining to sample, fraction, partition, spatial location, interacting neighboring molecule(s), cycle number, etc. Additionally, the presence of UMI information can also be classified as identifying information. In certain embodiments, after a binding agent binds to a polypeptide, information from a coding tag linked to a binding agent can be transferred to the recording tag associated with the polypeptide while the binding agent is bound to the polypeptide. In other embodiments, after a binding agent binds to a polypeptide, information from a recording tag associated with the polypeptide can be transferred to the coding tag linked to the binding agent while the binding agent is bound to the polypeptide. A recording tag may be directly linked to a polypeptide, linked to a polypeptide via a multifunctional linker, or associated with a polypeptide by virtue of its proximity (or co-localization) on a support. A recording tag may be linked via its 5' end or 3' end or at an internal site, as long as the linkage is compatible with the method used to transfer coding tag information to the recording tag or vice versa. A recording tag may further comprise other functional components, e.g., a universal priming site, unique molecular identifier, a barcode (e.g., a sample barcode, a fraction barcode, spatial barcode, a compartment tag, etc.), a spacer sequence that is complementary to a spacer sequence of a coding tag, or any combination thereof. The spacer sequence of a recording tag is preferably at the 3'-end of the recording tag in embodiments where polymerase extension is used to transfer coding tag information to the recording tag.

As used herein, the term "primer extension", also referred to as "polymerase extension", refers to a reaction catalyzed by a nucleic acid polymerase (e.g., DNA polymerase) whereby a nucleic acid molecule (e.g., oligonucleotide primer, spacer sequence) that anneals to a complementary strand is extended by the polymerase, using the complementary strand as template.

As used herein, the term "unique molecular identifier" or "UMI" refers to a nucleic acid molecule of about 3 to about 40 bases (3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases) in length providing a unique identifier tag for each macromolecule, polypeptide or binding agent to which the UMI is linked. A polypeptide UMI can be used to computationally deconvolute sequencing data from a plurality of extended recording tags to identify extended recording tags that originated from an individual polypeptide. A polypeptide UMI can be used to accurately count originating polypeptide molecules by collapsing NGS reads to unique UMIs. A binding agent UMI can be used to identify each individual molecular binding agent that binds to a particular polypeptide. For example, a UMI can be used to identify the number of individual binding events for a binding agent specific for a single amino acid that occurs for a particular peptide molecule. It is understood that when UMI and barcode are both referenced in the context of a binding agent or polypeptide, that the barcode refers to identifying information other that the UMI for the individual binding agent or polypeptide (e.g., sample barcode, compartment barcode, binding cycle barcode).

As used herein, the term "universal priming site" or "universal primer" or "universal priming sequence" refers to a nucleic acid molecule, which may be used for library amplification and/or for sequencing reactions. A universal priming site may include, but is not limited to, a priming site (primer sequence) for PCR amplification, flow cell adaptor sequences that anneal to complementary oligonucleotides on flow cell surfaces enabling bridge amplification in some next generation sequencing platforms, a sequencing priming site, or a combination thereof. Universal priming sites can be used for other types of amplification, including those commonly used in conjunction with next generation digital sequencing. For example, extended recording tag molecules may be circularized and a universal priming site used for rolling circle amplification to form DNA nanoballs that can be used as sequencing templates (Drmanac et al., 2009, Science 327:78-81). Alternatively, recording tag molecules may be circularized and sequenced directly by polymerase extension from universal priming sites (Korlach et al., 2008, Proc. Natl. Acad. Sci. 105:1176-1181). The term "forward" when used in context with a "universal priming site" or "universal primer" may also be referred to as "5'" or "sense". The term "reverse" when used in context with a "universal priming site" or "universal primer" may also be referred to as "3'" or "antisense".

As used herein, the term "extended recording tag" refers to a recording tag to which information of at least one binding agent's coding tag (or its complementary sequence) has been transferred following binding of the binding agent to a polypeptide. Information of the coding tag may be transferred to the recording tag directly (e.g., ligation) or indirectly (e.g., primer extension). Information may be transferred to the recording tag directly (e.g., ligation) or indirectly (e.g., primer extension) from a secondary tag of an adaptor molecule. Information of a coding tag may be transferred to the recording tag enzymatically or chemically. An extended recording tag may comprise binding agent information of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 125, 150, 175, 200 or more coding tags. The base sequence of an extended recording tag may reflect the temporal and sequential order of binding of the binding agents identified by their coding tags, may reflect a partial sequential order of binding of the binding agents identified by the coding tags, or may not reflect any order of binding of the binding agents identified by the coding tags. In certain embodiments, the coding tag information present in the extended recording tag represents with at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% identity the polypeptide sequence being analyzed. In certain embodiments where the extended recording tag does not represent the polypeptide sequence being analyzed with 100% identity, errors may be due to off-target binding by a binding agent, or to a "missed" binding cycle (e.g., because a binding agent fails to bind to a polypeptide during a binding cycle, because of a failed primer extension reaction), or both.

As used herein, the term "solid support", "solid surface", or "solid substrate", or "sequencing substrate", or "substrate" refers to any solid material, including porous and non-porous materials, to which a polypeptide can be associated directly or indirectly, by any means known in the art, including covalent and non-covalent interactions, or any combination thereof. A solid support may be two-dimensional (e.g., planar surface) or three-dimensional (e.g., gel matrix or bead). A solid support can be any support surface including, but not limited to, a bead, a microbead, an array, a glass surface, a silicon surface, a plastic surface, a filter, a membrane, a PTFE membrane, a PTFE membrane, a nitrocellulose membrane, a nitrocellulose-based polymer surface, nylon, a silicon wafer chip, a flow through chip, a flow cell, a biochip including signal transducing electronics, a channel, a microtiter well, an ELISA plate, a spinning interferometry disc, a nitrocellulose membrane, a nitrocellulose-based polymer surface, a polymer matrix, a nanoparticle, or a microsphere. Materials for a solid support include but are not limited to acrylamide, agarose, cellulose, dextran, nitrocellulose, glass, gold, quartz, polystyrene, polyethylene vinyl acetate, polypropylene, polyester, polymethacrylate, polyacrylate, polyethylene, polyethylene oxide, polysilicates, polycarbonates, poly vinyl alcohol (PVA), Teflon, fluorocarbons, nylon, silicon rubber, polyanhydrides, polyglycolic acid, polyvinylchloride, polylactic acid, polyorthoesters, functionalized silane, polypropylfumerate, collagen, glycosaminoglycans, polyamino acids, dextran, or any combination thereof. Solid supports further include thin film, membrane, bottles, dishes, fibers, woven fibers, shaped polymers such as tubes, particles, beads, microspheres, microparticles, or any combination thereof. For example, when solid surface is a bead, the bead can include, but is not limited to, a ceramic bead, a polystyrene bead, a polymer bead, a polyacrylate bead, a methylstyrene bead, an agarose bead, a cellulose bead, a dextran bead, an acrylamide bead, a solid core bead, a porous bead, a paramagnetic bead, a glass bead, a controlled pore bead, a silica-based bead, or any combinations thereof. A bead may be spherical or an irregularly shaped. A bead or support may be porous. A bead's size may range from nanometers, e.g., 100 nm, to millimeters, e.g., 1 mm. In certain embodiments, beads range in size from about 0.2 micron to about 200 microns, or from about 0.5 micron to about 5 micron. In some embodiments, beads can be about 1, 1.5, 2, 2.5, 2.8, 3, 3.5, 4, 4.5, 5, 5.5, 6, 6.5, 7, 7.5, 8, 8.5, 9, 9.5, 10, 10.5, 15, or 20 µm in diameter. In certain embodiments, "a bead" solid support may refer to an individual bead or a plurality of beads. In some embodiments, the solid surface is a nanoparticle. In certain embodiments, the nanoparticles range in size from about 1 nm to about 500 nm in diameter, for example, between about 1 nm and about 20 nm, between about 1 nm and about 50 nm, between about 1 nm and about 100 nm, between about 10 nm and about 50 nm, between about 10 nm and about 100 nm, between about 10 nm and about 200 nm, between about 50 nm and about 100 nm, between about 50 nm and about 150, between about 50 nm and about 200 nm, between about 100 nm and about 200 nm, or between about 200 nm and about 500 nm in diameter. In some embodiments, the nanoparticles can be about 10 nm, about 50 nm, about 100 nm, about 150 nm, about 200 nm, about 300 nm, or about 500 nm in diameter. In some embodiments, the nanoparticles are less than about 200 nm in diameter.

As used herein, the term "nucleic acid molecule" or "polynucleotide" refers to a single- or double-stranded polynucleotide containing deoxyribonucleotides or ribonucleotides that are linked by 3'-5' phosphodiester bonds, as well as polynucleotide analogs. A nucleic acid molecule includes, but is not limited to, DNA, RNA, and cDNA. A polynucleotide analog may possess a backbone other than a standard phosphodiester linkage found in natural polynucleotides and, optionally, a modified sugar moiety or moieties other than ribose or deoxyribose. Polynucleotide analogs contain bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide. Examples of polynucleotide analogs include, but are not limited to xeno nucleic acid (XNA), bridged nucleic acid (BNA), glycol nucleic acid (GNA), peptide nucleic acids (PNAs), yPNAs, morpholino polynucleotides, locked nucleic acids (LNAs), threose nucleic acid (TNA), 2'-O-Methyl polynucleotides, 2'-O-alkyl ribosyl substituted polynucleotides, phosphorothioate polynucleotides, and boronophosphate polynucleotides. A polynucleotide analog may possess purine or pyrimidine analogs, including for example, 7-deaza purine analogs, 8-halopurine analogs, 5-halopyrimidine analogs, or universal base analogs that can pair with any base, including hypoxanthine, nitroazoles, isocarbostyril analogues, azole carboxamides, and aromatic triazole analogues, or base analogs with additional functionality, such as a biotin moiety for affinity binding. In some embodiments, the nucleic acid molecule or oligonucleotide is a modified oligonucleotide. In some embodiments, the nucleic acid molecule or oligonucleotide is a DNA with pseudo-complementary bases, a DNA with protected bases, an RNA molecule, a BNA molecule, an XNA molecule, a LNA molecule, a PNA molecule, a γPNA molecule, or a morpholino DNA, or a combination thereof. In some embodiments, the nucleic acid molecule or oligonucleotide is backbone modified, sugar modified, or nucleobase modified. In some embodiments, the nucleic acid molecule or oligonucleotide has nucleobase protecting groups such as Alloc, electrophilic protecting groups such as thiranes, acetyl protecting groups, nitrobenzyl protecting groups, sulfonate protecting groups, or traditional base-labile protecting groups.

As used herein, "nucleic acid sequencing" means the determination of the order of nucleotides in a nucleic acid molecule or a sample of nucleic acid molecules.

As used herein, "next generation sequencing" refers to high-throughput sequencing methods that allow the sequencing of millions to billions of molecules in parallel. Examples of next generation sequencing methods include sequencing by synthesis, sequencing by ligation, sequencing by hybridization, polony sequencing, ion semiconductor sequencing, and pyrosequencing. By attaching primers to a solid substrate and a complementary sequence to a nucleic acid molecule, a nucleic acid molecule can be hybridized to the solid substrate via the primer and then multiple copies can be generated in a discrete area on the solid substrate by using polymerase to amplify (these groupings are sometimes referred to as polymerase colonies or polonies). Consequently, during the sequencing process, a nucleotide at a particular position can be sequenced multiple times (e.g., hundreds or thousands of times)—this depth of coverage is referred to as "deep sequencing." Examples of high throughput nucleic acid sequencing technology include platforms provided by Illumina, BGI, Qiagen, Thermo-Fisher, and Roche, including formats such as parallel bead arrays, sequencing by synthesis, sequencing by ligation, capillary electrophoresis, electronic microchips, "biochips," microarrays, parallel microchips, and single-molecule arrays (See e.g., Service, *Science* (2006) 311:1544-1546).

As used herein, "single molecule sequencing" or "third generation sequencing" refers to next-generation sequencing methods wherein reads from single molecule sequencing instruments are generated by sequencing of a single molecule of DNA. Unlike next generation sequencing methods that rely on amplification to clone many DNA molecules in parallel for sequencing in a phased approach, single molecule sequencing interrogates single molecules of DNA and does not require amplification or synchronization. Single molecule sequencing includes methods that need to pause the sequencing reaction after each base incorporation ('wash-and-scan' cycle) and methods which do not need to halt between read steps. Examples of single molecule sequencing methods include single molecule real-time sequencing (Pacific Biosciences), nanopore-based sequencing (Oxford Nanopore), duplex interrupted nanopore sequencing, and direct imaging of DNA using advanced microscopy.

As used herein, "analyzing" the polypeptide means to identify, detect, quantify, characterize, distinguish, or a combination thereof, all or a portion of the components of the polypeptide. For example, analyzing a peptide, polypeptide, or protein includes determining all or a portion of the amino acid sequence (contiguous or non-continuous) of the peptide. Analyzing a polypeptide also includes partial identification of a component of the polypeptide. For example, partial identification of amino acids in the polypeptide protein sequence can identify an amino acid in the protein as belonging to a subset of possible amino acids. Analysis typically begins with analysis of the n NTAA, and then proceeds to the next amino acid of the peptide (i.e., n−1, n−2, n−3, and so forth). This is accomplished by elimination of the n NTAA, thereby converting the n−1 amino acid of the peptide to an N-terminal amino acid (referred to herein as the "n−1 NTAA"). Analyzing the peptide may also include determining the presence and frequency of post-translational modifications on the peptide, which may or may not include information regarding the sequential order of the post-translational modifications on the peptide. Analyzing the peptide may also include determining the presence and frequency of epitopes in the peptide, which may or may not include information regarding the sequential order or location of the epitopes within the peptide. Analyzing the peptide may include combining different types of analysis, for example obtaining epitope information, amino acid sequence information, post-translational modification information, or any combination thereof.

It is understood that aspects and embodiments of the invention described herein include "consisting of" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present invention will become apparent from the following specification taken in conjunction with the accompanying drawings.

I. BINDING REACTION

Provided herein are methods and kits for performing a binding reaction comprising contacting a binding agent with a target, wherein the binding agent and the target each comprises or is associated with a stabilizing component, allowing the binding agent to interact with a binding site located on the target, and linking the stabilizing components to form a stable complex. In a preferred embodiment, binding is reversible and no covalent bonds are formed during binding. To stabilize binding, a stabilizing component may be directly or indirectly associated with or joined to the target. The stabilizing component may be directly or indirectly associated with or joined to the binding agent. In some embodiments, each of the stabilizing components is attached to or associated with the binding agent and the target, respectively, at a site different from the binding site between the binding agent and the target. In some particular embodiments, the stabilizing component and the binding moiety of the binding agent are separate. In some examples, the target in the binding reaction is a macromolecule, e.g., a peptide, polypeptide, and protein. In some aspects, the binding reaction is performed with a plurality of binding agents and a plurality of macromolecules, e.g., peptides, polypeptides, and proteins. The plurality of binding agents may include a mixture of binding agents.

In some embodiments, the provided methods for performing a binding reaction is performed in an assay for sequencing or analysis of the peptides, polypeptides, and proteins. Before or after performing a binding reaction, other steps of an assay for analysis of the target may be performed (see e.g., FIG. 1A-1D and FIG. 2A-2D). In some embodiments, the provided methods for performing a binding reaction are compatible with a further information transfer step, such as information transfer between nucleic acids associated with the binding agent and the target. In some examples, the information transfer is between a nucleic acid tag associated with the binding agent and a nucleic acid tag associated with the target (e.g., by extension or ligation).

To form a stable complex, a binding agent is contacted with a target, and the binding agent and the target each comprises, is joined to, or is associated with a stabilizing component. The binding agent is allowed to interact with the target, then the stabilizing components are linked to form a stable complex. In some embodiments, the linking of the stabilizing components can be controlled and/or inducible. In some cases, the linking of the stabilizing components does not occur until the stabilizing components are "activated". For example, the stabilizing components are linked upon introduction to light. In some cases, the stabilizing components are linked upon introduction to a linking agent. For example, the linking agent comprises a chemical reagent, a non-biological reagent, a biological reagent, or a combination thereof. In some examples, the linking agent comprises a protein or a polypeptide. In some examples, the linking agent comprises metal ions. Once activated, the linking of the stabilizing components, either directly with each other or indirectly via a linker or other components, allows formation of a stable complex with the binding agent and target.

A. Forming a Stable Complex with Linked Stabilizing Components

Provided herein are methods for performing a binding reaction that forms a stable complex. The stable complex comprises a binding agent and a target, wherein the binding agent and the target is each associated with or joined to a stabilizing component. The binding agent is configured to bind to the target at a binding site located on the target. The method comprises linking the stabilizing components associated with the binding agent and the target, thereby forming a stable complex. In some embodiments, the linking of the stabilizing components (directly or indirectly) forms a complex adequately or sufficiently stable for performing other steps or analysis of the target. In some cases, the complex containing the binding agent and the target is adequately or sufficiently stable for information transfer to occur. In some cases, within the stable complex, the interaction between the binding agent and the target is maintained.

In some embodiments, the method for performing a binding reaction is reversible, where the stable complex is formed and then can be disassembled. In some embodiments, the method for performing a binding reaction is temporally controlled. In some embodiments, the linking of the stabilizing components is inducible. In some embodiments, the method for performing a binding reaction includes an activation step for the stable complex to form. In some embodiments, the method for performing a binding reaction includes an activation step for linking the stabilizing components. For example, the linking of the stabilizing components can involve photosensitive step (e.g. photoisomerization) or can involve hybridization-based interactions. In some cases, the stabilizing components comprise caged compounds or caged molecules, such as small organic molecules. In some cases, the stabilizing component is a photosensitive caged molecule. In some aspects, once activated, the stable complex may form quickly, e.g. the stabilizing components are linked quickly once activated.

In some embodiments, the provided methods may provide the advantage of providing specificity and stability in forming the complex comprising the binding agent and the target. For example, specificity is provided by first contacting the binding agent with the target. After the binding agent interacts with the target, the stabilizing component associated with the binding agent is linked to the stabilizing component associated with the target, thereby forming a stable complex. In some embodiments, the method is performed with a mixture of binding agents and a mixture of targets, and each binding agent in the mixture is configured to exhibit at least partial specificity towards some particular target(s). In some embodiments, within a mixture containing molecules that are not target of the binding agent, the binding agent is allowed to bind to the appropriate target before the stabilizing components are linked. In some embodiments, the binding agents and stabilizing components with the desired binding affinity are selected and used for the methods provided herein for the binding reaction. In some embodiments, the stabilizing components and linking agents with the desired binding affinity are selected and used for the methods provided herein for the binding reaction. In some examples, the relative affinity of stabilizing components to each other and/or to the linking agent is at least as high as the affinity of the binding agent to the target. In some cases, the method includes a wash step after allowing the binding agent to interact with the binding site located on the target. The wash step may remove non-specific binding of binding agents to non-target molecules. In some cases, the linking agent for linking the stabilizing components is provided and introduced after the wash step.

The binding reaction can be accomplished by a number of different ways depending on the design of the components in the complex. For example, the binding agent may be joined to a stabilizing component and a nucleic acid molecule by a linker of various lengths and the distance between the components may vary. In particular embodiments, the target is associated or joined to a stabilizing component via a linker of various lengths based on the interaction of the components in the complex.

The methods for performing the binding reaction includes a binding agent associated with, joined to, attached to, or comprising a stabilizing component and a target associated with, joined to, attached to, or comprising a stabilizing component. In some embodiments, the binding agent and the target are each associated with a stabilizing component. In some cases, the stabilizing component itself comprises one or more sub-components. In some embodiments, the binding agent is associated with a first stabilizing component and the target is associated with a second stabilizing component. In some aspects, the first and second stabilizing components are the same or different. In some cases, the binding agent and target may each be associated with one or more stabilizing components. The binding agent may be directly associated with, joined to, attached to the stabilizing component(s). The binding agent may be indirectly associated with, joined to, attached to the stabilizing component(s), such as via a linker. In some embodiments, the binding agent can be joined to the stabilizing component via any suitable linker, such as of various lengths and flexibility. For example, the stabilizing component and the binding agent is joined via a flexible linker (e.g., PEG linker).

In some embodiments, the binding agent is joined to a nucleic acid molecule (e.g., a coding tag) that is joined the stabilizing component via a linker (e.g., PEG linker). The target may be directly associated with, joined to, attached to the stabilizing component(s). The target may be indirectly associated with, joined to, attached to the stabilizing component(s), such as via a linker. In some embodiments, the target is joined to the stabilizing component via any suitable linker, such as of various lengths and flexibility. For example, the stabilizing component and the target is joined via a flexible linker (e.g., PEG linker). In some embodiments, the target is joined to a nucleic acid molecule (e.g., a capture nucleic acid molecule) that is joined the stabilizing component via a linker (e.g., PEG linker). For example, the target is joined to a bait nucleic acid molecule which hybridizes with at least a portion of the capture nucleic acid molecule that is immobilized on a solid support and the capture nucleic acid molecule is joined to the stabilizing component. In certain embodiments, a linker joins two molecules (binding agent and stabilizing component or target and stabilizing component) via enzymatic reaction or chemistry reaction (e.g., click chemistry). In some embodiments, the stabilizing components are joined to the target or binding agent via a functional moiety, such as a click chemistry moiety, an aldehyde, an azide/alkyne, or a maleimide/thiol, or an epoxide/nucleophile, an inverse electron demand Diels-Alder (iEDDA) group, or a moiety for a Staudinger reaction. In some embodiments, the stabilizing components are joined to the target or binding agent via hybridization of attached nucleic acid molecules or oligonucleotides.

In some embodiments, a stabilizing component is joined or attached (directly or indirectly via a linker) to a nucleic acid molecule or oligonucleotide. For example, the nucleic acid molecule or oligonucleotide joined or associated with the stabilizing component is configured for hybridization to a complementary nucleic acid molecule or oligonucleotide. In some embodiments, the complementary nucleic acid molecule or oligonucleotide is associated or joined to a binding molecule or a binding pair member such as a biotin.

Figure 3:
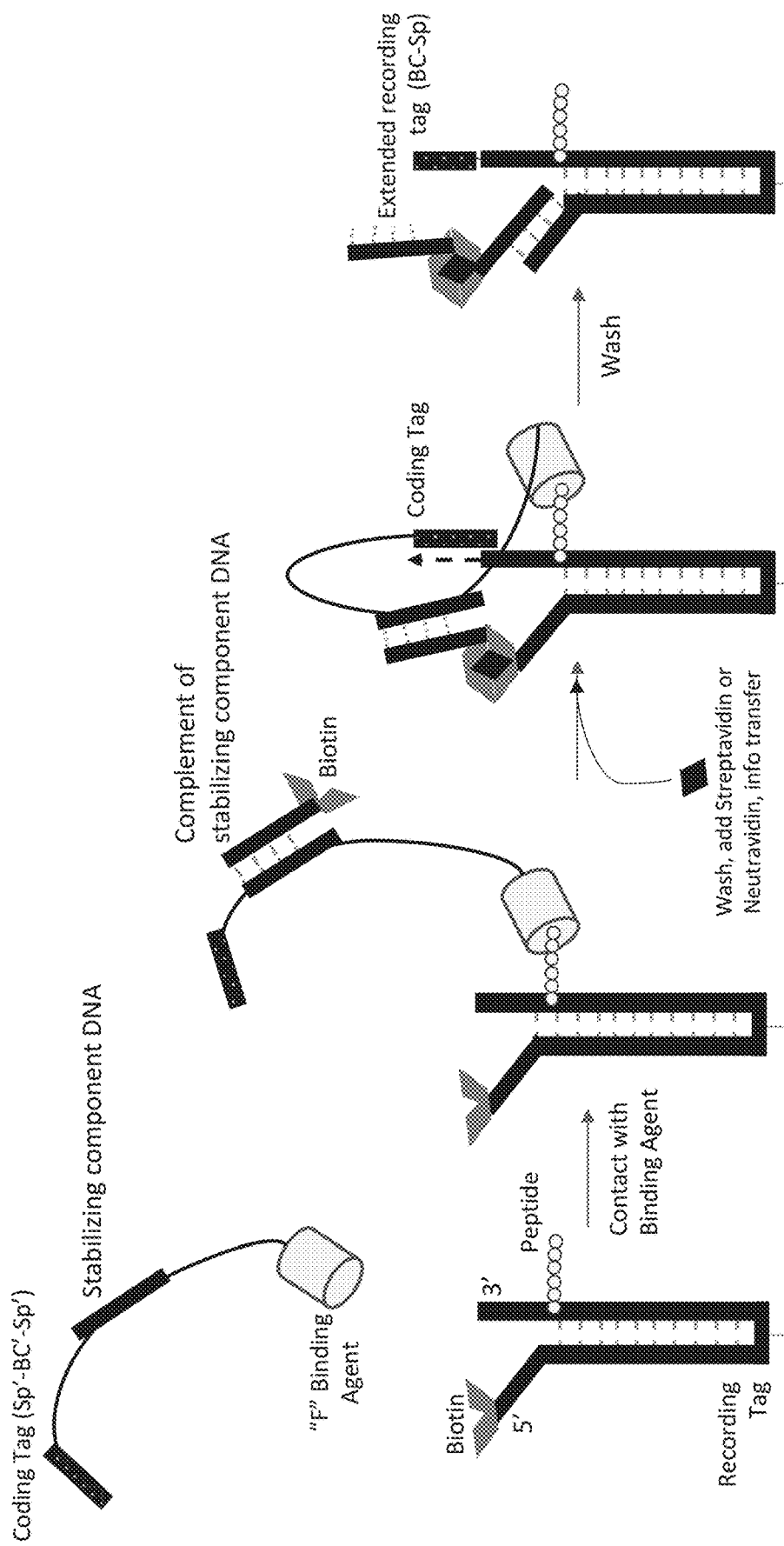
FIG. 3A-3D depict an exemplary binding reaction and formation of a stable complex for information transfer (using interactions between a binding pair, e.g., biotin and streptavidin or neutravidin).

In some embodiments, a recording tag is joined to a binding pair member, e.g., a biotin molecule (or similar molecule) at the 5' end. In some embodiments, a recording tag is joined to a stabilizing component DNA and the stabilizing component can be associated with its complementary stabilizing component nucleic acid which is joined to a binding pair member, e.g., a biotin (or similar molecule). In some embodiments, a binding agent is joined via a linker to a coding tag which is joined via a linker to a biotin molecule. In some embodiments, a binding agent is joined via a linker to a coding tag (nucleic acid hairpin) which is joined via a linker to a biotin or similar molecule (in the following order: binding agent-linker-hairpin coding tag-linker-biotin). In some embodiments, a binding agent is joined via a linker to a stabilizing component DNA which is joined via a linker to a coding tag (in the following order: binding agent-linker-stabilizing component DNA-linker-coding tag) (FIG. 3A). In some examples, the stabilizing component can be associated with its complementary stabilizing component nucleic acid which is joined to a biotin (or similar molecule) (FIG. 3B).

In some embodiments, the linking of the stabilizing components to form the stable complex includes interaction of the stabilizing component associated with the binding agent with the stabilizing component associated with the target. In some embodiments, the linking of the stabilizing components include interaction of the stabilizing components with a linking agent. In some embodiments, the linking of the stabilizing components include interaction of nucleic acid molecules associated with each of the stabilizing components. In some embodiments, the interaction of the stabilizing components with each other or with the linking agent is covalent or non-covalent.

A variety of binding partners or pairs are known to those of skill in the art and may be used in the subject binding reactions to stabilize the interaction of the binding agent and target (e.g., as stabilizing components). The stabilizing components can be joined to the binding agent or target using standard conjugation chemistries (Hermanson, Bioconjugate Techniques, (2013) Academic Press). Selection of the stabilizing component may be based on affinity of the stabilizing components to each other or for the linking agent, speed of interaction, strength of the interaction, reversibility of the interaction, etc. In some embodiments, the stabilizing components each comprises a biological molecule, a chemical molecule, a small molecule or a combination thereof. In some embodiments, the stabilizing components comprises any appropriate binding partners, host-guest molecules or motifs, other interacting molecules, or portions thereof (see e.g. Liu et al., Chem Soc Rev. (2017); 46(9): 2391-2403; Mantooth et al., Macromol Biosci. (2019) 19(1):e1800281). Exemplar host-guest interactions include the supramolecular cyclic cucurbit[N]uril (N=5-8) host molecules which interact, in a reversible manner, with guest molecules with extremely high affinity (Ka~$10^{12}$ to $10^{15}$). For instance, cucurbit[7]uril rapidly (within minutes) forms host-guest complexes with ferrocene or adamantane derivatives with an binding affinity of $10^{12}$-$10^{13}$, respectively (Barrow, S. J., et al. (2015). "Cucurbituril-Based Molecular Recognition." Chem Rev 115(22): 12320-12406, incorporated by reference herein). In some aspects, the stabilizing component comprises an organic molecule or a synthetic molecule. In some examples, the stabilizing component is or comprises a small molecule, a compound, a protein, a protein complex, polypeptide, peptide, nucleic acid molecule, carbohydrate, lipid, macrocycle, a chimeric macromolecule, a synthetic host, or any combinations thereof. In some embodiments, the stabilizing component is or comprises an antibody, a catalytic antibody, an antigen, an enzyme, an inhibitor, a ligand, a protein, a substrate, or an organic compound. In some embodiments, the stabilizing component is or comprises a hapten. A hapten molecule may be attached at different positions in the hapten molecule to the binding agent or the target (or an associated polynucleotide or nucleic acid molecule).

In some embodiments, at least one of the stabilizing components may comprise a photosensitive molecule (e.g. photolabile or photoisomerization). In some embodiments, the stabilizing components are configured for nucleic acid hybridization-based interactions. In some cases, the stabilizing components comprise or are associated with caged compounds or caged molecules, such as small organic molecules. In some other embodiments, the stabilizing components comprise or are associated with one or more components of a known host-guest interaction.

In some embodiments, the introduction of the light, activating the stabilizing component, or providing the linking agent provides temporal control over the linking of the stabilizing components. In some embodiments, the stabilizing components are linked to each other (directly or indirectly) upon introduction of a linking agent or light. In some embodiments, the stabilizing components remain inactive, or are generally not linked to each other or to a linking agent until activated. In some cases, activation may refer to the introduction of a molecule, photoactivation (e.g., introduction of light, for example, UV or blue light), change in pH of the reaction, change in condition of the reaction (e.g., change in temperature), or destruction or removal of inhibition (e.g., uncaging of a molecule). In some aspects, upon activation, one or more of the stabilizing components undergoes a conformational change. In some cases, one or more of the stabilizing components is under allosteric control and upon activation (e.g., by binding to a linking agent), the stabilizing component is made available for interactions/binding. In some embodiments, to form the stable complex, the light or linking agent induces uncaging of one or both of the stabilizing components, deblocking of one or both of the stabilizing components, isomerization of the stabilizing components, hybridization of the stabilizing components, and/or binding of the stabilizing components. In some embodiments, once activated, the linking of the stabilizing components occurs in less than about 10 seconds, less than about 30 seconds, less than about 60 seconds, less than about 80 seconds, less than about 100 seconds, less than about 2 minutes, less than about 5 minutes, less than about 10 minutes, or less than about 15 minutes. It may be desirable to select stabilizing components that may be linked in an amount of time less than the time for the binding agent to dissociate from the target, to maintain specificity of the binding agent with the target.

In some embodiments, linking of the stabilizing components is specific or occurs within the complex between a stabilizing component associated with the binding agent and a stabilizing component associated with the target bound by said binding agent. For example, the method is performed such that linking of stabilizing components is not intermolecular, e.g., between stabilizing components of different complexes. It may be preferred that linking does not occur between a stabilizing component of a binding agent and a target bound by a different binding agent. In some aspects, linking of intramolecular stabilizing components within a complex can be achieved by titrating or controlling the density of target macromolecules on a support or within the volume of a substrate. In some cases, the control of density of the target macromolecules is performed by controlling the density of functional coupling groups for attaching the targets or by spiking a competitor or "dummy" reactive molecule when immobilizing the targets to the support.

In some examples, the linking agent comprises a chemical reagent, a non-biological reagent, a biological reagent, or a combination thereof. In some cases, the linking agent comprises one or more proteins. In some cases, the linking agent comprises metal ions. In some examples, the stabilizing components are linked upon a change in pH of the reaction or reaction mixture or environment. In some embodiments, the linking agent comprises at least one polynucleotide or nucleic acid comprising a sequence which hybridizes to at least one of the stabilizing components. In some particular embodiments, the linking agent is a polynucleotide or nucleic acid comprising two hybridization regions: one region for hybridizing to a nucleic acid joined to a target and one region for hybridizing to a nucleic acid joined to the binding agent. In some cases, one stabilizing component is associated with the binding agent via hybridization of a polynucleotide or nucleic acid joined to the stabilizing component to a nucleic acid joined to the binding agent. In some cases, one stabilizing component is associated with the target via hybridization of a polynucleotide or nucleic acid joined to the stabilizing component to a nucleic acid joined to the recording tag joined to the target. In some embodiments, the stabilizing component is or comprises a biotin or an analog thereof (e.g. desthiobiotin) and the linking agent is or comprises an avidin (e.g., streptavidin or neutravidin). In another particular embodiment, the first stabilizing component is or comprises a first antibody or an antigen-recognizing fragment thereof; the second stabilizing component is or comprises a second antibody or an antigen-recognizing fragment thereof recognizing a different epitope from the first antibody; and the linking agent comprises two epitopes recognized by the first and second antibodies, so after introduction of the linking agent a stable complex forms comprising the first and second antibodies (or antigen-recognizing fragments thereof) and the linking agent.

In some embodiments, once the stabilizing components are linked, the binding agent and the target remains bound. In some embodiments, once the stabilizing components are linked, the binding agent and the target are released from each other, remaining in the vicinity of each other by virtue of the linked stabilizing components. In this case, when the stabilizing components remain linked, the process of information (encoding) transfer can occur.

The described stabilization approach operates by transiently "cross-linking" the binding agent and the target on a support after binding event forming a stable complex. Several kinds of stabilizing components can be employed, but in a preferred embodiment the stabilization methods rely on a rapid means of reversibly coupling the DNA-target polypeptide complex to the binding agent after it binds to the target polypeptide.

The following embodiment illustrates an exemplary workflow including a binding reaction: a large collection of polypeptides (e.g., 50 million-1 billion or more) from a proteolytic digest are immobilized randomly on a substrate (e.g., beads) at an appropriate intramolecular spacing with nucleic acid capture molecules; the targets are joined to nucleic acid capture molecules which are each joined to a desthiobiotin molecule (the first stabilizing component); binding agents each joined to a biotin molecule (the second stabilizing component) and an associated nucleic acid molecule containing information regarding the binding agent are contacted with the targets and allowed to interact; a wash is preformed to remove non-specific binding; streptavidin is added to the reaction as a linking agent and associates with the biotin and desthiobiotin; a streptavidin molecule binds a biotin joined to the binding agent and a desthiobiotin joined to the target, thereby forming a stable complex containing the binding agent and target. In some examples, the biotin-nucleic acid conjugates can be added after the binding agent interacts with the target. In some embodiments, each of the biotin or desthiobiotin may use any similar molecule or analog, depending on desired strength of the interaction.

In one embodiment, the first stabilizing component is the same as the second stabilizing component. For example, in the exemplary workflow from the previous paragraph, a biotin molecule can be used instead of desthiobiotin molecule, and two biotin molecules will interact with the linking agent and form the stable complex. In another embodiment, the first stabilizing component has a lower affinity to the linking agent in comparison to an affinity of the second stabilizing component to the linking agent as shown in the exemplary workflow from the previous paragraph. In some embodiment, it will be preferable to use this combination of different stabilizing components such as desthiobiotin (DSB) and biotin. The use of a rapid high-affinity stabilizing component on the binding agent (biotin) and a lower affinity stabilizing component (DSB) associated with a target polypeptide provides for both rapid formation of the stable complex and controllable release (disruption of the stable complex) at the target polypeptide side, for example, by elution with biotin, which opens the target polypeptide for the next binding cycle.

In some embodiments, formation of the stable complex is reversible and no covalent bonds are formed during formation of the stable complex. Preferably, only non-covalent interactions are involved in the formation of the stable complex. Examples of non-covalent interactions are electrostatic, π-effects, van der Waals forces, formation of hydrogen bonds or other types of dipole-dipole interactions, hydrophobic interactions. In some embodiments, the disrupting is conducted by removing the linking agent. In some cases, the disrupting is conducted by introducing a destabilizing agent. For example, the destabilizing agent comprises heat, a denaturing agent, an enzyme, a competitor molecule, or a combination thereof. In some cases, the competitor molecule is a competitor for binding of or to the binding agent, the linking agent, and/or the stabilizing components. In other embodiments, reversible covalent bonds can be formed during formation of the stable complex.

In some embodiments, the method for performing the binding reaction further comprises disrupting or destabilizing the stable complex comprising the binding agent, target, stabilizing components and, optionally, the linking agent. In some aspects, the disrupting allows the stabilizing component (e.g., associated with the recording tag) to become available for interacting. In some cases, the method includes a repeated cycle of forming a stable complex and disrupting the stable complex such that the binding agent is released from the target, allowing the target to be available for other reactions or treatments. In some embodiments, the first stabilizing component associated with a target peptide or macromolecule has a lower affinity to the linking agent in comparison to an affinity of the second stabilizing component to the linking agent. This setup allows for efficient disruption of the stable complex and binder dissociation. Several types of stabilizing components can be utilized in this setup. One particular type includes using dethiobiotin (DSB) and biotin linked via streptavidin during the stable complex formation, and then using biotin for dissociation. Other linking agents can also be used, preferably ones that have affinity sites for two different interacting partners. These partners can be included as stabilizing components and will be linked together upon introduction of the linking agent.

In some embodiments, one or more of the stabilizing components are cleavable. In some examples, two different cleavable stabilizing components (e.g., haptens) are attached to the target and binding agent respectively, directly or indirectly via a nucleic acid molecule. Specific cleaving agents (e.g. chemical reagent for cleaving) can be used to cleave one stabilizing component while leaving the other stabilizing component intact. For example, the method may include using linking the stabilizing components to form a stable complex comprising the binding agent, the target and the stabilizing components, then cleaving the stabilizing component associated with the binding agent while the stabilizing component remains associated with the target.

Figure 13B:
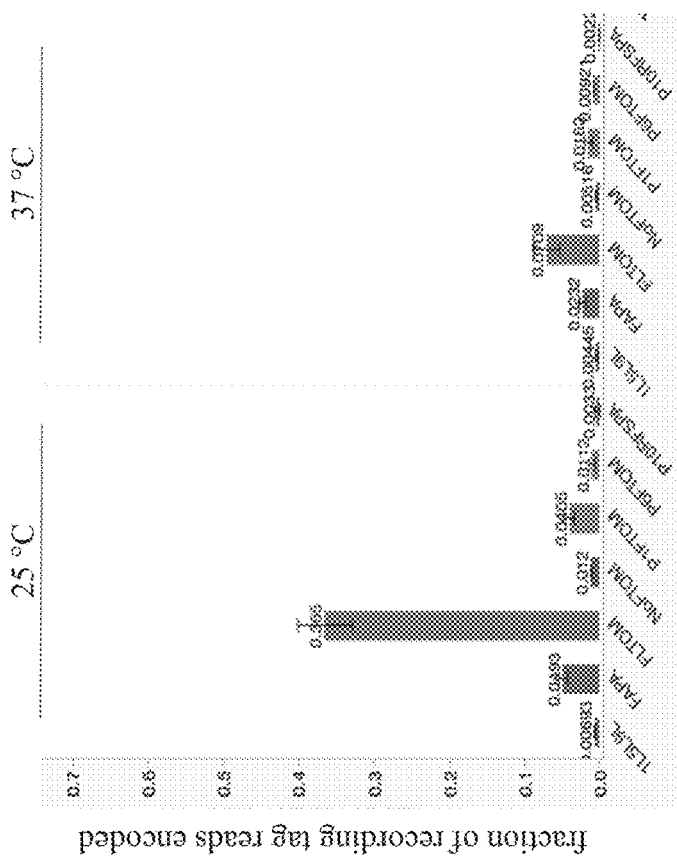
FIGS. 13A and 13B show dependence of encoding efficiencies on the encoding temperature. 7 targeted peptides were tested with the 31-F binding agent labeled with biotin. SA was added as the linking agent in all samples.
Figure 13A:
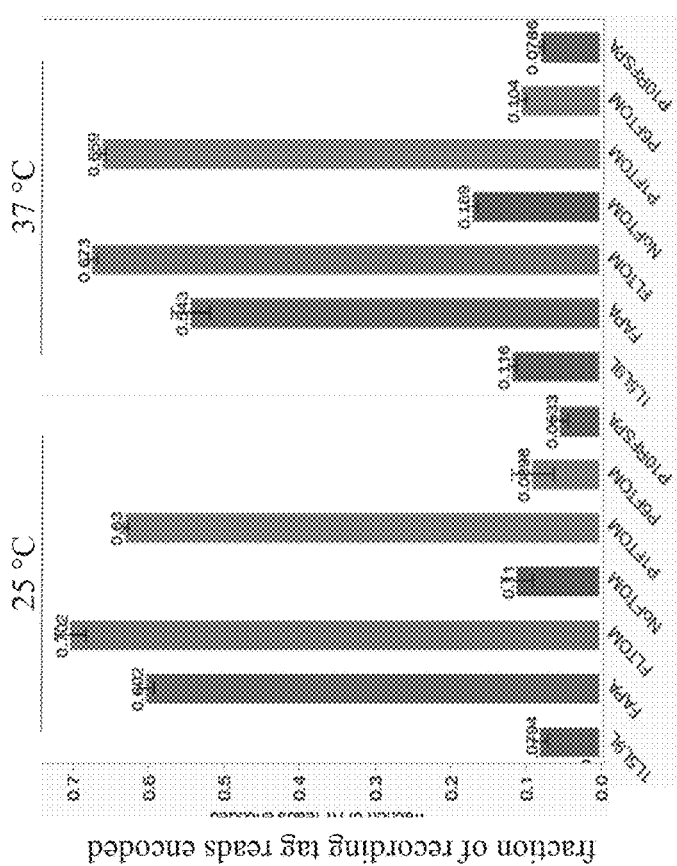
Figure 14B:
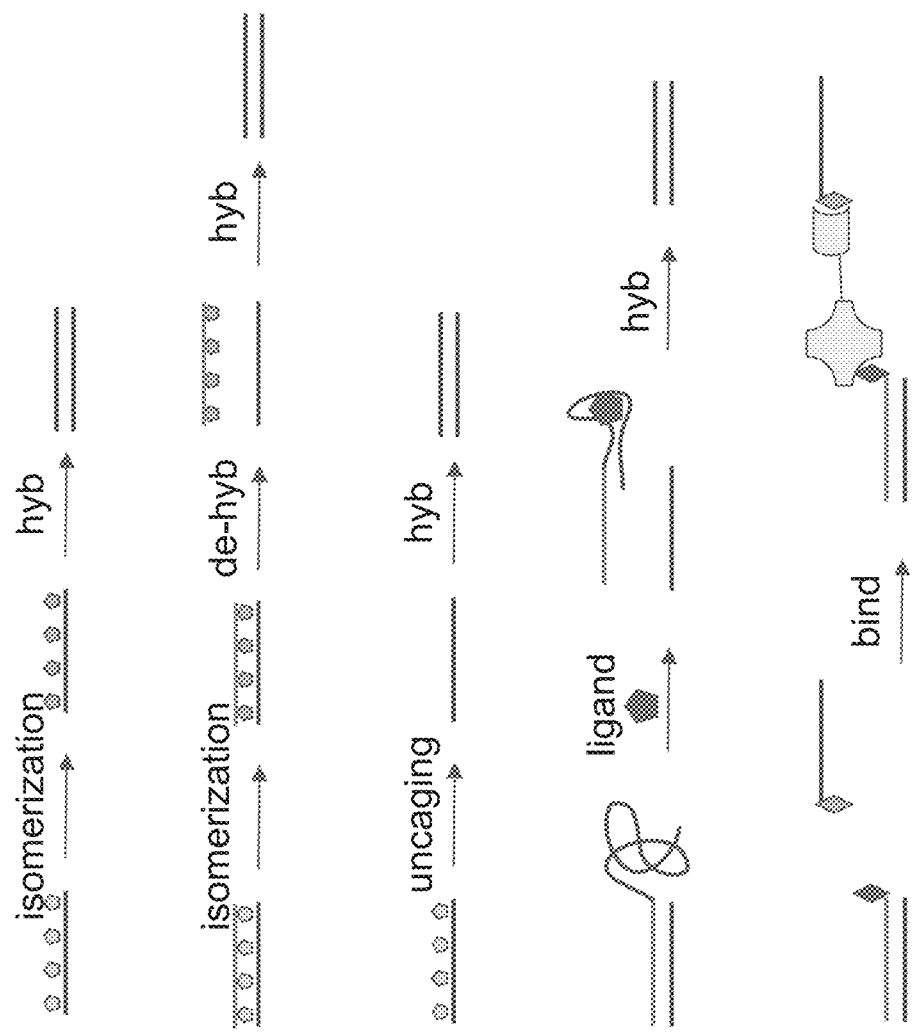
FIGS. 14A and 14B show exemplary embodiments of controllable hybridization of two polynucleotides used as stabilizing components.
Figure 14A:
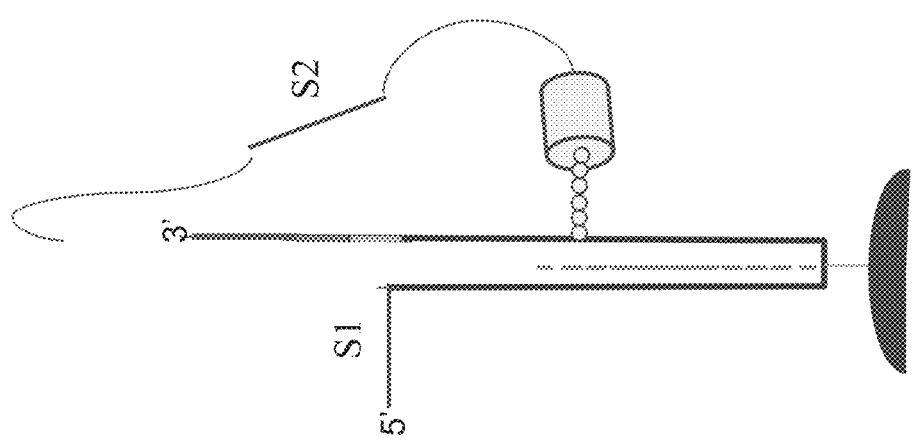

In some embodiments, the first or second stabilizing component comprises a polynucleotide, and the linking agent comprises a linking polynucleotide that hybridizes to the polynucleotide of one of the stabilizing components. In some embodiments, known approaches can be used to generate controllable hybridization of two polynucleotides that will result in formation of the stable complex containing binding agent and target. Several potential embodiments of controllable hybridization of two polynucleotides (used as stabilizing components) are illustrated in FIGS. 13A and 13B. For example, photoisomerization or uncaging can trigger hybridization, as disclosed in Szymański W, et al., Reversible photocontrol of biological systems by the incorporation of molecular photoswitches. Chem Rev. 2013 Aug. 14; 113(8):6114-78; Asanuma H, et al., Synthesis of azobenzene-tethered DNA for reversible photo-regulation of DNA functions: hybridization and transcription. Nat Protoc. 2007; 2(1):203-12; Yunqi Yan et al., Photocontrolled DNA hybridization stringency with fluorescence detection in heterogeneous assays, ACS Sens. 2016, 1, 5, 566-571; Goldau T, et al., Azobenzene C-Nucleosides for Photocontrolled Hybridization of DNA at Room Temperature. Chemistry. 2015 Dec. 1; 21(49):17870-6; Menge C, Heckel A. Coumarin-caged dG for improved wavelength-selective uncaging of DNA. Org Lett. 2011 Sep. 2; 13(17):4620-3; Ruble B K, et al., Caged oligonucleotides for studying biological systems, J Inorg Biochem. 2015 September; 150: 182-188; Adam V, et al., Expanding the Toolbox of Photoswitches for DNA Nanotechnology Using Arylazopyrazoles. Chemistry. 2018 Jan. 24; 24(5):1062-1066, which are incorporated herein by reference. "Caged" compounds have inactivating groups bonded to bioactive molecules that can be readily removed in an orthogonal manner, for example, by UV light or visible light photoirradiation. By using light to turn on activity, high spatial and temporal control of polynucleotide hybridization can be attained.

The following embodiment illustrates another exemplary workflow including a binding reaction: a large collection of polypeptides (e.g., 50 million-1 billion or more) from a proteolytic digest are immobilized randomly on a substrate (e.g., beads) at an appropriate intramolecular spacing with nucleic acid capture molecules; the target polypeptides are joined to nucleic acid capture molecules which are each joined to a hybridizable polynucleotide (the first stabilizing component); binding agents each joined to a complementary hybridizable polynucleotide (the second stabilizing component) and an associated coding tag containing information regarding the binding agent are contacted with the target polypeptides and allowed to interact; a wash is preformed to remove non-specific binding. The hybridizable polynucleotide is modified by introducing photoswitchable nucleotides or caged nucleotides to prevent hybridization with its complementary polynucleotide. Light of a certain wavelength is introduced to the reaction as a linking agent, inducing uncaging of nucleotides and allowing hybridization and formation of a stable complex containing the binding agent and target polypeptide. Several caged or modified nucleotide variants can be used. First, diethylaminocoumarin (DEACM) as a photoremovable protecting group for 2'-deoxyguanosine can be used, and light with 405 nm wavelength can be used for uncaging as disclosed in Menge C, Heckel A. Coumarin-caged dG for improved wavelength-selective uncaging of DNA. Org Lett. 2011 Sep. 2; 13(17):4620-3. Second, azobenzene moieties can be introduced into certain DNA nucleotides on a conventional DNA synthesizer using a phosphoramidite monomer bearing an azobenzene synthesized from D-threoninol as disclosed in Asanuma H, et al., Synthesis of azobenzene-tethered DNA for reversible photo-regulation of DNA functions: hybridization and transcription. Nat Protoc. 2007; 2(1):203-12. Hybridization of a polynucleotide having azobenzene-modified DNA can be reversibly photo-controlled by controlling cis-trans isomerization of the azobenzene. The hybridization can be photo-induced by cis-trans isomerization of the azobenzene moiety by irradiation of a visible light (wavelength is more than 400 nm). When azobenzene is in a trans-form, a stable duplex can be formed with a complementary strand. Importantly, hybridization is reversible and can be disrupted by UV light irradiation (wavelength between 300 nm and 400 nm), which induces isomerization of the trans-azobenzene to its cis-form. Thus, several cycles of formation and disruption of the stable complex containing binding agent and target polypeptide can be achieved. In addition to azobenzenes, other known groups that undergo photo-induced structural switches include stilbenes, hemithioindigos, spiropyrans, diarylethenes and fulgides (Szymański W, et al., Reversible photocontrol of biological systems by the incorporation of molecular photoswitches. Chem Rev. 2013 Aug. 14; 113(8):6114-78). Photoswitchable units can be introduced to nucleotide monophosphates in nucleic acid oligomers via two methods: alkylation of a thiophosphate-modified backbone and amidation of the ribose moiety on a 2'-aminodeoxyuridylate analog as disclosed in Szymański W, et al., Reversible photocontrol of biological systems by the incorporation of molecular photoswitches. Chem Rev. 2013 Aug. 14; 113(8):6114-78 and references therein.

In some embodiments, the linking agent comprises a metal ion that links two stabilizing components together. One particular example of such embodiment is described in Nakamura T, et al., A metal-ion-responsive adhesive material via switching of molecular recognition properties. Nat Commun. 2014 Aug. 7; 5:4622, where divalent metal ions ($Fe^{2+}$, $co^{2+}$, $Ni^{2+}$, $cu^{2+}$, $zn^{2+}$) are used specifically for adherence of two hydrogels. Metal ions can bring together spartially separated metal-chelating or metal-coordinating groups to form a stable complex having a metal ion in its center. In this embodiment, a solid support contains a N-tert-butyl (tBu)-modified capture DNA for immobilizing a target macromolecule (e.g. polypeptide). During binding reaction a binding agent is added that comprises b-cyclodextrin (bCD) blocked by 2,2'-bipyridyl (bpy). For stabilization reaction, a metal ion ($Fe^{2+}$, $Co^{2+}$, $Ni^{2+}$, $Cu^{2+}$ or $Zn^{2+}$) is added to trigger bCD-tBu interaction to clamp the binding agent and capture DNA, keeping the binding agent near the target macromolecule for information transfer. To reverse stabilization and disrupt the stable complex, 2,2'-bipyridyl (bpy) is further added. In another embodiment, a Ni-NTA/HisTag interaction can be utilize for the stabilization reaction. In this embodiment, a solid support contains N-terminal protected 6*His-tagged capture DNA for immobilizing a target macromolecule (e.g. polypeptide). During binding reaction a binding agent is added that comprises chelating ligand nitrilotriacetic acid (NTA). For stabilization reaction, a metal ion (Ni') is added to trigger interaction. To reverse stabilization and disrupt the stable complex, imidazole is further added. In another embodiment, an Azide/Alkyne linkage can be utilize for the stabilization reaction. In this embodiment, a solid support contains an aldehyde-modified capture DNA for immobilizing a target macromolecule (e.g. polypeptide). During binding reaction a binding agent is added that comprises TMS or TIPS-protected Aldehyde-Azide. For stabilization reaction, a metal ion (copper) is added to trigger Azide/Aldehyde click reaction. To reverse stabilization and disrupt the stable complex, deprotection of TMS or TIPS is used to generate new aldehyde on the capture DNA.

Provided herein are methods and kits for analysis of macromolecules, e.g., peptides, polypeptides, and proteins, which includes a step of transferring information to a recording tag. In some embodiments, the analysis employs barcoding and nucleic acid encoding of molecular recognition events, and/or detectable labels. In some examples, the information transferred comprises identifying information regarding a binding agent that is configured to bind to the macromolecule. The information transfer can be achieved by any suitable means such as by extension or ligation, and can be between nucleic acid molecules, e.g., between a nucleic acid tag associated with the macromolecule for analysis and a secondary tag on an adaptor molecule. The provided method for information transfer comprises: (a) providing a macromolecule and an associated recording tag joined to a support; (b) contacting the macromolecule with a binding agent capable of binding to the macromolecule, wherein the binding agent comprises a coding tag with identifying information regarding the binding agent, to allow binding between the macromolecule and the binding agent; (c) providing an adaptor molecule comprising a first hybridization sequence substantially complementary to at least a portion of the coding tag (or portion thereof), and a secondary tag, to allow hybridization between the adaptor molecule (or the first hybridization sequence) and the coding tag (or the portion of the coding tag); (d) transferring the information of the secondary tag to the recording tag to generate an extended recording tag; and analyzing the extended recording tag. The methods provided herein may include providing a plurality of binding agents and a plurality of macromolecules and allowing the binding agents and macromolecules to interact. In some embodiments, a plurality of adaptor molecules are provided. In some embodiments, the present methods comprise contacting a single macromolecule with a single binding agent, contacting a plurality of macromolecules with a single binding agent, or contacting a plurality of macromolecules with a plurality of binding agents.

In a preferred embodiment, macromolecule comprises a polypeptide.

In some embodiments, the present disclosure provides, in part, methods for analyzing a macromolecule which includes information transfer, with direct applications to protein and peptide characterization, quantitation, and/or sequencing. Provided herein are methods for transferring information from a secondary tag of an adaptor molecule to a recording tag associated with the macromolecule (e.g., polypeptide) bound by the binding agent.

Transfer of information may be performed via ligation, extension or other methods known in the art. The information transferred from the secondary tag of an adaptor molecule includes identifying information regarding the identity of the binding agent, the macromolecule or portion thereof bound by the binding agent. For example, if a protein macromolecule is bound by the binding agent, the identifying information may comprise information regarding the identity of the one or more amino acid(s) on the peptide bound by the binding agent (see 6A-6D and FIG. 7A-7D). In some embodiments, the information regarding the identity of the macromolecule bound by the binding agent is from the coding tag associated with said binding agent, and transferred to the recording tag via the hybridized adaptor molecule. The macromolecule analysis assay may include one or more cycles of transferring identifying information of a binding agent to a recording tag associated with the macromolecule to be analyzed. The extended recording tag associated with the macromolecule for analysis can comprise the information from one or more secondary tags. If multiple cycles are performed, the resulting extended recording tag then contains information built up from a series of binding events and multiple information transfer events using adaptor molecules comprising secondary tags. In general, improvements for the transfer of information may provide certain benefits to the macromolecule analysis assay.

In particular, the adaptor molecules provided in step (c) used in this method for analyzing macromolecules provides certain advantages to the overall design of the assay. In this system, the adaptor molecule serves as an intermediate between the information on the coding tag associated with the binding agent and the transferred information on the recording tag. The adaptor molecules comprise a first hybridization sequence and a secondary tag, wherein the first hybridization sequence or portion thereof is substantially complementary or complementary to the coding tag or a region therein. The first hybridization sequence allows each coding tag to be associated with an adaptor molecule and its contained secondary tag. In some aspects, the use of the adaptor molecules provides the ability to adjust the information transferred to the recording tag (via the secondary tag) quickly and conveniently, by obviating the need to remake binding agent-coding tag conjugates, which may be a time consuming process. In some cases, the use of the adaptor molecule provides some flexibility such as the ability to collapse information at the level of the secondary tag. In some embodiments, the adaptor molecules may be designed to contain suitable barcodes (e.g. as part of the secondary tag) based on the sequencing system used for the readout. For example, the barcode may be suitable for less accurate NGS such as nanopore sequencing (e.g., more error correction).

In some embodiments related, for example, to polypeptide sequencing, multiple cycle of transferring information from a binding agent-fused coding tag to the polypeptide-associated recording tag occur, similar to the cycles shown in FIGS. 1, 2, 6 and 7. In preferred embodiments, at the end of each cycle, the terminal amino acid of the polypeptide gets cleaved off, so the next amino acid of the polypeptide becomes a new terminal amino acid and a target for binding agents on the next cycle.

Provided herein are methods for transferring information from a secondary tag of an adaptor molecule to a recording tag associated with the macromolecule (e.g., polypeptide) bound by the binding agent. Transfer of information may be performed via ligation, extension or other methods known in the art. The information transferred from the secondary tag of an adaptor molecule includes identifying information regarding the identity of the binding agent, the macromolecule or portion thereof bound by the binding agent. For example, if a protein macromolecule is bound by the binding agent, the identifying information may comprise information regarding the identity of the one or more amino acid(s) on the peptide bound by the binding agent For the multicycle ProteoCode assay, which can comprise >15 cycles of cycle-specific binding and encoding events, the use of cycle-specific adapter molecules rather than cycle-specific DNA-tagged binding agents recognizing a particular NTAA greatly decreases the manufacturing burden of creating and maintaining a set of 20 or more binders (this set would recognize all 20 NTAA and/or post-translationally modified NTAA) multiply by 15+ cycles. For 20 binders and 15 cycles, this equates to a set of 300 binders. Rather, than a new pool of binders for each cycle, a new pool of cycle-specific adapter molecules can be used to translate NTAA binding information into cycle-specific NTAA binding information. As such, a single universal set of 15-20 DNA-conjugated binding agents would be employed in each cycle, and cycle-specific information would be conferred by the use of cycle-specific pools of adapter molecules.

The analysis assay includes the use of a plurality of binding agents and each binding agent is associated with a coding tag containing identifying information regarding the identity of the macromolecule. An example of collapsing information from multiple binding agents is as follows: the macromolecule "X" may be bound by two binding agents (such as at different motifs on the molecule) with corresponding coding tags B1 and B2, two adaptor molecules which contain a secondary tag and B1' and B2' as the first hybridization region, respectively, can both be associated with "X". Thus the information from two binding agents is collapsed at the level of the secondary tag and transferred as the same information to the recording tag. In this case, the option also remains to switch in adaptor molecules that retain the information of the B1 and B2 binding agents while using the same binding agents and associated coding tags, simply by using different adaptor molecules. In some cases, the adaptor molecules can be exchanged or modified without the need for modifying the binding agent and associated coding tags.

In some embodiments, a spacer is added to the end of the recording tag with the secondary tag, and the spacer comprises a sequence that is capable of hybridizing with a sequence on the adaptor molecule to facilitate transfer of the identifying information.

In some embodiments, the adaptor molecule further comprises a second hybridization sequence substantially complementary or complementary to a portion of the recording tag. The second hybridization sequence on the adaptor molecule may be substantially complementary or complementary to a sequence at the 3' terminus of the recording tag, such as a region on the recording tag generated from a previous information transfer of the secondary tag from the adaptor molecule to the recording tag. In some cases, information transfer of the secondary tag from the adaptor molecule to the recording tag occurs if both the first hybridization sequence on the adaptor molecule hybridizes to the coding tag of a binding agent and the second hybridization sequence of the adaptor molecule hybridizes to a portion of the recording tag. In this case, a set of adaptor molecules is used such that combinations of the first hybridization sequence and the second hybridization sequence covers all combinations needed to hybridize to potential complementary sequences on the recording tags and coding tags. In some embodiments, the provided method for information transfer using the adaptor molecule comprising a second hybridization sequence enables a "spacer-less" approach of transferring information from an adaptor molecule to a recording tag. For example, this may remove the need for inserting a spacer sequence for hybridization purposes into the extended recording tag. In some cases, since each cycle of the method includes extending the recording tag, a spacer-less approach provides the benefit that the extended recording tag length can be reduced.

Identifying information associated with a specific binding agent may be transferred to a recording tag using a variety of methods. The transfer in the methods provided herein are from the secondary tag of an adaptor molecule to the recording tag to generate an extended recording tag. In some embodiments, the transfer of identifying information (e.g., from a secondary tag to a recording tag) can be accomplished by ligation (e.g., an enzymatic or chemical ligation, a splint ligation, a sticky end ligation, a single-strand (ss) ligation such as a ssDNA ligation, or any combination thereof), a polymerase-mediated reaction (e.g., primer extension of single-stranded nucleic acid or double-stranded nucleic acid), or any combination thereof.

Identifying information associated with a specific binding agent may be transferred to a nucleic acid on the recording tag associated with the immobilized macromolecule via ligation (FIG. 6A-6D). Ligation may be a blunt end ligation or sticky end ligation. Ligation may be an enzymatic ligation reaction. Examples of ligases include, but are not limited to CV DNA ligase, T4 DNA ligase, T7 DNA ligase, T3 DNA ligase, Taq DNA ligase, E. coli DNA ligase, 9° N DNA ligase (See e.g., U.S. Patent Publication No. US20140378315). After ligation of the secondary tag to the recording tag, the other portions of the adaptor molecule (e.g., the first hybridization sequence) if no longer needed may be cleaved and released. In some embodiments, the adaptor molecule comprises one or more uracil bases, which can be targeted for digestion with a uracil-specific excision reagent (e.g., USER™).

In another embodiment, transfer of PNAs can be accomplished with chemical ligation using published techniques. The structure of PNA is such that it has a 5' N-terminal amine group and an unreactive 3' C-terminal amide. Chemical ligation of PNA requires that the termini be modified to be chemically active. This is typically done by derivatizing the 5' N-terminus with a cysteinyl moiety and the 3' C-terminus with a thioester moiety. Such modified PNAs easily couple using standard native chemical ligation conditions (Roloff et al., (2013) Bioorgan. Med. Chem. 21:3458-3464).

In some embodiments, identifying information from a secondary tag can be transferred to a recording tag using topoisomerase. Topoisomerase can be used be used to ligate a topo-charged 3' phosphate on the recording tag (or extensions thereof or any nucleic acids attached) to the 5' end of the coding tag, or complement thereof (Shuman et al., 1994, J. Biol. Chem. 269:32678-32684).

In certain embodiments, information is transferred to a recording tag via primer extension (Chan et al. (2015) Curr Opin Chem Biol 26: 55-61). A sequence on the 3'-terminus of a recording tag or an extended recording tag anneals with complementary sequence on the 3' terminus of an adaptor molecule and a polymerase (e.g., strand-displacing polymerase) extends the recording tag sequence, using the secondary tag of the annealed adaptor molecule as a template (FIG. 7). In some cases, the complementary sequence on the 3' terminus of an adaptor molecule may be a spacer sequence. In some cases, the complementary sequence on the 3' terminus of an adaptor molecule may be the second hybridization sequence. In some examples, the adaptor molecule comprises a spacer or linker to stop extension after transfer of information from the secondary tag to the recording tag.

In some embodiments, a DNA polymerase that is used for primer extension possesses strand-displacement activity and has limited or is devoid of 3'-5 exonuclease activity. Several of many examples of such polymerases include Klenow exo- (Klenow fragment of DNA Pol 1), T4 DNA polymerase exo-, T7 DNA polymerase exo (Sequenase 2.0), Pfu exo-, Vent exo-, Deep Vent exo-, Bst DNA polymerase large fragment exo-, Bca Pol, 9° N Pol, and Phi29 Pol exo-. In a preferred embodiment, the DNA polymerase is active at room temperature and up to 45° C. In another embodiment, a "warm start" version of a thermophilic polymerase is employed such that the polymerase is activated and is used at about 40° C.-50° C. An exemplary warm start polymerase is Bst 2.0 Warm Start DNA Polymerase (New England Biolabs).

Additives useful in strand-displacement replication include any of a number of single-stranded DNA binding proteins (SSB proteins) of bacterial, viral, or eukaryotic origin, such as SSB protein of E. coli, phage T4 gene 32 product, phage T7 gene 2.5 protein, phage Pf3 SSB, replication protein A RPA32 and RPA14 subunits (Wold, Annu. Rev. Biochem. (1997) 66:61-92); other DNA binding proteins, such as adenovirus DNA-binding protein, herpes simplex protein ICP8, BMRF1 polymerase accessory subunit, herpes virus UL29 SSB-like protein; any of a number of replication complex proteins known to participate in DNA replication, such as phage T7 helicase/primase, phage T4 gene 41 helicase, E. coli Rep helicase, E. coli recBCD helicase, recA, E. coli and eukaryotic topoisomerases (Annu Rev Biochem. (2001) 70:369-413).

Mis-priming or self-priming events, such as when the terminal spacer sequence of the recording tag primes extension self-extension may be minimized by inclusion of single stranded binding proteins (T4 gene 32, E. coli SSB, etc.), DMSO (1-10%), formamide (1-10%), BSA (10-100 ug/ml), TMAC1 (1-5 mM), ammonium sulfate (10-50 mM), betaine (1-3 M), glycerol (5-40%), or ethylene glycol (5-40%), in the primer extension reaction.

Most type A polymerases devoid of 3' exonuclease activity (endogenous or engineered removal), such as Klenow exo-, T7 DNA polymerase exo- (Sequenase 2.0), and Taq polymerase catalyze non-templated addition of a nucleotide, preferably an adenosine base (to lesser degree a G base, dependent on sequence context) to the 3' blunt end of a duplex extension product. For Taq polymerase, a 3' pyrimidine (C>T) minimizes non-templated adenosine addition, whereas a 3' purine nucleotide (G>A) favours non-templated adenosine addition. Alternatively, addition of non-templated base can be reduced by employing a mutant polymerase (mesophilic or thermophilic) in which non-templated terminal transferase activity has been greatly reduced by one or more point mutations, especially in the O-helix region (see U.S. Pat. No. 7,501,237) (Yang et al., Nucleic Acids Res. (2002) 30(19): 4314-4320). Pfu exo-, which is 3' exonuclease deficient and has strand-displacing ability, also does not have non-templated terminal transferase activity.

In another embodiment, polymerase extension buffers are comprised of 40-120 mM buffering agent such as Tris-Acetate, Tris-HCl, HEPES, etc. at a pH of 6-9.

Self-priming/mis-priming events initiated by self-annealing of the terminal spacer sequence of the extended recording tag with internal regions of the extended recording tag may be minimized by including pseudo-complementary bases in the recording/extended recording tag (Lahoud, Timoshchuk et al. 2008), (Hoshika, Chen et al. 2010). Pseudo-complementary bases show significantly reduced hybridization affinities for the formation of duplexes with each other due the presence of chemical modification. However, many pseudo-complementary modified bases can form strong base pairs with natural DNA or RNA sequences. In certain embodiments, the coding tag spacer sequence is comprised of multiple A and T bases, and commercially available pseudo-complementary bases 2-aminoadenine and 2-thiothymine are incorporated in the recording tag using phosphoramidite oligonucleotide synthesis. Additional pseudocomplementary bases can be incorporated into the extended recording tag during primer extension by adding pseudo-complementary nucleotides to the reaction (Gamper, Arar et al. 2006).

In certain embodiments, the binding event information of the binding agent to the macromolecule (e.g., peptide) is transferred from a secondary tag of an adaptor molecule to the recording tag associated with the immobilized macromolecule in a cyclic fashion. In some embodiments, steps repeated one or more times include: (b) contacting the macromolecule with a binding agent capable of binding to the macromolecule, wherein the binding agent comprises a coding tag with identifying information regarding the binding agent; (c) providing an adaptor molecule comprising a first hybridization sequence substantially complementary or complementary to at least a portion of the coding tag or the entire coding tag, and a secondary tag; and (d) transferring the information of the secondary tag to the recording tag to generate an extended recording tag. In some cases, the method further includes one or more wash steps between any of steps (b), (c), and (d). In some cases, the method further includes removing the binding agent and/or the adaptor molecule.

In some embodiments, a set of adaptor molecules used in a cycle of binding and information transfer may include cycle information, such as using cycle specific sequences. In one embodiment, the adaptor molecules comprise binding cycle-specific sequences. In one embodiment, the secondary tags comprise binding cycle-specific sequences. Binding cycle-specific sequences may be accomplished either via the use of completely unique binding cycle barcodes or through unique combinations of sub-barcodes. In some aspects, embedding binding cycle information directly in the secondary tag sequence may allow the total length of the coding tag to be minimized when employing error-correcting barcodes. The use of error-tolerant barcodes allows highly accurate barcode identification using sequencing platforms and approaches that are more error-prone, but have other advantages such as rapid speed of analysis, lower cost, and/or more portable instrumentation.

In some aspects, the provided methods also allow the use of adaptor molecules with secondary tags that are of preferred lengths, such as a length suitable for a particular sequencing method. In some embodiments, adaptor molecules may comprise secondary tags containing error-tolerant barcodes. In some embodiments, various libraries or sets of adaptor molecules can be designed to be compatible with a particular sequencing method and switched interchangeably if another sequencing method is preferred for the downstream analysis step.

B. Adaptor Molecules

Provided herein are methods for analysing a macromolecule comprising use of an adaptor molecule comprising a first hybridization sequence and a secondary tag. The methods provided may include preparing, selecting, and providing a single adaptor molecule or a plurality of adaptor molecules. The library or set of adaptor molecules used in the provided methods comprises at least one adaptor molecule configured to hybridize to at least one coding tag associated with the binding agents used for analyzing the macromolecule (or a portion of the coding tag). In some embodiments, the adaptor molecule further comprises a second hybridization sequence. The first hybridization sequence comprises a sequence substantially complementary or complementary to particular coding tags, allowing adaptor molecules to hybridize to corresponding coding tags and associate the secondary tag with the corresponding binding agents. In some embodiments, the information from the secondary tag can be transferred from the adaptor molecule to the recording tag after the coding tag associated with the binding agent hybridizes with the first hybridization sequence on the adaptor molecule. The adaptor molecule may comprise any suitable nucleic acid molecule including a DNA molecule, an RNA molecule, a PNA molecule, a BNA molecule, an XNA, molecule, an LNA molecule, a γPNA molecule, or a combination thereof. In some examples, the adaptor molecule comprises a spacer or linker. In some examples, the linker or spacer is provided to stop extension after transfer of information from the secondary tag to the recording tag. In some examples, a linker may be In some embodiments, the adaptor molecule may further comprise a universal priming site, a binding cycle specific spacer, binding cycle-specific barcode, a UMI or any combination thereof.

In some embodiments, multiple coding tags associated with a binding agent is configured to hybridize to adaptor molecules comprising the same secondary tag. For example, two binding agents that provide the same identifying information regarding a binding agent and the corresponding cognate target may be designed such that each binding agent is associated with the same secondary tag. In some examples for analyzing peptides, a binding agent that binds peptides with a terminal alanine (P1)-alanine (P2) and a binding agent that binds peptides with a terminal alanine (P1)-arginine (P2) both provide information that a peptide has a NTAA (P1) that is alanine, regardless of the amino acid at the penultimate position (P2). The coding tag associated with both binding agents hybridize with adaptor molecules which share the same secondary tag providing information of the terminal alanine on the peptide, thus collapsing the information of multiple binders into one piece of information at the level of the secondary tag.

In some embodiments, the first hybridization sequence ($1^{st}$ Hyb Sequence in FIGS. 7C and 7C) of the adaptor molecule comprises a single stranded region for hybridizing to the coding tag (or region therein) associated with the binding agent. In some embodiments, the first hybridization sequence comprises at least one nucleic acid region which is substantially complementary to a coding tag or portion thereof. In some embodiments, the first hybridization sequence in the adaptor molecule is complementary to a portion of the coding tag. In some embodiments, the first hybridization sequence in the adaptor molecule is complementary to the entire coding tag. In some examples, the first hybridization sequence comprises a sequence of nucleotides that binds selectively to the coding tag sequence or portion thereof. In some embodiments, the first hybridization sequence comprises a single stranded region which is substantially complementary to the coding tag sequence. "Substantially complementary" refers to sequences that are capable of hybridizing to a target nucleic acid sequence under the conditions employed. In preferred embodiments, a "substantially complementary" single-stranded region is exactly complementary to a target nucleic acid sequence. For example, the single-stranded region of the first hybridization sequence complementary to the coding tag may have at least 4 bases, at least 5 bases, at least 6 bases, at least 7 bases, at least 8 bases, at least 9 bases, at least 10 bases, at least 12 bases, at least 14 bases, at least 16 bases, at least 20 bases, at least 24 bases, at least 30 bases, or at least 34 bases. In some embodiments, the single-stranded region of the first hybridization sequence complementary to the coding tag has fewer than 40 bases, fewer than 30 bases, or fewer than 25 bases. One skilled in the art may select complementary regions with number of bases that is sufficient for forming stable hybridization regions between the first hybridization sequence and the coding tag. In some embodiments, the first hybridization sequence for hybridizing to the coding tag is located at the 3' or the 5' terminus of the adaptor molecule. In some specific embodiments, the first hybridization sequence for hybridizing to the coding tag is located at the 5' terminus of the adaptor molecule. In some examples, the first hybridization sequence is 5' to the secondary tag in the adaptor molecule.

In some embodiments, the second hybridization sequence (2nd Hyb Sequence in FIG. 7C) of the adaptor molecule comprises a single stranded region for hybridizing to a portion of the recording tag associated with the macromolecule for analysis. For example, the second hybridization sequence on the adaptor molecule is substantially complementary or complementary to a region on the recording tag generated from a previous information transfer of the secondary tag from the adaptor molecule to the recording tag. In some aspects, the second hybridization sequence on the adaptor molecule comprises the secondary tag information or portion thereof on a different adaptor molecule. In some embodiments, the second hybridization sequence comprises at least one nucleic acid region which is substantially complementary to a portion of the recording tag or portion thereof. In some embodiments, the second hybridization sequence is substantially complementary or complementary to a sequence at the 3' terminus of the recording tag. In some examples, the second hybridization sequence comprises a sequence of nucleotides that binds selectively to a portion of the recording tag associated with the macromolecule for analysis. In some embodiments, the second hybridization sequence comprises a single stranded region which is substantially complementary to a portion of the recording tag associated with the macromolecule for analysis. For example, the single-stranded region of the second hybridization sequence complementary to the recording tag or portion thereof may have at least 4 bases, at least 5 bases, at least 6 bases, at least 7 bases, at least 8 bases, at least 9 bases, at least 10 bases, at least 12 bases, at least 14 bases, at least 16 bases, at least 20 bases, at least 24 bases, at least 30 bases, or at least 34 bases. In some embodiments, the single-stranded region of the second hybridization sequence complementary to the recording tag or portion thereof has fewer than 40 bases, fewer than 30 bases, or fewer than 25 bases. One skilled in the art may select complementary regions with number of bases that is sufficient for forming stable hybridization regions between the second hybridization sequence and the portion of the recording tag. In some embodiments, the second hybridization sequence for hybridizing to the portion of the recording tag is located at the 3' or the 5' terminus of the adaptor molecule. In some specific embodiments, the second hybridization sequence is located at the 3' terminus of the adaptor molecule.

The secondary tag of an adaptor molecule can be a polynucleotide of any suitable length, e.g., a nucleic acid molecule of about 2 bases to about 100 bases, including any integer including 2 and 100 and in between, that comprises identifying information for a binding agent. Information of a secondary tag can be associated to a binding agent via the first hybridization sequence (which is substantially complementary or complementary to the coding tag (or portion thereof) associated with a binding agent) comprised by the same adaptor molecule. A secondary tag can made from a sequenceable polymer. The secondary tag may be optionally flanked by one spacer on one side or optionally flanked by a spacer on each side. A secondary tag may also be comprised of an optional UMI and/or an optional binding cycle-specific barcode. In certain embodiments, a secondary tag may be flanked by a binding cycle specific spacer. A secondary tag may be single stranded or double stranded. A double stranded secondary tag may comprise blunt ends, overhanging ends, or both. A secondary tag may refer to the secondary tag that is part of the adaptor molecule or to a complementary sequence that is capable of hybridizing to the secondary tag, or to the information present in an extended recording tag transferred from the secondary tag. In certain embodiments, a secondary tag may further comprise a binding cycle specific barcode, a unique molecular identifier, or both. In some specific embodiments, the secondary tag is a binding cycle specific sequence. For example, one set or plurality of adaptor molecules is used with a first cycle and a second set or plurality of adaptor molecules is used with a second cycle, etc.

In some aspects, a secondary tag comprises a sequence that provides identifying information regarding the binding agent associated via the first hybridization region on the adaptor molecule. The sequence providing identifying information is about 3 bases to about 30 bases, about 3 bases to about 20 bases, about 3 bases to about 10 bases, or about 3 bases to about 8 bases. In some embodiments, an sequence providing identifying information is about 3 bases, 4 bases, 5 bases, 6 bases, 7 bases, 8 bases, 9 bases, 10 bases, 11 bases, 12 bases, 13 bases, 14 bases, 15 bases, 20 bases, 25 bases, or 30 bases in length. The length of the sequence providing identifying information may be adjusted based on the size of the binding agent library used.

In some embodiments, each unique binding agent within a library of binding agents is associated with a sequence providing identifying information regarding the binding agent. The secondary tag comprises this sequence providing identifying information regarding the binding agent. For example, 20 unique sequences may be used as secondary tags for providing identifying information for a library of 20 binding agents that bind to the 20 standard amino acids. Additional sequences may be used to identify modified amino acids (e.g., post-translationally modified amino acids). In another example, 30 unique sequence may be used as secondary tags for a library of 30 binding agents that bind to the 20 standard amino acids and 10 post-translational modified amino acids (e.g., phosphorylated amino acids, acetylated amino acids, methylated amino acids). In other embodiments, two or more different binding agents may be associated with the same sequence (secondary tags) providing identifying information regarding the binding agent. In some cases, 20 unique sequences may be used as secondary tags for a library of 30 binding agents that bind to the 20 standard amino acids in an overlapping manner.

In some embodiments, the secondary tag sequence can be optimized for a particular sequencing analysis platform. In a particular embodiment, the sequencing platform is nanopore sequencing. In some embodiments, the sequencing platform has a per base error rate of >1%, >5%, >10%, >15%, >20%, >25%, or >30%. For example, if the extended nucleic acid is to be analyzed using a nanopore sequencing instrument, the barcode sequences (e.g., sequences comprising information from the secondary tag) can be designed to be optimally electrically distinguishable in transit through a nanopore. In some embodiments, the length of the barcode sequences is optimally designed to implement an appropriate level of error detection and/or correction.

In certain embodiments, the adaptor molecule further comprises a spacer sequence at one end or both ends. In some embodiments, the adaptor molecule comprises a spacer at the 3' terminus. A spacer sequence is about 1 base to about 20 bases, about 1 base to about 10 bases, about 5 bases to about 9 bases, or about 4 bases to about 8 bases. In some embodiments, a spacer is about 1 base, 2 bases, 3 bases, 4 bases, 5 bases, 6 bases, 7 bases, 8 bases, 9 bases, 10 bases, 11 bases, 12 bases, 13 bases, 14 bases, 15 bases or 20 bases in length. In some embodiments, a spacer is shorter than the sequence providing identifying information comprised in the secondary tag, e.g., at least 1 base, 2, bases, 3 bases, 4 bases, 5 bases, 6, bases, 7 bases, 8 bases, 9 bases, 10 bases, 11 bases, 12 bases, 13 bases, 14 bases, 15 bases, 20 bases, or 25 bases shorter than the sequence providing identifying information comprised in the secondary tag. In other embodiments, a spacer is the same length as the sequence providing identifying information comprised in the secondary tag. In certain embodiments, the spacer is specific to the adaptor molecule. In some cases, a spacer is designed such that a spacer from a previous binding cycle only interacts with a spacer from the appropriate adaptor molecule in a current binding cycle. A spacer sequence may be used as the primer annealing site for a primer extension reaction, or a splint or sticky end in a ligation reaction. A 5' spacer on an adaptor molecule may optionally contain pseudo complementary bases to a 3' spacer on the recording tag to increase $T_M$ (Lehoud et al., 2008, Nucleic Acids Res. 36:3409-3419). In other embodiments, the adaptor molecules do not have a binding cycle specific spacer sequence. In some embodiments, the adaptor molecules do not have a spacer sequence.

In some embodiments, a set (e.g. a library) or plurality of adaptor molecules share a common spacer sequence used in an assay (e.g. the entire library of adaptor molecules used in a multiple binding cycle method possess a common spacer). In another embodiment, the adaptor molecules are comprised of a binding cycle tags, identifying a particular binding cycle. In other embodiments, the adaptor molecules within a library or set of adaptor molecules have a binding cycle specific spacer sequence. In some embodiments, adaptor molecules comprises one binding cycle specific spacer sequence. For example, adaptor molecules used in the first binding cycle comprise a "cycle 1" specific spacer sequence, adaptor molecules used in the second binding cycle comprise a "cycle 2" specific spacer sequence, and so on up to "n" binding cycles. In some embodiments, a spacer sequence comprises a sufficient number of bases to anneal to a complementary spacer sequence in a recording tag or extended recording tag to initiate a primer extension reaction or sticky end ligation reaction.

In some embodiments, adaptor molecules used to bind in an alternating cycles comprises different binding cycle specific spacer sequences. For example, adaptor molecules used in the first binding cycle comprise a "cycle 1" specific spacer sequence, adaptor molecules used in the second binding cycle comprise a "cycle 2" specific spacer sequence, adaptor molecules used in the third binding cycle also comprises the "cycle 1" specific spacer sequence, adaptor molecules used in the fourth binding cycle comprises the "cycle 2" specific spacer sequence. In this manner, alternating spacers can be used and cycle specific spacers are not needed for every cycle.

The adaptor molecules may also be designed to contain palindromic sequences. Inclusion of a palindromic sequence into the adaptor molecule allows a nascent, growing, extended recording tag to fold upon itself as information is transferred from the secondary tag. The extended recording tag is folded into a more compact structure, effectively decreasing undesired inter-molecular binding and primer extension events.

The adaptor molecules may include a terminator nucleotide incorporated at the 3' end of the 3' spacer sequence. After a binding agent binds to a polypeptide, an adaptor molecule hybridizes, and their corresponding hybridization sequences and recording tags anneal via complementary spacer sequences, it is possible for primer extension to transfer information from the secondary tag to the recording tag. Addition of a terminator nucleotide on the 3' end of the secondary tag prevents transfer of recording tag information to the secondary tag.

In some specific embodiments, the adaptor molecule comprises from 5' to 3' direction the secondary tag and the first hybridization sequence, optionally with a linker in between said components. In some specific embodiments, the adaptor molecule comprises from 5' to 3' direction: the first hybridization sequence, the secondary tag, and the second hybridization sequence. In some specific embodiments, the adaptor molecule comprises from 5' to 3' direction: the first hybridization sequence, the secondary tag, and a spacer sequence. In some specific embodiments, the adaptor molecule comprises from 5' to 3' direction: the first hybridization sequence, a spacer or linker to stop extension, the secondary tag, and the second hybridization sequence. In some specific embodiments, the adaptor molecule comprises from 5' to 3' direction: the first hybridization sequence, a spacer or linker to stop extension, the secondary tag, and a spacer sequence.

In some embodiments, the method further includes adding a universal priming site from an adaptor molecule to the extended recording tag, prior to or during the last binding cycle. In some embodiments, the universal reverse priming site is added to the recording tag (e.g., extended recording tag) from an adaptor molecule. The adaptor molecules used in the final binding cycle may comprise a universal priming site. After transfer of the final secondary tag information to the extended recording tag, the tag can be capped by addition of a universal reverse priming site via ligation, primer extension or other methods known in the art. In some embodiments, a capping reaction may be performed in any binding cycle to add a capping sequence (e.g., a universal priming site) to recording tags that did not extend with information from a secondary tag in that cycle. In some cases, such a step is useful to indicate that an information transfer event did not happen in a particular binding cycle.

C. Recording Tag

In some embodiments, the macromolecule (e.g., protein or polypeptide) for analysis may be labeled with a nucleic acid molecule or an oligonucleotide (e.g., DNA recording tag). In some aspects, a plurality of macromolecules in the sample is provided with recording tags. The recording tags may be associated or attached, directly or indirectly to the macromolecules using any suitable means. In some embodiments, a macromolecule may be associated with one or more recording tags. In some aspects, the recording tag may be any suitable sequenceable moiety to which identifying information can be transferred (e.g., information from one or more secondary tags). In some aspects, the recording tags may be associated or attached, directly or indirectly to the macromolecules prior to contacting with a binding agent.

In some embodiments, at least one recording tag is associated or co-localized directly or indirectly with the macromolecule (e.g., polypeptide). In a particular embodiment, a single recording tag is attached to a polypeptide, such as via the attachment to a N- or C-terminal amino acid. In another embodiment, multiple recording tags are attached to the polypeptide, such as to the lysine residues or peptide backbone. In some embodiments, a polypeptide labeled with multiple recording tags is fragmented or digested into smaller peptides, with each peptide labeled on average with one recording tag.

A recording tag may comprise DNA, RNA, or polynucleotide analogs including PNA, gPNA, GNA, HNA, BNA, XNA, TNA, or a combination thereof. A recording tag may be single stranded, or partially or completely double stranded. A recording tag may have a blunt end or overhanging end. In certain embodiments, all or a substantial amount of the macromolecules (e.g., at least 50%, 55%, 60%, 65%, 70%, 75%, 80%, 85%, 90%, 95%, 96%, 97%, 98%, 99%, or 100%) within a sample are labeled with a recording tag. In other embodiments, a subset of macromolecules within a sample are labeled with recording tags. In a particular embodiment, a subset of macromolecules from a sample undergo targeted (analyte specific) labeling with recording tags. For example, targeted recording tag labeling of proteins may be achieved using target protein-specific binding agents (e.g., antibodies, aptamers, etc.). In some embodiments, the recording tags are attached to the macromolecules prior to providing the sample on a support. In some embodiments, the recording tags are attached to the macromolecules after providing the sample on the support.

In some embodiments, the recording tag may comprise other nucleic acid components. In some embodiments, the recording tag may comprise a unique molecular identifier, a compartment tag, a partition barcode, sample barcode, a fraction barcode, a spacer sequence, a universal priming site, or any combination thereof. In some embodiments, the recording tag may comprise a blocking group, such as at the 3'-terminus of the recording tag. In some cases, the 3'-terminus of the recording tag is blocked to prevent extension of the recording tag by a polymerase.

In some embodiments, the recording tag can include a sample identifying barcode. A sample barcode is useful in the multiplexed analysis of a set of samples in a single reaction vessel or immobilized to a single solid substrate or collection of solid substrates (e.g., a planar slide, population of beads contained in a single tube or vessel, etc.). For example, macromolecules from many different samples can be labeled with recording tags with sample-specific barcodes, and then all the samples pooled together prior to immobilization to a support, cyclic binding of the binding agent, and recording tag analysis. Alternatively, the samples can be kept separate until after creation of a DNA-encoded library, and sample barcodes attached during PCR amplification of the DNA-encoded library, and then mixed together prior to sequencing. This approach could be useful when assaying analytes (e.g., proteins) of different abundance classes.

In certain embodiments, a recording tag comprises an optional, unique molecular identifier (UMI), which provides a unique identifier tag for each macromolecules (e.g., polypeptide) to which the UMI is associated with. A UMI can be about 3 to about 40 bases, about 3 to about 30 bases, about 3 to about 20 bases, or about 3 to about 10 bases, or about 3 to about 8 bases. In some embodiments, a UMI is about 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 25 bases, 30 bases, 35 bases, or 40 bases in length. A UMI can be used to de-convolute sequencing data from a plurality of extended recording tags to identify sequence reads from individual macromolecules. In some embodiments, within a library of macromolecules, each macromolecule is associated with a single recording tag, with each recording tag comprising a unique UMI. In other embodiments, multiple copies of a recording tag are associated with a single macromolecule, with each copy of the recording tag comprising the same UMI. In some embodiments, a UMI has a different base sequence than the spacer or secondary tags to facilitate distinguishing these components during sequence analysis. In some embodiments, the UMI may provide function as a location identifier and also provide information in the macromolecule analysis assay. For example, the UMI may be used to identify molecules that are identical by descent, and therefore originated from the same initial molecule. In some aspects, this information can be used to correct for variations in amplification, and to detect and correct sequencing errors.

In some embodiments, the recording tag comprises a spacer polymer. In certain embodiments, a recording tag comprises a spacer at its terminus, e.g., 3' end. As used herein reference to a spacer sequence in the context of a recording tag includes a spacer sequence that is identical to the spacer sequence associated with its cognate binding agent, or a spacer sequence that is complementary to the spacer sequence associated with its cognate binding agent. The terminal, e.g., 3', spacer on the recording tag permits transfer of identifying information of a cognate binding agent from a secondary tag to the recording tag during the first binding cycle (e.g., via annealing of complementary spacer sequences for primer extension or sticky end ligation). In one embodiment, the spacer sequence is about 1-20 bases in length, about 2-12 bases in length, or 5-10 bases in length. The length of the spacer may depend on factors such as the temperature and reaction conditions of the primer extension reaction for transferring secondary tag information to the recording tag.

In some embodiments using spacer sequences, the recording tags associated with a library of polypeptides share a common spacer sequence. In other embodiments, the recording tags associated with a library of polypeptides have binding cycle specific spacer sequences that are complementary to the binding cycle specific spacer sequences of adaptor molecules. In some aspects, the spacer sequence in the recording tag is designed to have minimal complementarity to other regions in the recording tag; likewise, the spacer sequence in the adaptor molecules should have minimal complementarity to other regions in the adaptor molecule. In some cases, the spacer sequence of the recording tags and adaptor molecules should have minimal sequence complementarity to components such unique molecular identifiers, barcodes (e.g., compartment, partition, sample, spatial location), universal primer sequences, secondary tag sequences, cycle specific sequences, etc. present in the tags.

In certain embodiments, a recording tag comprises a universal priming site, e.g., a forward or 5' universal priming site. A universal priming site is a nucleic acid sequence that may be used for priming a library amplification reaction and/or for sequencing. A universal priming site may include, but is not limited to, a priming site for PCR amplification, flow cell adaptor sequences that anneal to complementary oligonucleotides on flow cell surfaces (e.g., Illumina next generation sequencing), a sequencing priming site, or a combination thereof. A universal priming site can be about 10 bases to about 60 bases. In some embodiments, a universal priming site comprises an Illumina P5 primer (5'-AATGATACGGCGACCACCGA-3'-SEQ ID NO:1) or an Illumina P7 primer (5'-CAAGCAGAAGACGGCATACGAGAT-3'-SEQ ID NO:2).

In certain embodiments, a recording tag comprises a compartment tag. In some embodiments, the compartment tag is a component within a recording tag. In some embodiments, the recording tag can also include a barcode which represents a compartment tag in which a compartment, such as a droplet, microwell, physical region on a support, etc. is assigned a unique barcode. The association of a compartment with a specific barcode can be achieved in any number of ways such as by encapsulating a single barcoded bead in a compartment, e.g., by direct merging or adding a barcoded droplet to a compartment, by directly printing or injecting a barcode reagents to a compartment, etc. The barcode reagents within a compartment are used to add compartment-specific barcodes to the macromolecule or fragments thereof within the compartment. Applied to protein partitioning into compartments, the barcodes can be used to map analyzed peptides back to their originating protein molecules in the compartment. This can greatly facilitate protein identification. Compartment barcodes can also be used to identify protein complexes. In other embodiments, multiple compartments that represent a subset of a population of compartments may be assigned a unique barcode representing the subset. In some embodiments, the recording tag comprises fraction barcode which contains identifying information for the macromolecules within a fraction.

In some embodiments, one or more of the tags (e.g., compartment tag, a partition barcode, sample barcode, a fraction barcode, etc.) further comprise a functional moiety capable of reacting with an internal amino acid, the peptide backbone, or N-terminal amino acid on the plurality of protein complexes, proteins, or polypeptides. In some embodiments, the functional moiety is a click chemistry moiety, an aldehyde, an azide/alkyne, or a maleimide/thiol, or an epoxide/nucleophile, an inverse electron demand Diels-Alder (iEDDA) group, or a moiety for a Staudinger reaction. In some specific embodiments, a plurality of compartment tags is formed by printing, spotting, ink-jetting the compartment tags into the compartment, or a combination thereof. In some embodiments, the tag is attached to a polypeptide to link the tag to the macromolecule via a polypeptide-polypeptide linkage. In some embodiments, the tag-attached polypeptide comprises a protein ligase recognition sequence.

In certain embodiments, a peptide or polypeptide macromolecule can be immobilized to a support by an affinity capture reagent (and optionally covalently crosslinked), wherein the recording tag is associated with the affinity capture reagent directly, or alternatively, the macromolecule can be directly immobilized to the support with a recording tag. In one embodiment, the macromolecule is attached to a bait nucleic acid which hybridizes to a capture nucleic acid and is ligated to a capture nucleic acid which comprises a reactive coupling moiety for attaching to the support. In some examples, the bait or capture nucleic acid may serve as a recording tag to which information regarding the polypeptide can be transferred. In some embodiments, the macromolecule is attached to a bait nucleic acid to form a nucleic acid-macromolecule chimera. In some embodiments, the immobilization methods comprise bringing the nucleic acid-macromolecule chimera into proximity with a support by hybridizing the bait nucleic acid to a capture nucleic acid attached to the support, and covalently coupling the nucleic acid-macromolecule chimera to the solid support. In some cases, the nucleic acid-macromolecule chimera is coupled indirectly to the solid support, such as via a linker. In some embodiments, a plurality of the nucleic acid-macromolecule chimeras is coupled on the solid support and any adjacently coupled nucleic acid-macromolecule chimeras are spaced apart from each other at an average distance of about 50 nm or greater.

In some embodiments, the density or number of macromolecules provided with a recording tag is controlled or titrated. In some examples, the desired spacing, density, and/or amount of recording tags in the sample may be titrated by providing a diluted or controlled number of recording tags. In some examples, the desired spacing, density, and/or amount of recording tags may be achieved by spiking a competitor or "dummy" competitor molecule when providing, associating, and/or attaching the recording tags. In some cases, the "dummy" competitor molecule reacts in the same way as a recording tag being associated or attached to a macromolecule in the sample but the competitor molecule does not function as a recording tag. In some specific examples, if a desired density is 1 functional recording tag per 1,000 available sites for attachment in the sample, then spiking in 1 functional recording tag for every 1,000 "dummy" competitor molecules is used to achieve the desired spacing. In some examples, the ratio of functional recording tags is adjusted based on the reaction rate of the functional recording tags compared to the reaction rate of the competitor molecules.

In some examples, the labeling of the macromolecule with a recording tag is performed using standard amine coupling chemistries. For example, the e-amino group (e.g., of lysine residues) and the N-terminal amino group may be susceptible to labeling with amine-reactive coupling agents, depending on the pH of the reaction (Mendoza et al., Mass Spectrom Rev (2009) 28(5): 785-815). In a particular embodiment, the recording tag comprises a reactive moiety (e.g., for conjugation to a solid surface, a multifunctional linker, or a macromolecule), a linker, a universal priming sequence, a barcode (e.g., compartment tag, partition barcode, sample barcode, fraction barcode, or any combination thereof), an optional UMI, and a spacer (Sp) sequence for facilitating information transfer. In another embodiment, the protein can be first labeled with a universal DNA tag, and the barcode-Sp sequence (representing a sample, a compartment, a physical location on a slide, etc.) are attached to the protein later through and enzymatic or chemical coupling step. A universal DNA tag comprises a short sequence of nucleotides that are used to label a protein or polypeptide macromolecule and can be used as point of attachment for a barcode (e.g., compartment tag, recording tag, etc.). For example, a recording tag may comprise at its terminus a sequence complementary to the universal DNA tag. In certain embodiments, a universal DNA tag is a universal priming sequence. Upon hybridization of the universal DNA tags on the labeled protein to complementary sequence in recording tags (e.g., bound to beads), the annealed universal DNA tag may be extended via primer extension, transferring the recording tag information to the DNA tagged protein. In a particular embodiment, the protein is labeled with a universal DNA tag prior to proteinase digestion into peptides. The universal DNA tags on the labeled peptides from the digest can then be converted into an informative and effective recording tag.

The recording tags may comprise a reactive moiety for a cognate reactive moiety present on the macromolecule, e.g., protein, (e.g., click chemistry labeling, photoaffinity labeling). For example, recording tags may comprise an azide moiety for interacting with alkyne-derivatized proteins, or recording tags may comprise a benzophenone for interacting with native proteins, etc. After binding of the target protein by the target protein specific binding agent, the recording tag and target protein are coupled via their corresponding reactive moieties. After the target protein is labeled with the recording tag, the target-protein specific binding agent may be removed by digestion of the DNA capture probe linked to the target-protein specific binding agent. For example, the DNA capture probe may be designed to contain uracil bases, which are then targeted for digestion with a uracil-specific excision reagent (e.g., USER™), and the target-protein specific binding agent may be dissociated from the target protein. In some embodiments, other types of linkages besides hybridization can be used to link the recording tag to a macromolecule. A suitable linker can be attached to various positions of the recording tag, such as the 3' end, at an internal position, or within the linker attached to the 5' end of the recording tag.

In some aspects, the spacer sequence in the recording is designed to have minimal complementarity to other regions in the recording tag. In some aspects, the spacer sequence of the recording tags and adaptor molecules should have minimal sequence complementarity to components such unique molecular identifiers, barcodes (e.g., compartment, partition, sample, spatial location), universal primer sequences, secondary tag sequences, cycle specific sequences, etc. present in the recording tags, adaptor molecules, and/or coding tags.

The information from one or more secondary tags of adaptor molecules is transferred to the recording tag to generate an extended recording tag. In some embodiments, an extended recording tag comprises from 5' to 3' direction: a universal forward (or 5') priming sequence, information transferred from one or more secondary tag(s), and a spacer sequence. In some embodiments, an extended recording tag comprises from 5' to 3' direction: a universal forward (or 5') priming sequence, information transferred from one or more secondary tag(s), optionally other barcodes (e.g., sample barcode, partition barcode, compartment barcode, or any combination thereof), a spacer sequence, and a universal reverse (or 3') priming sequence. In some other embodiments, a recording tag comprises from 5' to 3' direction: a universal forward (or 5') priming sequence, information transferred from one or more secondary tag(s), optionally other barcodes (e.g., sample barcode, partition barcode, compartment barcode, or any combination thereof), an optional UMI, a spacer sequence, and a universal reverse (or 3') priming sequence.

D. Binding Agent

The methods described herein use a binding agent configured for interacting with the macromolecules to be analyzed (e.g., polypeptides, peptides, proteins). The assay can include contacting a plurality of binding agents to a plurality of macromolecules, or a plurality of targets. In some embodiments, the present methods comprise contacting a single macromolecule with a single binding agent, contacting a plurality of macromolecules (a plurality of targets) with a single binding agent, or contacting a plurality of macromolecules with a plurality of binding agents. In some embodiments, the plurality of binding agents includes a mixture of binding agents.

A binding agent can be any molecule (e.g., peptide, polypeptide, protein, nucleic acid, carbohydrate, small molecule, and the like) capable of binding to a component or feature of a polypeptide. A binding agent can be a naturally occurring, synthetically produced, or recombinantly expressed molecule. In some embodiments, the scaffold used to engineer a binding agent can be from any species, e.g., human, non-human, transgenic. A binding agent may bind to a portion of a target macromolecule or a motif. A binding agent may bind to a single monomer or subunit of a polypeptide (e.g., a single amino acid) or bind to multiple linked subunits of a polypeptide (e.g., dipeptide, tripeptide, or higher order peptide of a longer polypeptide molecule).

In some examples, the binding agent comprises an antibody, an antigen-binding antibody fragment, a single-domain antibody (sdAb), a recombinant heavy-chain-only antibody (VHH), a single-chain antibody (scFv), a shark-derived variable domain (vNARs), a Fv, a Fab, a Fab', a F(ab')2, a linear antibody, a diabody, an aptamer, a peptide mimetic molecule, a fusion protein, a reactive or non-reactive small molecule, or a synthetic molecule.

In certain embodiments, a binding agent may be designed to bind covalently. Covalent binding can be designed to be conditional or favored upon binding to the correct moiety. For example, an target and its cognate binding agent may each be modified with a reactive group such that once the target-specific binding agent is bound to the target, a coupling reaction is carried out to create a covalent linkage between the two. Non-specific binding of the binding agent to other locations that lack the cognate reactive group would not result in covalent attachment. In some embodiments, the target comprises a ligand that is capable of forming a covalent bond to a binding agent. In some embodiments, the target comprises a ligand group that is capable of covalent binding to a binding agent. Covalent binding between a binding agent and its target may allow for more stringent washing to be used to remove binding agents that are non-specifically bound, thus increasing the specificity of the assay. In some embodiments, the method includes a wash step after contacting the binding agent to the macromolecule to remove non-specifically bound binding agents. The stringency of the wash step may be tuned depending on the affinity of the binding agent to the target and/or the strength and stability of the complex formed.

In some embodiments, the binding agents are configured to provide specificity for binding of the binding agent to the macromolecule. In certain embodiments, a binding agent may be a selective binding agent. As used herein, selective binding refers to the ability of the binding agent to preferentially bind to a specific ligand (e.g., amino acid or class of amino acids) relative to binding to a different ligand (e.g., amino acid or class of amino acids). Selectivity is commonly referred to as the equilibrium constant for the reaction of displacement of one ligand by another ligand in a complex with a binding agent. Typically, such selectivity is associated with the spatial geometry of the ligand and/or the manner and degree by which the ligand binds to a binding agent, such as by hydrogen bonding, hydrophobic binding, and Van der Waals forces (non-covalent interactions) or by reversible or non-reversible covalent attachment to the binding agent. It should also be understood that selectivity may be relative, and as opposed to absolute, and that different factors can affect the same, including ligand concentration. Thus, in one example, a binding agent selectively binds one of the twenty standard amino acids. In some examples, a binding agent binds to an N-terminal amino acid residue, a C-terminal amino acid residue, or an internal amino acid residue.

In some embodiments, the binding agent is partially specific or selective. In some aspects, the binding agent preferentially binds one or more amino acids. In some examples, a binding agent may bind to or is capable of binding to two or more of the twenty standard amino acids. For example, a binding agent may preferentially bind the amino acids A, C, and G over other amino acids. In some other examples, the binding agent may selectively or specifically bind more than one amino acid. In some aspects, the binding agent may also have a preference for one or more amino acids at the second, third, fourth, fifth, etc. positions from the terminal amino acid. In some cases, the binding agent preferentially binds to a specific terminal amino acid and a penultimate amino acid. For example, a binding agent may preferentially bind AA, AC, and AG or a binding agent may preferentially bind AA, CA, and GA. In some specific examples, binding agents with different specificities can be associated with coding tags that hybridize to adaptor molecules comprising the same secondary tag. In some embodiments, a binding agent may exhibit flexibility and variability in target binding preference in some or all of the positions of the targets. In some examples, a binding agent may have a preference for one or more specific target terminal amino acids and have a flexible preference for a target at the penultimate position. In some other examples, a binding agent may have a preference for one or more specific target amino acids in the penultimate amino acid position and have a flexible preference for a target at the terminal amino acid position. In some embodiments, a binding agent is selective for a target comprising a terminal amino acid and other components of a macromolecule. In some examples, a binding agent is selective for a target comprising a terminal amino acid and at least a portion of the peptide backbone. In some particular examples, a binding agent is selective for a target comprising a terminal amino acid and an amide peptide backbone. In some cases, the peptide backbone comprises a natural peptide backbone or a post-translational modification. In some embodiments, the binding agent exhibits allosteric binding.

In some embodiments, the method comprises contacting a mixture of binding agents with a mixture of macromolecules and selectivity need only be relative to the other binding agents to which the target is exposed. It should also be understood that selectivity of a binding agent need not be absolute to a specific molecule but could be to a portion of a molecule. In some examples, selectivity of a binding agent need not be absolute to a specific amino acid, but could be selective to a class of amino acids, such as amino acids with polar or non-polar side chains, or with electrically (positively or negatively) charged side chains, or with aromatic side chains, or some specific class or size of side chains, and the like. In some embodiments, the ability of a binding agent to selectively bind a feature or component of a macromolecule is characterized by comparing binding abilities of binding agents. For example, the binding ability of a binding agent to the target can be compared to the binding ability of a binding agent which binds to a different target, for example, comparing a binding agent selective for a class of amino acids to a binding agent selective for a different class of amino acids. In some examples, a binding agent selective for non-polar side chains is compared to a binding agent selective for polar side chains. In some embodiments, a binding agent selective for a feature, component of a peptide, or one or more amino acid exhibits at least 1×, at least 2×, at least 5×, at least 10×, at least 50×, at least 100×, or at least 500× more binding compared to a binding agent selective for a different feature, component of a peptide, or one or more amino acid.

In a particular embodiment, the binding agent has a high affinity and high selectivity for the macromolecule, e.g., the polypeptide, of interest. In particular, a high binding affinity with a low off-rate may be efficacious for hybridization of the adaptor molecule to the coding tag. In certain embodiments, a binding agent has a Kd of about <500 nM, <200 nM, <100 nM, <50 nM, <10 nM, <5 nM, <1 nM, <0.5 nM, or <0.1 nM. In a particular embodiment, the binding agent is added to the polypeptide at a concentration >1×, >5×, >10×, >100×, or >1000× its Kd to drive binding to completion. For example, binding kinetics of an antibody to a single protein molecule is described in Chang et al., J Immunol Methods (2012) 378(1-2): 102-115.

In certain embodiments, a binding agent may bind to a terminal amino acid of a peptide, an intervening amino acid, dipeptide (sequence of two amino acids), tripeptide (sequence of three amino acids), or higher order peptide of a peptide molecule. In some embodiments, each binding agent in a library of binding agents selectively binds to a particular amino acid, for example one of the twenty standard naturally occurring amino acids. In some embodiments, the binding agent binds to an unmodified or native (e.g., natural) amino acid. In some examples, the binding agent binds to an unmodified or native dipeptide (sequence of two amino acids), tripeptide (sequence of three amino acids), or higher order peptide of a peptide molecule. A binding agent may be engineered for high affinity for a native or unmodified N-terminal amino acid (NTAA), high specificity for a native or unmodified NTAA, or both. In some embodiments, binding agents can be developed through directed evolution of promising affinity scaffolds using phage display.

In certain embodiments, a binding agent may bind to a post-translational modification of an amino acid. In some embodiments, a peptide comprises one or more post-translational modifications, which may be the same of different. The NTAA, CTAA, an intervening amino acid, or a combination thereof of a peptide may be post-translationally modified. Post-translational modifications to amino acids include acylation, acetylation, alkylation (including methylation), biotinylation, butyrylation, carbamylation, carbonylation, deamidation, deiminiation, diphthamide formation, disulfide bridge formation, eliminylation, flavin attachment, formylation, gamma-carboxylation, glutamylation, glycylation, glycosylation, glypiation, heme C attachment, hydroxylation, hypusine formation, iodination, isoprenylation, lipidation, lipoylation, malonylation, methylation, myristolylation, oxidation, palmitoylation, pegylation, phosphopantetheinylation, phosphorylation, prenylation, propionylation, retinylidene Schiff base formation, S-glutathionylation, S-nitrosylation, S-sulfenylation, selenation, succinylation, sulfination, ubiquitination, and C-terminal amidation (see, also, Seo and Lee, 2004, J. Biochem. Mol. Biol. 37:35-44).

In certain embodiments, a lectin is used as a binding agent for detecting the glycosylation state of a protein, polypeptide, or peptide. Lectins are carbohydrate-binding proteins that can selectively recognize glycan epitopes of free carbohydrates or glycoproteins. A list of lectins recognizing various glycosylation states (e.g., core-fucose, sialic acids, N-acetyl-D-lactosamine, mannose, N-acetyl-glucosamine) include: A, AAA, AAL, ABA, ACA, ACG, ACL, AOL, ASA, BanLec, BC2L-A, BC2LCN, BPA, BPL, Calsepa, CGL2, CNL, Con, ConA, DBA, Discoidin, DSA, ECA, EEL, F17AG, Gal1, Gal1-S, Gal2, Gal3, Gal3C-S, Gal7-S, Gal9, GNA, GRFT, GS-I, GS-II, GSL-I, GSL-II, HHL, HIHA, HPA, I, II, Jacalin, LBA, LCA, LEA, LEL, Lentil, Lotus, LSL-N, LTL, MAA, MAH, MAL_I, Malectin, MOA, MPA, MPL, NPA, Orysata, PA-IIL, PA-IL, PALa, PHA-E, PHA-L, PHA-P, PHAE, PHAL, PNA, PPL, PSA, PSL1a, PTL, PTL-I, PWM, RCA120, RS-Fuc, SAMB, SBA, SJA, SNA, SNA-I, SNA-II, SSA, STL, TJA-I, TJA-II, TxLCI, UDA, UEA-I, UEA-II, VFA, VVA, WFA, WGA (see, Zhang et al., 2016, MABS 8:524-535).

In some embodiments, a binding agent may bind to a native or unmodified or unlabeled terminal amino acid. Moreover, in some cases, these natural amino acid binders don't recognize N-terminal labels. Directed evolution of aaRS scaffolds can be used to generate higher affinity, higher specificity binding agents that recognized the N-terminal amino acids in the context of an N-terminal label. In another example, Havranak et al. (U.S. Patent Publication No. US 2014/0273004) describes engineering aminoacyl tRNA synthetases (aaRSs) as specific NTAA binders. The amino acid binding pocket of the aaRSs has an intrinsic ability to bind cognate amino acids, but generally exhibits poor binding affinity and specificity. Moreover, these natural amino acid binders don't recognize N-terminal labels. Directed evolution of aaRS scaffolds can be used to generate higher affinity, higher specificity binding agents that recognized the N-terminal amino acids in the context of an N-terminal label.

In certain embodiments, a binding agent may bind to a modified or labeled terminal amino acid (e.g., an NTAA that has been functionalized or modified). In some embodiments, a binding agent may bind to a chemically or enzymatically modified terminal amino acid. A modified or labeled NTAA can be one that is functionalized with phenylisothiocyanate, PITC, 1-fluoro-2,4-dinitrobenzene (Sanger's reagent, DNFB), benzyloxycarbonyl chloride or carbobenzoxy chloride (Cbz-Cl), N-(Benzyloxycarbonyloxy)succinimide (Cbz-OSu or Cbz-O-NHS), dansyl chloride (DNS-Cl, or 1-dimethylaminonaphthalene-5-sulfonyl chloride), 4-sulfonyl-2-nitrofluorobenzene (SNFB), N-Acetyl-Isatoic Anhydride, Isatoic Anhydride, 2-Pyridinecarboxaldehyde, 2-Formylphenylboronic acid, 2-Acetylphenylboronic acid, 1-Fluoro-2,4-dinitrobenzene, Succinic anhydride, 4-Chloro-7-nitrobenzofurazan, Pentafluorophenylisothiocyanate, 4-(Trifluoromethoxy)-phenylisothiocyanate, 4-(Trifluoromethyl)-phenylisothiocyanate, 3-(Carboxylic acid)-phenylisothiocyanate, 3-(Trifluoromethyl)-phenylisothiocyanate, 1-Naphthylisothiocyanate, N-nitroimidazole-1-carboximidamide, N,N,Äs-Bis(pivaloyl)-1H-pyrazole-1-carboxamidine, N,N,Äs-Bis(benzyloxycarbonyl)-1H-pyrazole-1-carboxamidine, an acetylating reagent, a guanidinylation reagent, a thioacylation reagent, a thioacetylation reagent, or a thiobenzylation reagent, or a diheterocyclic methanimine reagent. In some examples, the binding agent binds an amino acid labeled by contacting with a reagent or using a method as described in International Patent Publication No. WO 2019/089846. In some cases, the binding agent binds an amino acid labeled by an amine modifying reagent.

A binding agent may bind to an N-terminal peptide, a C-terminal peptide, or an intervening peptide of a peptide, polypeptide, or protein molecule. A binding agent may bind to an N-terminal amino acid, C-terminal amino acid, or an intervening amino acid of a peptide molecule. A binding agent may bind to an N-terminal or C-terminal diamino acid moiety. An N-terminal diamino acid is comprised of the N-terminal amino acid and the penultimate N-terminal amino acid. A C-terminal diamino acid is similarly defined for the C-terminus. In some embodiments, the binding agent binds to a chemically modified N-terminal amino acid residue or a chemically modified C-terminal amino acid residue. To increase the affinity of a binding agent to small N-terminal amino acids (NTAAs) of peptides, the NTAA may be modified with an "immunogenic" hapten, such as dinitrophenol (DNP). This can be implemented in a cyclic sequencing approach using Sanger's reagent, dinitrofluorobenzene (DNFB), which attaches a DNP group to the amine group of the NTAA. Commercial anti-DNP antibodies have affinities in the low nM range (~8 nM, LO-DNP-2) (Bilgicer et al., J Am Chem Soc (2009) 131(26): 9361-9367); as such it stands to reason that it should be possible to engineer high-affinity NTAA binding agents to a number of NTAAs modified with DNP (via DNFB) and simultaneously achieve good binding selectivity for a particular NTAA. In another example, an NTAA may be modified with sulfonyl nitrophenol (SNP) using 4-sulfonyl-2-nitrofluorobenzene (SNFB). Similar affinity enhancements may also be achieved with alternative NTAA modifiers, such as an acetyl group or an amidinyl (guanidinyl) group.

In certain embodiments, a binding agent can be an aptamer (e.g., peptide aptamer, DNA aptamer, or RNA aptamer), a peptoid, an antibody or a specific binding fragment thereof, an amino acid binding protein or enzyme, an antibody binding fragment, an antibody mimetic, a peptide, a peptidomimetic, a protein, or a polynucleotide (e.g., DNA, RNA, peptide nucleic acid (PNA), a gPNA, bridged nucleic acid (BNA), xeno nucleic acid (XNA), glycerol nucleic acid (GNA), or threose nucleic acid (TNA), or a variant thereof).

As used herein, the terms antibody and antibodies are used in a broad sense, to include not only intact antibody molecules, for example but not limited to immunoglobulin A, immunoglobulin G, immunoglobulin D, immunoglobulin E, and immunoglobulin M, but also any immunoreactive component(s) of an antibody molecule or portion thereof that immuno-specifically bind to at least one epitope. An antibody may be naturally occurring, synthetically produced, or recombinantly expressed. An antibody may be a fusion protein. An antibody may be an antibody mimetic. Examples of antibodies include but are not limited to, Fab fragments, Fab' fragments, F(ab'), fragments, single chain antibody fragments (scFv), miniantibodies, nanobodies, diabodies, crosslinked antibody fragments, Affibody™, nanobodies, single domain antibodies, DVD-Ig molecules, alphabodies, affimers, affitins, cyclotides, molecules, and the like. Immunoreactive products derived using antibody engineering or protein engineering techniques are also expressly within the meaning of the term antibodies. Detailed descriptions of antibody and/or protein engineering, including relevant protocols, can be found in, among other places, J. Maynard and G. Georgiou, 2000, Ann. Rev. Biomed. Eng. 2:339-76; Antibody Engineering, R. Kontermann and S. Dubel, eds., Springer Lab Manual, Springer Verlag (2001); U.S. Pat. No. 5,831,012; and S. Paul, Antibody Engineering Protocols, Humana Press (1995).

As with antibodies, nucleic acid and peptide aptamers that specifically recognize a macromolecule, e.g., a peptide or a polypeptide, can be produced using known methods. Aptamers bind target molecules in a highly specific, conformation-dependent manner, typically with very high affinity, although aptamers with lower binding affinity can be selected if desired. Aptamers have been shown to distinguish between targets based on very small structural differences such as the presence or absence of a methyl or hydroxyl group and certain aptamers can distinguish between D- and L-enantiomers. Aptamers have been obtained that bind small molecular targets, including drugs, metal ions, and organic dyes, peptides, biotin, and proteins, including but not limited to streptavidin, VEGF, and viral proteins. Aptamers have been shown to retain functional activity after biotinylation, fluorescein labeling, and when attached to glass surfaces and microspheres. (see, e.g., Jayasena, 1999, Clin Chem 45:1628-50; Kusser2000, J. Biotechnol. 74: 27-39; Colas, 2000, Curr Opin Chem Biol 4:54-9). Aptamers which specifically bind arginine and AMP have been described as well (see, Patel and Suri, 2000, J. Biotech. 74:39-60). Oligonucleotide aptamers that bind to a specific amino acid have been disclosed in Gold et al. (1995, Ann. Rev. Biochem. 64:763-97). RNA aptamers that bind amino acids have also been described (Ames and Breaker, 2011, RNA Biol. 8; 82-89; Mannironi et al., 2000, RNA 6:520-27; Famulok, 1994, J. Am. Chem. Soc. 116:1698-1706).

A binding agent can be made by modifying naturally-occurring or synthetically-produced proteins by genetic engineering to introduce one or more mutations in the amino acid sequence to produce engineered proteins that bind to a specific component or feature of a polypeptide (e.g., NTAA, CTAA, or post-translationally modified amino acid or a peptide). For example, exopeptidases (e.g., aminopeptidases, carboxypeptidases, dipeptidyl peptidase, dipeptidyl aminopeptidase), exoproteases, mutated exoproteases, mutated anticalins, mutated ClpSs, antibodies, or tRNA synthetases can be modified to create a binding agent that selectively binds to a particular NTAA. In another example, carboxypeptidases can be modified to create a binding agent that selectively binds to a particular CTAA. A binding agent can also be designed or modified, and utilized, to specifically bind a modified NTAA or modified CTAA, for example one that has a post-translational modification (e.g., phosphorylated NTAA or phosphorylated CTAA) or one that has been modified with a label (e.g., PTC, 1-fluoro-2,4-dinitrobenzene (using Sanger's reagent, DNFB), dansyl chloride (using DNS-Cl, or 1-dimethylaminonaphthalene-5-sulfonyl chloride), or using a thioacylation reagent, a thioacetylation reagent, an acetylation reagent, an amidination (guanidinylation) reagent, or a thiobenzylation reagent). Strategies for directed evolution of proteins are known in the art (e.g., Yuan et al., 2005, Microbiol. Mol. Biol. Rev. 69:373-392), and include phage display, ribosomal display, mRNA display, CIS display, CAD display, emulsions, cell surface display method, yeast surface display, bacterial surface display, etc.

In some embodiments, a binding agent that selectively binds to a labeled or functionalized NTAA can be utilized. For example, the NTAA may be reacted with phenylisothiocyanate (PITC) to form a phenylthiocarbamoyl-NTAA derivative. In this manner, the binding agent may be fashioned to selectively bind both the phenyl group of the phenylthiocarbamoyl moiety as well as the alpha-carbon R group of the NTAA. Use of PITC in this manner allows for subsequent elimination of the NTAA by Edman degradation as discussed below. In another embodiment, the NTAA may be reacted with Sanger's reagent (DNFB), to generate a DNP-labeled NTAA. Optionally, DNFB is used with an ionic liquid such as 1-ethyl-3-methylimidazolium bis[(trifluoromethyl)sulfonyl]imide ([emim][Tf2N]), in which DNFB is highly soluble. In this manner, the binding agent may be engineered to selectively bind the combination of the DNP and the R group on the NTAA. The addition of the DNP moiety provides a larger "handle" for the interaction of the binding agent with the NTAA, and should lead to a higher affinity interaction.

In yet another embodiment, a binding agent may be a modified aminopeptidase. In some embodiments, the binding agent may be a modified aminopeptidase that has been engineered to recognize the DNP-labeled NTAA providing cyclic control of aminopeptidase degradation of the peptide. Once the DNP-labeled NTAA is eliminated, another cycle of DNFB derivatization is performed in order to bind and eliminate the newly exposed NTAA. In preferred particular embodiment, the aminopeptidase is a monomeric metalloprotease, such an aminopeptidase activated by zinc (Calcagno et al., Appl Microbiol Biotechnol. (2016) 100(16): 7091-7102). In another example, a binding agent may selectively bind to an NTAA that is modified with sulfonyl nitrophenol (SNP), e.g., by using 4-sulfonyl-2-nitrofluorobenzene (SNFB). Other reagents that may be used to functionalize the NTAA include trifluoroethyl isothiocyanate, allyl isothiocyanate, and dimethylaminoazobenzene isothiocyanate, or a reagent as described in International Patent Publication No. WO 2019/089846.

In some embodiments, the binding agent binds to an unmodified or native amino acid. In some examples, the binding agent binds to an unmodified or native dipeptide (sequence of two amino acids), tripeptide (sequence of three amino acids), or higher order peptide of a peptide molecule. A binding agent may be engineered for high affinity for a modified NTAA, high specificity for a modified NTAA, or both. In some embodiments, binding agents can be developed through directed evolution of promising affinity scaffolds using phage display.

In another example, highly-selective engineered ClpSs have also been described in the literature. Emili et al. describe the directed evolution of an E. coli. ClpS protein via phage display, resulting in four different variants with the ability to selectively bind NTAAs for aspartic acid, arginine, tryptophan, and leucine residues (U.S. Pat. No. 9,566,335, incorporated by reference in its entirety). In one embodiment, the binding moiety of the binding agent comprises a member of the evolutionarily conserved ClpS family of adaptor proteins involved in natural N-terminal protein recognition and binding or a variant thereof (See e.g., Schuenemann et al., (2009) EMBO Reports 10(5); Roman-Hernandez et al., (2009) PNAS 106(22):8888-93; Guo et al., (2002) JBC 277(48): 46753-62; Wang et al., (2008) Molecular Cell 32: 406-414). In some embodiments, the amino acid residues corresponding to the ClpS hydrophobic binding pocket identified in Schuenemann et al. are modified in order to generate a binding moiety with the desired selectivity.

In one embodiment, the binding moiety comprises a member of the UBR box recognition sequence family, or a variant of the UBR box recognition sequence family. UBR recognition boxes are described in Tasaki et al., (2009), JBC 284(3): 1884-95. For example, the binding moiety may comprise UBR1, UBR2, or a mutant, variant, or homologue thereof.

In certain embodiments, the binding agent further comprises one or more detectable labels such as fluorescent labels, in addition to the binding moiety. In some embodiments, the binding agent does not comprise a polynucleotide such as a coding tag. Optionally, the binding agent comprises a synthetic or natural antibody. In some embodiments, the binding agent comprises an aptamer. In one embodiment, the binding agent comprises a polypeptide, such as a modified member of the ClpS family of adaptor proteins, such as a variant of an E. coli ClpS binding polypeptide, and a detectable label. In one embodiment, the detectable label is optically detectable. In some embodiments, the detectable label comprises a fluorescently moiety, a color-coded nanoparticle, a quantum dot or any combination thereof. In one embodiment the label comprises a polystyrene dye encompassing a core dye molecule such as a FluoSphere™, Nile Red, fluorescein, rhodamine, derivatized rhodamine dyes, such as TAMRA, phosphor, polymethadine dye, fluorescent phosphoramidite, TEXAS RED, green fluorescent protein, acridine, cyanine, cyanine 5 dye, cyanine 3 dye, 5-(2'-aminoethyl)-aminonaphthalene-1-sulfonic acid (EDANS), BODIPY, 120 ALEXA or a derivative or modification of any of the foregoing. In one embodiment, the detectable label is resistant to photobleaching while producing lots of signal (such as photons) at a unique and easily detectable wavelength, with high signal-to-noise ratio.

In some embodiments, the binding agents are fluorescently labeled with a fluorophore such that when a binding agent binds to a macromolecule, fluorescence emitted by the fluorophore can be detected by an appropriate detector. When binding agents are polypeptide molecules, the fluorophores can be coupled to free amine groups (e.g., lysine side chains) of the binding agents. When binding agents are nucleic acid aptamers, the fluorophores can be coupled to nucleotides by methods known in the art such that the fluorophores would not disrupt 3D structure of an aptamer.

Fluorescence can suitably be detected by detectors known in the art. For example, single molecule detection of bound fluorescently labeled binding agent can be done by total internal reflection fluorescence (TIRF) microscopy, as shown in U.S. Pat. No. 9,435,810 B2, incorporated herein. Based on the fluorescence detected from a specific binding agent, information about the macromolecule can be collected and/or recorded, and, sometimes, a portion of the macromolecule can be identified (for example, the N-terminal amino acid of the polypeptide). In some embodiments, where the contacting step comprises contacting a macromolecule with more than one binding agents (a mixture of two or more binding agents) capable of binding to the macromolecule, each of the binding agents is suitably labeled with different fluorophores having different fluorescence emission spectra.

In a particular embodiment, anticalins are engineered for both high affinity and high specificity to labeled NTAAs (e.g. PTC, modified-PTC, Cbz, DNP, SNP, acetyl, guanidinyl, amino guanidinyl, heterocyclic methanimine, etc.). Certain varieties of anticalin scaffolds have suitable shape for binding single amino acids, by virtue of their beta barrel structure. An N-terminal amino acid (either with or without modification) can potentially fit and be recognized in this "beta barrel" bucket. High affinity anticalins with engineered novel binding activities have been described (reviewed by Skerra, 2008, FEBS J. 275: 2677-2683). For example, anticalins with high affinity binding (low nM) to fluorescein and digoxygenin have been engineered (Gebauer et al., 2012, Methods Enzymol 503: 157-188). Engineering of alternative scaffolds for new binding functions has also been reviewed by Banta et al. (2013, Annu. Rev. Biomed. Eng. 15:93-113).

The functional affinity (avidity) of a given monovalent binding agent may be increased by at least an order of magnitude by using a bivalent or higher order multimer of the monovalent binding agent (Vauquelin et al., 2013, Br J Pharmacol 168(8): 1771-1785. 2013). Avidity refers to the accumulated strength of multiple, simultaneous, non-covalent binding interactions. An individual binding interaction may be easily dissociated. However, when multiple binding interactions are present at the same time, transient dissociation of a single binding interaction does not allow the binding protein to diffuse away and the binding interaction is likely to be restored. An alternative method for increasing avidity of a binding agent is to include complementary sequences in the coding tag attached to the binding agent and the recording tag associated with the polypeptide.

In some embodiments, the binding agent is linked, directly or indirectly, to a multimerization domain. Thus, monomeric, dimeric, and higher order (e.g., 3, 4, 5, or more) multimeric polypeptides comprising one or more binding agents are provided herein. In some specific embodiments, the binding agent is dimeric. In some examples, two polypeptides of the invention can be covalently or non-covalently attached to each other to form a dimer.

In some embodiments, the binding agent is derived from a biological, naturally occurring, non-naturally occurring, or synthetic source. In some examples, the binding agent is derived from de novo protein design (Huang et al., (2016) 537(7620):320-327). In some examples, the binding agent has a structure, sequence, and/or activity designed from first principles.

In some embodiments, a binding agent can be utilized that selectively binds a modified C-terminal amino acid (CTAA). Carboxypeptidases are proteases that cleave/eliminate terminal amino acids containing a free carboxyl group. A number of carboxypeptidases exhibit amino acid preferences, e.g., carboxypeptidase B preferentially cleaves at basic amino acids, such as arginine and lysine. A carboxypeptidase can be modified to create a binding agent that selectively binds to particular amino acid. In some embodiments, the carboxypeptidase may be engineered to selectively bind both the modification moiety as well as the alpha-carbon R group of the CTAA. Thus, engineered carboxypeptidases may specifically recognize 20 different CTAAs representing the standard amino acids in the context of a C-terminal label. Control of the stepwise degradation from the C-terminus of the peptide is achieved by using engineered carboxypeptidases that are only active (e.g., binding activity or catalytic activity) in the presence of the label. In one example, the CTAA may be modified by a para-Nitroanilide or 7-amino-4-methylcoumarinyl group.

Other potential scaffolds that can be engineered to generate binding agents for use in the methods described herein include: an anticalin, a lipocalin, an amino acid tRNA synthetase (aaRS), ClpS, an Affilin®, an Adnectin™, a T cell receptor, a zinc finger protein, a thioredoxin, GST A1-1, DARPin, an affimer, an affitin, an alphabody, an avimer, a monobody, an antibody, a single domain antibody, a nanobody, EETI-II, HPSTI, intrabody, PHD-finger, V(NAR) LDTI, evibody, Ig(NAR), knottin, maxibody, microbody, neocarzinostatin, pVIII, tendamistat, VLR, protein A scaffold, MTI-II, ecotin, GCN4, Im9, kunitz domain, PBP, trans-body, tetranectin, WW domain, CBM4-2, DX-88, GFP, iMab, Ldl receptor domain A, Min-23, PDZ-domain, avian pancreatic polypeptide, charybdotoxin/10Fn3, domain antibody (Dab), a2p8 ankyrin repeat, insect defensing A peptide, Designed AR protein, C-type lectin domain, staphylococcal nuclease, Src homology domain 3 (SH3), or Src homology domain 2 (SH2). See e.g., El-Gebali et al., (2019) Nucleic Acids Research 47:D427-D432 and Finn et al., (2013) Nucleic Acids Res. 42 (Database issue):D222-D230. In some embodiments, a binding agent is derived from an enzyme which binds one or more amino acids (e.g., an aminopeptidase). In certain embodiments, a binding agent can be derived from an anticalin or a Clp protease adaptor protein (ClpS).

A binding agent may preferably bind to a modified or labeled amino acid, by chemical or enzymatic means, (e.g., an amino acid that has been functionalized by a reagent (e.g., a compound)) over a non-modified or unlabeled amino acid. For example, a binding agent may preferably bind to an amino acid that has been functionalized with an acetyl moiety, Cbz moiety, guanyl moiety, dansyl moiety, PTC moiety, DNP moiety, SNP moiety, diheterocyclic methanimine moiety, etc., over an amino acid that does not possess said moiety. In some embodiments, a binding agent may preferably bind to an amino acid that has been functionalized or modified as described in International Patent Publication No. WO 2019/089846. In some cases, a binding agent may bind to a post-translationally modified amino acid. Thus, in certain embodiments, an extended nucleic acid comprises coding tag information relating to amino acid sequence and post-translational modifications of the polypeptide. In one example, a peptide is contacted with binding agents for PTM modifications, and associated coding tag information are transferred to the recording tag associated with the immobilized peptide. Once the detection and transfer of coding tag information relating to amino acid modifications is complete, the PTM modifying groups can be removed before detection and transfer of coding tag information for the primary amino acid sequence using N-terminal or C-terminal degradation methods.

In some embodiments, the N-terminal amino acid (or labeled N-terminal amino acid, e.g., PITC-NTAA, Cbz-NTAA, DNP-NTAA, SNP-NTAA, acetyl-NTAA, guanidinylated-NTAA, heterocyclic methanimine-NTAA) of each immobilized peptide is bound by a cognate NTAA binding agent which is attached to a coding tag.

In some embodiments, detection of internal post-translationally modified amino acids (e.g., phosphorylation, glycosylation, succinylation, ubiquitination, S-Nitrosylation, methylation, N-acetylation, lipidation, etc.) is be accomplished prior to detection and elimination of terminal amino acids (e.g., NTAA or CTAA). In one example, a peptide is contacted with binding agents for PTM modifications, and information from a corresponding secondary tag is transferred to the recording tag associated with the immobilized peptide. Once the detection and transfer of information relating to amino acid modifications is complete, the PTM modifying groups can be removed before detection and transfer of secondary tag information for the primary amino acid sequence using N-terminal or C-terminal degradation methods. Thus, resulting extended nucleic acids indicate the presence of post-translational modifications in a peptide sequence, though not the sequential order, along with primary amino acid sequence information.

In some embodiments, detection of internal post-translationally modified amino acids may occur concurrently with detection of primary amino acid sequence. In one example, an NTAA (or CTAA) is contacted with a binding agent specific for a post-translationally modified amino acid, either alone or as part of a library of binding agents (e.g., library composed of binding agents for the 20 standard amino acids and selected post-translational modified amino acids). Successive cycles of terminal amino acid elimination and contact with a binding agent (or library of binding agents) follow. Thus, resulting extended nucleic acids on the recording tag associated with the immobilized peptide indicate the presence and order of post-translational modifications in the context of a primary amino acid sequence.

In certain embodiments, a macromolecule, e.g., a polypeptide, is also contacted with a non-cognate binding agent. As used herein, a non-cognate binding agent is referring to a binding agent that is selective for a different target (e.g. polypeptide feature or component) than the particular target being considered. For example, if the n NTAA is phenylalanine, and the peptide is contacted with three binding agents selective for phenylalanine, tyrosine, and asparagine, respectively, the binding agent selective for phenylalanine would be first binding agent capable of selectively binding to the $n^{th}$ NTAA (i.e., phenylalanine), while the other two binding agents would be non-cognate binding agents for that peptide (since they are selective for NTAAs other than phenylalanine). The tyrosine and asparagine binding agents may, however, be cognate binding agents for other peptides in the sample. If the n NTAA (phenylalanine) was then cleaved from the peptide, thereby converting the n−1 amino acid of the peptide to the n−1 NTAA (e.g., tyrosine), and the peptide was then contacted with the same three binding agents, the binding agent selective for tyrosine would be second binding agent capable of selectively binding to the n−1 NTAA (i.e., tyrosine), while the other two binding agents would be non-cognate binding agents (since they are selective for NTAAs other than tyrosine).

Thus, it should be understood that whether an agent is a binding agent or a non-cognate binding agent will depend on the nature of the particular polypeptide feature or component currently available for binding. Also, if multiple polypeptides are analyzed in a multiplexed reaction, a binding agent for one polypeptide may be a non-cognate binding agent for another, and vice versa. According, it should be understood that the following description concerning binding agents is applicable to any type of binding agent described herein (i.e., both cognate and non-cognate binding agents).

In certain embodiments, the concentration of the binding agents in a solution is controlled to reduce background and/or false positive results of the assay.

In some embodiments, the concentration of a binding agent can be at any suitable concentration, e.g., at about 0.0001 nM, about 0.001 nM, about 0.01 nM, about 0.1 nM, about 1 nM, about 2 nM, about 5 nM, about 10 nM, about 20 nM, about 50 nM, about 100 nM, about 200 nM, about 500 nM, or about 1,000 nM. In other embodiments, the concentration of a soluble conjugate used in the assay is between about 0.0001 nM and about 0.001 nM, between about 0.001 nM and about 0.01 nM, between about 0.01 nM and about 0.1 nM, between about 0.1 nM and about 1 nM, between about 1 nM and about 2 nM, between about 2 nM and about 5 nM, between about 5 nM and about 10 nM, between about 10 nM and about 20 nM, between about 20 nM and about 50 nM, between about 50 nM and about 100 nM, between about 100 nM and about 200 nM, between about 200 nM and about 500 nM, between about 500 nM and about 1000 nM, or more than about 1,000 nM.

In some embodiments, the ratio between the soluble binding agent molecules and the immobilized macromolecule, e.g., polypeptides, can be at any suitable range, e.g., at about 0.00001:1, about 0.0001:1, about 0.001:1, about 0.01:1, about 0.1:1, about 1:1, about 2:1, about 5:1, about 10:1, about 15:1, about 20:1, about 25:1, about 30:1, about 35:1, about 40:1, about 45:1, about 50:1, about 55:1, about 60:1, about 65:1, about 70:1, about 75:1, about 80:1, about 85:1, about 90:1, about 95:1, about 100:1, about $10^4$:1, about $10^5$:1, about $10^6$:1, or higher, or any ratio in between the above listed ratios. Higher ratios between the soluble binding agent molecules and the immobilized polypeptide(s) and/or the nucleic acids can be used to drive the binding and/or the secondary tag information transfer to completion. This may be particularly useful for detecting and/or analyzing low abundance polypeptides in a sample.

E. Coding Tag

The coding tag associated with the binding agent is or comprises a polynucleotide with any suitable length, e.g., a nucleic acid molecule of about 2 bases to about 100 bases, including any integer including 2 and 100 and in between, that comprises identifying information for its associated binding agent. A coding tag comprises a sequence for hybridizing to a first hybridization sequence of an adaptor molecule. A "coding tag" may also be made from a "sequenceable polymer" (see, e.g., Niu et al., 2013, Nat. Chem. 5:282-292; Roy et al., 2015, Nat. Commun. 6:7237; Lutz, 2015, Macromolecules 48:4759-4767; each of which are incorporated by reference in its entirety). A coding tag may comprise an encoder sequence or a sequence with identifying information. The coding tag or portion thereof may comprise a sequence substantially complementary or complementary to a first hybridization sequence of an adaptor molecule, thus the coding tag can be associated with the secondary tag which contains identifying information regarding the binding agent. The first hybridization sequence on an adaptor molecule comprises a substantially complementary or complementary sequence configured to hybridize to the coding tag (or portion thereof) directly attached to a binding agent. In some aspects, the coding tag is used in the provided methods to hybridize to said first hybridization on the adaptor molecule and localize the appropriate adaptor molecule for information transfer.

A coding tag may be a single stranded molecule, a double stranded molecule, or a partially double stranded. A coding tag may comprise blunt ends, overhanging ends, or one of each. In some embodiments, a coding tag is partially double stranded. In some embodiments, the coding tag may comprise a hairpin. In certain embodiments, the hairpin comprises mutually complementary nucleic acid regions are connected through a nucleic acid strand. In some embodiments, the nucleic acid hairpin can also further comprise 3' and/or 5' single-stranded region(s) extending from the double-stranded stem segment. In some examples, the hairpin comprises a single strand of nucleic acid.

In some embodiments, a binding agent described comprises a coding tag containing identifying information regarding (e.g., representing or correlating to) the binding agent. In some embodiments, the identifying information from the secondary tag corresponds to the coding tag and comprises information regarding the identity of the target bound by the binding agent. In some embodiments, the identifying information from the coding tag comprises or is associated with information regarding the identity of the one or more amino acid(s) on the peptide bound by the binding agent.

A coding tag is a nucleic acid molecule of about 3 bases to about 100 bases that provides unique identifying information for its associated binding agent. A coding tag may comprise about 3 to about 90 bases, about 3 to about 80 bases, about 3 to about 70 bases, about 3 to about 60 bases, about 3 bases to about 50 bases, about 3 bases to about 40 bases, about 3 bases to about 30 bases, about 3 bases to about 20 bases, about 3 bases to about 10 bases, or about 3 bases to about 8 bases. In some embodiments, a coding tag is about 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 25 bases, 30 bases, 35 bases, 40 bases, 55 bases, 60 bases, 65 bases, 70 bases, 75 bases, 80 bases, 85 bases, 90 bases, 95 bases, or 100 bases in length. A coding tag may be composed of DNA, RNA, polynucleotide analogs, or a combination thereof. Polynucleotide analogs include PNA, gPNA, BNA, GNA, TNA, LNA, morpholino polynucleotides, 2'-O-Methyl polynucleotides, alkyl ribosyl substituted polynucleotides, phosphorothioate polynucleotides, and 7-deaza purine analogs.

A coding tag can be joined to a binding agent directly or indirectly, by any means known in the art, including covalent and non-covalent interactions. In some embodiments, a coding tag may be joined to binding agent enzymatically or chemically. In some embodiments, a coding tag may be joined to a binding agent via ligation. In other embodiments, a coding tag is joined to a binding agent via affinity binding pairs (e.g., biotin and streptavidin). In some cases, a coding tag may be joined to a binding agent to an unnatural amino acid, such as via a covalent interaction with an unnatural amino acid.

In some embodiments, a binding agent is joined to a coding tag via SpyCatcher-SpyTag interaction. The SpyTag peptide forms an irreversible covalent bond to the SpyCatcher protein via a spontaneous isopeptide linkage, thereby offering a genetically encoded way to create peptide interactions that resist force and harsh conditions (Zakeri et al., 2012, Proc. Natl. Acad. Sci. 109:E690-697; Li et al., 2014, J. Mol. Biol. 426:309-317). A binding agent may be expressed as a fusion protein comprising the SpyCatcher protein. In some embodiments, the SpyCatcher protein is appended on the N-terminus or C-terminus of the binding agent. The SpyTag peptide can be coupled to the coding tag using standard conjugation chemistries (Hermanson, Bioconjugate Techniques, (2013) Academic Press).

In some embodiments, an enzyme-based strategy is used to join the binding agent to a coding tag. For example, the binding agent may be joined to a coding tag using a formylglycine (FGly)-generating enzyme (FGE). In one example, a protein, e.g., SpyLigase, is used to join the binding agent to the coding tag (Fierer et al., Proc Natl Acad Sci USA. 2014; 111(13): E1176-E1181).

In other embodiments, a binding agent is joined to a coding tag via SnoopTag-SnoopCatcher peptide-protein interaction. The SnoopTag peptide forms an isopeptide bond with the SnoopCatcher protein (Veggiani et al., Proc. Natl. Acad. Sci. USA, 2016, 113:1202-1207). A binding agent may be expressed as a fusion protein comprising the SnoopCatcher protein. In some embodiments, the SnoopCatcher protein is appended on the N-terminus or C-terminus of the binding agent. The SnoopTag peptide can be coupled to the coding tag using standard conjugation chemistries.

In yet other embodiments, a binding agent is joined to a coding tag via the HaloTag® protein fusion tag and its chemical ligand. HaloTag is a modified haloalkane dehalogenase designed to covalently bind to synthetic ligands (HaloTag ligands) (Los et al., 2008, ACS Chem. Biol. 3:373-382). The synthetic ligands comprise a chloroalkane linker attached to a variety of useful molecules. A covalent bond forms between the HaloTag and the chloroalkane linker that is highly specific, occurs rapidly under physiological conditions, and is essentially irreversible.

In some cases, a binding agent is joined to a coding tag by attaching (conjugating) using an enzyme, such as sortase-mediated labeling (See e.g., Antos et al., Curr Protoc Protein Sci. (2009) CHAPTER 15: Unit-15.3; International Patent Publication No. WO2013003555). The sortase enzyme catalyzes a transpeptidation reaction (See e.g., Falck et al, Antibodies (2018) 7(4):1-19). In some aspects, the binding agent is modified with or attached to one or more N-terminal or C-terminal glycine residues.

In some embodiments, a binding agent is joined to a coding tag using a cysteine bioconjugation method. In some embodiments, a binding agent is joined to a coding tag using π-clamp-mediated cysteine bioconjugation (See e.g., Zhang et al., Nat Chem. (2016) 8(2):120-128). In some cases, a binding agent is joined to a coding tag using 3-arylpropiolonitriles (APN)-mediated tagging (e.g. Koniev et al., Bioconjug Chem. 2014; 25(2):202-206).

II. MACROMOLECULE ANALYSIS ASSAY

The provided methods for analysis of macromolecules, e.g., peptides, polypeptides, and proteins, which includes a step of transferring information to a recording tag may include additional steps, treatments, and reactions. In some embodiments, the macromolecule analysis assay is a next generation protein assay (NGPA) using multiple binding agents and enzymatically-mediated sequential information transfer. In some cases, the analysis assay is performed on immobilized target molecules bound a cognate binding agent (e.g., antibody) and forming a stable complex, then hybridizing an adaptor molecule comprising a sequence that is complementary to the coding tag and a secondary tag, and transferring information from the secondary tags of bound antibodies to the recording tag associated with the macromolecule. In some cases, the analysis assay is performed on immobilized macromolecules bound by two or more cognate binding agents (e.g., antibodies). After a cognate antibody binding event, an adaptor molecule hybridizes, and a combined primer extension and DNA nicking step is used to transfer information from the secondary tags of the adaptor molecules to the recording tag. In some cases, polyclonal antibodies (or mixed population of monoclonal antibody) to multivalent epitopes on a protein can be used for the assay. See e.g., International Patent Publication No. WO 2017/192633.

In some embodiments, the macromolecule is a polypeptide and a polypeptide analysis assay is performed. In some embodiments, the sequence (or a portion of the sequence thereof) and/or the identity of a target protein is determined using a polypeptide analysis assay. In some examples, the polypeptide analysis assay includes assessing at least a partial sequence or identity of the polypeptide using suitable techniques or procedures. For example, at least a partial sequence of the polypeptide can be assessed by N-terminal amino acid analysis or C-terminal amino acid analysis. In some embodiments, at least a partial sequence of the polypeptide can be assessed using a ProteoCode assay. In some examples, at least a partial sequence of the polypeptide can be assessed by the techniques or procedures disclosed and/or claimed in U.S. Provisional Patent Application Nos. 62/330,841, 62/339,071, 62/376,886, 62/579,844, 62/582,312, 62/583,448, 62/579,870, 62/579,840, and 62/582,916, and International Patent Publication Nos. WO 2017/192633, and WO/2019/089836, and WO 2019/089851.

In some embodiments, the polypeptide analysis assay includes performing an assay which utilizes the recording tag associated with the macromolecule, e.g., the polypeptide. The recording tag is used to record information gathered from one or more binding events between a binding agent and the macromolecule to be analyzed.

Provided herein is a method for analyzing a macromolecule comprising the steps of: (a) providing a macromolecule and an associated recording tag joined to a support; (b) contacting the macromolecule with a binding agent capable of binding to the macromolecule, wherein the binding agent comprises a coding tag with identifying information regarding the binding agent, to allow binding between the macromolecule and the binding agent; (c) providing an adaptor molecule comprising a first hybridization sequence substantially complementary or complementary to at least a portion of the coding tag, and a secondary tag, to allow hybridization between the adaptor molecule (or the first hybridization sequence) and the coding tag (or the portion of the coding tag); (d) transferring the information of the secondary tag to the recording tag to generate an extended recording tag; and analyzing the extended recording tag. In some cases, the binding agent is removed after step (d). In some embodiments, the method further includes adding a universal priming site to the extended recording tag, prior to analyzing the extended recording tag.

In some examples, step (a) is performed before steps (b), (c), and (d). In some embodiments, step (b) is performed before step (c) and step (d). In some cases, step (c) is performed before step (d). In some particular embodiments, the steps are performed in the order: (a), (b), (c), and (d), optionally repeating steps (b), (c), and (d) one or more times.

In some embodiments, the method is performed with one or more macromolecules and the method further includes step (e) removing the terminal amino acid (e.g., N-terminal amino acid (NTAA)) of the polypeptide, protein or peptide to expose a new terminal amino acid of the polypeptide, protein or peptide. In some cases, a cycle of steps (b), (c), (d) and (e) is repeated one or more times prior to analyzing the extended recording tag. In some particular embodiments, the steps are performed in the order: (a), (b), (c), (d) and (e), optionally repeating steps (b), (c), (d) and (e) one or more times.

In some embodiments, the method includes treating the target polypeptide, protein or peptide with a reagent for modifying a terminal amino acid of the polypeptide, protein or peptide. In some aspects, the reagent for modifying a terminal amino acid of a polypeptide comprises a chemical agent or an enzymatic agent. In some embodiments, the target polypeptide, protein or peptide is contacted with the reagent for modifying a terminal amino acid before step (b). In some embodiments, the target polypeptide, protein or peptide is contacted with the reagent for modifying a terminal amino acid before removing the terminal amino acid.

In some embodiments, the method further includes removing the binding agent after transferring information from the secondary tag to the recording tag. In some aspects, the binding agent is removed after step (d). In some aspects, the binding agent is removed before step (e). In some aspects, removing the binding agent is performed after transferring information from the secondary tag of the adaptor molecule to the recording tag associated with the target.

In some embodiments, the provided methods for analysis of macromolecules can be used in combination with a method for performing a binding reaction that forms a stable complex. In some aspects, the step of contacting the macromolecule with a binding agent capable of binding to the macromolecule further includes components and/or steps for stabilizing the complex. For example, the binding reaction comprises contacting a binding agent with a target macromolecule, wherein the binding agent and the target each comprises or is associated with a stabilizing component, allowing the binding agent to interact with the target, and allowing linking of the stabilizing components to form a stable complex. In some aspects, the stable complex may include the binding agent and associated coding tag, the adaptor molecule, the stabilizing component associated with the binding agent, the target and associated stabilizing component, and optionally a linking agent. In some embodiments, the stabilizing component associated with the binding agent is joined to the coding tag associated with the binding agent.

and/or an oligonucleotide. Once activated, the linking of the stabilizing components, either directly with each other or indirectly via a linker (e.g., a linking agent) or other components, allows formation of a stable complex with the binding agent and target. In some embodiments, a stabilizing component is joined or attached (directly or indirectly via a linker) to a nucleic acid molecule or oligonucleotide.

In some embodiments, the linking agent comprises an oligonucleotide comprising a sequence complementary to a nucleic acid joined to the binding agent (e.g., stabilizing component associated with the coding tag) and the adaptor molecule comprises a first hybridization region complementary to the coding tag. In this aspect, a stable complex is formed that includes a recording tag joined to the macromolecule target, the macromolecule target bound by the binding agent associated with a coding tag, the coding tag hybridized to both the adaptor molecule and the linking agent (hybridized to the stabilizing component), and the linking agent is also hybridized to the stabilizing component of the recording tag.

In some embodiments, information is transferred from the coding tag to the linking agent, and this information is subsequently transferred to the recording tag. In some aspects, information is transferred from an adaptor molecule by ligation, wherein the adaptor molecule is part of the linking agent joining the stabilizing component associated with the recording tag with the stabilizing component associated with the binding agent.

In a specific example, a linking agent comprises two DNA pieces joined by a linker (a first DNA for hybridizing to the stabilizing component associated with the recording tag and a second DNA comprising the adaptor molecule with a secondary tag for transferring information to the recording tag). In this example, the secondary tag of the adaptor molecule is ligated to the recording tag, USER enzyme can be used to cleave the U residue and remove the remaining portion of the linking agent from the extended recording tag. In some cases, this approach may be useful for reducing or removing the requirement for spacers in the information transfer step. In some embodiments, single stranded DNA ligation is used for information transfer.

In some embodiments, the macromolecule analysis assay comprises: providing a macromolecule and an associated recording tag joined to a support, wherein the macromolecule is also associated with a stabilizing component; contacting the macromolecule with a binding agent capable of binding to the macromolecule, wherein the binding agent comprises a coding tag with identifying information regarding the binding agent, wherein the binding agent is also associated with a stabilizing component; providing a linking agent and linking the stabilizing components to form a stable complex comprising the macromolecule, the binding agent and the stabilizing components; providing an adaptor molecule comprising a first hybridization sequence substantially complementary to at least a portion of the coding tag, and a secondary tag, to allow hybridization between the adaptor molecule (or the first hybridization sequence) and the coding tag (or the portion of the coding tag); and transferring the information of the secondary tag to the recording tag to generate an extended recording tag; and analyzing the extended recording tag. In some cases, information is transferred from the secondary tag of the adaptor molecule to the recording tag. In some cases, information is transferred from the adaptor molecule to the linking agent, then from the linking agent to the recording tag.

The methods disclosed herein can be used for analysis, including detection, identification, quantitation and/or sequencing, of a plurality of macromolecules simultaneously (multiplexing). Multiplexing as used herein refers to analysis of a plurality of macromolecules (e.g. polypeptides) in the same assay. The plurality of macromolecules can be derived from the same sample or different samples. The plurality of macromolecules can be derived from the same subject or different subjects. The plurality of macromolecules that are analyzed can be different macromolecules, or the same macromolecule derived from different samples. A plurality of macromolecules includes 2 or more macromolecules, 5 or more macromolecules, 10 or more macromolecules, 50 or more macromolecules, 100 or more macromolecules, 500 or more macromolecules, 1000 or more macromolecules, 5,000 or more macromolecules, 10,000 or more macromolecules, 50,000 or more macromolecules, 100,000 or more macromolecules, 500,000 or more macromolecules, or 1,000,000 or more macromolecules.

F. Target

The methods provided herein describe a binding reaction with a binding agent and a target. Prior to performing the binding reaction, a target may be obtained from a source and treated in various ways to prepare the target for the binding reaction, such as by joining to a stabilizing component. The binding reaction may be performed on a plurality of targets. In some embodiments, the target is immobilized on a support. In some embodiments, a target is a macromolecule or portion thereof. In some cases, the targets are molecules (e.g., macromolecules) obtained from a sample and are of unknown identity. In some cases, the targets are molecules (e.g., macromolecules) from a mixture of molecules obtained from a sample. A macromolecule can be a large molecule composed of smaller subunits. In certain embodiments, a macromolecule is a protein, a protein complex, polypeptide, peptide, nucleic acid molecule, carbohydrate, lipid, macrocycle, or a chimeric macromolecule. A macromolecule (e.g., protein, polypeptide, peptide) in the methods disclosed herein may be obtained from any suitable source or sample. In some embodiments, the target is or comprises macromolecules (e.g., proteins, polypeptides, or peptides) obtained from a sample that is a biological sample. In some embodiments, the sample comprises but is not limited to, mammalian or human cells, yeast cells, and/or bacterial cells. In some embodiments, the sample contains cells that are from a sample obtained from a multicellular organism. For example, the sample may be isolated from an individual. In some embodiments, the sample may comprise a single cell type or multiple cell types. In some embodiments, the sample may be obtained from a mammalian organism or a human, for example by puncture, or other collecting or sampling procedures. In some embodiments, the sample comprises two or more cells.

In some embodiments, the biological sample may contain whole cells and/or live cells and/or cell debris. In some examples, a suitable source or sample, may include but is not limited to: biological samples, such as biopsy samples, cell cultures, cells (both primary cells and cultured cell lines), sample comprising cell organelles or vesicles, tissues and tissue extracts; of virtually any organism. For example, a suitable source or sample, may include but is not limited to: biopsy; fecal matter; bodily fluids (such as blood, whole blood, serum, plasma, urine, lymph, bile, aqueous humor, breast milk, cerumen (earwax), chyle, chyme, endolymph, perilymph, exudates, cerebrospinal fluid, interstitial fluid, aqueous or vitreous humor, colostrum, sputum, amniotic fluid, saliva, anal and vaginal secretions, gastric acid, gastric juice, lymph, mucus (including nasal drainage and phlegm), pericardial fluid, peritoneal fluid, pleural fluid, pus, rheum, saliva, sebum (skin oil), sputum, synovial fluid, perspiration and semen, a transudate, vomit and mixtures of one or more thereof, an exudate (e.g., fluid obtained from an abscess or any other site of infection or inflammation) or fluid obtained from a joint (normal joint or a joint affected by disease such as rheumatoid arthritis, osteoarthritis, gout or septic arthritis) of virtually any organism, with mammalian-derived samples, including microbiome-containing samples, being preferred and human-derived samples, including microbiome-containing samples, being particularly preferred; environmental samples (such as air, agricultural, water and soil samples); microbial samples including samples derived from microbial biofilms and/or communities, as well as microbial spores; tissue samples including tissue sections, research samples including extracellular fluids, extracellular supernatants from cell cultures, inclusion bodies in bacteria, cellular components including mitochondria and cellular periplasm. In some embodiments, the biological sample comprises a body fluid or is derived from a body fluid, wherein the body fluid is obtained from a mammal or a human. In some embodiments, the sample includes bodily fluids, or cell cultures from bodily fluids.

In some embodiments, prior to performing the binding reaction, the macromolecules (e.g., polypeptides and proteins) may be obtained and prepared from a single cell type or multiple cell types. In some embodiments, the sample comprises a population of cells. In some embodiments, the macromolecules (e.g., proteins, polypeptides, or peptides) are from a cellular or subcellular component, an extracellular vesicle, an organelle, or an organized subcomponent thereof. The macromolecules (e.g., proteins, polypeptides, or peptides) may be from organelles, for example, mitochondria, nuclei, or cellular vesicles. In one embodiment, one or more specific types of single cells or subtypes thereof may be isolated. In some embodiments, the sample may include but are not limited to cellular organelles, (e.g., nucleus, golgi apparatus, ribosomes, mitochondria, endoplasmic reticulum, chloroplast, cell membrane, vesicles, etc.).

In certain embodiments, the target comprises a macromolecule that is a protein, a protein complex, a polypeptide, or peptide. Amino acid sequence information and post-translational modifications of a peptide, polypeptide, or protein are transduced into a nucleic acid encoded library that can be analyzed via next generation sequencing methods. A peptide may comprise L-amino acids, D-amino acids, or both. A peptide, polypeptide, protein, or protein complex may comprise a standard, naturally occurring amino acid, a modified amino acid (e.g., post-translational modification), an amino acid analog, an amino acid mimetic, or any combination thereof. In some embodiments, a peptide, polypeptide, or protein is naturally occurring, synthetically produced, or recombinantly expressed. In any of the aforementioned peptide embodiments, a peptide, polypeptide, protein, or protein complex may further comprise a post-translational modification. Non-standard amino acids include selenocysteine, pyrrolysine, and N-formylmethionine, β-amino acids, homo-amino acids, Proline and Pyruvic acid derivatives, 3-substituted Alanine derivatives, Glycine derivatives, ring-substituted Phenylalanine and Tyrosine Derivatives, linear core amino acids, and N-methyl amino acids.

A post-translational modification (PTM) of a peptide, polypeptide, or protein may be a covalent modification or enzymatic modification. Examples of post-translation modifications include, but are not limited to, acylation, acetylation, alkylation (including methylation), biotinylation, butyrylation, carbamylation, carbonylation, deamidation, deiminiation, diphthamide formation, disulfide bridge formation, eliminylation, flavin attachment, formylation, gamma-carboxylation, glutamylation, glycylation, glycosylation (e.g., N-linked, O-linked, C-linked, phosphoglycosylation), glypiation, heme C attachment, hydroxylation, hypusine formation, iodination, isoprenylation, lipidation, lipoylation, malonylation, methylation, myristolylation, oxidation, palmitoylation, pegylation, phosphopantetheinylation, phosphorylation, prenylation, propionylation, retinylidene Schiff base formation, S-glutathionylation, S-nitrosylation, S-sulfenylation, selenation, succinylation, sulfination, ubiquitination, and C-terminal amidation. A post-translational modification includes modifications of the amino terminus and/or the carboxyl terminus of a peptide, polypeptide, or protein. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl). A post-translational modification also includes modifications, such as but not limited to those described above, of amino acids falling between the amino and carboxy termini of a peptide, polypeptide, or protein. Post-translational modification can regulate a protein's "biology" within a cell, e.g., its activity, structure, stability, or localization. For example, phosphorylation plays an important role in regulation of protein, particularly in cell signaling (Prabakaran et al., 2012, Wiley Interdiscip Rev Syst Biol Med 4: 565-583). In another example, the addition of sugars to proteins, such as glycosylation, has been shown to promote protein folding, improve stability, and modify regulatory function and the attachment of lipids to proteins enables targeting to the cell membrane. A post-translational modification can also include peptide, polypeptide, or protein modifications to include one or more detectable labels.

In certain embodiments, a peptide, polypeptide, or protein can be fragmented. Peptides, polypeptides, or proteins can be fragmented by any means known in the art, including fragmentation by a protease or endopeptidase. In some embodiments, fragmentation of a peptide, polypeptide, or protein is targeted by use of a specific protease or endopeptidase. A specific protease or endopeptidase binds and cleaves at a specific consensus sequence (e.g., TEV protease). In other embodiments, fragmentation of a peptide, polypeptide, or protein is non-targeted or random by use of a non-specific protease or endopeptidase. A non-specific protease may bind and cleave at a specific amino acid residue rather than a consensus sequence (e.g., proteinase K is a non-specific serine protease). In some embodiments, proteinases and endopeptidases, such as those known in the art, can be used to cleave a protein or polypeptide into smaller peptide fragments include proteinase K, trypsin, chymotrypsin, pepsin, thermolysin, thrombin, Factor Xa, furin, endopeptidase, papain, pepsin, subtilisin, elastase, enterokinase, Genenase™ I, Endoproteinase LysC, Endoproteinase AspN, Endoproteinase GluC, etc. (Granvogl et al., 2007, Anal Bioanal Chem 389: 991-1002). In certain embodiments, a peptide, polypeptide, or protein is fragmented by proteinase K, or optionally, a thermolabile version of proteinase K to enable rapid inactivation. In some cases, Proteinase K is stable in denaturing reagents, such as urea and SDS, and enables digestion of completely denatured proteins. Protein and polypeptide fragmentation into peptides can be performed before or after attachment of a DNA tag or DNA recording tag.

Chemical reagents can also be used to digest proteins into peptide fragments. A chemical reagent may cleave at a specific amino acid residue (e.g., cyanogen bromide hydrolyzes peptide bonds at the C-terminus of methionine residues). Chemical reagents for fragmenting polypeptides or proteins into smaller peptides include cyanogen bromide (CNBr), hydroxylamine, hydrazine, formic acid, BNPS-skatole [2-(2-nitrophenylsulfenyl)-3-methylindole], iodosobenzoic acid, .NTCB+Ni (2-nitro-5-thiocyanobenzoic acid), etc.

In certain embodiments, following enzymatic or chemical cleavage, the resulting peptide fragments are approximately the same desired length, e.g., from about 10 amino acids to about 70 amino acids, from about 10 amino acids to about 60 amino acids, from about 10 amino acids to about 50 amino acids, about 10 to about 40 amino acids, from about 10 to about 30 amino acids, from about 20 amino acids to about 70 amino acids, from about 20 amino acids to about 60 amino acids, from about 20 amino acids to about 50 amino acids, about 20 to about 40 amino acids, from about 20 to about 30 amino acids, from about 30 amino acids to about 70 amino acids, from about 30 amino acids to about 60 amino acids, from about 30 amino acids to about 50 amino acids, or from about 30 amino acids to about 40 amino acids. A cleavage reaction may be monitored, preferably in real time, by spiking the protein or polypeptide sample with a short test FRET (fluorescence resonance energy transfer) peptide comprising a peptide sequence containing a proteinase or endopeptidase cleavage site. In the intact FRET peptide, a fluorescent group and a quencher group are attached to either end of the peptide sequence containing the cleavage site, and fluorescence resonance energy transfer between the quencher and the fluorophore leads to low fluorescence. Upon cleavage of the test peptide by a protease or endopeptidase, the quencher and fluorophore are separated giving a large increase in fluorescence. A cleavage reaction can be stopped when a certain fluorescence intensity is achieved, allowing a reproducible cleavage endpoint to be achieved.

In some aspects, a target is or comprises a sample of macromolecules (e.g., peptides, polypeptides, or proteins) which can undergo protein fractionation methods where proteins or peptides are separated by one or more properties such as cellular location, molecular weight, hydrophobicity, isoelectric point, or protein enrichment methods. In some embodiments, a subset of macromolecules (e.g., proteins) within a sample is fractionated such that a subset of the macromolecules is sorted from the rest of the sample. For example, the sample may undergo fractionation methods prior to attachment to a support. Alternatively, or additionally, protein enrichment methods may be used to select for a specific protein or peptide (see, e.g., Whiteaker et al., 2007, Anal. Biochem. 362:44-54, incorporated by reference in its entirety) or to select for a particular post translational modification (see, e.g., Huang et al., 2014. J. Chromatogr. A 1372:1-17, incorporated by reference in its entirety). Alternatively, a particular class or classes of proteins such as immunoglobulins, or immunoglobulin (Ig) isotypes such as IgG, can be affinity enriched or selected for analysis. In the case of immunoglobulin molecules, analysis of the sequence and abundance or frequency of hypervariable sequences involved in affinity binding are of particular interest, particularly as they vary in response to disease progression or correlate with healthy, immune, and/or or disease phenotypes. Overly abundant proteins can also be subtracted from the sample using standard immunoaffinity methods. Depletion of abundant proteins can be useful for plasma samples where over 80% of the protein constituent is albumin and immunoglobulins. Several commercial products are available for depletion of plasma samples of overly abundant proteins, including depletion spin columns that remove top 2-20 plasma proteins (Pierce, Agilent), or PROTIA and PROT20 (Sigma-Aldrich).

In certain embodiments, a protein sample dynamic range can be modulated by fractionating the protein sample using standard fractionation methods, including electrophoresis and liquid chromatography (Zhou et al., 2012, Anal Chem 84(2): 720-734), or partitioning the fractions into compartments (e.g., droplets) loaded with limited capacity protein binding beads/resin (e.g. hydroxylated silica particles) (McCormick, 1989, Anal Biochem 181(1): 66-74) and eluting bound protein. Excess protein in each compartmentalized fraction is washed away. Examples of electrophoretic methods include capillary electrophoresis (CE), capillary isoelectric focusing (CIEF), capillary isotachophoresis (CITP), free flow electrophoresis, gel-eluted liquid fraction entrapment electrophoresis (GELFrEE). Examples of liquid chromatography protein separation methods include reverse phase (RP), ion exchange (IE), size exclusion (SE), hydrophilic interaction, etc. Examples of compartment partitions include emulsions, droplets, microwells, physically separated regions on a flat substrate, etc. Exemplary protein binding beads/resins include silica nanoparticles derivatized with phenol groups or hydroxyl groups (e.g., StrataClean Resin from Agilent Technologies, RapidClean from LabTech, etc.). By limiting the binding capacity of the beads/resin, highly-abundant proteins eluting in a given fraction will only be partially bound to the beads, and excess proteins removed.

In some embodiments, a partition barcode is used which comprises assignment of a unique barcode to a subsampling of macromolecules from a population of macromolecules within a sample. This partition barcode may be comprised of identical barcodes arising from the partitioning of macromolecules within compartments labeled with the same barcode (e.g., a barcoded bead population in which multiple beads share the same barcode). The use of physical compartments effectively subsamples the original sample to provide assignment of partition barcodes. For instance, a set of beads labeled with 10,000 different compartment barcodes is provided. Furthermore, suppose in a given assay, that a population of 1 million beads are used in the assay. On average, there are 100 beads per compartment barcode (Poisson distribution). Further suppose that the beads capture an aggregate of 10 million macromolecules. On average, there are 10 macromolecules per bead, with 100 compartments per compartment barcode, there are effectively 1,000 macromolecules per partition barcode (comprised of 100 compartment barcodes for 100 distinct physical compartments).

In another embodiment, single molecule partitioning and partition barcoding of polypeptides is accomplished by labeling polypeptides (chemically or enzymatically) with an amplifiable DNA UMI tag (e.g., recording tag) at the N or C terminus, or both. DNA tags are attached to the body of the polypeptide (internal amino acids) via non-specific photo-labeling or specific chemical attachment to reactive amino acids such as lysines. Information from the recording tag attached to the terminus of the peptide is transferred to the DNA tags via an enzymatic emulsion PCR (Williams et al., Nat Methods, (2006) 3(7):545-550; Schutze et al., Anal Biochem. (2011) 410(1):155-157) or emulsion in vitro transcription/reverse transcription (IVT/RT) step. In the preferred embodiment, a nanoemulsion is employed such that, on average, there is fewer than a single polypeptide per emulsion droplet with size from 50 nm-1000 nm (Nishikawa et al., J Nucleic Acids. (2012) 2012: 923214; Gupta et al., Soft Matter. (2016) 12(11):2826-41; Sole et al., Langmuir (2006, 22(20):8326-8332). Additionally, all the components of PCR are included in the aqueous emulsion mix including primers, dNTPs, Mg2+, polymerase, and PCR buffer. If IVT/RT is used, then the recording tag is designed with a T7/SP6 RNA polymerase promoter sequence to generate transcripts that hybridize to the DNA tags attached to the body of the polypeptide (Ryckelynck et al., RNA. (2015) 21(3):458-469). A reverse transcriptase (RT) copies the information from the hybridized RNA molecule to the DNA tag. In this way, emulsion PCR or IVT/RT can be used to effectively transfer information from the terminus recording tag to multiple DNA tags attached to the body of the polypeptide.

In some embodiments, a sample of macromolecule targets (e.g., peptides, polypeptides, or proteins) can be processed into a physical area or volume e.g., into a compartment. Various processing and/or labeling steps may be performed on the sample prior to performing the binding reaction. In some embodiments, the compartment separates or isolates a subset of macromolecules from a sample of macromolecules. In some examples, the compartment may be an aqueous compartment (e.g., microfluidic droplet), a solid compartment (e.g., picotiter well or microtiter well on a plate, tube, vial, bead), or a separated region on a surface. In some cases, a compartment may comprise one or more beads to which macromolecules may be immobilized. In some embodiments, macromolecules in a compartment is labeled with a compartment tag including a barcode. For example, the macromolecules in one compartment can be labeled with the same barcode or macromolecules in multiple compartments can be labeled with the same barcode. See e.g., Valihrach et al., Int J Mol Sci. 2018 Mar. 11; 19(3). pii: E807. Encapsulation of cellular contents via gelation in beads is a useful approach to single cell analysis (Tamminen et al., Front Microbiol (2015) 6: 195; Spencer et al., ISME J (2016) 10(2): 427-436). Barcoding single cell droplets enables all components from a single cell to be labeled with the same identifier (Klein et al., Cell (2015) 161(5): 1187-1201; Zilionis et al., Nat Protoc (2017) 12(1): 44-73; International Patent Publication No. WO 2016/130704). Compartment barcoding can be accomplished in a number of ways including direct incorporation of unique barcodes into each droplet by droplet joining (Bio-Rad Laboratories), by introduction of barcoded beads into droplets (10× Genomics), or by combinatorial barcoding of components of the droplet post encapsulation and gelation using and split-pool combinatorial barcoding as described by Gunderson et al. (International Patent Publication No. WO 2016/130704, incorporated by reference in its entirety). A similar combinatorial labeling scheme can also be applied to nuclei (Vitak et al., Nat Methods (2017) 14(3):302-308).

In some embodiments, the target (e.g., macromolecule) is joined to a support before performing the binding reaction. In some cases, it is desirable to use a support with a large carrying capacity to immobilize a large number of targets (e.g., macromolecules). In some embodiments, it is preferred to immobilize the targets using a three-dimensional support (e.g., a porous matrix or a bead). For example, the preparation of the targets including joining the target to a support is performed prior to performing the binding reaction. In some examples, the preparation of the target including joining the macromolecule to nucleic acid molecule or a oligonucleotide may be performed prior to or after immobilizing the target. In some embodiments, a plurality of targets are attached to a support prior to the binding reaction and contacting with a binding agent.

A support can be any solid or porous support including, but not limited to, a bead, a microbead, an array, a glass surface, a silicon surface, a plastic surface, a filter, a membrane, a PTFE membrane, nylon, a microtiter well, an ELISA plate, a spinning interferometry disc, a nitrocellulose membrane, a nitrocellulose-based polymer surface, a nanoparticle, or a microsphere. Materials for a support include but are not limited to acrylamide, agarose, cellulose, dextran, nitrocellulose, glass, gold, quartz, polystyrene, polyethylene vinyl acetate, polypropylene, polyester, polymethacrylate, polyacrylate, polyethylene, polyethylene oxide, polysilicates, polycarbonates, poly vinyl alcohol (PVA), Teflon, fluorocarbons, nylon, silicon rubber, silica, polyanhydrides, polyglycolic acid, polyvinylchloride, polylactic acid, polyorthoesters, functionalized silane, polypropylfumerate, collagen, glycosaminoglycans, polyamino acids, or any combination thereof. In certain embodiments, a support is a bead, for example, a polystyrene bead, a polymer bead, a polyacrylate bead, an agarose bead, a cellulose bead, a dextran bead, an acrylamide bead, a solid core bead, a porous bead, a paramagnetic bead, a glass bead, a silica-based bead, or a controlled pore bead, or any combinations thereof. In some specific embodiments, the support is a porous agarose bead.

In some embodiments, the support may comprise any suitable solid material, including porous and non-porous materials, to which a macromolecule, e.g., a polypeptide, can be associated directly or indirectly, by any means known in the art, including covalent and non-covalent interactions, or any combination thereof. A support may be two-dimensional (e.g., planar surface) or three-dimensional (e.g., gel matrix or bead). A support can be any support surface including, but not limited to, a bead, a microbead, an array, a glass surface, a silicon surface, a plastic surface, a filter, a membrane, a PTFE membrane, a PTFE membrane, a nitrocellulose membrane, a nitrocellulose-based polymer surface, nylon, a microtiter well, an ELISA plate, a spinning interferometry disc, a polymer matrix, a nanoparticle, or a microsphere. Materials for a support include but are not limited to acrylamide, agarose, cellulose, dextran, nitrocellulose, glass, gold, quartz, polystyrene, polyethylene vinyl acetate, polypropylene, polyester, polymethacrylate, polyacrylate, polyethylene, polyethylene oxide, polysilicates, polycarbonates, poly vinyl alcohol (PVA), Teflon, fluorocarbons, nylon, silicon rubber, polyanhydrides, polyglycolic acid, polyvinylchloride, polylactic acid, polyorthoesters, functionalized silane, polypropylfumerate, collagen, glycosaminoglycans, polyamino acids, dextran, or any combination thereof. Supports further include thin film, membrane, bottles, dishes, fibers, woven fibers, shaped polymers such as tubes, particles, beads, microspheres, microparticles, or any combination thereof. For example, when solid surface is a bead, the bead can include, but is not limited to, a ceramic bead, a polystyrene bead, a polymer bead, a polyacrylate bead, a methylstyrene bead, an agarose bead, a cellulose bead, a dextran bead, an acrylamide bead, a solid core bead, a porous bead, a paramagnetic bead, a glass bead, or a controlled pore bead, a silica-based bead, or any combinations thereof. A bead may be spherical or an irregularly shaped. A bead or support may be porous. A bead's size may range from nanometers, e.g., 100 nm, to millimeters, e.g., 1 mm. In certain embodiments, beads range in size from about 0.2 micron to about 200 microns, or from about 0.5 micron to about 5 micron. In some embodiments, beads can be about 1, 1.5, 2, 2.5, 2.8, 3, 3.5, 4, 4.5, 5, 5.5, 6, 6.5, 7, 7.5, 8, 8.5, 9, 9.5, 10, 10.5, 15, or 20 µm in diameter. In certain embodiments, "a bead" support may refer to an individual bead or a plurality of beads. In some embodiments, the solid surface is a nanoparticle. In certain embodiments, the nanoparticles range in size from about 1 nm to about 500 nm in diameter, for example, between about 1 nm and about 20 nm, between about 1 nm and about 50 nm, between about 1 nm and about 100 nm, between about 10 nm and about 50 nm, between about 10 nm and about 100 nm, between about 10 nm and about 200 nm, between about 50 nm and about 100 nm, between about 50 nm and about 150, between about 50 nm and about 200 nm, between about 100 nm and about 200 nm, or between about 200 nm and about 500 nm in diameter. In some embodiments, the nanoparticles can be about 10 nm, about 50 nm, about 100 nm, about 150 nm, about 200 nm, about 300 nm, or about 500 nm in diameter. In some embodiments, the nanoparticles are less than about 200 nm in diameter.

Various reactions may be used to attach the targets (e.g., macromolecules) to a support (e.g., a solid or a porous support). The targets (e.g., macromolecules) may be attached directly or indirectly to the support. In some cases, the targets (e.g., macromolecules) are attached to the support via a nucleic acid. Exemplary reactions include the copper catalyzed reaction of an azide and alkyne to form a triazole (Huisgen 1,3-dipolar cycloaddition), strain-promoted azide alkyne cycloaddition (SPAAC), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse electron demand Diels-Alder (IEDDA) reaction (e.g., m-tetrazine (mTet) or phenyl tetrazine (pTet) and trans-cyclooctene (TCO)); or pTet and an alkene), alkene and tetrazole photoreaction, Staudinger ligation of azides and phosphines, and various displacement reactions, such as displacement of a leaving group by nucleophilic attack on an electrophilic atom (Horisawa 2014, Knall, Hollauf et al. 2014). Exemplary displacement reactions include reaction of an amine with: an activated ester; an N-hydroxysuccinimide ester; an isocyanate; an isothioscyanate, an aldehyde, an epoxide, or the like. In some embodiments, iEDDA click chemistry is used for immobilizing macromolecules (e.g., polypeptides) to a support since it is rapid and delivers high yields at low input concentrations. In another embodiment, m-tetrazine rather than tetrazine is used in an iEDDA click chemistry reaction, as m-tetrazine has improved bond stability. In another embodiment, phenyl tetrazine (pTet) is used in an iEDDA click chemistry reaction. In one case, a polypeptide is labeled with a bifunctional click chemistry reagent, such as alkyne-NHS ester (acetylene-PEG-NETS ester) reagent or alkyne-benzophenone to generate an alkyne-labeled polypeptide. In some embodiments, an alkyne can also be a strained alkyne, such as cyclooctynes including Dibenzocyclooctyl (DBCO), etc.

In certain embodiments where multiple targets are immobilized on the same support, the target molecules can be spaced appropriately to accommodate methods of performing the binding reaction and any downstream analysis steps to be used to assess the target. For example, it may be advantageous to space the target molecules that optimally to allow a nucleic acid-based method for assessing and sequencing the proteins to be performed. In some embodiments, the method for assessing and sequencing protein targets involve a binding agent which binds to the target molecules and the binding agent comprises a coding tag with information that is transferred to a nucleic acid attached to the target molecules. In some cases, spacing of the targets on the support is determined based on the consideration that information transfer from a coding tag of a binding agent bound to one target molecule may reach a neighboring molecule.

In some embodiments, the surface of the support is passivated (blocked). A "passivated" surface refers to a surface that has been treated with outer layer of material. Methods of passivating surfaces include standard methods from the fluorescent single molecule analysis literature, including passivating surfaces with polymer like polyethylene glycol (PEG) (Pan et al., 2015, Phys. Biol. 12:045006), polysiloxane (e.g., Pluronic F-127), star polymers (e.g., star PEG) (Groll et al., 2010, Methods Enzymol. 472:1-18), hydrophobic dichlorodimethylsilane (DDS)+self-assembled Tween-20 (Hua et al., 2014, Nat. Methods 11:1233-1236), diamond-like carbon (DLC), DLC+PEG (Stavis et al., 2011, Proc. Natl. Acad. Sci. USA 108:983-988), and zwitterionic moiety (e.g., U.S. Patent Application Publication US 2006/0183863). In addition to covalent surface modifications, a number of passivating agents can be employed as well including surfactants like Tween-20, polysiloxane in solution (Pluronic series), poly vinyl alcohol (PVA), and proteins like BSA and casein. Alternatively, density of macromolecules (e.g., proteins, polypeptide, or peptides) can be titrated on the surface or within the volume of a solid substrate by spiking a competitor or "dummy" reactive molecule when immobilizing the proteins, polypeptides or peptides to the solid substrate.

To control spacing of the immobilized targets on the support, the density of functional coupling groups for attaching the target (e.g., TCO or carboxyl groups (COOH)) may be titrated on the substrate surface. In some embodiments, multiple target molecules (e.g., macromolecules) are spaced apart on the surface or within the volume (e.g., porous supports) of a support such that adjacent molecules are spaced apart at a distance of about 50 nm to about 500 nm, or about 50 nm to about 400 nm, or about 50 nm to about 300 nm, or about 50 nm to about 200 nm, or about 50 nm to about 100 nm. In some embodiments, multiple molecules are spaced apart on the surface of a support with an average distance of at least 50 nm, at least 60 nm, at least 70 nm, at least 80 nm, at least 90 nm, at least 100 nm, at least 150 nm, at least 200 nm, at least 250 nm, at least 300 nm, at least 350 nm, at least 400 nm, at least 450 nm, or at least 500 nm. In some embodiments, multiple molecules are spaced apart on the surface of a support with an average distance of at least 50 nm. In some embodiments, molecules are spaced apart on the surface or within the volume of a support such that, empirically, the relative frequency of inter- to intra-molecular events (e.g. transfer of information) is <1:10; <1:100; <1:1,000; or <1:10,000.

In some embodiments, the plurality of target molecules (e.g., macromolecules) is coupled on the support spaced apart at an average distance between two adjacent molecules which ranges from about 50 to 100 nm, from about 50 to 250 nm, from about 50 to 500 nm, from about 50 to 750 nm, from about 50 to 1,000 nm, from about 50 to 1,500 nm, from about 50 to 2,000 nm, from about 100 to 250 nm, from about 100 to 500 nm, from about 200 to 500 nm, from about 300 to 500 nm, from about 100 to 1000 nm, from about 500 to 600 nm, from about 500 to 700 nm, from about 500 to 800 nm, from about 500 to 900 nm, from about 500 to 1,000 nm, from about 500 to 2,000 nm, from about 500 to 5,000 nm, from about 1,000 to 5,000 nm, or from about 3,000 to 5,000 nm.

In some embodiments, appropriate spacing of the target molecules (e.g., macromolecules) on the support is accomplished by titrating the ratio of available attachment molecules on the substrate surface. In some examples, the substrate surface (e.g., bead surface) is functionalized with a carboxyl group (COOH) which is treated with an activating agent (e.g., activating agent is EDC and Sulfo-NHS). In some examples, the substrate surface (e.g., bead surface) comprises NHS moieties. In some embodiments, a mixture of $mPEG_n$-$NH_2$ and $NH_2$-$PEG_n$-mTet is added to the activated beads (wherein n is any number, such as 1-100). The ratio between the $mPEG_3$-$NH_2$ (not available for coupling) and $NH_2$-$PEG_{24}$-mTet (available for coupling) is titrated to generate an appropriate density of functional moieties available to attach the polypeptides on the substrate surface. In certain embodiments, the mean spacing between coupling moieties (e.g., $NH_2$-$PEG_4$-mTet) on the solid surface is at least 50 nm, at least 100 nm, at least 250 nm, or at least 500 nm. In some specific embodiments, the ratio of $NH_2$-$PEG_n$-mTet to $mPEG_3$-$NH_2$ is about or greater than 1:1000, about or greater than 1:10,000, about or greater than 1:100,000, or about or greater than 1:1,000,000. In some further embodiments, the recording tag attaches to the $NH_2$-$PEG_n$-mTet. In some embodiments, the spacing of the target molecules (e.g., macromolecules) on the support is achieved by controlling the concentration and/or number of available COOH or other functional groups on the support.

III. METHODS OF ASSAYING MACROMOLECULES

The provided methods for performing a binding reaction may be used in or in combination with an assay for analyzing the target, such as in a macromolecule analysis assay. In some embodiments, additional treatments and reactions may be performed with the target before or after the binding reaction. In some cases, some of the additional reactions and treatments may be performed while the stable complex comprising the binding agent, target, and stabilizing components are intact. In some cases, prior to performing the binding reaction, the target or plurality of targets is obtained from a sample and immobilized on a support (e.g., on a bead). In some embodiments, the binding reaction is useful for identifying the target or a portion thereof, such as by using a binding agent with a known binding profile. In certain embodiments, the binding agent comprises one or more detectable labels.

In some aspects, the macromolecule analysis assay includes contacting the macromolecule with a binding agent capable of binding to the macromolecule and forming a stable complex, wherein the binding agent comprises a coding tag with identifying information regarding the binding agent; and transferring the information of the coding tag to a recording tag (associated with the target macromolecule) to generate an extended recording tag. The stable complex is formed by linking the stabilizing components (associated or joined to the target and binding agent). In some further embodiments, transferring the information of the coding tag to the recording tag to extend the recording tag may be repeated one or more times. In some cases, the analysis assay is performed on immobilized target molecules bound by two or more cognate binding agents (e.g., antibodies). After a cognate antibody binding event, a stable complex can be formed, and a combined primer extension and DNA nicking step may be used to transfer information from the coding tags of bound antibodies to the recording tag.

Provided herein is a method for analyzing a macromolecule comprising the steps of: (a) providing a macromolecule and an associated recording tag joined to a support; (b) contacting the macromolecule with a binding agent capable of binding to the macromolecule, wherein the binding agent comprises a coding tag with identifying information regarding the binding agent and the binding agent and the macromolecule each comprises or is associated with a stabilizing component; (c) linking the stabilizing components to form a stable complex; (d) transferring the information of the coding tag to the recording tag to generate an extended recording tag; and analyzing the extended recording tag.

In some examples, step (a) is performed before steps (b), (c) and (d). In some embodiments, step (b) is performed before step (c) and step (d). In some cases, step (c) is performed before step (d). In some embodiments, the method further comprises removing the one or more binding agents. In some embodiments, removing the one or more binding agents is performed after step (d).

In some embodiments, the method is performed with one or more target peptides and the method further includes step (e) removing the terminal amino acid (e.g., N-terminal amino acid (NTAA)) of the peptide to expose a new terminal amino acid of the peptide.

In some embodiments, the method includes treating the target peptide with a reagent for modifying a terminal amino acid of the peptide. In some embodiments, the target peptide is contacted with the reagent for modifying a terminal amino acid before step (b). In some embodiments, the target peptide is contacted with the reagent for modifying a terminal amino acid before removing the terminal amino acid.

In some embodiments, the method further includes the step of removing the binding agent after transferring information from the coding tag to the recording tag. In some cases, the stable complex is disrupted prior to removing the binding agent. The disrupting may be performed by introducing a destabilizing agent, such as heat, a denaturing agent, an enzyme or a competitor molecule. In some embodiments, the bound binding agent and annealed coding tag can be removed following transfer of the identifying information (e.g., primer extension) by using highly denaturing conditions (e.g., 0.1-0.2 N NaOH, 6M Urea, 2.4 M guanidinium isothiocyanate, 95% formamide, etc.).

In some embodiments, the provided methods for analysis of macromolecules can further include providing a plurality of adaptor molecules each comprising a first hybridization sequence substantially complementary to at least a portion of the coding tag (or portion thereof), and a secondary tag; and transferring the information of the secondary tag to the recording tag to generate an extended recording tag. In some embodiments, the information transferred from the secondary tag of an adaptor molecule includes identifying information regarding the identity of the macromolecule or portion thereof bound by the binding agent. The extended recording tag associated with the macromolecule for analysis can comprise the information from one or more secondary tags.

The methods provided may include preparing, selecting, and providing a plurality of adaptor molecules. In some embodiments, more than one coding tag associated a binding agent is configured to hybridize to adaptor molecules comprising the same secondary tag. The adaptor molecules comprise a first hybridization sequence and a secondary tag, wherein the first hybridization sequence or portion thereof is complementary to the coding tag or region therein. In some embodiments, the first hybridization sequence of the adaptor molecule comprises a single stranded region for hybridizing to the coding tag (or region therein) associated with the binding agent. In some embodiments, the adaptor molecule further comprises a second hybridization sequence substantially complementary to at least a portion of the recording tag.

In some embodiments, the macromolecule analysis assay comprises: providing a macromolecule and an associated recording tag joined to a support, wherein the macromolecule is also associated with a stabilizing component; contacting the macromolecule with a binding agent capable of binding to the macromolecule, wherein the binding agent comprises a coding tag with identifying information regarding the binding agent, to allow binding between the macromolecule and the binding agent, wherein the binding agent is also associated with a stabilizing component; providing a linking agent and linking the stabilizing components to form a stable complex; providing a plurality of adaptor molecules each comprising a first hybridization sequence substantially complementary to at least a portion of the coding tag, and a secondary tag, to allow hybridization between the adaptor molecule (or the first hybridization sequence) and the coding tag (or the portion of the coding tag); transferring the information of the secondary tag to the recording tag to generate an extended recording tag; and analyzing the extended recording tag. In some cases, information is transferred from the secondary tag of the adaptor molecule to the recording tag. In some cases, information is transferred from the adaptor molecule to the linking agent, then from the linking agent to the recording tag.

Information Transfer

In some embodiments, the method further comprises transferring information of a coding tag associated with the binding agent to the recording tag associated with the target to generate an extended recording tag, thereby generating an extended recording tag. In some cases, transferring information of the coding tag to the recording tag is performed after the stabilizing components are linked. In some cases, transferring information of the coding tag to the recording tag is performed after the stable complex is formed. In some cases, transferring information of the coding tag to the recording tag is performed after introducing the linking agent or introducing light to the binding reaction.

In embodiments relating to methods of analyzing peptides or polypeptides, the method generally includes contacting a binding agent to terminal amino acid (e.g., NTAA or CTAA) of a polypeptide, protein or peptide, providing an adaptor molecule and allowing hybridization of complementary sequences, and transferring the information from the secondary tag to the recording tag associated with the polypeptide, protein or peptide, thereby generating a first order extended recording tag (see FIG. 1, 2, 6 or 7). In some further embodiment, the method comprises labeling or modifying the macromolecule (e.g. peptide) prior to or after the polypeptide, protein or peptide is contacted with the binding agent. For example, the terminal amino acid of the polypeptide, protein or peptide bound by the binding agent may be a chemically labeled or modified terminal amino acid. In some further embodiments, the method further includes removing or eliminating the terminal amino acid (e.g., NTAA or CTAA) from the polypeptide, protein or peptide after the information transfer step. The terminal amino acid eliminated may be a chemically labeled or modified terminal amino acid. Removal of the NTAA by contacting with an enzyme or chemical reagents converts the penultimate amino acid of the polypeptide, protein or peptide to a terminal amino acid. The polypeptide analysis may include one or more cycles of binding with additional binding agents to the terminal amino acid, providing a plurality of adaptor molecules and allow hybridization between the coding tag and first hybridization sequence of the adaptor molecule, and transferring information from the secondary tags to the extended nucleic acid thereby generating a higher order extended recording tag containing information regarding two or more binding agents, and eliminating the terminal amino acid in a cyclic manner. Additional binding, hybridizing, transferring information, and removal, can occur as described above up to n amino acids to generate an $n^{th}$ order extended nucleic acid, which collectively represent the polypeptide, protein or peptide. In some of any provided embodiments, steps including the NTAA in the described exemplary approach can be performed instead with a C terminal amino acid (CTAA).

In some embodiments, the order of the steps in the process for a degradation-based peptide or polypeptide sequencing assay can be reversed or be performed in various orders. For example, in some embodiments, the terminal amino acid labeling can be conducted before and/or after the polypeptide is bound to the binding agent.

In some embodiments, the polypeptide analysis assay includes performing an assay which utilizes the recording tag associated with the target macromolecule, e.g., the polypeptide. The recording tag associated with the target polypeptide is used in the polypeptide analysis assay which includes transferring identifying information from one or more coding tags to the recording tag.

In some embodiments, contacting of the first binding agent and second binding agent to the target, and optionally any further binding agents (e.g., third binding agent, fourth binding agent, fifth binding agent, and so on), are performed at the same time. For example, the first binding agent and second binding agent, and optionally any further order binding agents, can be pooled together, for example to form a library of binding agents. In another example, the first binding agent and second binding agent, and optionally any further order binding agents, rather than being pooled together, are added simultaneously to the polypeptide. In one embodiment, a library of binding agents comprises at least 20 binding agents that selectively bind to the 20 standard, naturally occurring amino acids. In some embodiments, a library of binding agents may comprise binding agents that selectively bind to the modified amino acids.

In other embodiments, the first binding agent and second binding agent, and optionally any further order binding agents, are each contacted with the polypeptide in separate binding cycles, added in sequential order. In certain embodiments, multiple binding agents are used at the same time in parallel. This parallel approach saves time and reduces non-specific binding by non-cognate binding agents to a site that is bound by a cognate binding agent (because the binding agents are in competition).

In the methods described herein, after binding of a binding agent to a target macromolecule, e.g., a protein or peptide, identifying information of its linked coding tag is transferred to the recording tag (e.g., recording tag) associated with the peptide, thereby generating an extended recording tag. The nucleic acid associated with the protein or peptide for analysis can comprise the recording tag and information from one or more coding tags. In some embodiments, the recording tag further comprises barcodes and/or other nucleic acid components. In particular embodiments, the identifying information from the coding tag of the binding agent is transferred to the recording tag (or other nucleic acid components) attached thereto. The transfer of the identifying information can be achieved by any suitable means such as by extension or ligation. In some embodiments, a spacer is added to the end of the recording tag, and the spacer comprises a sequence that is capable of hybridizing with a sequence on the coding tag to facilitate transfer of the identifying information.

Coding tag information associated with a specific binding agent may be transferred to a recording tag using a variety of methods. In certain embodiments, information of a coding tagA spacer sequence on the 3'-terminus of a recording tag or an extended recording tag anneals with complementary spacer sequence on the 3' terminus of a coding tag and a polymerase (e.g., strand-displacing polymerase) extends the recording tag sequence, using the annealed coding tag as a template. In some embodiments, oligonucleotides complementary to coding tag encoder sequence and 5' spacer can be pre-annealed to the coding tags to prevent hybridization of the coding tag to internal encoder and spacer sequences present in an extended recording tag. The 3' terminal spacer, on the coding tag, remaining single stranded, preferably binds to the terminal 3' spacer on the recording tag. In other embodiments, a nascent recording tag can be coated with a single stranded binding protein to prevent annealing of the coding tag to internal sites. Alternatively, the nascent recording tag can also be coated with RecA (or related homologues such as uvsX) to facilitate invasion of the 3' terminus into a completely double stranded coding tag (Bell et al., 2012, Nature 491:274-278). This configuration prevents the double stranded coding tag from interacting with internal recording tag elements, yet is susceptible to strand invasion by the RecA coated 3' tail of the extended recording tag (Bell, et al., 2015, Elife 4: e08646). The presence of a single-stranded binding protein can facilitate the strand displacement reaction. In certain embodiments, after a binding agent binds to a polypeptide, information from a coding tag linked to a binding agent can be transferred to the nucleic acid associated with the polypeptide while the binding agent is bound to the polypeptide.

An extended nucleic acid associated with the macromolecule, e.g., the peptide, with identifying information from the coding tag may comprise information from a binding agent's coding tag representing each binding cycle performed. However, in some cases, an extended nucleic acid may also experience a "missed" binding cycle, e.g., if a binding agent fails to bind to the polypeptide, because the coding tag was missing, damaged, or defective, because the primer extension reaction failed. Even if a binding event occurs, transfer of information from the coding tag may be incomplete or less than 100% accurate, e.g., because a coding tag was damaged or defective, because errors were introduced in the primer extension reaction). Thus, an extended nucleic acid may represent 100%, or up to 95%, 90%, 85%, 80%, 75%, 70%, 65%, 60%, 65%, 55%, 50%, 45%, 40%, 35%, 30%, or any subrange thereof, of binding events that have occurred on its associated polypeptide. Moreover, the coding tag information present in the extended nucleic acid may have at least 30%, 35%, 40%, 45%, 50%, 55%, 60%, 65%, 70%, 75%, 80%, 85%, 90%, 95%, or 100% identity the corresponding coding tags.

In certain embodiments, an extended recording tag associated with the immobilized peptide may comprise information from multiple coding tags representing multiple, successive binding events. In these embodiments, a single, concatenated extended recording tag associated with the immobilized peptide can be representative of a single polypeptide. As referred to herein, transfer of coding tag information to the recording tag associated with the immobilized peptide also includes transfer to an extended recording tag as would occur in methods involving multiple, successive binding events.

Coding tag information associated with a specific binding agent may be transferred using a variety of methods. In certain embodiments, information of a coding tag is transferred to a recording tag associated with the immobilized peptide via primer extension (Chan et al., Curr Opin Chem Biol. (2015) 26: 55-61). A spacer sequence on the 3'-terminus of a recording tag anneals with complementary spacer sequence on the 3' terminus of a coding tag and a polymerase (e.g., strand-displacing polymerase) extends the nucleic acid sequence on the recording tag, using the annealed coding tag as a template. In some embodiments, oligonucleotides complementary to coding tag encoder sequence and 5' spacer can be pre-annealed to the coding tags to prevent hybridization of the coding tag to internal encoder and spacer sequences present in an extended nucleic acid. The 3' terminal spacer, on the coding tag, remaining single stranded, preferably binds to the terminal 3' spacer on the recording tag (or any barcodes or other nucleic acid components associated). In other embodiments, a nascent recording tag associated with the immobilized peptide can be coated with a single stranded binding protein to prevent annealing of the coding tag to internal sites.

In any of the preceding embodiments, the transfer of identifying information (e.g., from a coding tag to a recording tag) can be accomplished by ligation (e.g., an enzymatic or chemical ligation, a splint ligation, a sticky end ligation, a single-strand (ss) ligation such as a ssDNA ligation, or any combination thereof), a polymerase-mediated reaction (e.g., primer extension of single-stranded nucleic acid or double-stranded nucleic acid), or any combination thereof.

Most type A polymerases are devoid of 3' exonuclease activity (endogenous or engineered removal), such as Klenow exo-, T7 DNA polymerase exo- (Sequenase 2.0), and Taq polymerase catalyzes non-templated addition of a nucleotide, preferably an adenosine base (to lesser degree a G base, dependent on sequence context) to the 3' blunt end of a duplex amplification product. In some embodiments, using Taq polymerase for primer extension, placement of a thymidine base in the coding tag between the spacer sequence distal from the binding agent and the adjacent barcode sequence (e.g., encoder sequence or cycle specific sequence) accommodates the sporadic inclusion of a non-templated adenosine nucleotide on the 3' terminus of the spacer sequence of the recording tag. In this manner, the extended recording tag associated with the immobilized peptide (with or without a non-templated adenosine base) can anneal to the coding tag and undergo primer extension.

In some embodiments, to minimize non-specific interaction of the coding tag labeled binding agents in solution with the nucleic acids of immobilized proteins, competitor (also referred to as blocking) oligonucleotides complementary to nucleic acids containing spacer sequences (e.g., on the recording tag) can be added to binding reactions to minimize non-specific interactions. In some embodiments, the blocking oligonucleotides contain a sequence that is complementary to the coding tag or a portion thereof attached to the binding agent. In some embodiments, blocking oligonucleotides are relatively short. Excess competitor oligonucleotides are washed from the binding reaction prior to primer extension, which effectively dissociates the annealed competitor oligonucleotides from the nucleic acids on the recording tag, especially when exposed to slightly elevated temperatures (e.g., 30-50° C.). Blocking oligonucleotides may comprise a terminator nucleotide at its 3' end to prevent primer extension.

In certain embodiments, the annealing of the spacer sequence on the recording tag to the complementary spacer sequence on the coding tag is metastable under the primer extension reaction conditions (i.e., the annealing Tm is similar to the reaction temperature). This allows the spacer sequence of the coding tag to displace any blocking oligonucleotide annealed to the spacer sequence of the recording tag (or extensions thereof).

Coding tag information associated with a specific binding agent may be transferred to a nucleic acid on the recording tag associated with the immobilized peptide via ligation, Electroligase®. Alternatively, a ligation may be a chemical ligation reaction, such as chemical ligation using standard chemical ligation or "click chemistry" (Gunderson et al., Genome Res (1998) 8(11): 1142-1153; Peng et al., European J Org Chem (2010) (22): 4194-4197; El-Sagheer et al., Proc Natl Acad Sci USA (2011) 108(28): 11338-11343; El-Sagheer et al., Org Biomol Chem (2011) 9(1): 232-235; Sharma et al., Anal Chem (2012) 84(14): 6104-6109; Roloff et al., Bioorg Med Chem (2013) 21(12): 3458-3464;

Litovchick et al., Artif DNA PNA XNA (2014) 5(1): e27896; Roloff et al., Methods Mol Biol (2014) 1050:131-141).

In some embodiments, coding tag information can be transferred using topoisomerase. In certain embodiments, the binding event information is transferred from a coding tag to the recording tag associated with the immobilized peptide in a cyclic fashion. Cross-reactive binding events can be informatically filtered out after sequencing by requiring that at least two different coding tags, identifying two or more independent binding events, map to the same class of binding agents (cognate to a particular protein). The coding tag may contain an optional UMI sequence in addition to one or more spacer sequences. Universal priming sequences may also be included in extended nucleic acids on the recording tag associated with the immobilized peptide for amplification and NGS sequencing.

In some examples, the final extended recording tag containing information from one or more binding agents is optionally flanked by universal priming sites to facilitate downstream amplification and/or DNA sequencing. The forward universal priming site (e.g., Illumina's P5-S1 sequence) can be part of the original design of the recording tag and the reverse universal priming site (e.g., Illumina's P7-S2' sequence) can be added as a final step in the extension of the nucleic acid. In some embodiments, the addition of forward and reverse priming sites can be done independently of a binding agent.

In some embodiments, the target macromolecule (e.g., protein or polypeptide) may be labeled with a nucleic acid molecule or a oligonucleotide (e.g., DNA recording tag). In some aspects, a plurality of target macromolecules in the sample is provided with recording tags. The recording tags may be associated or attached, directly or indirectly to the target macromolecules using any suitable means. In some aspects, the recording tags may be associated or attached, directly or indirectly to the target macromolecules prior to contacting the target with a binding agent.

In some embodiments, at least one recording tag is associated or co-localized directly or indirectly with the target macromolecule. In some embodiments, a UMI has a different base sequence than the spacer or encoder sequences within the binding agents' coding tags to facilitate distinguishing these components during sequence analysis.

In some embodiments, the recording tags associated with a library of polypeptides share a common spacer sequence. In other embodiments, the recording tags associated with a library of polypeptides have binding cycle specific spacer sequences that are complementary to the binding cycle specific spacer sequences of their cognate binding agents. In some aspects, the spacer sequence in the recording tag is designed to have minimal complementarity to other regions in the recording tag; likewise, the spacer sequence in the coding tag should have minimal complementarity to other regions in the coding tag. In some cases, the spacer sequence of the recording tags and coding tags should have minimal sequence complementarity to components such unique molecular identifiers, barcodes (e.g., compartment, partition, sample, spatial location), universal primer sequences, encoder sequences, cycle specific sequences, etc. present in the recording tags or coding tags. In some embodiments, information of one or more tags are transferred to the recording tag (e.g., via primer extension or ligation) to extend the recording tag. The spacer sequence in the coding tag should have minimal complementarity to other regions in the coding tag. In other words, the spacer sequence of the recording tags and coding tags should have minimal sequence complementarity to components such unique molecular identifiers, barcodes (e.g., compartment, partition, sample, spatial location), universal primer sequences, encoder sequences, cycle specific sequences, etc. present in the recording tags or coding tags.

In some embodiments, a recording tag comprises from 5' to 3' direction: a universal forward (or 5') priming sequence, information transferred from the coding tag, and a spacer sequence. In some embodiments, an extended recording tag comprises from 5' to 3' direction: a universal forward (or 5') priming sequence, information transferred from the coding tag, optionally other barcodes (e.g., sample barcode, partition barcode, compartment barcode, or any combination thereof), a spacer sequence, a universal reverse (or 3') priming sequence. In some other embodiments, a recording tag comprises from 5' to 3' direction: a universal forward (or 5') priming sequence, information transferred from the coding tag, optionally other barcodes (e.g., sample barcode, partition barcode, compartment barcode, or any combination thereof), an optional UMI, and a spacer sequence.

The coding tag associated with the binding agent is or comprises a polynucleotide with any suitable length, e.g., a nucleic acid molecule of about 2 bases to about 100 bases, including any integer including 2 and 100 and in between, that comprises identifying information for its associated binding agent. A coding tag may comprise an encoder sequence or a sequence with identifying information, which is optionally flanked by one spacer on one side or optionally flanked by a spacer on each side. A coding tag may also be comprised of an optional UMI and/or an optional binding cycle-specific barcode. A coding tag may refer to the coding tag that is directly attached to a binding agent, to a complementary sequence hybridized to the coding tag directly attached to a binding agent (e.g., for double stranded coding tags), or to coding tag information present in an extended nucleic acid on the recording tag. In certain embodiments, a coding tag may further comprise a binding cycle specific spacer or barcode, a unique molecular identifier, a universal priming site, or any combination thereof. In some embodiments, a coding tag is partially double stranded, which prevents annealing of the coding tag to internal encoder and spacer sequences in a growing extended recording tag the binding agent. In some embodiments, the identifying information from the coding tag comprises information regarding the identity of the target bound by the binding agent. In some aspects, a coding tag comprises an encoder sequence that provides identifying information regarding the associated binding agent. An encoder sequence is about 3 bases to about 30 bases, about 3 bases to about 20 bases, about 3 bases to about 10 bases, or about 3 bases to about 8 bases. In some embodiments, an encoder sequence is about 3 bases, 4 bases, 5 bases, 6 bases, 7 bases, 8 bases, 9 bases, 10 bases, 11 bases, 12 bases, 13 bases, 14 bases, 15 bases, 20 bases, 25 bases, or 30 bases in length. The length of the encoder sequence determines the number of unique encoder sequences that can be generated. Shorter encoding sequences generate a smaller number of unique encoding sequences, which may be useful when using a small number of binding agents. In a specific embodiment, a set of >50 unique encoder sequences are used for a binding agent library.

In some embodiments, each unique binding agent within a library of binding agents has a unique encoder sequence. For example, 20 unique encoder sequences may be used for a library of 20 binding agents that bind to the 20 standard amino acids. In another example, 30 unique encoder sequences may be used. In other embodiments, two or more different binding agents may share the same encoder sequence. For example, two binding agents that each bind to a different standard amino acid may share the same encoder sequence.

In certain embodiments, a coding tag further comprises a spacer sequence at one end or both ends. In some embodiments, a spacer within a coding tag is shorter than the encoder sequence, e.g., at least 1 base, 2, bases, 3 bases, 4 bases, 5 bases, 6, bases, 7 bases, 8 bases, 9 bases, 10 bases, 11 bases, 12 bases, 13 bases, 14 bases, 15 bases, 20 bases, or 25 bases shorter than the encoder sequence. In other embodiments, a spacer within a coding tag is the same length as the encoder sequence. In certain embodiments, the spacer is binding agent specific so that a spacer from a previous binding cycle only interacts with a spacer from the appropriate binding agent in a current binding cycle. An example would be pairs of cognate antibodies containing spacer sequences that only allow information transfer if both antibodies sequentially bind to the polypeptide. A spacer sequence may be used as the primer annealing site for a primer extension reaction, or a splint or sticky end in a ligation reaction. A 5' spacer on a coding tag may optionally contain pseudo complementary bases to a 3' spacer on the recording tag to increase T. In other embodiments, the coding tags within a library of binding agents do not have a binding cycle specific spacer sequence.

In one example, two or more binding agents that each bind to different targets have associated coding tags share the same spacers. In some cases, coding tags associated with two or more binding agents share coding tags with the same sequence or a portion thereof.

In some embodiments, the coding tags within a collection of binding agents share a common spacer sequence used in an assay (e.g. the entire library of binding agents used in a multiple binding cycle method possess a common spacer in their coding tags). In another embodiment, the coding tags are comprised of a binding cycle tags, identifying a particular binding cycle. In other embodiments, the coding tags within a library of binding agents have a binding cycle specific spacer sequence. In some embodiments, a coding tag comprises one binding cycle specific spacer sequence. For example, a coding tag for binding agents used in the first binding cycle comprise a "cycle 1" specific spacer sequence, a coding tag for binding agents used in the second binding cycle comprise a "cycle 2" specific spacer sequence, and so on up to "n" binding cycles. In further embodiments, coding tags for binding agents used in the first binding cycle comprise a "cycle 1" specific spacer sequence and a "cycle 2" specific spacer sequence, coding tags for binding agents used in the second binding cycle comprise a "cycle 2" specific spacer sequence and a "cycle 3" specific spacer sequence, and so on up to "n" binding cycles. In some embodiments, coding tags associated with binding agents used to bind in an alternating cycles comprises different binding cycle specific spacer sequences. For example, a coding tag for binding agents used in the first binding cycle comprise a "cycle 1" specific spacer sequence, a coding tag for binding agents used in the second binding cycle comprise a "cycle 2" specific spacer sequence, a coding tag for binding agents used in the third binding cycle also comprises the "cycle 1" specific spacer sequence, a coding tag for binding agents used in the fourth binding cycle comprises the "cycle 2" specific spacer sequence. In this manner, cycle specific spacers are not needed for every cycle.

A cycle specific spacer sequence can also be used to concatenate information of coding tags onto a single recording tag when a population of recording tags is associated with a polypeptide. The first binding cycle transfers information from the coding tag to a randomly-chosen recording tag, and subsequent binding cycles can prime only the extended recording tag using cycle dependent spacer sequences. More specifically, coding tags for binding agents used in the first binding cycle comprise a "cycle 1" specific spacer sequence and a "cycle 2" specific spacer sequence, coding tags for binding agents used in the second binding cycle comprise a "cycle 2" specific spacer sequence and a "cycle 3" specific spacer sequence, and so on up to "n" binding cycles. Coding tags of binding agents from the first binding cycle are capable of annealing to recording tags via complementary cycle 1 specific spacer sequences. Upon transfer of the coding tag information to the recording tag, the cycle 2 specific spacer sequence is positioned at the 3' terminus of the extended recording tag at the end of binding cycle 1. Coding tags of binding agents from the second binding cycle are capable of annealing to the extended recording tags via complementary cycle 2 specific spacer sequences. Upon transfer of the coding tag information to the extended recording tag, the cycle 3 specific spacer sequence is positioned at the 3' terminus of the extended recording tag at the end of binding cycle 2, and so on through "n" binding cycles. This embodiment provides that transfer of binding information in a particular binding cycle among multiple binding cycles will only occur on (extended) recording tags that have experienced the previous binding cycles. However, sometimes a binding agent may fail to bind to a cognate polypeptide. Oligonucleotides comprising binding cycle specific spacers after each binding cycle as a "chase" step can be used to keep the binding cycles synchronized even if the event of a binding cycle failure. For example, if a cognate binding agent fails to bind to a polypeptide during binding cycle 1, adding a chase step following binding cycle 1 using oligonucleotides comprising both a cycle 1 specific spacer, a cycle 2 specific spacer, and a "null" encoder sequence. The "null" encoder sequence can be the absence of an encoder sequence or, preferably, a specific barcode that positively identifies a "null" binding cycle. The "null" oligonucleotide is capable of annealing to the recording tag via the cycle 1 specific spacer, and the cycle 2 specific spacer is transferred to the recording tag. Thus, binding agents from binding cycle 2 are capable of annealing to the extended recording tag via the cycle 2 specific spacer despite the failed binding cycle 1 event. The "null" oligonucleotide marks binding cycle 1 as a failed binding event within the extended recording tag.

In some embodiments, a coding tag comprises a cleavable or nickable DNA strand within the second (3') spacer sequence proximal to the binding agent. For example, the 3' spacer may have one or more uracil bases that can be nicked by uracil-specific excision reagent (USER). USER generates a single nucleotide gap at the location of the uracil. In another example, the 3' spacer may comprise a recognition sequence for a nicking endonuclease that hydrolyzes only one strand of a duplex. Preferably, the enzyme used for cleaving or nicking the 3' spacer sequence acts only on one DNA strand (the 3' spacer of the coding tag), such that the other strand within the duplex belonging to the (extended) recording tag is left intact. These embodiments is particularly useful in assays analyzing proteins in their native conformation, as it allows the non-denaturing removal of the binding agent from the (extended) recording tag after primer extension has occurred and leaves a single stranded DNA spacer sequence on the extended recording tag available for subsequent binding cycles.

The coding tags may also be designed to contain palindromic sequences. Inclusion of a palindromic sequence into a coding tag allows a nascent, growing, extended recording tag to fold upon itself as coding tag information is transferred. An extended recording tag can be built up from a series of binding events using coding tags comprising analyte-specific spacers and encoder sequences. In one embodiment, a first binding event employs a binding agent with a coding tag comprised of a generic 3' spacer primer sequence and an analyte-specific spacer sequence at the 5' terminus for use in the next binding cycle; subsequent binding cycles then use binding agents with encoded analyte-specific 3' spacer sequences. This design results in amplifiable library elements being created only from a correct series of cognate binding events. Off-target and cross-reactive binding interactions will lead to a non-amplifiable extended recording tag. In one example, a pair of cognate binding agents to a particular polypeptide analyte is used in two binding cycles to identify the analyte. The first cognate binding agent contains a coding tag comprised of a generic spacer 3' sequence for priming extension on the generic spacer sequence of the recording tag, and an encoded analyte-specific spacer at the 5' end, which will be used in the next binding cycle. For matched cognate binding agent pairs, the 3' analyte-specific spacer of the second binding agent is matched to the 5' analyte-specific spacer of the first binding agent. In this way, only correct binding of the cognate pair of binding agents will result in an amplifiable extended recording tag. Cross-reactive binding agents will not be able to prime extension on the recording tag, and no amplifiable extended recording tag product generated. This approach greatly enhances the specificity of the methods disclosed herein. The same principle can be applied to triplet binding agent sets, in which 3 cycles of binding are employed. In a first binding cycle, a generic 3' Sp sequence on the recording tag interacts with a generic spacer on a binding agent coding tag. Primer extension transfers coding tag information, including an analyte specific 5' spacer, to the recording tag. Subsequent binding cycles employ analyte specific spacers on the binding agents' coding tags.

A coding tag may include a terminator nucleotide incorporated at the 3' end of the 3' spacer sequence. After a binding agent binds to a polypeptide and their corresponding coding tag and recording tags anneal via complementary spacer sequences, it is possible for primer extension to transfer information from the coding tag to the recording tag, or to transfer information from the recording tag to the coding tag. Addition of a terminator nucleotide on the 3' end of the coding tag prevents transfer of recording tag information to the coding tag. It is understood that for embodiments described herein involving generation of extended coding tags, it may be preferable to include a terminator nucleotide at the 3' end of the recording tag to prevent transfer of coding tag information to the recording tag.

In some embodiments, the coding tag sequence can be optimized for the particular sequencing analysis platform. Sequences comprising identifying information from the coding tag can be designed to be optimally electrically distinguishable in transit through a nanopore.

In certain embodiments, a coding tag may further comprise a unique molecular identifier for the binding agent to which the coding tag is linked. A UMI for the binding agent may be useful in embodiments utilizing extended coding tags or di-tag molecules for sequencing readouts, which in combination with the encoder sequence provides information regarding the identity of the binding agent and number of unique binding events for a polypeptide.

G. Amino Acid Cleavage

In embodiments relating to methods of analyzing target peptides or polypeptides using a degradation based approach, following contacting and binding of a first binding agent to an n NTAA of a peptide of n amino acids, forming a stable complex, and transferring of the first binding agent's coding tag information to a nucleic acid associated with the peptide, thereby generating a first order extended nucleic acid (e.g., on the recording tag), then NTAA is eliminated. Removal of the n labeled NTAA by contacting with an enzyme or chemical reagents converts the n−1 amino acid of the peptide to an N-terminal amino acid, which is referred to herein as an n−1 NTAA. A second binding agent is contacted with the peptide and binds to the n−1 NTAA, and the second binding agent's coding tag information is transferred to the first order extended nucleic acid thereby generating a second order extended nucleic acid (e.g., for generating a concatenated $n^{th}$ order extended nucleic acid representing the peptide). Elimination of the n−1 labeled NTAA converts the n−2 amino acid of the peptide to an N-terminal amino acid, which is referred to herein as n−2 NTAA. Additional binding, transfer, labeling, and removal, can occur as described above up to n amino acids to generate an $n^{th}$ order extended nucleic acid or n separate extended nucleic acids, which collectively represent the peptide. As used herein, an n "order" when used in reference to a binding agent, coding tag, or extended nucleic acid, refers to the n binding cycle, wherein the binding agent and its associated coding tag is used or the n binding cycle where the extended nucleic acid is created (e.g. on recording tag). In some embodiments, steps including the NTAA in the described exemplary approach can be performed instead with a C terminal amino acid (CTAA).

In certain embodiments relating to analyzing peptides, following binding of a terminal amino acid (N-terminal or C-terminal) by a binding agent and transfer of coding tag information, the terminal amino acid is removed or cleaved from the peptide to expose a new terminal amino acid. In some embodiments, the terminal amino acid is an NTAA. In other embodiments, the terminal amino acid is a CTAA. Cleavage of a terminal amino acid can be accomplished by any number of known techniques, including chemical cleavage and enzymatic cleavage. In some embodiments, an engineered enzyme that catalyzes or reagent that promotes the removal of the PITC-derivatized or other labeled N-terminal amino acid is used. In some embodiments, the terminal amino acid is removed or eliminated using any of the methods as described in International Patent Publication No. WO 2019/089846. In some embodiments, cleavage of a terminal amino uses a carboxypeptidase, an aminopeptidase, a dipeptidyl peptidase, a dipeptidyl aminopeptidase or a variant, mutant, or modified protein thereof; a hydrolase or a variant, mutant, or modified protein thereof; a mild Edman degradation reagent; an Edmanase enzyme; anhydrous TFA, a base; or any combination thereof. In some embodiments, the mild Edman degradation uses a dichloro or monochloro acid; the mild Edman degradation uses TFA, TCA, or DCA; or the mild Edman degradation uses triethylamine, triethanolamine, or triethylammonium acetate ($Et_3NHOAc$).

In some cases, the reagent for removing the amino acid comprises a base. In some embodiments, the base is a hydroxide, an alkylated amine, a cyclic amine, a carbonate buffer, trisodium phosphate buffer, or a metal salt. In some examples, the hydroxide is sodium hydroxide; the alkylated amine is selected from methylamine, ethylamine, propylamine, dimethylamine, diethylamine, dipropylamine, trimethylamine, triethylamine, tripropylamine, cyclohexylamine, benzylamine, aniline, diphenylamine, N,N-Diisopropylethylamine (DIPEA), and lithium diisopropylamide (LDA); the cyclic amine is selected from pyridine, pyrimidine, imidazole, pyrrole, indole, piperidine, prolidine, 1,8-diazabicyclo[5.4.0]undec-7-ene (DBU), and 1,5-diazabicyclo[4.3.0]non-5-ene (DBN); the carbonate buffer comprises sodium carbonate, potassium carbonate, calcium carbonate, sodium bicarbonate, potassium bicarbonate, or calcium bicarbonate; the metal salt comprises silver; or the metal salt is $AgClO_4$.

Enzymatic cleavage of a NTAA may be accomplished by an aminopeptidase or other peptidases. Aminopeptidases naturally occur as monomeric and multimeric enzymes, and may be metal or ATP-dependent. Natural aminopeptidases have very limited specificity, and generically cleave N-terminal amino acids in a processive manner, cleaving one amino acid off after another. For the methods described here, aminopeptidases (e.g., metalloenzymatic aminopeptidase) may be engineered to possess specific binding or catalytic activity to the NTAA only when modified with an N-terminal label. For example, an aminopeptidase may be engineered such than it only cleaves an N-terminal amino acid if it is modified by a group such as PTC, modified-PTC, Cbz, DNP, SNP, acetyl, guanidinyl, diheterocyclic methanimine, etc. In this way, the aminopeptidase cleaves only a single amino acid at a time from the N-terminus, and allows control of the degradation cycle. In some embodiments, the modified aminopeptidase is non-selective as to amino acid residue identity while being selective for the N-terminal label. In other embodiments, the modified aminopeptidase is selective for both amino acid residue identity and the N-terminal label. Engineered aminopeptidase mutants that bind to and cleave individual or small groups of labelled (biotinylated) NTAAs have been described (see, PCT Publication No. WO2010/065322).

Engineered aminopeptidase mutants that bind to and cleave individual or small groups of labelled (biotinylated) NTAAs have been described (see, PCT Publication No. WO2010/065322, incorporated by reference in its entirety). Aminopeptidases are enzymes that cleave amino acids from the N-terminus of proteins or peptides. Natural aminopeptidases have very limited specificity, and generically eliminate N-terminal amino acids in a processive manner, cleaving one amino acid off after another (Kishor et al., 2015, Anal. Biochem. 488:6-8). However, residue specific aminopeptidases have been identified (Eriquez et al., J. Clin. Microbiol. 1980, 12:667-71; Wilce et al., 1998, Proc. Natl. Acad. Sci. USA 95:3472-3477; Liao et al., 2004, Prot. Sci. 13:1802-10). Aminopeptidases may be engineered to specifically bind to 20 different NTAAs representing the standard amino acids that are labeled with a specific moiety (e.g., PTC, DNP, SNP, etc.). Control of the stepwise degradation of the N-terminus of the peptide is achieved by using engineered aminopeptidases that are only active (e.g., binding activity or catalytic activity) in the presence of the label. In another example, Havranak et al. (U.S. Patent Publication No. US 2014/0273004) describes engineering aminoacyl tRNA synthetases (aaRSs) as specific NTAA binders. The amino acid binding pocket of the aaRSs has an intrinsic ability to bind cognate amino acids, but generally exhibits poor binding affinity and specificity. Moreover, these natural amino acid binders don't recognize N-terminal labels. Directed evolution of aaRS scaffolds can be used to generate higher affinity, higher specificity binding agents that recognized the N-terminal amino acids in the context of an N-terminal label.

In certain embodiments, the aminopeptidase may be engineered to be non-specific, such that it does not selectively recognize one particular amino acid over another, but rather just recognizes the labeled N-terminus. In yet another embodiment, cyclic cleavage is attained by using an engineered acylpeptide hydrolase (APH) to cleave an acetylated NTAA. In yet another embodiment, amidination (guanidinylation) of the NTAA is employed to enable mild cleavage of the labeled NTAA using NaOH (Hamada, (2016) Bioorg Med Chem Lett 26(7): 1690-1695).

In some embodiments, the method further comprises contacting the polypeptide with a proline aminopeptidase under conditions suitable to cleave an N-terminal proline before step (b). In some examples, a proline aminopeptidase (PAP) is an enzyme that is capable of specifically cleaving an N-terminal proline from a polypeptide. PAP enzymes that cleave N-terminal prolines are also referred to as proline iminopeptidases (PIPs). Known monomeric PAPs include family members from *B. coagulans, L. delbrueckii, N. gonorrhoeae, F. meningosepticum, S. marcescens, T. acidophilum, L. plantarum* (MEROPS 533.001) Nakajima et al., J Bacteriol. (2006) 188(4):1599-606; Kitazono et al., Bacteriol (1992) 174(24):7919-7925). Known multimeric PAPs including *D. hansenii* (Bolumar et al., (2003) 86(1-2):141-151) and similar homologues from other species (Basten et al., Mol Genet Genomics (2005) 272(6):673-679). Either native or engineered variants/mutants of PAPs may be employed.

For embodiments relating to CTAA binding agents, methods of cleaving CTAA from polypeptides are also known in the art. For example, U.S. Pat. No. 6,046,053 discloses a method of reacting the peptide or protein with an alkyl acid anhydride to convert the carboxy-terminal into oxazolone, liberating the C-terminal amino acid by reaction with acid and alcohol or with ester. Enzymatic cleavage of a CTAA may also be accomplished by a carboxypeptidase. Several carboxypeptidases exhibit amino acid preferences, e.g., carboxypeptidase B preferentially cleaves at basic amino acids, such as arginine and lysine. As described above, carboxypeptidases may also be modified in the same fashion as aminopeptidases to engineer carboxypeptidases that specifically bind to CTAAs having a C-terminal label. In this way, the carboxypeptidase cleaves only a single amino acid at a time from the C-terminus, and allows control of the degradation cycle. In some embodiments, the modified carboxypeptidase is non-selective as to amino acid residue identity while being selective for the C-terminal label. In other embodiments, the modified carboxypeptidase is selective for both amino acid residue identity and the C-terminal label.

H. Analysis

In some embodiments, the extended recording tag generated from performing the provided methods comprises information transferred from one or more coding tags. In some embodiments, the extended recording tags further comprise identifying information from one or more coding tags. In some embodiments, the extended recording tags are amplified (or a portion thereof) prior to determining at least the sequence of the coding tag(s) in the extended recording tag. In some embodiments, the extended recording tags (or a portion thereof) are released prior to determining at least the sequence of the coding tag(s) in the extended recording tag. In some embodiments, the transferred secondary sequences are analyzed.

The extended nucleic acid (e.g., recording tag) is any nucleic acid molecule or sequenceable polymer molecule (see, e.g., Niu et al., 2013, Nat. Chem. 5:282-292; Roy et al., 2015, Nat. Commun. 6:7237; Lutz, 2015, Macromolecules 48:4759-4767; each of which are incorporated by reference in its entirety) that comprises identifying information for a macromolecule, e.g., a polypeptide. The length of the final extended recording tag generated by the methods described herein is dependent upon multiple factors, including the length of the coding tag(s) (e.g., barcode and spacer), the length of the nucleic acids (e.g., optionally including any unique molecular identifier, spacer, universal priming site, barcode, or combinations thereof). After transfer of the final tag information to the extended nucleic acid (e.g., from any coding tags), the tag can be capped by addition of a universal reverse priming site via ligation, primer extension or other methods known in the art. In some embodiments, the universal forward priming site in the nucleic acid (e.g., on the recording tag) is compatible with the universal reverse priming site that is appended to the final extended nucleic acid. In some embodiments, a universal reverse priming site is an Illumina P7 primer (5'-CAAGCAGAAGACGGCATACGAGAT-3'-SEQ ID NO:2) or an Illumina P5 primer (5'-AATGATACGGCGACCACCGA-3'-SEQ ID NO:1). The sense or antisense P7 may be appended, depending on strand sense of the nucleic acid to which the identifying information from the secondary or coding tag is transferred to. An extended nucleic acid library can be cleaved or amplified directly from the support (e.g., beads) and used in traditional next generation sequencing assays and protocols.

In some embodiments, a primer extension reaction is performed on a library of single stranded extended nucleic acids (e.g., extended on the recording tag) to copy complementary strands thereof. In some embodiments, the polypeptide sequencing assay (e.g., ProteoCode assay), comprises several chemical and enzymatic steps in a cyclical progression.

Extended nucleic acid recording tags can be processed and analysed using a variety of nucleic acid sequencing methods. In some embodiments, extended recording tags containing the information from one or more secondary or coding tags and any other nucleic acid components are processed and analysed. In some embodiments, the collection of extended recording tags can be concatenated. In some embodiments, the extended recording tag can be amplified prior to determining the sequence.

In some embodiments, the recording tag or extended recording tag comprises information from one or more secondary or coding tags is analysed and/or sequenced. In some embodiments, the method includes analyzing the identifying information regarding the binding agent of the macromolecule analysis assay transferred to the recording tag.

Examples of sequencing methods include, but are not limited to, chain termination sequencing (Sanger sequencing); next generation sequencing methods, such as sequencing by synthesis, sequencing by ligation, sequencing by hybridization, polony sequencing, ion semiconductor sequencing, and pyrosequencing; and third generation sequencing methods, such as single molecule real time sequencing, nanopore-based sequencing, duplex interrupted sequencing, and direct imaging of DNA using advanced microscopy.

Suitable sequencing methods for use in the invention include, but are not limited to, the following methods known in the art, such as sequencing by hybridization, sequencing by synthesis technology (e.g., HiSeq™ and Solexa™, Illumina), SMRT™ (Single Molecule Real Time) technology (Pacific Biosciences), true single molecule sequencing (e.g., HeliScope™, Helicos Biosciences), massively parallel next generation sequencing (e.g., SOLiD™, Applied Biosciences; Solexa and HiSeq™, Illumina), massively parallel semiconductor sequencing (e.g., Ion Torrent), pyrosequencing technology (e.g., GS FLX and GS Junior Systems, Roche/454), nanopore sequence (e.g., Oxford Nanopore Technologies).

A library of nucleic acids (e.g., extended nucleic acids) may be amplified in a variety of ways. A library of nucleic acids (e.g., recording tags comprising information from one or more secondary or coding tags) undergo exponential amplification, e.g., via PCR or emulsion PCR. Emulsion PCR is known to produce more uniform amplification (Hori, Fukano et al., Biochem Biophys Res Commun (2007) 352 (2): 323-328). Alternatively, a library of nucleic acids (e.g., extended nucleic acids) may undergo linear amplification, e.g., via in vitro transcription of template DNA using T7 RNA polymerase. The library of nucleic acids (e.g., extended nucleic acids) can be amplified using primers compatible with the universal forward priming site and universal reverse priming site contained therein. A library of nucleic acids (e.g., the recording tag) can also be amplified using tailed primers to add sequence to either the 5'-end, 3'-end or both ends of the extended nucleic acids. Sequences that can be added to the termini of the extended nucleic acids include library specific index sequences to allow multiplexing of multiple libraries in a single sequencing run, adaptor sequences, read primer sequences, or any other sequences for making the library of extended nucleic acids compatible for a sequencing platform. An example of a library amplification in preparation for next generation sequencing is as follows: a 20 µl PCR reaction volume is set up using an extended nucleic acid library eluted from ~1 mg of beads (~10 ng), 200 µM dNTP, 1 µM of each forward and reverse amplification primers, 0.5 µl (1 U) of Phusion Hot Start enzyme (New England Biolabs) and subjected to the following cycling conditions: 98° C. for 30 sec followed by 20 cycles of 98° C. for 10 sec, 60° C. for 30 sec, 72° C. for 30 sec, followed by 72° C. for 7 min, then hold at 4° C.

In certain embodiments, either before, during or following amplification, the library of nucleic acids (e.g., extended nucleic acids) can undergo target enrichment. In some embodiments, target enrichment can be used to selectively capture or amplify extended nucleic acids representing macromolecules (e.g., polypeptides) of interest from a library of extended nucleic acids before sequencing. In some aspects, target enrichment for protein sequencing is challenging because of the high cost and difficulty in producing highly-specific binding agents for target proteins. In some cases, antibodies are notoriously non-specific and difficult to scale production across thousands of proteins. In some embodiments, the methods of the present disclosure circumvent this problem by converting the protein code into a nucleic acid code which can then make use of a wide range of targeted DNA enrichment strategies available for DNA libraries. In some cases, peptides of interest can be enriched in a sample by enriching their corresponding extended nucleic acids. Methods of targeted enrichment are known in the art, and include hybrid capture assays, PCR-based assays such as TruSeq custom Amplicon (Illumina), padlock probes (also referred to as molecular inversion probes), and the like (see, Mamanova et al., (2010) Nature Methods 7: 111-118; Bodi et al., J. Biomol. Tech. (2013) 24:73-86; Ballester et al., (2016) Expert Review of Molecular Diagnostics 357-372; Mertes et al., (2011) Brief Funct. Genomics 10:374-386; Nilsson et al., (1994) Science 265:2085-8; each of which are incorporated herein by reference in their entirety).

In one embodiment, a library of nucleic acids (e.g., extended recording tags) is enriched via a hybrid capture-based assay. In a hybrid-capture based assay, the library of extended nucleic acids is hybridized to target-specific oligonucleotides that are labeled with an affinity tag (e.g., biotin). Extended nucleic acids hybridized to the target-specific oligonucleotides are "pulled down" via their affinity tags using an affinity ligand (e.g., streptavidin coated beads), and background (non-specific) extended nucleic acids are washed away. The enriched extended nucleic acids (e.g., extended nucleic acids) are then obtained for positive enrichment (e.g., eluted from the beads). In some embodiments, oligonucleotides complementary to the corresponding extended nucleic acid library representations of peptides of interest can be used in a hybrid capture assay. In some embodiments, sequential rounds or enrichment can also be carried out, with the same or different bait sets.

To enrich the entire length of a polypeptide in a library of extended nucleic acids representing fragments thereof (e.g., peptides), "tiled" bait oligonucleotides can be designed across the entire nucleic acid representation of the protein.

In another embodiment, primer extension and ligation-based mediated amplification enrichment (AmpliSeq, PCR, TruSeq TSCA, etc.) can be used to select and module fraction enriched of library elements representing a subset of polypeptides. Competing oligonucleotides can also be employed to tune the degree of primer extension, ligation, or amplification. In the simplest implementation, this can be accomplished by having a mix of target specific primers comprising a universal primer tail and competing primers lacking a 5' universal primer tail. After an initial primer extension, only primers with the 5' universal primer sequence can be amplified. The ratio of primer with and without the universal primer sequence controls the fraction of target amplified. In other embodiments, the inclusion of hybridizing but non-extending primers can be used to modulate the fraction of library elements undergoing primer extension, ligation, or amplification.

Targeted enrichment methods can also be used in a negative selection mode to selectively remove extended nucleic acids from a library before sequencing. Examples of undesirable extended nucleic acids that can be removed are those representing over abundant polypeptide species, e.g., for proteins, albumin, immunoglobulins, etc.

A competitor oligonucleotide bait, hybridizing to the target but lacking a biotin moiety, can also be used in the hybrid capture step to modulate the fraction of any particular locus enriched. The competitor oligonucleotide bait competes for hybridization to the target with the standard biotinylated bait effectively modulating the fraction of target pulled down during enrichment. The ten orders dynamic range of protein expression can be compressed by several orders using this competitive suppression approach, especially for the overly abundant species such as albumin. Thus, the fraction of library elements captured for a given locus relative to standard hybrid capture can be modulated from 100% down to 0% enrichment.

Additionally, library normalization techniques can be used to remove overly abundant species from the extended nucleic acid library. This approach works best for defined length libraries originating from peptides generated by site-specific protease digestion such as trypsin, LysC, GluC, etc. In one example, normalization can be accomplished by denaturing a double-stranded library and allowing the library elements to re-anneal. The abundant library elements re-anneal more quickly than less abundant elements due to the second-order rate constant of bimolecular hybridization kinetics (Bochman, Paeschke et al. 2012). The ssDNA library elements can be separated from the abundant dsDNA library elements using methods known in the art, such as chromatography on hydroxyapatite columns (VanderNoot, et al., 2012, Biotechniques 53:373-380) or treatment of the library with a duplex-specific nuclease (DSN) from Kamchatka crab (Shagin et al., (2002) Genome Res. 12:1935-42) which destroys the dsDNA library elements.

Any combination of fractionation, enrichment, and subtraction methods, of the polypeptides before attachment to the support and/or of the resulting extended nucleic acid library can economize sequencing reads and improve measurement of low abundance species.

In some embodiments, a library of nucleic acids (e.g., extended nucleic acids) is concatenated by ligation or end-complementary PCR to create a long DNA molecule comprising multiple different extended recorder tags, extended coding tags, or di-tags, respectively (Du et al., (2003) BioTechniques 35:66-72; Muecke et al., (2008) Structure 16:837-841; U.S. Pat. No. 5,834,252, each of which is incorporated by reference in its entirety). This embodiment is preferable for nanopore sequencing in which long strands of DNA are analyzed by the nanopore sequencing device.

In some embodiments, direct single molecule analysis is performed on the nucleic acids (e.g., extended nucleic acids) (see, e.g., Harris et al., (2008) Science 320:106-109). The nucleic acids (e.g., extended nucleic acids) can be analysed directly on the support, such as a flow cell or beads that are compatible for loading onto a flow cell surface (optionally microcell patterned), wherein the flow cell or beads can integrate with a single molecule sequencer or a single molecule decoding instrument. For single molecule decoding, hybridization of several rounds of pooled fluorescently-labeled of decoding oligonucleotides (Gunderson et al., (2004) Genome Res. 14:970-7) can be used to ascertain both the identity and order of the secondary or coding tags within the extended nucleic acids (e.g., on the recording tag). In some embodiments, the binding agents may be labeled with cycle-specific coding tags as described above (see also, Gunderson et al., (2004) Genome Res. 14:970-7).

Following sequencing of the nucleic acid libraries (e.g., of extended nucleic acids), the resulting sequences can be collapsed by their UMIs if used and then associated to their corresponding polypeptides and aligned to the totality of the proteome. Resulting sequences can also be collapsed by their compartment tags and associated to their corresponding compartmental proteome, which in a particular embodiment contains only a single or a very limited number of protein molecules. Both protein identification and quantification can easily be derived from this digital peptide information.

The methods disclosed herein can be used for analysis, including detection, quantitation and/or sequencing, of a plurality of macromolecules simultaneously (multiplexing). Multiplexing as used herein refers to analysis of a plurality of macromolecules (e.g. polypeptides) in the same assay. The plurality of macromolecules can be derived from the same sample or different samples. The plurality of macromolecules can be derived from the same subject or different subjects. The plurality of macromolecules that are analyzed can be different macromolecules, or the same macromolecule derived from different samples. A plurality of macromolecules includes 2 or more macromolecules, 5 or more macromolecules, 10 or more macromolecules, 50 or more macromolecules, 100 or more macromolecules, 500 or more macromolecules, 1,000 or more macromolecules, 5,000 or more macromolecules, 10,000 or more macromolecules, 50,000 or more macromolecules, 100,000 or more macromolecules, 500,000 or more macromolecules, or 1,000,000 or more macromolecules.

Kits and Articles of Manufacture

Provided herein are kits and articles of manufacture comprising components for preforming a binding reaction by forming a stable complex of binding agents, targets, and the stabilizing components associated. In some embodiments, the kits further contain other reagents for treating and analyzing the target macromolecules (e.g., proteins, polypeptides, or peptides). The kits and articles of manufacture may include any one or more of the reagents and components used in the methods described in Section I and II. In some embodiments, the kit comprises reagents for preparing samples for preforming the binding reaction, such as for preparing targets from a sample and joining with stabilizing components. In some embodiments, the kit comprises a plurality of binding agents wherein each binding agent is associated with one or more stabilizing components. In some aspects, the kits contain components for performing a binding reaction comprising contacting a binding agent with a target, wherein the binding agent and the target each comprises or is associated with a stabilizing component; allowing the binding agent to interact with a binding site located on the target; and linking the stabilizing components to form a stable complex; wherein each of the stabilizing components is attached to or associated with the binding agent and the target, respectively, at a site different from the binding site between the binding agent and the target. In some embodiments, the kits optionally include instructions for performing the binding reaction.

In some embodiments, the kits comprise one or more of the following components: binding agent(s), stabilizing component(s), linking agent(s), solid support(s), recording tag(s), reagent(s) for attaching the stabilizing components, reagent(s) for transferring information, sequencing reagent(s), and/or any reagents as described in the methods for performing the binding reaction and analyzing macromolecules (e.g., proteins, polypeptides, or peptides), enzyme(s), buffer(s), etc.

In some embodiments, the kits also include other components for treating the macromolecules (e.g., proteins, polypeptides, or peptides), preforming a binding reaction, and analysis of the same including other reagent(s) for analysis of the target. In one aspect, provided herein are components used to prepare a reaction mixture. In preferred embodiments, the reaction mixture is a solution. In preferred embodiments, the reaction mixture includes one or more of the following: stabilizing component(s), linking agent(s), solid support(s), recording tag(s), reagent(s) for attaching or associating the stabilizing components, reagent(s) for transferring information, sequencing reagent(s), binding agent(s) with associated stabilizing component(s) and/or coding tag(s), buffer(s).

In another aspect, disclosed herein is a kit for performing a binding reaction comprising a library of binding agents, wherein each binding agent comprises or is associated with one or more stabilizing components, and a coding tag comprising identifying information regarding the binding moiety. In some examples, the binding moiety is capable of binding to one or more N-terminal, internal, or C-terminal amino acids of the target peptide, or capable of binding to the one or more N-terminal, internal, or C-terminal amino acids of a peptide modified by a functionalizing reagent. In some cases, the kit also includes linking agents, wherein the linking agent comprises a chemical reagent, a non-biological reagent, a biological reagent, or a combination thereof. In some cases, the linking agent comprises a polypeptide or protein. In some cases, the linking agent comprises a metal ion.

In some embodiments, the kit includes a binding agent comprising a coding tag, which comprises identifying information regarding the binding agent; an adaptor molecule comprising a first hybridization sequence substantially complementary to at least a portion of the coding tag, and a secondary tag. In some embodiment, the binding agent is configured to bind a macromolecule associated with a recording tag and reagents for transferring information from the secondary tag from the adaptor molecule to the recording tag are also provided. In some aspects, the kit includes a plurality or set of adaptor molecules. In some aspects, the kit includes a plurality or set of binding agents. In some embodiments, the set of binding agents is configured to be compatible with the set of adaptor molecules. In one aspect, provided herein are components used to prepare a reaction mixture. In some preferred embodiments, the reaction mixture is a solution. In preferred embodiments, the reaction mixture includes one or more of the following: adaptor molecule(s), binding agent(s) and associated coding tag(s), solid support(s), recording tag(s), reagent(s) for transferring information, sequencing reagent(s), and/or buffer(s). In some embodiments, the kit comprises: a binding agent comprising a coding tag, which comprises identifying information regarding the binding agent, wherein the binding agent is configured to bind a macromolecule associated with a first stabilizing component and with a recording tag joined to a support, and wherein the binding agent is associated with a second stabilizing component; the recording tag associated with the first stabilizing component; a linking agent configured to linking the first and second stabilizing components together after binding of the binding agent to the macromolecule to form a stable complex comprising the binding agent, the macromolecule and the stabilizing components. The kit may also comprise an adaptor molecule comprising a first hybridization sequence substantially complementary to at least a portion of the coding tag, and a secondary tag, wherein an information of the secondary tag is configured for transfer from the adaptor molecule to the recording tag to generate an extended recording tag after the coding tag associated with the binding agent hybridizes with the first hybridization sequence on the adaptor molecule.

In some embodiments, the kits and articles of manufacture further comprise a plurality of nucleic acid molecules or oligonucleotides. In some embodiments, the kits include a plurality of barcodes. The barcode(s) may include a compartment barcode, a partition barcode, a sample barcode, a fraction barcode, or any combination thereof. In some cases, the barcode comprises a unique molecule identifier (UMI). In some examples, the barcode comprises a DNA molecule, DNA with pseudo-complementary bases, an RNA molecule, a BNA molecule, an XNA molecule, a LNA molecule, a PNA molecule, a γPNA molecule, a non-nucleic acid sequenceable polymer, e.g., a polysaccharide, a polypeptide, a peptide, or a polyamide, or a combination thereof. In some embodiments, the barcodes are configured to attach the target macromolecules, e.g., the proteins, in the sample or to attach to nucleic components associated with the targets.

In some embodiments, the kit further comprises reagents for treating the target macromolecules, e.g., the proteins. Any combination of fractionation, enrichment, and subtraction methods, of the proteins may be performed. For example, the reagent may be used to fragment or digest the proteins. In some cases, the kit comprises reagents and components to fractionate, isolate, subtract, enrich proteins. In some examples, the kits further comprises a protease such as trypsin, LysN, or LysC. In some embodiments, the kit comprises a support for immobilizing the one or more targets and reagents for immobilizing the target on a support.

In some embodiments, the kit also comprises one or more buffers or reaction fluids necessary for any of the binding reaction to occur. Buffers including wash buffers, reaction buffers, and binding buffers, elution buffers and the like are known to those or ordinary skill in the arts. In some embodiments, the kits further include buffers and other components to accompany other reagents described herein. The reagents, buffers, and other components may be provided in vials (such as sealed vials), vessels, ampules, bottles, jars, flexible packaging (e.g., sealed Mylar or plastic bags), and the like. Any of the components of the kits may be sterilized and/or sealed.

In some embodiments, the kit includes one or more reagents for nucleic acid sequence analysis. In some examples, the reagent for sequence analysis is for use in sequencing by synthesis, sequencing by ligation, single molecule sequencing, single molecule fluorescent sequencing, sequencing by hybridization, polony sequencing, ion semiconductor sequencing, pyrosequencing, single molecule real-time sequencing, nanopore-based sequencing, or direct imaging of DNA using advanced microscopy, or any combination thereof.

In addition to above-mentioned components, the subject kits may further include instructions for using the components of the kit to practice the subject methods, i.e., instructions for sample preparation, treatment and/or analysis. In some embodiments, the instructions are directed to methods of performing the binding reaction with target macromolecules (e.g., proteins, polypeptides, or peptides). The kits described herein may also include other materials desirable from a commercial and user standpoint, including other buffers, diluents, filters, syringes, and package inserts with instructions for performing any methods described herein.

Any of the above-mentioned kit components, and any molecule, molecular complex or conjugate, reagent (e.g., chemical or biological reagents), agent, structure (e.g., support, surface, particle, or bead), reaction intermediate, reaction product, binding complex, or any other article of manufacture disclosed and/or used in the exemplary kits and methods, may be provided separately or in any suitable combination in order to form a kit.

IV. EXEMPLARY EMBODIMENTS

Among the provided embodiments are:

1. A method for performing a binding reaction, comprising:
contacting a binding agent with a target, wherein the binding agent and the target each comprises or is associated with a stabilizing component;
allowing the binding agent to interact with a binding site located on the target; and
linking the stabilizing components to form a stable complex comprising the binding agent, the target and the stabilizing components;
wherein the stabilizing components are attached to or associated with the binding agent and the target, respectively, at a site different from the binding site between the binding agent and the target.

2. The method of embodiment 1, wherein the stabilizing components are linked directly or indirectly to the binding agent and the target, respectively.

3. The method of embodiment 1 or embodiment 2, wherein the stabilizing components are linked upon introduction to light.

4. The method of embodiment 1 or embodiment 2, wherein the stabilizing components are linked upon introduction to a linking agent.

5. The method of embodiment 4, wherein the linking agent comprises a chemical reagent, a non-biological reagent, a biological reagent, or a combination thereof.

6. The method of embodiment 4, wherein the linking agent comprises a polypeptide or a protein.

7. The method of embodiment 4, wherein the linking agent comprises a metal ion.

8. The method of any one of embodiments 1-7, wherein the stabilizing components each comprises a biological molecule, a chemical molecule, a small molecule or a combination thereof.

9. The method of embodiment 8, wherein the stabilizing components each comprises a polynucleotide.

10. The method of embodiment 9, wherein the linking agent comprises at least one polynucleotide or nucleic acid comprising a sequence which hybridizes to at least one of the stabilizing components.

11. The method of any one of embodiments 4-10, wherein after introduction of the linking agent, the stabilizing components interact with each other and/or the stabilizing components interact with the linking agent.

12. The method of any one of embodiments 3-11, wherein the light or linking agent induces uncaging of one or both of the stabilizing components, deblocking of one or both of the stabilizing components, isomerization of the stabilizing components, hybridization of the stabilizing components, and/or binding of the stabilizing components.

13. The method of any one of embodiments 1-12, wherein the target is immobilized on a support, e.g., a solid support.

14. The method of embodiment 13, wherein the target is directly or indirectly immobilized on a support, e.g., a solid support.

15. The method of any one of embodiments 1-14, wherein the target is associated or joined with a recording tag.

16. The method of embodiment 15, wherein the associated or joined recording tag is covalently joined to a support, e.g., a solid support.

17. The method of any one of embodiments 13-16, wherein the support is a three-dimensional support (e.g., a porous matrix or a bead).

18. The method of embodiment 17, wherein the support is a polystyrene bead, a polyacrylate bead, a polymer bead, an agarose bead, a cellulose bead, a dextran bead, an acrylamide bead, a solid core bead, a porous bead, a paramagnetic bead, a glass bead, a controlled pore bead, a silica-based bead, or a combination thereof.

19. The method of any one of embodiments 15-18, wherein the recording tag is a DNA molecule, an RNA molecule, a PNA molecule, a BNA molecule, an XNA, molecule, an LNA molecule, a γPNA molecule, or a combination thereof.

20. The method of any one of embodiments 1-19, wherein the method comprises contacting a single binding agent with a single target, a single binding agent with a plurality of targets, a plurality of binding agents with a single target, or a plurality of binding agents with a plurality of targets.

21. The method of any one of embodiments 1-20, wherein the binding agent provides specificity for binding of the binding agent to the target.

22. The method of any one of embodiments 1-21, wherein the stabilizing components associated with the binding agent and the target are linked after the binding agent interacts with the target.

23. The method of any one of embodiments 3-22, wherein introduction of the light or linking agent provides temporal control over the linking of the stabilizing components.

24. The method of any one of embodiments 1-23, wherein the relative affinity of stabilizing components to each other or to the linking agent is at least as high as the affinity of the binding agent to the target.

25. The method of any one of embodiments 15-24, further comprising transferring information of a coding tag with identifying information regarding the binding agent to the recording tag associated with the target to generate an extended recording tag.

26. The method of embodiment 25, wherein transferring information of the coding tag to the recording tag is performed after introducing the light or linking agent.

27. The method of embodiment 25 or embodiment 26, wherein the transferring information comprises contacting the stable complex with a reagent for transferring the identifying information.

28. The method of embodiment 27, wherein the reagent for transferring the identifying information is a chemical ligation reagent or a biological ligation reagent.

29. The method of embodiment 27, wherein the reagent for transferring the identifying information is a reagent for primer extension of single-stranded nucleic acid or double-stranded nucleic acid.

30. The method of any one of embodiments 1-29, further comprising disrupting the stable complex.

31. The method of embodiment 30, wherein the stable complex is disrupted after the transfer of information from the coding tag to the recording tag.

32. The method of embodiment 30 or embodiment 31, wherein the disrupting is conducted by removing the linking agent from the stable complex.

33. The method of any one of embodiments 30-32, wherein the disrupting is conducted by introducing a destabilizing agent.

34. The method of embodiment 33, wherein the destabilizing agent comprises heat, a denaturing agent, an enzyme, or a competitor molecule.

35. The method of embodiment 34, wherein the competitor molecule is a competitor for binding of or to the binding agent, the linking agent, and/or the stabilizing component(s).

36. The method of any one of embodiments 1-35, wherein the method further comprises a wash step after allowing the binding agent to interact with the binding site located on the target.

37. The method of embodiment 36, wherein the linking agent is added after the wash step.

38. The method of any one of embodiments 25-37, wherein the linking of the stabilizing components forms a complex adequately or sufficiently stable for information transfer to occur from the coding tag to the recording tag.

39. The method of any one of embodiments 25-38, wherein contacting the binding agent with the target is performed before transferring information from the coding tag associated with the binding agent to the recording tag associated with the target.

40. The method of any one of embodiments 1-39, further comprising removing the binding agent.

41. The method of embodiment 40, wherein removing the binding agent is performed after transferring information from the coding tag associated with the binding agent to the recording tag associated with the target.

42. The method of any one of embodiments 1-41, wherein the target is a macromolecule.

43. The method of embodiment 42, wherein the macromolecule comprises a polypeptide.

44. The method of embodiment 43, wherein the macromolecule comprises a protein or peptide.

45. The method of embodiment 44, wherein the peptide is obtained by fragmenting protein(s), e.g., protein(s) from a biological sample.

46. The method of embodiment 45, wherein the fragmenting is performed by contacting the protein(s) with a protease.

47. A method for analyzing a macromolecule comprising the steps of:
(a) providing a macromolecule and an associated recording tag joined to a support;
(b) contacting the macromolecule with a binding agent capable of binding to the macromolecule, wherein the binding agent comprises a coding tag with identifying information regarding the binding agent and the binding agent and the macromolecule each comprises or is associated with a stabilizing component;
(c) linking the stabilizing components to form a stable complex comprising the binding agent, the macromolecule and the stabilizing components;
(d) transferring the information of the coding tag to the recording tag to generate an extended recording tag; and analyzing the extended recording tag.

48. The method of embodiment 47, optionally repeating a cycle of steps (b), (c), and (d) one or more times prior to analyzing the extended recording tag.

49. The method of embodiment 47 or embodiment 48, wherein the stabilizing components are linked directly or indirectly to the binding agent and the macromolecule, respectively.

50. The method of any one of embodiments 47-49, wherein the stabilizing components are linked upon introduction to light.

51. The method of any one of embodiments 47-50, wherein the stabilizing components are linked upon introduction to a linking agent.

52. The method of embodiment 51, wherein the linking agent comprises a chemical reagent, a non-biological reagent, a biological reagent, or a combination thereof.

53. The method of embodiment 51, wherein the linking agent comprises a polypeptide or a protein.

54. The method of embodiment 51, wherein the linking agent comprises a metal ion.

55. The method of any one of embodiments 47-54, wherein the stabilizing components each comprises a biological molecule, a chemical molecule, a small molecule or a combination thereof.

56. The method of embodiment 55, wherein the stabilizing components each comprises a polynucleotide.

57. The method of embodiment 56, wherein the linking agent comprises at least one polynucleotide or nucleic acid comprising a sequence which hybridizes to at least one of the stabilizing components.

58. The method of any one of embodiments 51-57, wherein after introduction of the linking agent, the stabilizing components interact with each other and/or the stabilizing components interact with the linking agent.

59. The method of any one of embodiments 50-58, wherein the light or linking agent induces uncaging of one or both of the stabilizing components, deblocking of one or both of the stabilizing components, isomerization of the stabilizing components, hybridization of the stabilizing components, and/or binding of the stabilizing components.

60. The method of any one of embodiments 47-59, wherein the method comprises contacting a single binding agent with a single target, a single binding agent with a plurality of targets, a plurality of binding agents with a single target, or a plurality of binding agents with a plurality of macromolecules.

61. The method of any one of embodiments 47-60, wherein the binding agent provides specificity for binding of the binding agent to the macromolecule.

62. The method of any one of embodiments 47-61, wherein the stabilizing components associated with the binding agent and the macromolecule are linked after the binding agent interacts with the macromolecule.

63. The method of any one of embodiments 50-62, wherein introduction of the light or linking agent provides temporal control over the linking of the stabilizing components.

64. The method of any one of embodiments 47-63, wherein the relative affinity of stabilizing components to each other or to the linking agent is at least as high as the affinity of the binding agent to the target.

65. The method of any one of embodiments 47-64, wherein transferring the identifying information of the coding tag to the recording tag is effected by primer extension.

66. The method of any one of embodiments 47-64, wherein transferring the identifying information of the coding tag to the recording tag is effected by ligation.

67. The method of any one of embodiments 47-66, wherein the macromolecule comprises a polypeptide.

68. The method of embodiment 67, wherein the macromolecule comprises a protein or peptide.

69. The method of embodiment 68, wherein the peptide is obtained by fragmenting protein(s), e.g., protein(s) from a biological sample.

70. The method of embodiment 69, wherein the fragmenting is performed by contacting the protein(s) with a protease.

71. The method of any one of embodiments 47-70, wherein the associated recording tag is covalently joined to a support.

72. The method of any one of embodiments 47-71, wherein the macromolecule is indirectly joined to a support.

73. The method of any one of embodiments 47-72, wherein the support is a three-dimensional support (e.g., a porous matrix or a bead).

74. The method of embodiment 73, wherein the support is a polystyrene bead, a polyacrylate bead, a polymer bead, an agarose bead, a cellulose bead, a dextran bead, an acrylamide bead, a solid core bead, a porous bead, a paramagnetic bead, a glass bead, a controlled pore bead, a silica-based bead, or a combination thereof.

75. The method of any one of embodiments 47-74, wherein the recording tag is a DNA molecule, an RNA molecule, a PNA molecule, a BNA molecule, an XNA, molecule, an LNA molecule, a γPNA molecule, or a combination thereof.

76. The method of any one of embodiments 47-75, wherein the recording tag comprises a unique molecular identifier (UMI).

77. The method of any one of embodiments 47-76, wherein the stabilizing components are attached to or associated with the binding agent and the macromolecule, respectively, at a site different from the binding site between the binding agent and the macromolecule.

78. The method of any one of embodiments 68-77, wherein the binding agent is configured to bind to a C-terminal amino acid residue of the protein or peptide.

79. The method of any one of embodiments 68-77, wherein the binding agent is configured to bind to an N-terminal amino acid residue of the protein or peptide.

80. The method of any one of embodiments 68-79, further comprising (e) removing the N-terminal amino acid (NTAA) of the protein or peptide to expose a new NTAA of the protein or peptide.

81. The method of embodiment 80, wherein a cycle of steps (b), (c), (d) and (e) is repeated one or more times prior to analyzing the extended recording tag.

82. The method of any one of embodiments 68-81, further comprising treating the protein or peptide with a reagent for modifying a terminal amino acid of the protein or peptide.

83. The method of embodiment 82, wherein the reagent for modifying a terminal amino acid of a polypeptide comprises a chemical agent or an enzymatic agent.

84. The method of any one of embodiments 1-83, further comprising removing the binding agent.

85. The method of any one of embodiments 47-84, further comprising adding a universal priming site to the extended recording tag.

86. The method of any one of embodiments 47-85, wherein one or more extended recording tags are amplified prior to analysis.

87. The method of any one of embodiments 47-86, wherein the extended recording tag is analyzed using a nucleic acid sequencing method.

88. The method of embodiment 87, wherein the nucleic acid sequencing method is sequencing by synthesis, sequencing by ligation, sequencing by hybridization, polony sequencing, ion semiconductor sequencing, or pyrosequencing.

89. The method of embodiment 87 or embodiment 88, wherein the nucleic acid sequencing method is single molecule real-time sequencing, nanopore-based sequencing, or direct imaging of DNA using advanced microscopy.

90. The method of any one of embodiments 25-89, wherein the binding agent and the coding tag are joined by a linker.

91. The method of any one of embodiments 25-90, wherein the coding tag comprises a UMI.

92. The method of any one of embodiments 25-91, wherein the coding tag comprises a universal priming site.

93. The method of any one of embodiments 15-89, wherein the recording tag comprises a universal priming site.

94. The method of any one of embodiments 1-93, wherein the binding agent is a polypeptide or protein.

95. The method of embodiment 94, wherein the binding agent is an aminopeptidase or variant, mutant, or modified protein thereof; an aminoacyl tRNA synthetase or variant, mutant, or modified protein thereof; an anticalin or variant, mutant, or modified protein thereof; a ClpS, ClpS2, or variant, mutant, or modified protein thereof; a UBR box protein or variant, mutant, or modified protein thereof; or a modified small molecule that binds amino acid(s), i.e. vancomycin or a variant, mutant, or modified molecule thereof; or an antibody or binding fragment thereof; or any combination thereof.

96. The method of any one of embodiments 1-95, wherein the binding agent binds to a single amino acid residue, a dipeptide, a tripeptide or a post-translational modification of the polypeptide.

97. A method for analyzing a macromolecule comprising the steps of:

(a) providing a macromolecule joined to a support, wherein the macromolecule comprises or is associated with a first stabilizing component;

(b) contacting the macromolecule with a binding agent capable of binding to the macromolecule, wherein the binding agent comprises or is associated with a second stabilizing component;

(c) after binding of the binding agent to the macromolecule, linking the first and second stabilizing components together to form a stable complex comprising the binding agent, the macromolecule and the stabilizing components;

(d) analyzing the macromolecule by obtaining an information about the binding agent bound to the macromolecule.

98. The method of embodiment 97, wherein the stabilizing components are linked upon introduction of a linking agent, and no covalent bonds are formed during formation of the stable complex.

99. The method of embodiment 97, wherein the stabilizing components are linked upon introduction to light.

100. The method of embodiment 97 or 98, wherein the linking agent comprises a polypeptide.

101. The method of embodiment 97 or 98, wherein the binding agent is fluorescently labeled to enable detection of the contact between the macromolecule and the binding agent; and analyzing the macromolecule comprises detecting fluorescence from the binding agent after contacting the macromolecule.

102. The method of any one of embodiments 97-101, wherein the first or second stabilizing component comprises a polynucleotide, and the linking agent comprises a linking polynucleotide that hybridizes to the polynucleotide of one of the stabilizing components.

103. The method of any one of embodiments 97-102, wherein the first stabilizing component is the same as the second stabilizing component.

104. The method of any one of embodiments 97-102, wherein the first stabilizing component has a lower affinity to the linking agent in comparison to an affinity of the second stabilizing component to the linking agent.

105. The method of any one of embodiments 97-104, wherein the method comprises contacting a plurality of binding agents with a single macromolecule, or contacting a plurality of binding agents with a plurality of macromolecules, and wherein at least one binding agent of the plurality of binding agents is capable of binding to the macromolecule and each binding agent of the plurality of binding agents comprises or is associated with the second stabilizing component.

106. The method of any one of embodiments 97-105, wherein the macromolecule comprises a polypeptide and the binding agent or a binding agent from the plurality of binding agents is capable of binding to a N-terminal amino acid (NTAA) of the polypeptide or to a modified NTAA of the polypeptide.

107. The method of embodiment 106, wherein analyzing the macromolecule comprises identifying at least one amino acid residue of the polypeptide.

108. The method of embodiment 107, wherein providing a macromolecule comprises providing the polypeptide associated with a recording tag; the binding agent or each binding agent from the plurality of binding agents comprises or is associated with a coding tag with identifying information regarding the binding agent; obtaining an information about the binding agent comprises transferring an information from the coding tag to the recording tag after binding of the binding agent to the macromolecule to generate an extended recording tag; and identifying at least one amino acid residue of the polypeptide comprises analyzing the extended recording tag.

109. The method of embodiment 108, further comprising: providing an adaptor molecule comprising a first hybridization sequence and a secondary tag, wherein the first hybridization sequence is substantially complementary to at least a portion of the coding tag, to allow hybridization between the first hybridization sequence and the coding tag; and transferring information of the secondary tag to the recording tag to generate an extended recording tag, wherein the information of the secondary tag is transferred from the adaptor molecule to the recording tag after the coding tag associated with the binding agent hybridizes with the first hybridization sequence on the adaptor molecule.

110. The method of embodiments 108 or embodiment 109, wherein transferring information of the coding tag to the recording tag or from secondary tag to the recording tag is performed after the stabilizing components are linked together.

111. The method of any one of embodiments 108-110, wherein the transferring information comprises contacting the coding tag with a reagent for transferring the identifying information, the reagent comprising a reagent for primer extension reaction, a chemical ligation reagent or a biological ligation reagent.

112. The method of any one of embodiments 108-111, wherein the stable complex is disrupted after the transfer of information from the coding tag to the recording tag by removing the linking agent from the stable complex or by introducing a destabilizing agent.

113. The method of any one of embodiments 108-112, further comprising contacting the polypeptide with a N-terminal modifier agent prior to binding of the binding agent to the polypeptide to form the modified NTAA of the polypeptide.

114. The method of embodiment 113, further comprising removing the modified NTAA of the polypeptide after transferring the information from the coding tag to the recording tag to expose a new NTAA of the polypeptide.

115. The method of embodiment 114, further comprising repeating steps of:

contacting the polypeptide with a N-terminal modifier agent to form the modified NTAA of the polypeptide; contacting the polypeptide with a binding agent capable of binding to the modified NTAA of the polypeptide or with a plurality of binding agents wherein at least one binding agent of the plurality of binding agents is capable of binding to the modified NTAA of the polypeptide, wherein each binding agent of the plurality of binding agents comprises or is associated with the second stabilizing component; and linking the first and second stabilizing components together to form a stable complex comprising the binding agent, the macromolecule and the stabilizing components; optionally, removing the modified NTAA of the polypeptide; at least one more time prior to analyzing the extended recording tag.

116. The method of any one of embodiments 108-115, wherein the extended recording tag is analyzed using a nucleic acid sequencing method.

117. A kit for analyzing a macromolecule, comprising: a binding agent comprising a coding tag, which comprises identifying information regarding the binding agent, wherein the binding agent is configured to bind a macromolecule associated with a first stabilizing component and with a recording tag joined to a support, and wherein the binding agent is associated with a second stabilizing component; the recording tag associated with the first stabilizing component; a linking agent configured to linking the first and second stabilizing components together after binding of the binding agent to the macromolecule to form a stable complex comprising the binding agent, the macromolecule and the stabilizing components.

118. The kit of embodiment 117, wherein the kit comprises a plurality of binding agents and wherein at least one binding agent of the plurality of binding agents is capable of binding to the macromolecule and each binding agent of the plurality of binding agents comprises or is associated with the second stabilizing component.

119. The kit of embodiment 117 or 118, wherein the macromolecule comprises a polypeptide.

120. The kit of any one of embodiments 117-119, wherein the coding tag and/or the recording tag comprises a unique molecular identifier (UMI) or a barcode sequence.

121. The kit of any one of embodiments 117-120, further comprising:

an adaptor molecule comprising a first hybridization sequence substantially complementary to at least a portion of the coding tag, and a secondary tag, wherein an information of the secondary tag is configured for transfer from the adaptor molecule to the recording tag to generate an extended recording tag after the coding tag associated with the binding agent hybridizes with the first hybridization sequence on the adaptor molecule.

122. A method for analyzing a macromolecule, comprising the steps of:

(a) providing a macromolecule and an associated recording tag joined to a support;

(b) contacting the macromolecule with a binding agent capable of binding to the macromolecule, wherein the binding agent comprises a coding tag with identifying information regarding the binding agent, to allow binding between the macromolecule and the binding agent;

(c) providing an adaptor molecule comprising a first hybridization sequence and a secondary tag, wherein the first hybridization sequence is substantially complementary to at least a portion of the coding tag, to allow hybridization between the first hybridization sequence and the coding tag, wherein step (c) is performed before, after or simultaneously with step (b);

(d) transferring information of the secondary tag to the recording tag to generate an extended recording tag, wherein the information of the secondary tag is transferred from the adaptor molecule to the recording tag after the coding tag associated with the binding agent hybridizes with the first hybridization sequence on the adaptor molecule; and (e) analyzing the extended recording tag.

123. The method of embodiment 122, wherein step (b) comprises contacting a plurality of macromolecules with a plurality of binding agents and step (c) comprises providing a plurality of adaptor molecules, wherein the plurality of adaptor molecules comprises at least one adaptor molecule capable of hybridizing to at least one coding tag associated with the binding agent.

124. The method of embodiment 122, wherein multiple coding tags associated with the binding agent are configured to hybridize to adaptor molecules comprising the same secondary tag.

125. The method of embodiment 122 or 123, wherein the adaptor molecule further comprises a second hybridization sequence substantially complementary to a sequence at the 3' terminus of the recording tag or substantially complementary to a region on the recording tag generated from a previous information transfer of the secondary tag from the adaptor molecule to the recording tag, and wherein information transfer of the secondary tag from the adaptor molecule to the recording tag occurs after: the first hybridization sequence on the adaptor molecule hybridizes to the coding tag of the binding agent; and the second hybridization sequence of the adaptor molecule hybridizes to a portion of the recording tag.

V. EXAMPLES

The following examples are offered to illustrate but not to limit the methods, compositions, and uses provided herein. Certain aspects of the present invention, including, but not limited to, embodiments for information transfer between coding tags and recording tags, methods for attachment of nucleotide-polypeptide chimera to a support, methods of making nucleotide-polypeptide chimera, methods of generating barcodes, methods of generating specific binders recognizing an N-terminal amino acid of a polypeptide, reagents and methods for modifying and/or removing an N-terminal amino acid from a polypeptide were disclosed in US 20190145982 A1, US 20200348308 A1, US 20200348307 A1, WO 2020/223000, the contents of which are incorporated herein by reference in its entirety.

Example 1. Generation of Specific N-Terminal Amino Acid (NTAA) Binders by Phage Display Library Screening Library construction, phage panning, and clone characterization. High diversity (~$10^{10}$) phage libraries using NNK variant site encoding were constructed targeting residues positions within the pocket of the anticalin. The phage library construction is known in the art and disclosed, for example, in Miersch S, et al., Scalable high throughput selection from phage-displayed synthetic antibody libraries. J Vis Exp. 2015 Jan. 17; (95):51492. doi: 10.3791/51492, which is incorporated herein by reference. Three rounds of selection were used. A pin-based magnetic particle processor (Kingfisher, Thermo) was used for unit-automation of the panning procedure, which enables the handling of 96 magnetic pins, corresponding to the positions of a 96-well microtitre plate, essentially as described in Zoltan Konthur et al., Semi-automated Magnetic Bead-Based Antibody Selection from Phage Display Libraries, Springer Protocols Handbook, Antibody Engineering, pp 267-287, 2010, DOI 10.1007/978-3-642-01144-3_18, which is incorporated herein by reference. Using the disclosed standard protocols, phage libraries were panned against different NTAA target peptides. Clones from the panning output were isolated and characterized using a panel of peptides in a multiplex Luminex binding assay. Specific binders were isolated against a variety of modified and non-modified NTAAs.

In one example, using phage display technology, a highly-selective engineered ClpS2 variant for a NTAA F binder (binder specifically recognizing F at the N-terminus of a polypeptide) was obtained. *Agrobacterium tumefaciens* ClpS2 (4YJM, starting scaffold MSDSPVDLKPKPKVK-PKLERPKLYKVMLLNDDYTPREFVTVVLKAVFRM-SEDTGRRV MMTAHRFGSAVVVVCERDIAETKAKE-ATDLGKEAGFPLMFTTEPEE as set forth in SEQ ID NO: 6) was cloned into a phage display vector with PelB leader sequence at N-terminus. From a subset of positions (L28, N30, D31, D32, Y33, T34, P35, R36, V39, M58, A61, H62, L95), we created different combinations of mutations using NNK degenerate codons (N=A/C/G/T, K=G/T). FA-PA peptide (SEQ ID NO: 3) with biotin was coated onto Streptavidin magnetic beads, and served as the target to pull down binders to FA-PA. AA-PA peptide (SEQ ID NO: 5) is used as a competitor to enrich for specific binders.

In another example, lipocalins were used as starting scaffolds for directed evolution toward modified NTAAs by phage display technology. Anticalins have an intrinsic cup-like binding pocket, highly stable structure, good recombinant expression in E. coli, binding pocket evolvability using phage display, and demonstrated potential for strong and specific binding to small molecules. Many anticalins have an intrinsic ability to bind a modified-dipeptide residue. Based on computational modeling, we designed N-terminal modifier agents (M) such that when combined with the P1 amino acid (N-terminal residue), the M-P1 moiety occupies the anticalin β-barrel core, with the P1 sidechain oriented closer to the surface of the pocket. This design forces the P2 residue (penultimate residue) of the peptide to be located just outside the pocket or affinity determining region and contribute less energy to binding. As one example, Pyrazole methanimine (PMI) is used as the N-terminal modifier agent. Two selective engineered NTAA binders were obtained based on lipocalin/anticalin scaffolds. 31-F binder specifically recognizing F at the N-terminus of a polypeptide was obtained from the following starting scaffold, SEQ ID NO: 7: QVSVQPNFQQDKFLGRWFSAGLASNSSWL-REKKAALSMAKSVVAPATDGGLNLTSTF LRKNQCE-TRTMLLQPAGSLGSYSYRSPHFGSTYSVSVVETD-YDQYALLYSQGSKGPGE DFRMATLYSRTQTPRAEL-KEKFTAFSKAQGFTEDTIVFLPQTDKCMTEQ. From a subset of positions (19, 22, 29, 33, 38, 41, 53, 55, 57, 66, 68, 81, 86, 90, 92, 105, 107, 117, 119, 121, 123), we created different combinations of mutations using NNK degenerate codons; PMI1-FXGG-peg9-K(biotin) peptide (SEQ ID NO: 8) was coated onto Streptavidin magnetic beads and served as the target to pull down binders that recognizes PMI1-F at the N-terminus of a polypeptide. Also, 44-L binder specifically recognizing L at the N-terminus of a polypeptide was obtained from the following starting scaffold, SEQ ID NO: 9: GPVPTPPDNIQVQENFNISRIYGKWYNLAIGST-SPWLKKIMDRMTVSTLVLGEGATEAEI SMTSTRWR-KGVCEETSGAYEKTDTDGKFLYHKSKWNITME-SYVVHTNYDEYAIFLTK KFSRHHGPTITAKLYGRAP-QLRETLLQDFRVVAQGVGIPEDSIFTMADRGEC-VPGEQ.

From a subset of positions (27, 30, 36, 37, 40, 43, 46, 48, 62, 64, 66, 75, 79, 99, 101, 114, 116, 128, 130, 132), we created different combinations of mutations using NNK degenerate codons; PMI1-LXGG-peg9-K(biotin) peptide (SEQ ID NO: 10) was coated onto Streptavidin magnetic beads and served as the target to pull down binders that recognizes PMI1-L at the N-terminus of a polypeptide.

Example 2. Stable Binding Reaction Performed in a Polypeptide Analysis Assay

This example describes a binding reaction performed to form a stable complex in a polypeptide analysis assay which involves information transfer for encoding amino acid sequence information of the target peptide into DNA sequence of an extended recording tag.

Target peptides attached to corresponding barcodes were joined to immobilized, bead-attached nucleic acid recording tags containing a biotin molecule (as the stabilizing component) at its 5' end (FIG. 3A). The target peptides assessed included two peptides with an N-terminal amino phenylalanine (F) ("FA", contained same peptides but different DNA barcode) and three peptides with an N-terminal alanine (A) ("AA" and "AFA"). A recording tag only control ("RT") was also performed which did not have a target peptide joined to the recording tag. F-binding agents configured to recognize peptide with a N-terminal phenylalanine were conjugated with nucleic acids (coding tag and DNA for associating with the biotin as the stabilizing component) and linker components. The nucleic acid associated with the binding agent contained a barcode (BC') with identifying information regarding the binding agent flanked by two spacer (SP') sequences useful for hybridization during information transfer extension reactions. The coding tag specific for each binder is attached to SpyTag via a PEG linker, and the resulting SpyTag-PL' is conjugated to binder-SpyCatcher fusion protein, so the corresponding stabilizing component contains DNA-PEG Linker-Sp'-Coding Tag BC'-Sp'.

The immobilized recording tags and target peptides were pre-washed with 0.1 M NaOH and 0.1% Tween20, 2 times of PBS+0.1% Tween20, incubated with Pierce™ Protein-Free T20 (PBS) Blocking Buffer (Thermo Scientific, Cat #37573) at 37° C. for 15 minutes, and washed two times with PBST (PBS+0.1% Tween20). After the washes, 200 nM of the DNA-conjugated F-binding agent and 300 nM of nucleic acids joined to a biotin which is complementary to the stabilizing component DNA was provided at 25° C. for 30 min, as shown in FIG. 3B. After two washes were performed (1.1 mM KH2PO4, 3 mM Na2HPO4, 500 mM NaCl, 0.1% Tween 20), 50 nM of neutravidin or streptavidin was added as the linking agent to connect biotin on the recording tag and the biotin associated with the binding agent and incubated at 25° C. for 5 min, as shown in FIG. 3C. A stable complex was formed between the recording tag and the DNA-conjugated F-binding agent, via the associated biotin molecules with the linking agent. Two washes were performed with PBST to remove extra streptavidin or neutravidin. The samples were then exposed to a long and stringent wash with PBST at 37° C. for 45 minutes to test stability of the complex, followed by a wash (1.1 mM KH2PO4, 3 mM Na2HPO4, 500 mM NaCl, 0.1% Tween 20) and then incubated with the encoding mixture for 5 minutes (0.125 U/μL Klenow fragment (3'->5' exo-), dNTP mixture (125 μM for each), 50 mM Tris-HCl (pH, 7.5), 2 mM MgSO4, 50 mM NaCl, 1 mM DTT, 0.1% Tween 20, and 0.1 mg/mL BSA) to copy the information from the coding tag to extend the recording tag, resulting BC and Sp at the 3' end, as shown in FIG. 3C-3D. As a negative control, PBST was added to the reaction instead of neutravidin and streptavidin. In the encoding control condition, the encoding mixture was added at the step that the linking agent was added in the other samples before the long and stringent wash with PBST at 37° C. for 45 minutes instead of the later step as described above.

After five additional washes (including 0.1 M NaOH and 0.1% Tween20 and PBS+0.1% Tween20), 0.4 mM of a nucleic acid (the capping oligonucleotide set forth in SEQ ID NO: 44) was added into the encoding mixture and incubated at 25° C. for 10 minutes to add a universal priming sequence to the recording tags (extended or unextended) using an extension reaction to generate a final product for NGS readout. The extended recording tags of the assay were subjected to PCR amplification and analyzed by next-generation sequencing (NGS).

Figure 4:
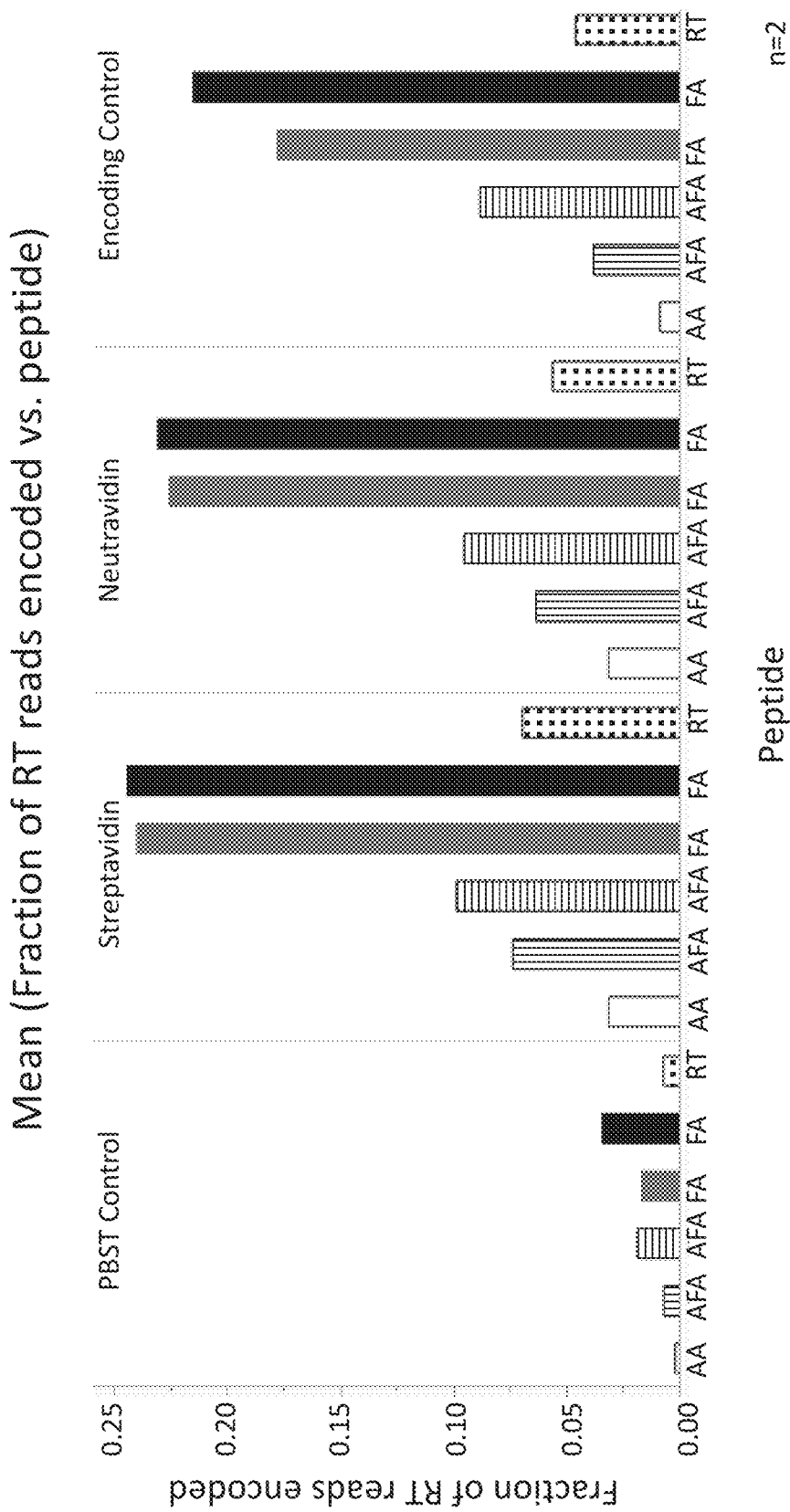
FIG. 4. depicts exemplary results from a polypeptide analysis assay (ProteoCode assay) performed which included forming a stable complex using interactions between biotin (stabilizing component) and streptavidin or neutravidin (linking agent). For comparison, a negative control where no linking agent was provided (PBST) and a encoding control was performed. The results show binding and encoding (transfer of information from a coding tag to recording tag) with a binding agent that recognizes the amino acid residue, phenylalanine.
Figure 5A:
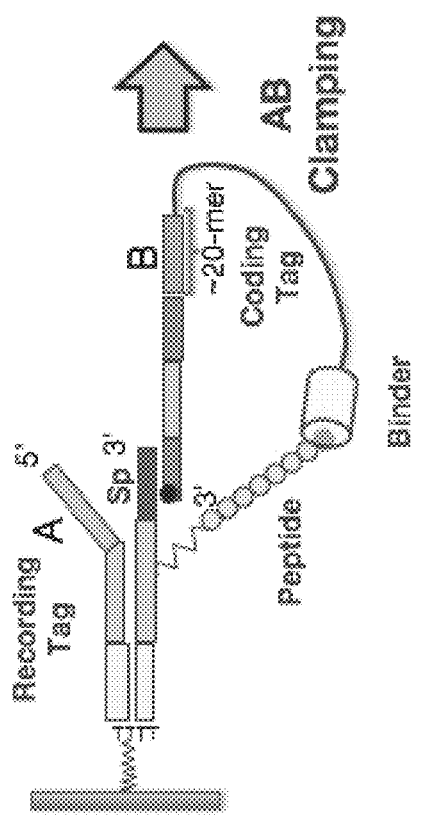
FIG. 5A and FIG. 5B show a bipartite clamping oligo, which anneals to an A region on the DNA-polypeptide chimera and a B region on the binding agent's coding tag. After binding and washing, the A'-B' clamping oligo is exposed to the system to stabilize the binding agent:DNA-polypeptide complex. Other types of bipartite affinity agents can also be employed for this stabilizing effect.
Figure 5B:
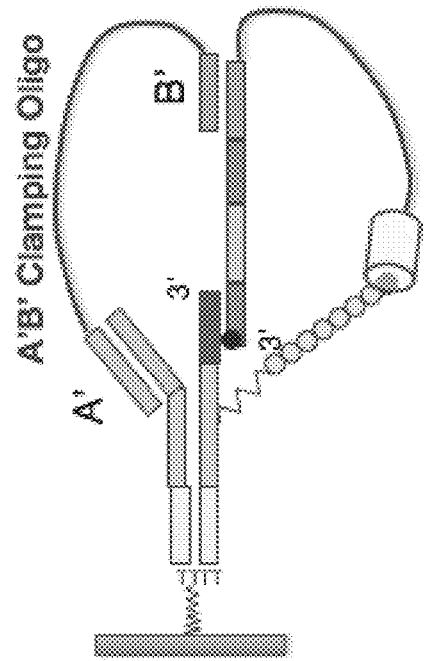
Figure 5C:
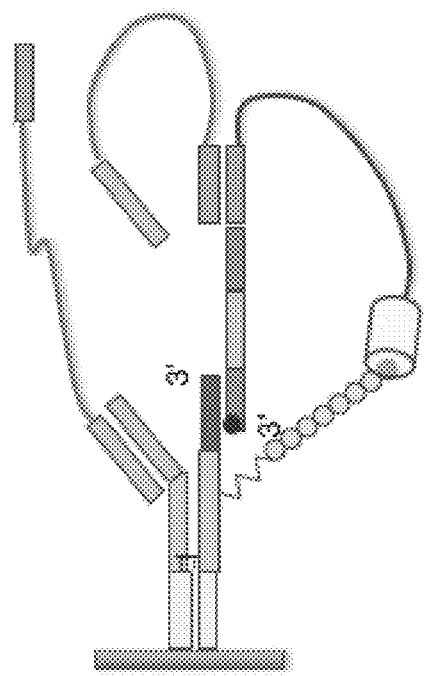
FIG. 5C shows that at high concentrations, stabilizing components can form a hindered clamping structure preventing efficient stabilization.

As shown in FIG. 4, when neutravidin or streptavidin was added as the linking agent to stabilize the complex, encoding (e.g. information transfer from the coding tag to the recording tag) indicating binding of the binding agent to the F-terminal peptides was observed as compared to negative control with PBST which showed only background signals, indicating that F-binding agent binding was not stably bound without the linking agent after the long and stringent wash (PBST at 37° C. for 45 min) for information transfer to occur. The results with streptavidin and neutravidin provided as the linking agent showed encoding efficiencies at least comparable to the encoding control where encoding is performed before the long and stringent wash (PBST at 37° C. for 45 min), serving as a control for the encoding/information transfer reaction. These results showed that the stable complex formed using the linking agents (streptavidin and neutravidin) with and stabilizing components (biotin molecules) was a useful tool to anchor the binding agent to bead-attached DNA recording tag, even in the presence of a long and stringent wash (PBST at 37° C. for 45 min), and the complex formed was adequately stable for information transfer from the coding tag to extend the recording tag in the exemplary polypeptide analysis assay.

Example 3. Exemplary Assay Including Information Transfer Via Splint Adaptor Molecule This example describes an exemplary assay system including information transfer using a splint adaptor molecule containing a first hybridization sequence complementary to a region on the coding tag and a second hybridization sequence complementary to a region on the recording tag.

Figure 8:
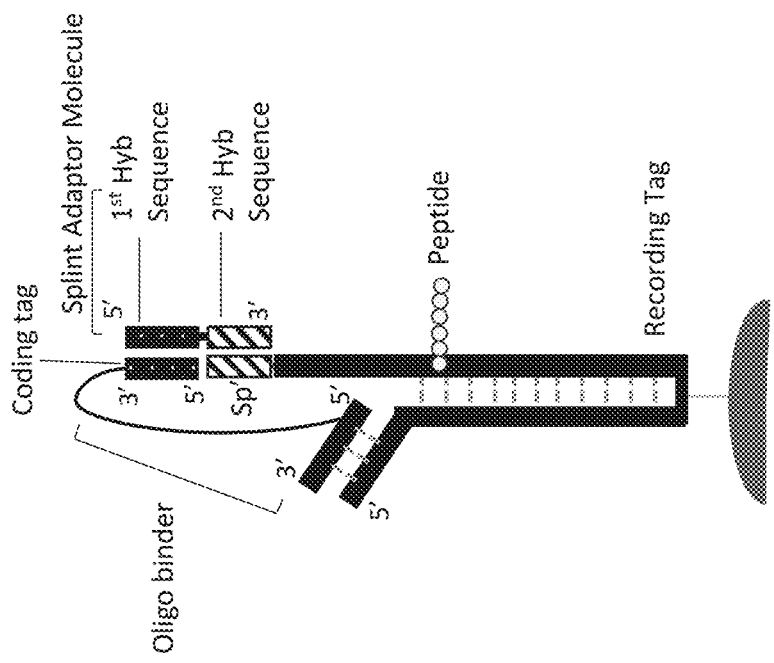
FIG. 8 depicts a model or exemplary assay system for information transfer using a splint adaptor molecule containing a first hybridization sequence complementary to a region on the coding tag and a second hybridization sequence complementary to a region on the recording tag.

Phosphorylated DNA recording tag was attached to three different peptides, with an amino-terminal sequence of FA, AFA and AA respectively (FA-peptide: FAGVAMPGAE-DDVVGSGSGK as set forth in SEQ ID NO: 3; AFA-peptide: AFAGVAMPGAEDDVVGSGSK as set forth in SEQ ID NO: 4; AA-peptide: AAGVAMPGAE-DDVVGSGSK as set forth in SEQ ID NO: 5). The DNA recording tag with no peptide attached was also used. The peptide-DNA conjugates and no-peptide DNA recording tags were immobilized on magnetic beads (Dynabeads, Thermo Fisher, USA). For the model assay, an oligo binder that is configured to hybridize to a sequence at the 5' end of the recording tag was used (FIG. 8). The oligo binder contained a nucleic acid coding tag containing a barcode. Two different coding tag sequences were tested. A DNA splint adaptor molecule was introduced that contained a first hybridization sequence complementary to the coding tag associated with the oligo binder and a second hybridization sequence that is complementary to the spacer region (Sp') in the recording tags (FIG. 8). To test the effect of mismatched nucleotides in the first hybridization sequence, which is configured to hybridize to the coding tag, or mismatched nucleotides in the second hybridization sequence, which is configured to hybridize to the recording tag, splint adaptor molecules comprising a first hybridization sequence that contained a 3 nucleotide mismatch, a 4 nucleotide mismatch, or a 7 nucleotide (full) mismatch, or a second hybridization sequence that contained a 4 nucleotide mismatch, or a 8 nucleotide (full) mismatch, were used.

The oligo binder and DNA-peptide chimera immobilized beads was incubated with the splint adaptor molecule at 37° C. for 30 minutes, then at room temperature for 15 minutes. After a 1-minute wash in PBST (PBS+ Tween20), the beads were incubated with encoding mixture containing 50 mM Tris-HCl, pH7.5, 2 mM $MgSO_4$, 50 mM NaCl, 1 mM DTT, 0.1% Tween 20, 0.1 mg/mL BSA, 0.125 mM dNTPs, 0.125 units/O_, Klenow fragment (3'->5' exo-) (MCLAB, USA) at 37° C. for 5 minutes. The beads were washed once with PBST with 10% formamide, once with 0.1 M NaOH and once with PBST with 10% formamide. The resulting beads were resuspended in PBST. The information of splint adaptor molecule (corresponding to the coding tag) was transferred to the recording tag, thereby generating an extended recording tag. The extended recording tag of the assay was subjected to qPCR with corresponding primers. As shown in Table 1, lower Ct values were obtained when the fully matched splint adaptor molecule was used (0 mismatch) indicating transferred information on the recording tag, whereas the splint adaptor molecule containing mismatches in either the 1st hyb sequence or 2nd hyb sequence produced higher Ct values relative to the 0 mismatch splint adaptor molecule. The data indicate that information corresponding to the coding tag was transferred from the splint adaptor molecule to the recording tag when hybridization occurred via a fully matched splint adaptor molecule.

TABLE 1 qPCR Assessment of Encoding (Information Transfer from Splint Adaptor Molecule)

| Condition | Coding Tag | Splint Mismatch in 1st Hyb Sequence (# nucleotides) | Splint Mismatch in 2nd Hyb Sequence (# nucleotides) | Ct Value |
|---|---|---|---|---|
| +Splint Adaptor Molecule | Coding Tag 1 | 0 | 0 | 23.4 |
| | | 3 | 0 | 29.7 |
| | | 4 | 0 | 29.9 |
| | | 7 (all) | 0 | 30.3 |
| | | 0 | 4 | 31.0 |
| | | 0 | 4 | 30.6 |
| | | 0 | 8 (all) | 30.9 |
| | Coding Tag 2 | 0 | 0 | 22.6 |
| | | 3 | 0 | 29.9 |
| | | 4 | 0 | 29.8 |
| | | 7 (all) | 0 | 29.7 |
| No Splint Adaptor Molecule | Coding Tag 1 | N/A | N/A | 31.1 |
| | Coding Tag 2 | N/A | N/A | 29.7 |
| No Klenow | Coding Tag 1 | 0 | 0 | 30.9 |
| | Coding Tag 2 | 0 | 0 | 29.9 |

For next-generation sequencing (NGS), the recoding tags were capped to add a universal priming sequence. Capping was done using an extension reaction. The extended recording tags of the assay were subjected to PCR amplification and analyzed by NGS. As shown in Table 2, information transfer from the splint adaptor molecule to the recording tag was observed when the splint adaptor contained 0 mismatched nucleotides with the coding tag. In comparison, low signal was observed when mismatches were present. This was also the case when the splint adaptor molecule was not provided (negative control) or when the Klenow polymerase was not provided (negative control). The data indicates that hybridization between the sequence on the splint adaptor molecule and corresponding complementary region on the coding tag and the recording tag was sufficient to facilitate transfer of information from the splint adaptor molecule, resulting in an extended recording tag.

TABLE 2

NGS Assessment of Encoding (Information Transfer from Splint Adaptor Molecule)

| Condition | Splint Mismatch 1st Hyb Sequence (# nucleotides) | Peptide | Fraction of RT reads enclosed |
|---|---|---|---|
| +Splint Adaptor Molecule | 0 | AA-PA | 0.168 |
| | 0 | AFA-PA | 0.378 |
| | 0 | FA-PA | 0.348 |
| | 0 | No Peptide | 0.336 |
| | 3 | AA-PA | 0.00 |

TABLE 2-continued

NGS Assessment of Encoding
(Information Transfer from Splint Adaptor Molecule)

| Condition | Splint Mismatch 1st Hyb Sequence (# nucleotides) | Peptide | Fraction of RT reads enclosed |
|---|---|---|---|
| | 3 | AFA-PA | 0.01 |
| | 3 | FA-PA | 0.00 |
| | 3 | No Peptide | 0.01 |
| | 4 | AA-PA | 0.00 |
| | 4 | AFA-PA | 0.00 |
| | 4 | FA-PA | 0.01 |
| | 4 | No Peptide | 0.01 |
| | 7 (all) | AA-PA | 0.00 |
| | 7 (all) | AFA-PA | 0.02 |
| | 7 (all) | FA-PA | 0.00 |
| | 7 (all) | No Peptide | 0.01 |
| No Splint | N/A | AA-PA | 0.00 |
| Adaptor | N/A | AFA-PA | 0.00 |
| Molecule | N/A | FA-PA | 0.01 |
| | N/A | No Peptide | 0.00 |
| No Klenow | 0 | AA-PA | 0.00 |
| | 0 | AFA-PA | 0.00 |
| | 0 | FA-PA | 0.01 |
| | 0 | No Peptide | 0.00 |

Figure 9A:
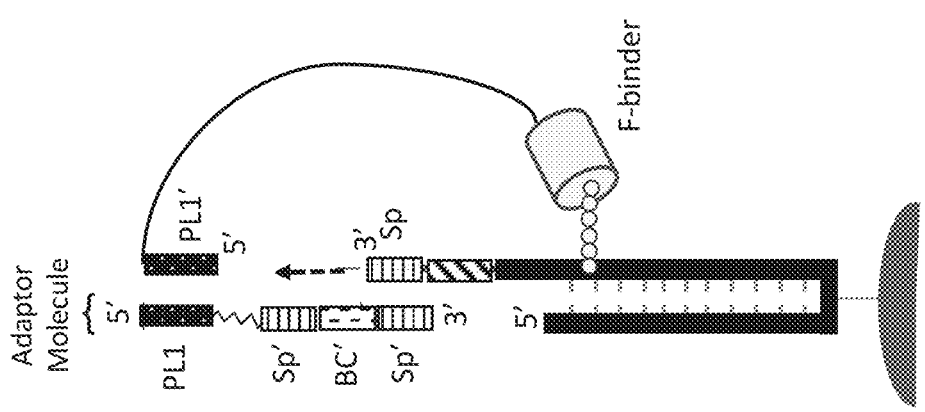
FIGS. 9A and 9B depict an exemplary embodiment for information transfer based on hybridization and extension reactions.
Figure 9B:
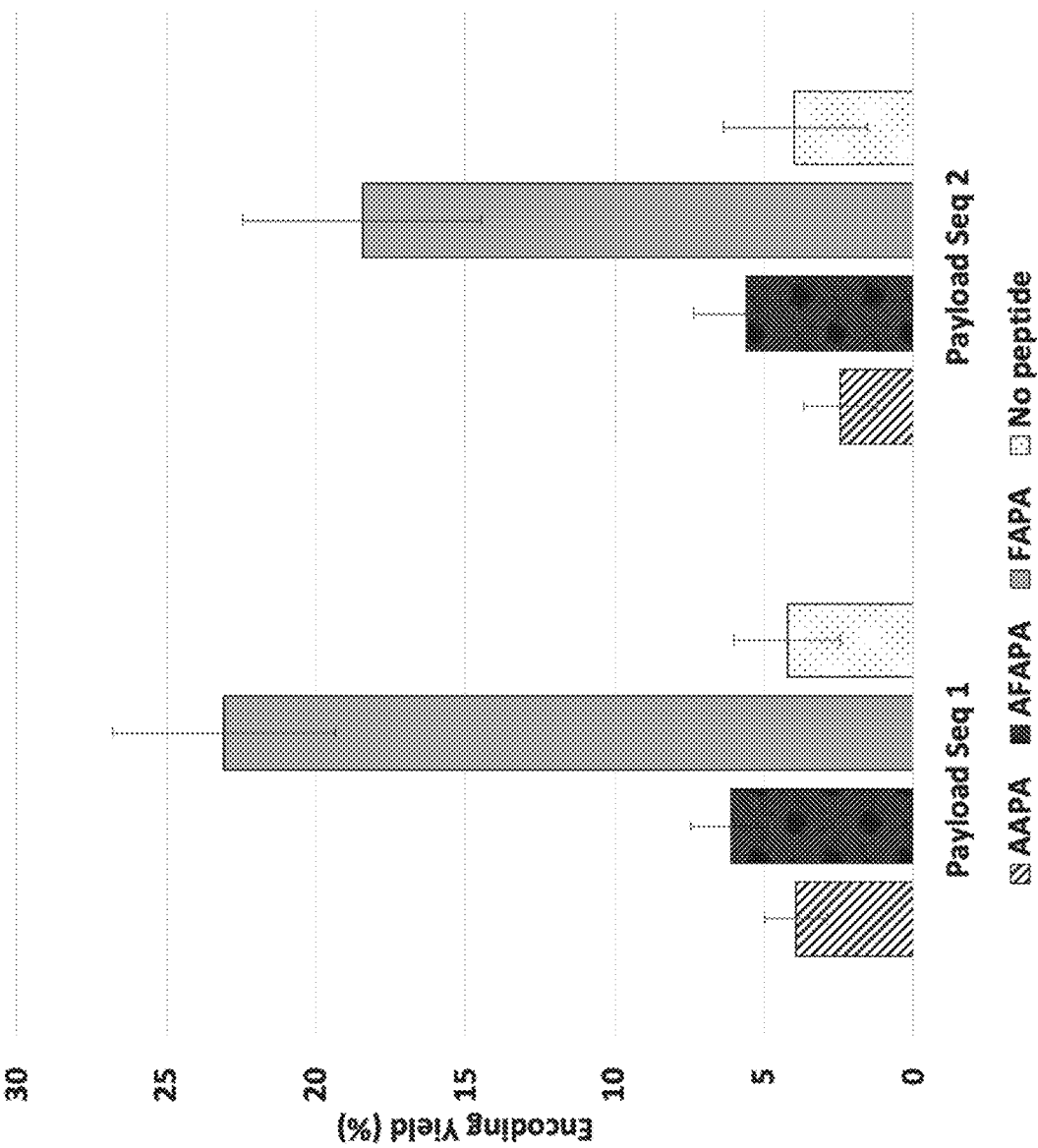
Figure 10B:
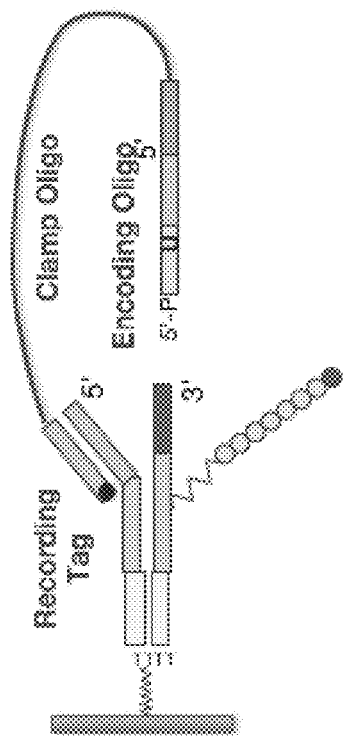
FIGS. 10A-10D show combined use of stabilizing components and adaptor molecules for encoding.
Figure 10D:
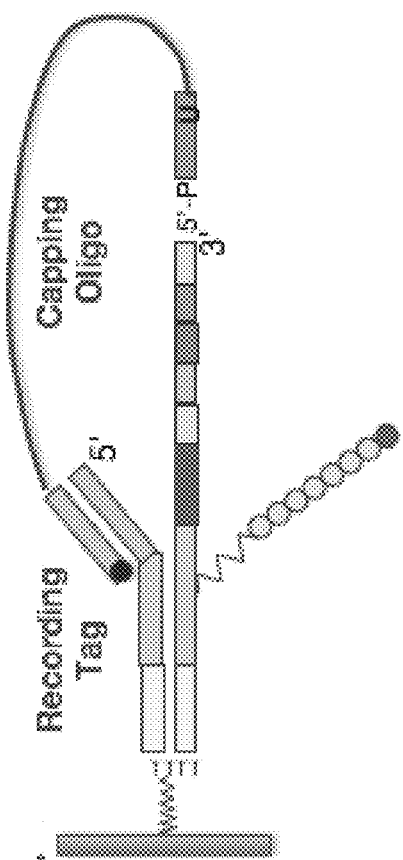
Figure 10A:
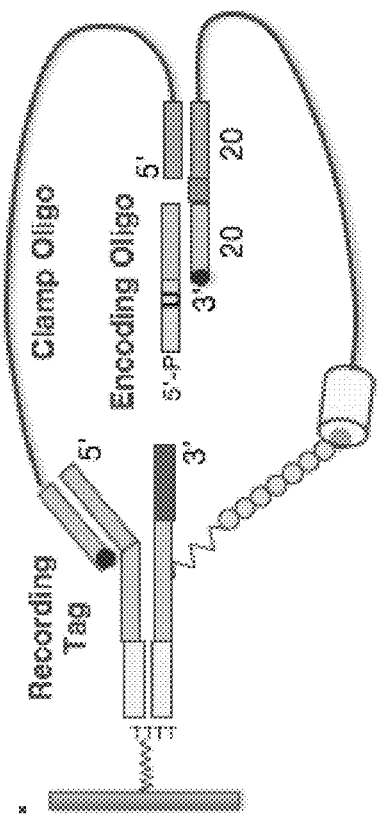
Figure 10C:
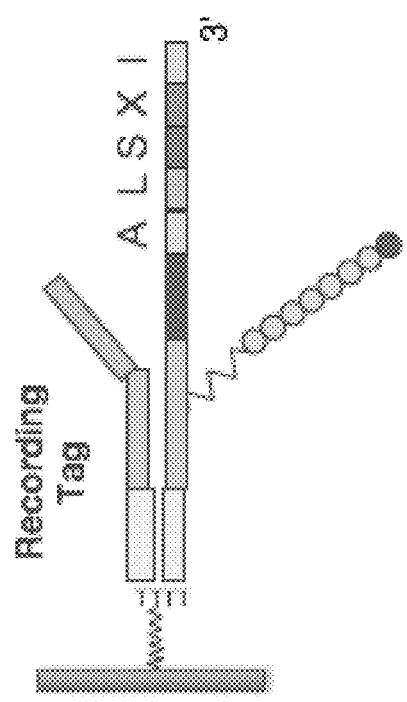

Example 4. Exemplary Assay Showing Information Transfer Via an Adaptor Molecule This example describes a specific embodiment for information transfer between a peptide molecule conjugated to a recording tag and a DNA-conjugated binder molecule conjugated that recognizes an N-terminal amino acid of the peptide molecule (FIGS. 9A-9B). Information transfer, in this embodiment, occurs via a splint adaptor molecule containing a first hybridization sequence (PL1') complementary to a region on the coding tag (PL1), followed by a PEG-based linker, a spacer sequence (Sp'), a barcode sequence (BC') and another spacer sequence (Sp') complementary to a region on the recording tag (Sp) (FIG. 9A).

In a particular example, a set of four recording tag (RT)-peptide chimeras were created by first "activating" the 5' amine on the RT oligonucleotides by coupling to TCO-PEG$_{12}$-NHS ester (Click Chemistry Tools). After TCO activation, the RT oligonucleotide, designed with an internal alkyne group, was coupled to azide-containing FA, AA and AF peptides (FA-peptide or FA-PA: FAGVAMPGAE-DDVVGSGSGK as set forth in SEQ ID NO: 3; AFA-peptide or AFA-PA: AFAGVAMPGAEDDVVGSGSK as set forth in SEQ ID NO: 4; AA-peptide or AA-PA: AAGVAMPGAE-DDVVGSGSK as set forth in SEQ ID NO: 5). These peptides having N-terminal FA, AA and AF amino acid sequences and an internal PA epitope were individually attached to recording tag oligonucleotides, amRT_Cs2, amRT_Cs4, and amRT_Cs5 (SEQ ID NOs: 11-13), respectively. A fourth recording tag, amRT_Cs1 (SEQ ID NOs: 14), was included as a no peptide control. An F-binder binding agent was conjugated to the coding tag oligonucleotide, amCT_s7 (SEQ ID NO: 10) comprised of the 8-mer barcode. The four chimeras that contain FA peptide, AA peptide, AF peptide or no peptide were combined and immobilized to mTet beads using iEDDA TCO-mTet chemistry. This 4-plex model system has been demonstrated an intra-molecular single molecule binding and specific encoding of an engineered F-binder on low recording tag density beads (1:10,000 and 1:100,000), see US 20200348308 A1. Absolute loading of the four different chimeras on beads was measured by an universal PA antibody since all three peptide types contained a PA antigen sequence, and all four chimeras were loaded in roughly equal amounts on the beads.

To increase efficiency of capture and immobilization of the four RT-peptide chimeras on beads, a hybridization-based immobilization was employed as disclosed in WO 2020/223000. The four RT-peptide chimeras were hybridized and ligated to hairpin capture DNAs attached to magnetic beads (Dynabeads, Thermo Fisher, USA). These capture beads were generated by attachment of hairpin capture nucleic acids to the beads using trans-cyclooctene (TCO) and methyltetrazine (mTet)-based click chemistry. TCO-modified short hairpin capture nucleic acids (16 basepair stem, 5 base loop, 24 base 5' overhang) were reacted with mTet-coated magnetic beads. To capture and ligate the RT-peptide chimeras to the beads, phosphorylated RT-peptide chimeras (10 nM) were annealed to the hairpin DNAs attached to beads in 5×SSC, 0.02% SDS, and incubated for 30 minutes at 37° C. The beads were washed once with PBST and resuspended in 1× Quick ligation solution (New England Biolabs, USA) with T4 DNA ligase. After a 30-minute incubation at 25° C., the beads were washed three times with 0.1 M NaOH+0.1% Tween 20 and three times with PBST. The total immobilized RT-peptide chimeras were quantified by qPCR using specific primer sets. Alternatively, peptides can be immobilized onto beads using a non-hybridization based method that did not involve a ligation step. The non-hybridization based method can be performed by incubating 30 μM TCO-modified DNA-tagged peptides including amino FA-terminal peptides, amino AFA-terminal peptides, and amino AA-terminal peptides, with mTet-coated magnetic beads overnight at 25° C. as described in US 20200348308 A1.

After capturing the four RT-peptide chimeras on beads, a binding and encoding assay was performed utilizing splint adaptor molecules as shown in FIG. 9A. A specific F-binder engineered from ClpS2 (obtained by Phage display library screening as disclosed in the previous example) conjugated with two different coding tags—hybridization sequences Payload seq 1 (PL1) and Payload seq 1 (PL2) was used for the assay. PL1 and PL2 were designed as random sequences that contain ~50% CG and do not interact with corresponding barcode and spacer sequences on the adaptor molecules. The complementary sequences of PL1 and PL2 (am-PL1' and am-PL2', SEQ ID NOs: 16-17) were attached to SpyTag via a PEG linker, and the resulting SpyTag-PL1' and Spy-Tag-PL2' were conjugated to F binder-SpyCatcher fusion protein, thus creating F binder-PL1' and F binder-PL2' fusions.

For the encoding assay, which comprises an information transfer between the coding tag and the recording tag, the F binder-PL1' and F binder-PL2' were mixed with splint adaptor molecules, CT_PL1_S6 and CT_PL2_S6 (SEQ ID NOs: 18-19), respectively, in 1:4 molar ratio, forming two binder mixes. Both adaptor molecules also include the C3 spacer at the 3' terminus of the oligonucleotide. The C3 spacer is a three carbon spacer. The C3 spacer located at the 3' terminus of the oligonucleotide prohibits extension of the oligonucleotide by a polymerase and prevents ligation at the 3' end. The architecture of splint adaptor molecules as shown in FIG. 9A allows for hybridization between splint adaptor molecule, coding tag and recording tag, providing conditions for transfer information between the coding tag and the recording tag. The bead-immobilized RT-peptide chimeras were incubated with 200 nM of each binder mix in 150 μL of PBST (PBS+ Tween20) at room temperature. After 30 minutes incubation, the beads were washed twice with 200 μL of PBST with 500 mM NaCl and resuspended in encoding mixture containing 50 mM Tris-HCl, pH7.5, 2 mM MgSO$_4$, 50 mM NaCl, 1 mM DTT, 0.1% Tween 20, 0.1 mg/mL BSA, 0.125 mM dNTPs, 0.125 units/μL Klenow fragment (3'->5' exo-) (MCLAB, USA) at 37° C. for 5 minutes. The beads were washed once with 0.1 M NaOH+ 0.01% Tween 20 and twice with PBST. The information of splint adaptor molecule (corresponding to the coding tag) was transferred to the recording tag, thereby generating an extended recording tag. For next-generation sequencing (NGS), the recording tags were capped to add a universal priming sequence. Capping was done using an extension reaction. The extended recording tags of the assay were subjected to PCR amplification and analyzed by NGS. Encoding yield on each peptide was obtained by evaluating percentage of recoding tags containing adaptor molecule's barcode information that was transferred during the assay. For both PL1 and PL2 sequences used, a high encoding yield during the assay was observed only for the target peptide FA-PA having F as the N-terminal amino acid (FIG. 9B), showing specificity of the information transfer for the cognate F-binder fusions. In an alternate embodiment, the splint adaptor molecule can be annealed to the binder-peptide complex post binding and washing.

Example 5. Exemplary Multi-Cycle Assay Showing Information Transfer Via an Adaptor Molecule An exemplary two-cycle encoding assay is performed as follows. The first cycle encoding is performed as described in Example 3. Chimeric molecules comprised of peptide-DNA recording tags are immobilized on magnetic beads as described in Example 3. A mixture of several N-terminal modified selective binders is used in the assay to interact with an immobilized polypeptide; each binder comprises an engineered protein specifically recognizing a particular N-terminal amino acid of the polypeptide and associated with a coding tag containing information about the binder. The coding tag specific for each binder (PL') is attached to SpyTag via a PEG linker, and the resulting SpyTag-PL' is conjugated to binder-SpyCatcher fusion protein.

A set of 20 exemplar coding tag adaptor sequences (PL' sequences) of 20 nucleotides in length include the following sequences (SEQ ID NOs: 20-39) based on Elmas, A., et al. (2013). "Designing DNA Barcodes Orthogonal in Melting Temperature by Simulated Annealing Optimization." Nucleic acid therapeutics 23: 140-151:

```
TGGTAGAGCCACAAACAGCC, GGTACAAGCAACGATCTCCA,
GGACCATCTGAATCATGCGC, GGATGACACGAACTCACGAC,
GGCGATCACAGACATTAACC, CACAGCCGATAATTGCAGAC,
GGTACAGACACTGCGACAAC, GTGGCAATTCGTCGCAATAC,
GGGTCATCACGGCTCATCAT, GCCAGATGTCAACACAGCTA,
CCGCCAAACAAATGTGTGCA, ATACACGCTCGGAAGACTGC,
ATGATGACCGCACTGACTGG, GGACAGCAGATCCACCTAAG,
CCTGTGAGAGAAGCAGACAC, CCGACAGATCAAGGCAGTTA,
AATCGCAGCCAAGTGAGTGA, ATAGATGACGCACCACGGTC,
AGACACGACACACTGGCTTA, AGGAGACGCCACATCGTATC.
```

For each binder, the binder-PL' conjugates are mixed with corresponding adaptor molecules, containing a complementary PL sequences, a spacer and a unique barcode (BC'), in 1:4 molar ratio. The binder-specific coding tag adapter sequences are comprised of 15 to 30-mer barcodes which have been designed to hybrid efficiently and orthogonally to other members barcodes. Exemplar approaches to generating orthogonal hybridizing sets of barcodes (20-25 nt.) are disclosed in: Elmas, A., et al. (2013). "Designing DNA Barcodes Orthogonal in Melting Temperature by Simulated Annealing Optimization." Nucleic acid therapeutics 23: 140-151; Pierce, S. E., et al. (2006). "A unique and universal molecular barcode array." Nat Methods 3(8): 601-603; Cook, M. A., et al. (2008). "Systematic validation and atomic force microscopy of non-covalent short oligonucleotide barcode microarrays." PLoS One 3(2): e1546; Xu, Q., et al. (2009). "Design of 240,000 orthogonal 25mer DNA barcode probes." Proc Natl Acad Sci USA 106(7): 2289-2294; Casini, A., et al. (2014). "R2oDNA designer: computational design of biologically neutral synthetic DNA sequences." ACS Synth Biol 3(8): 525-528.

In addition to good orthogonal hybridization properties amongst the members of the set, the barcodes can be further filtered to remove cross-reactivity with other DNA components of the ProteoCode system including universal priming sequences, spacer sequences, recording tag barcodes, etc.

In the case of two binders A and B used in the assay, conjugated to coding tag sequences, PLA1' (TGGTAGAGC-CACAAACAGCC, SEQ ID NO: 20) and PLB2' (GGTA-CAAGCAACGATCTCCA, SEQ ID NO: 21), respectively, beads with polypeptide-recording tag fusion molecules are incubated at 30° C. temperature with 150 μL of mixture containing 200 nM binder A-PLA1'+ adaptor A_$1^{st}$ cycle (GGCTGTTTGTGGCTCTACCA---GGTAAGAGCGACT-GTAGTGTG, SEQ ID NO: 40; where "---" is a C3 spacer) and 200 nM binder B-PLB2'+ adaptor B_$1^{st}$ cycle (TG-GAGATCGTTGCTTGTACC---GGTAAGAGCCGATG-TAGTGTG, SEQ ID NO: 41) in PBS-T (PBS+ Tween 20). Both adaptor molecules (adaptor A_$1^{st}$ cycle and adaptor B_$1^{st}$ cycle) also include the 3SpC3 spacer at the 3' terminus of the oligonucleotide. The C3 spacer is a three carbon spacer. The C3 spacer located at the 3' terminus of the oligonucleotide prohibits extension of the oligonucleotide by a polymerase and prevents ligation at the 3' end.

After 30 minutes incubation, the beads are washed twice with 200 μL PBS-T with 500 mM NaCl, and resuspended in encoding mixture containing 50 mM Tris-HCl, pH7.5, 2 mM MgSO4, 50 mM NaCl, 1 mM DTT, 0.1% Tween 20, 0.1 mg/mL BSA, 0.125 mM dNTPs, 0.125 units/uL Klenow fragment (3'-5' exo-) (MCLAB, USA) at 37° C. for 5 minutes. The beads are washed once with 0.1 M NaOH+ 0.01% Tween 20 and twice with PBS-T. If during the first cycle specific binding occurs between the NTAA of the polypeptide and the binder, the information regarding this binder is transferred from binding-specific barcode in the adaptor molecule to the recording tag (becomes encoded in the recording tag). In addition, the adaptor molecules may also contain a cycle-specific barcode (in this case a unique barcode for the first cycle) that will be also encoded in the recording tag after information transfer. After information transfer, the N-terminal amino acid of the polypeptide is cleaved off by mild Edman-like methods described, for example in US 20200348307 A1 or WO 2020223133 A1. Alternatively, the N-terminal amino acid of the polypeptide is cleaved off enzymatically by engineered cleavases described, for example in WO 2020198264 A1. The cleavage exposes a new N-terminal amino acid of the polypeptide, and the system is ready for the second cycle. During the second cycle of encoding the same set of binder coding tag combinations can be used (for example, binders A and B), but with a new set of adaptor molecules. For example, a mixture will contain 200 nM binder A-PLA1'+ adaptor A_$2^{nd}$ cycle (GGCTGTTTGTGGCTCTACCA---AGAGATGGCACGTGGTAAGAG, SEQ ID NO: 42) and 200 nM binder B-PL2'+ adaptor molecule2_$2^{nd}$ cycle (TG-GAGATCGTTGCTTGTACC---AGAGATGGTGCG-TGGTAAGAG, SEQ ID NO: 43) in PBS-T. Both adaptor molecules (adaptor molecule1_$2^{nd}$ cycle and adaptor molecule2_$2^{nd}$ cycle) also include the 3SpC3 spacer at the 3' terminus of the oligonucleotide. Adaptor molecules used for the second cycle will contain a cycle-specific barcode unique for the second cycle. The encoding conditions are the same for the first and the second cycle. After the second cycle encoding, either the third cycle can be done (following the NTAA cleavage) with new adaptor molecules containing a cycle-specific barcode unique for the third cycle, or the extended recording tag is capped by addition of a universal priming sequence to finish the encoding process. The capped recording tag is subjected to PCR amplification followed by sequencing and analysis using a next-generation sequencing method. The described approach overcomes a necessity to make and use a new pool of binder fusions for each cycle of encoding; rather, a new pool of cycle-specific adapter molecules is used for each cycle together with a single universal set of coding tag-conjugated binders.

Example 6. Stable Binding Reaction Performed in a Polypeptide Analysis Assay

This example describes "stabilizing" reaction immediately after a binding/washing event to form a stable complex of the binder with the polypeptide. The "stabilized" binding event enables robust information transfer without concern of binder dissociating from the polypeptide during encoding. This is particularly useful in a couple of different embodiments: 1) when using binders with appreciable off rates, and 2) when encoding using adapter molecules in which the adapter molecules are hybridized to the "clamped" (stabilized via use of stabilizing components) binder, stringent washing performed, and the extension step performed without regard to binder dissociation.

A model bead set comprised of target polypeptides attached to corresponding barcodes are immobilized to hairpin nucleic acid recording tags containing a desthiobiotin (DSB) molecule (as the stabilizing component) at its 5' end. The target polypeptides include two polypeptides with an N-terminal phenylalanine (F) ("FA", containing the same polypeptides but different DNA barcode) and three polypeptides with an N-terminal alanine (A) ("AA" and "AFA"). A recording tag only control ("RT") is also performed devoid of a target peptide. F-binding agents recognizing an N-terminal phenylalanine residue (obtained as described above using a phage display screening) are conjugated with "hybridizable" DNA coding tags. The nucleic acid associated with the binding agent contains a barcode (BC') with identifying information regarding the binding agent. The "hybridizable" coding tag barcodes for the binding agents are designed to be 15-25 mers DNA sequences with good hybridization properties and minimal cross-hybridization between the barcodes as described in (Elmas, A., et al. (2013). "Designing DNA Barcodes Orthogonal in Melting Temperature by Simulated Annealing Optimization." Nucleic acid therapeutics 23: 140-151).

The immobilized recording tags and target polypeptides are pre-washed with 0.1 M NaOH and 0.1% Tween 20, washed two times with PBST (PBS+0.1% Tween 20), incubated with Pierce™ Protein-Free T20 (PBS) Blocking Buffer (Thermo Scientific, Cat #37573) at 37° C. for 15 minutes, and washed two times with PBST. After the washes, 200 nM of the DNA-conjugated F-binding agent and 300 nM of a biotinylated splint adapter, complementary to a region of the binder coding tag, is added to the beads and incubated at 25° C. for 30 min. After two washes are performed with High Salt PBST (1.1 mM KH2PO4, 3 mM Na2HPO4, 500 mM NaCl, 0.1% Tween 20), 50 nM of streptavidin (SA) in PBST is added as the linking agent to connect DST on the recording tag and the biotin associated via the adapter sequence with the binding agent and incubated at 25° C. for 5 min. A stable complex is formed between the recording tag and the adapter sequence/DNA-conjugated F-binding agent, via the associated DSB/biotin molecules bound via the SA linking agent. Two washes are performed with PBST to remove extra SA.

The beads are then incubated with the extension mix for 5 minutes (0.125 U/µL Klenow fragment (3'->5' exo-), 125 uM dNTP mixture (dATP, dCTP, dGTP, and dTTP), 50 mM Tris-HCl (pH, 7.5), 2 mM MgSO$_4$, 50 mM NaCl, 1 mM DTT, 0.1% Tween 20, and 0.1 mg/mL BSA) to copy the information from the adapter molecule to the recording tag resulting in the extended recording tag having BC and Sp at the 3' end.

After extension of the recording tag and before the next encoding cycle, the linking agent (SA), adapter molecule, and binding agents are removed by incubation in 4 mM biotin in 0.1 M NaOH/0.1% Tween 20 for 10 min. This step takes advantage of the particular setup, in which the first stabilizing component (DSB) has a lower affinity to the linking agent (SA) in comparison to an affinity of the second stabilizing component (biotin) to the linking agent. This allows for efficient disruption of the stable complex before commencing the next encoding cycle. One or more additional encoding cycles can be performed similarly as described above. After all the encoding cycles are completed, 0.4 mM of a nucleic acid (the capping oligonucleotide set forth in SEQ ID NO: 44) was added into the encoding mixture and incubated at 25° C. for 10 minutes to add a universal priming sequence to the recording tags (extended or unextended) using an extension reaction to generate a final product for NGS readout. The extended recording tags of the assay were subjected to PCR amplification and analyzed by next-generation sequencing (NGS).

Figure 11:
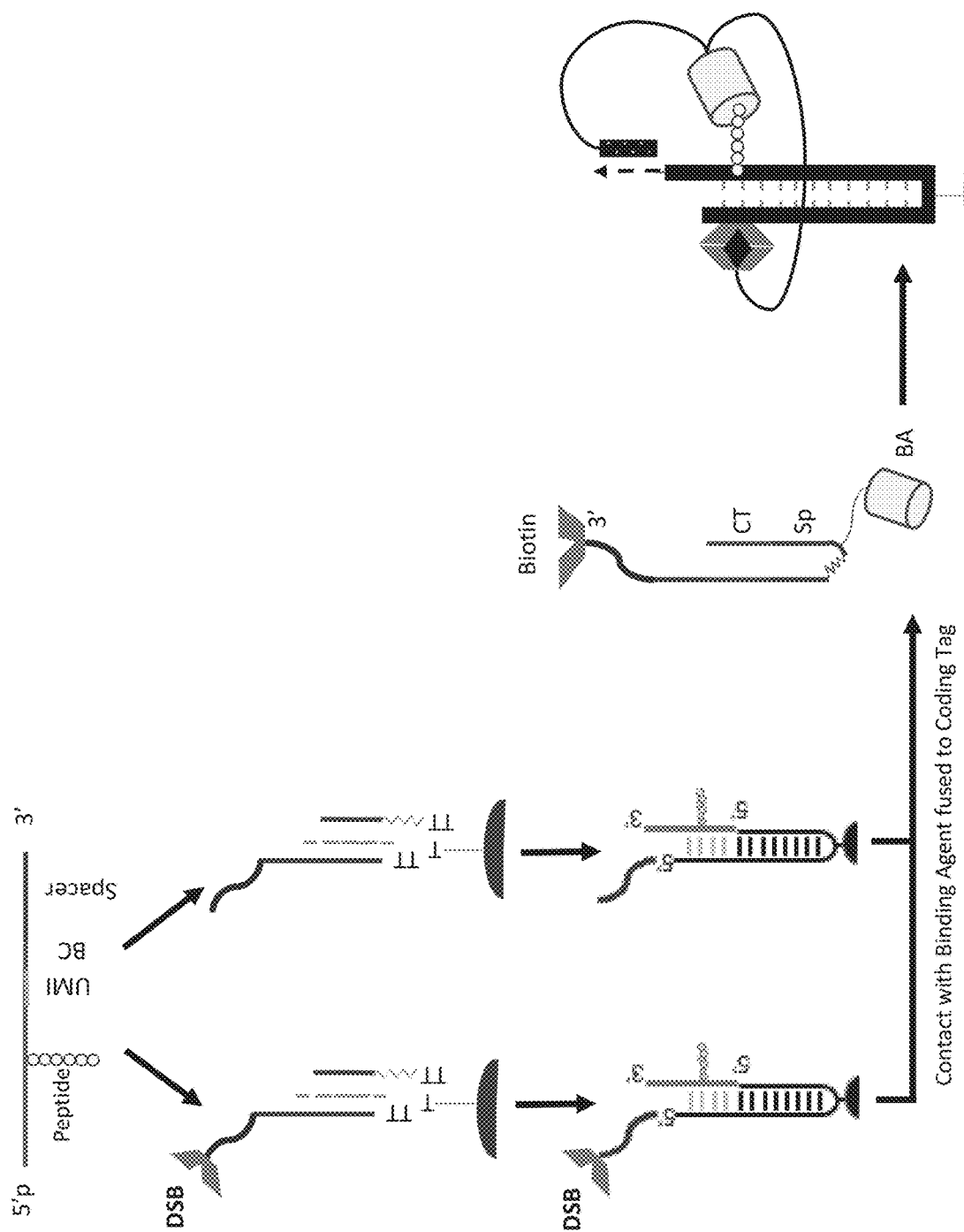
FIG. 11 depicts an exemplary arrangement of interacting components in the encoding assay. Target peptide fused to the recording tag is immobilized on a solid support via interaction with a hairpin DNA associated with the first stabilizing component (DSB). Then, a binding agent fused to the coding tag and labeled with biotin (the first stabilizing component) interacts with the target peptide. This interaction is stabilized upon addition of the linking agent.

Example 7. Use of Stabilizing Components for Efficient Encoding of Different Binders Two additional binders (31-F and 44-L) described in the Example 1 have been tested in the encoding assay using a setup similar to the Example 2. Several target peptides have been tested, having the following sequences: P1F[TOM]-FSGVARGDVRGGK (SEQ ID NO: 45), FL[TOM]-FLAEIRGDVRGGK (SEQ ID NO: 46); 1L5L9L LAGE-LAGELAGEIRGDVRGGK (SEQ ID NO: 47); P10RFSPA—dimethyl-AESAESASRFSGVAMPGAE-DDVVGSGSK (SEQ ID NO: 48); P6F[TOM]-LAESAFSG-VARGDVRGGK (SEQ ID NO: 49); FA-PA-FAGVAMP-GAEDDVVGSGSGK (SEQ ID NO: 3); NoF[TOM]-SGVARGDVRGGK (SEQ ID NO: 50). Target peptides attached to corresponding barcodes were joined to immobilized, bead-attached recording tags containing a desthiobiotin (DSB) molecule (as the stabilizing component) at its 5' end (FIG. 11). A recording tag only control ("RT") was also included in the experiments, which did not contain a target peptide joined to the recording tag. The beads were treated with an N-terminal modifier agent (pyrazole methanimine, PMI) to generate PMI-modified peptides as described in WO 2019/089846. 31-F and 44-L binding agents configured to recognize peptides with N-terminally PMI-modified phenylalanine or leucine residues were conjugated with nucleic acids (coding tag and DNA for associating with the biotin as the stabilizing component). The nucleic acid associated with the binding agent contained a barcode (BC') with identifying information regarding the binding agent flanked by two spacer (SP') sequences useful for hybridization during information transfer extension reactions. The coding tag specific for each binder is attached to SpyTag via a PEG linker, and the resulting SpyTag-PL' is conjugated to binder-SpyCatcher fusion protein, so the corresponding stabilizing component contains DNA-PEG Linker-Sp'-Coding Tag BC'-Sp'.

Figure 12A:
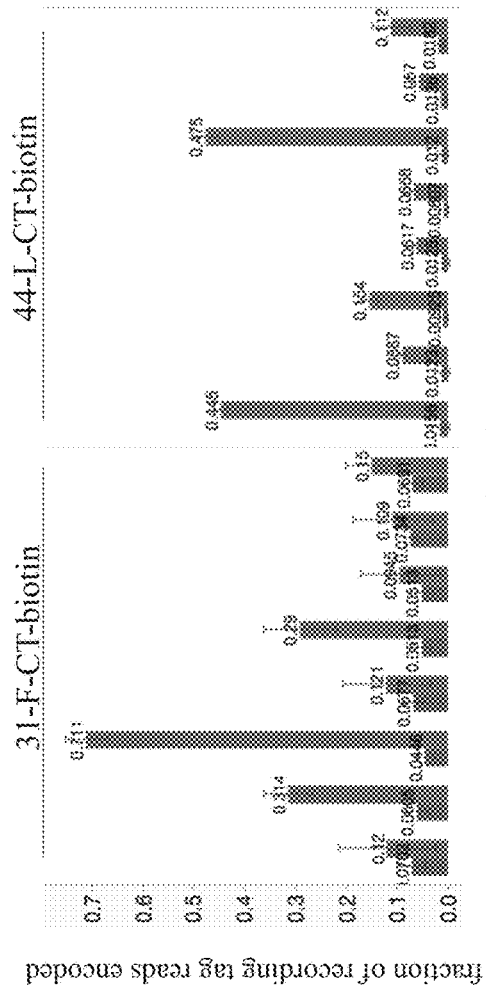
FIGS. 12A and 12B show dependence of encoding efficiencies on stabilization with a linking agent (SA) during stringent washing conditions.
Figure 12B:
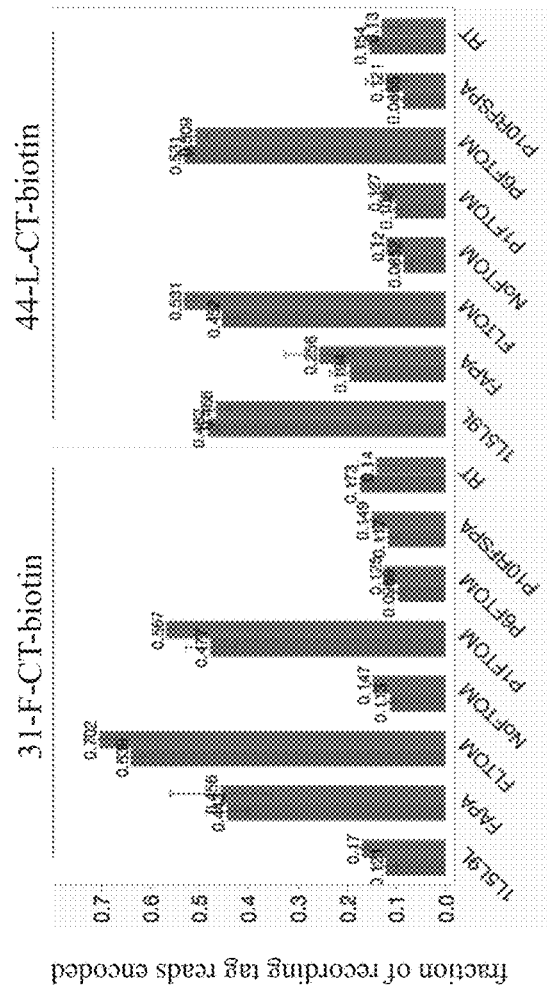

The immobilized recording tags and target peptides were pre-washed with 0.1 M NaOH and 0.1% Tween20, 2 times of PBS+0.1% Tween20, incubated with Pierce™ Protein-Free T20 (PBS) Blocking Buffer at 37° C. for 15 minutes, and washed with PBST (PBS+0.1% Tween20). After the wash, 200 nM of the DNA-conjugated binding agents and 300 nM of the nucleic acid complementary to the stabilizing component DNA joined to a biotin molecule was incubated at 25° C. for 30 min. After two washes performed (with 1.1 mM KH2PO4, 3 mM Na2HPO4, 500 mM NaCl, 0.1% Tween 20), either 50 nM of streptavidin (SA; shown in FIG. 12A) or PBST without SA (FIG. 12B) was added as a linking agent to connect DSB on the recording tag and biotin associated with the binding agent, and incubated at 25° C. for 5 min, followed by wash with PBST to remove excess of SA. The samples were then exposed either to a stringent wash with PBST at 37° C. for 45 minutes to test stability of the complex the during encoding assay (encoding efficiencies are indicated in FIGS. 12A and 12B by left bars for each combination of the targeted peptides and binders), or directly proceeded to the encoding without the stringent wash (encoding efficiencies are indicated in FIGS. 12A and 12B by right bars for each combination of the targeted peptides and binders). The samples were incubated with the encoding mixture for 5 minutes (0.125 U/µL Klenow fragment (3'->5' exo-), dNTP mixture (125 µM for each), 50 mM Tris-HCl (pH, 7.5), 2 mM MgSO4, 50 mM NaCl, 1 mM DTT, 0.1% Tween 20, and 0.1 mg/mL BSA) to copy the information from the coding tag to the recording tag (RT) to generate an extended recording tag, resulting BC and Sp at the 3' end of the RT. After additional washes (including 0.1 M NaOH and 0.1% Tween20 and PBS+0.1% Tween20), 0.4 mM of the capping oligonucleotide was added into the encoding mixture and incubated at 25° C. for 10 minutes to add a universal priming sequence to the recording tags (extended or unextended) using an extension reaction to generate a final product for NGS readout. The extended recording tags of the assay were subjected to PCR amplification and analyzed by next-generation sequencing (NGS), which quantified fractions of encoded recording tag reads for each combination of the targeted peptides and binders. The results shown in FIGS. 12A and 12B indicated that the stringent wash with PBST at 37° C. for 45 minutes greatly diminished the encoding efficiency for both binders, but addition of the linking agent (SA) reversed this effect, and encoding efficiencies have not been reduced.

To evaluate dependence of encoding efficiencies on the encoding temperature, the same combination of targeted peptides were tested with the 31-F binding agent labeled with biotin (FIGS. 13A and 13B). In some situations, encoding at a higher temperature may be desirable, since higher temperature may prevent unspecific interactions within complex components and decrease background signals during encoding. The encoding was performed as described above for FIGS. 12A and 12B with SA added as the linking agent in all samples. In FIG. 13A encoding efficiencies measured at two temperatures (25° C. and 37° C.) are shown for the setup where recording tags did not contain a DSB molecule at its 5' end (no stabilization during encoding), whereas in FIG. 13B DSB was attached to the recording tags (stabilization during encoding). The results shown in FIGS. 13A and 13B indicated that the interactions of the 31-F binder with the targeted peptides and corresponding encoding efficiencies are sensitive to temperature; addition of DSB and corresponding formation of the stable complex comprising the binder, peptide, SA (the linking agent), biotin and DSB (the stabilizing components) significantly increased encoding efficiencies and removed dependence on the encoding temperature (encoding efficiencies were similar for 25° C. and 37° C.).

Example 8. Exemplary Kit

The exemplary kit to perform an encoding assay for determining a portion of a macromolecule (an amino acid sequence of a target polypeptide in this particular case) comprises:

1) two binding agents (31-F and 44-L) prepared as described in Example 1, each binding agent is associated with a coding tag, which comprises identifying information regarding the binding agent (a unique barcode sequence) and is additionally associated with biotin (stabilizing component) as described in Example 2, Example 7, FIG. 11 and FIGS. 12A and 12B; optionally, the kit comprises additional binding agents that recognize other specific NTAA of a polypeptide; 2) a polynucleotide containing a unique molecular identifier (UMI) or a barcode sequence fused to dethiobiotin configured to be linked to a target polypeptide by means of a click chemistry (nucleotides are coupled to TCO-PEG12-NHS ester and then coupled to azide-containing polypeptide as described in Example 4); and 3) streptavidin. This kit can be used to determine an amino acid sequence of a target polypeptide by methods described in Examples 2-4 and 7.

The present disclosure is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

TABLE 3

SEQUENCE TABLE

| SEQ ID NO | Sequence (5'-3') | Description |
|---|---|---|
| 1 | AATGATACGGCGACCACCGA | P5 primer |
| 2 | CAAGCAGAAGACGGCATACGAGAT | P7 primer |
| 3 | FAGVAMPGAEDDVVGSGSGK | FA-PA |
| 4 | AFAGVAMPGAEDDVVGSGSK | AFA-PA |
| 5 | AAGVAMPGAEDDVVGSGSK | AA-PA |
| 6 | MSDSPVDLKPKPKVKPKLERPKLYKVMLLN DDYTPREFVTVVLKAVFRMSEDTGRRVMM TAHRFGSAVVVVCERDIAETKAKEATDLGK EAGFPL1VIFTTEPEE | scaffold for binder selection 1 |
| 7 | QVSVQPNFQQDKFLGRWFSAGLASNSSWLR EKKAALSMAKSVVAPATDGGLNLTSTFLRK NQCETRTMLLQPAGSLGSYSYRSPHFGSTYS VSVVETDYDQYALLYSQGSKGPGEDFRMAT LYSRTQTPRAELKEKFTAFSKAQGFTEDTIVF LPQTDKCMTEQ | scaffold for binder selection 2 |
| 8 | PMI1-FXGG-peg9-K(biotin) | bait peptide for binder selection 1 |
| 9 | GPVPTPPDNIQVQENFNISRIYGKWYNLAIGS TSPWLKKIMDRMTVSTLVLGEGATEAEISMT STRWRKGVCEETSGAYEKTDTDGKFLYHKS KWNITMESYVVHTNYDEYAIFLTKKFSRHH GPTITAKLYGRAPQLRETLLQDFRVVAQGVG IPEDSIFTMADRGECVPGEQ | scaffold for binder selection 3 |
| 10 | PMI1-LXGG-peg9-K(biotin) | bait peptide for binder selection 2 |
| 11 | ttcgtagtcc gcgacactag nnnnnnnnnn gttaatggac tgagtg | amRT_Cs2 oligonucleotide, n is a, c, g, or t |
| 12 | ttcgtagtcc gcgacactag nnnnnnnnnn cagtaccgac tgagtg | amRT_Cs4 oligonucleotide, n is a, c, g, or t |
| 13 | ttcgtagtcc gcgacactag nnnnnnnnnn gttggttaac tgagtg | amRT_Cs5 oligonucleotide, n is a, c, g, or t |
| 14 | ttcgtagtcc gcgacactag nnnnnnnnnn ttaagtcgac tgagtg | amRT_Cs1 oligonucleotide, n is a, C, g, or t |
| 15 | cactcagtca gactattcac tcagt | coding tag oligonucleotide |
| 16 | CATAGACTAGTAGCCGGAAC | am-PL1' oligonucleotide |
| 17 | TCGACGTAATGACACCGCTC | am-PL2' oligonucleotide |
| 18 | GTTCCGGCTACTAGTCTATG-peg6-CACTCAGTTTTTCCTGTCACTCAGT | CT_PL1_S6 adaptor molecule |
| 19 | GAGCGGTGTCATTACGTCGA-peg6-CACTCAGTTTTTCCTGTCACTCAGT | CT_PL2_S6 adaptor molecule |
| 20 | TGGTAGAGCCACAAACAGCC | coding tag barcode sequence 1 |
| 21 | GGTACAAGCAACGATCTCCA | coding tag barcode sequence 2 |
| 22 | GGACCATCTGAATCATGCGC | coding tag barcode sequence 3 |

TABLE 3-continued

SEQUENCE TABLE

| SEQ ID NO | Sequence (5'-3') | Description |
|---|---|---|
| 23 | GGATGACACGAACTCACGAC | coding tag barcode sequence 4 |
| 24 | GGCGATCACAGACATTAACC | coding tag barcode sequence 5 |
| 25 | CACAGCCGATAATTGCAGAC | coding tag barcode sequence 6 |
| 26 | GGTACAGACACTGCGACAAC | coding tag barcode sequence 7 |
| 27 | GTGGCAATTCGTCGCAATAC | coding tag barcode sequence 8 |
| 28 | GGGTCATCACGGCTCATCAT | coding tag barcode sequence 9 |
| 29 | GCCAGATGTCAACACAGCTA | coding tag barcode sequence 10 |
| 30 | CCGCCAAACAAATGTGTGCA | coding tag barcode sequence 11 |
| 31 | ATACACGCTCGGAAGACTGC | coding tag barcode sequence 12 |
| 32 | ATGATGACCGCACTGACTGG | coding tag barcode sequence 13 |
| 33 | GGACAGCAGATCCACCTAAG | coding tag barcode sequence 14 |
| 34 | CCTGTGAGAGAAGCAGACAC | coding tag barcode sequence 15 |
| 35 | CCGACAGATCAAGGCAGTTA | coding tag barcode sequence 16 |
| 36 | AATCGCAGCCAAGTGAGTGA | coding tag barcode sequence 17 |
| 37 | ATAGATGACGCACCACGGTC | coding tag barcode sequence 18 |
| 38 | AGACACGACACACTGGCTTA | coding tag barcode sequence 19 |
| 39 | AGGAGACGCCACATCGTATC | coding tag barcode sequence 20 |
| 40 | GGCTGTTTGTGGCTCTACCA-c3 spacer-GGTAAGAGCGACTGTAGTGTG/3SpC3/ | adaptor molecule 1 |
| 41 | TGGAGATCGTTGCTTGTACC-c3 spacer-GGTAAGAGCCGATGTAGTGTG/3SpC3/ | adaptor molecule 2 |
| 42 | GGCTGTTTGTGGCTCTACCA-c3 spacer-AGAGATGGCACGTGGTAAGAG/3SpC3/ | adaptor molecule 3 |
| 43 | TGGAGATCGTTGCTTGTACC-c3 spacer-AGAGATGGTGCGTGGTAAGAG/3SpC3/ | adaptor molecule 4 |
| 44 | GAC TGG AGT TCA GAC GTG TGC TCT TCC GAT CTT TCT ACT CTT CTC ACT CAG T/3SpC3/ | Capping oligonucleotide |
| 45 | FSGVARGDVRGGK | target peptide 1 |
| 46 | FLAEIRGDVRGGK | target peptide 2 |
| 47 | LAGELAGELAGEIRGDVRGGK | target peptide 3 |
| 48 | dimethyl-AESAESASRFSGVAMPGAEDDVVGSGSK | target peptide 4 |

TABLE 3-continued

SEQUENCE TABLE

| SEQ ID NO | Sequence (5'-3') | Description |
|---|---|---|
| 49 | LAESAFSGVARGDVRGGK | target peptide 5 |
| 50 | SGVARGDVRGGK | target peptide 6 |

PMI1 = Pyrazole methanimine modification at the N-terminus
peg9 spacer = internal nine atom polyethylene glycol spacer
peg6 spacer = internal six atom polyethylene glycol spacer
-c3 spacer- = an internal three-carbon spacer
/3SpC3/ = a 3'-terminal three-carbon spacer

What is claimed is:

1. A method for analyzing a macromolecule comprising the steps of:
   (a) providing the macromolecule joined to a support, wherein the macromolecule is associated with a first stabilizing component;
   (b) binding a binding agent to the macromolecule by contacting the macromolecule with the binding agent capable of specifically binding to the macromolecule, wherein the binding agent is associated with a second stabilizing component, and the binding of the binding agent to the macromolecule does not depend on the presence of the first stabilizing component and the second stabilizing component;
   (c) after binding of the binding agent to the macromolecule, linking the first and second stabilizing components together via a linking agent to form a stable complex comprising the binding agent, the macromolecule and the stabilizing components, wherein the first stabilizing component and the second stabilizing component are linked upon introduction of the linking agent that comprises a polypeptide that binds to the first stabilizing component and to the second stabilizing component; and
   (d) analyzing the macromolecule by obtaining information about the binding agent bound to the macromolecule.

2. The method of claim 1, wherein no covalent bonds are formed during formation of the stable complex.

3. The method of claim 1, wherein the stabilizing components are linked upon introduction to light.

4. The method of claim 1, wherein the first or second stabilizing component comprises a polynucleotide.

5. The method of claim 1, wherein the first stabilizing component is the same as the second stabilizing component.

6. The method of claim 1, wherein the first stabilizing component has a lower affinity to the linking agent in comparison to an affinity of the second stabilizing component to the linking agent.

7. The method of claim 1, wherein the method comprises contacting a plurality of binding agents with a single macromolecule, or contacting a plurality of binding agents with a plurality of macromolecules, and wherein at least one binding agent of the plurality of binding agents is capable of binding to the macromolecule and each binding agent of the plurality of binding agents is associated with the second stabilizing component.

8. The method of claim 1, wherein the binding agent is fluorescently labeled to enable detection of the contact between the macromolecule and the binding agent; and analyzing the macromolecule comprises detecting the fluorescence from the binding agent after contacting the macromolecule.

9. The method of claim 1, wherein the macromolecule comprises a polypeptide and the binding agent or a binding agent from the plurality of binding agents is capable of binding to a N-terminal amino acid (NTAA) of the polypeptide or to a modified NTAA of the polypeptide.

10. The method of claim 9, wherein analyzing the macromolecule comprises identifying at least one amino acid residue of the polypeptide.

11. The method of claim 10, wherein providing a macromolecule comprises providing the polypeptide associated with a recording tag; the binding agent or each binding agent from the plurality of binding agents is associated with a coding tag with identifying information regarding the binding agent; obtaining an information about the binding agent comprises transferring an information from the coding tag to the recording tag after binding of the binding agent to the macromolecule to generate an extended recording tag; and identifying at least one amino acid residue of the polypeptide comprises analyzing the extended recording tag.

12. The method of claim 11, further comprising:
providing an adaptor molecule comprising a first hybridization sequence and a secondary tag, wherein the first hybridization sequence is substantially complementary to at least a portion of the coding tag, to allow hybridization between the first hybridization sequence and the coding tag; and
transferring information of the secondary tag to the recording tag to generate an extended recording tag, wherein the information of the secondary tag is transferred from the adaptor molecule to the recording tag after the coding tag associated with the binding agent hybridizes with the first hybridization sequence on the adaptor molecule.

13. The method of claim 11, wherein transferring information of the coding tag to the recording tag is performed after the stabilizing components are linked together.

14. The method of claim 13, wherein transferring information comprises contacting the coding tag with a reagent for transferring the identifying information, the reagent comprising a reagent for primer extension reaction, a chemical ligation reagent or a biological ligation reagent.

15. The method of claim 14, wherein the stable complex is disrupted after the transfer of information from the coding tag to the recording tag by removing the linking agent from the stable complex or by introducing a destabilizing agent.

16. The method of claim 10, further comprising contacting the polypeptide with a N-terminal modifier agent prior to binding of the binding agent to the polypeptide to form the modified NTAA of the polypeptide.

17. The method of claim 16, further comprising removing the modified NTAA of the polypeptide after transferring the information from the coding tag to the recording tag to expose a new NTAA of the polypeptide.

18. The method of claim 17, further comprising repeating at least one more time prior to analyzing the extended recording tag the steps of:
contacting the polypeptide with a N-terminal modifier agent to form the modified NTAA of the polypeptide;
contacting the polypeptide with a binding agent capable of binding to the modified NTAA of the polypeptide or with a plurality of binding agents wherein at least one binding agent of the plurality of binding agents is capable of binding to the modified NTAA of the polypeptide, wherein each binding agent of the plurality of binding agents is associated with the second stabilizing component;
linking the first and second stabilizing components together to form a stable complex comprising the binding agent, the macromolecule and the stabilizing components; and/or
optionally, removing the modified NTAA of the polypeptide.

19. The method of claim 10, wherein the extended recording tag is analyzed using a nucleic acid sequencing method.

20. The method of claim 1, wherein the macromolecule comprises a first stabilizing component, and the binding agent comprises a second stabilizing component.

21. The method of claim 1, wherein the stable complex stabilizes interaction between the binding agent and the macromolecule during obtaining information about the binding agent bound to the macromolecule.

\* \* \* \* \*

SEQUENCE LISTING

<160> NUMBER OF SEQ ID NOS: 50

<210> SEQ ID NO 1
<211> LENGTH: 20
<212> TYPE: DNA
<213> ORGANISM: Artificial Sequence
<220> FEATURE:
<223> OTHER INFORMATION: P5 primer

<400> SEQUENCE: 1
aatgatacgg cgaccaccga                                                  20

<210> SEQ ID NO 2
<211> LENGTH: 24
<212> TYPE: DNA
<213> ORGANISM: Artificial Sequence
<220> FEATURE:
<223> OTHER INFORMATION: P7 primer

<400> SEQUENCE: 2
caagcagaag acggcatacg agat                                             24

<210> SEQ ID NO 3
<211> LENGTH: 20
<212> TYPE: PRT
<213> ORGANISM: Artificial Sequence
<220> FEATURE:
<223> OTHER INFORMATION: FA-PA

<400> SEQUENCE: 3

Phe Ala Gly Val Ala Met Pro Gly Ala Glu Asp Asp Val Val Gly Ser
1               5                   10                  15

Gly Ser Gly Lys
            20

<210> SEQ ID NO 4
<211> LENGTH: 20
<212> TYPE: PRT
<213> ORGANISM: Artificial Sequence
<220> FEATURE:
<223> OTHER INFORMATION: AFA-PA

<400> SEQUENCE: 4

Ala Phe Ala Gly Val Ala Met Pro Gly Ala Glu Asp Asp Val Val Gly
1               5                   10                  15

Ser Gly Ser Lys
            20

<210> SEQ ID NO 5

```
<211> LENGTH: 19
<212> TYPE: PRT
<213> ORGANISM: Artificial Sequence
<220> FEATURE:
<223> OTHER INFORMATION: AA-PA

<400> SEQUENCE: 5

Ala Ala Gly Val Ala Met Pro Gly Ala Glu Asp Val Val Gly Ser
1               5                   10                  15

Gly Ser Lys

<210> SEQ ID NO 6
<211> LENGTH: 103
<212> TYPE: PRT
<213> ORGANISM: Agrobacterium tumefaciens
<220> FEATURE:
<221> NAME/KEY: MISC_FEATURE
<222> LOCATION: (1)..(103)
<223> OTHER INFORMATION: Scaffold for binder selection 1

<400> SEQUENCE: 6

Met Ser Asp Ser Pro Val Asp Leu Lys Pro Lys Pro Lys Val Lys Pro
1               5                   10                  15

Lys Leu Glu Arg Pro Lys Leu Tyr Lys Val Met Leu Leu Asn Asp Asp
            20                  25                  30

Tyr Thr Pro Arg Glu Phe Val Thr Val Val Leu Lys Ala Val Phe Arg
        35                  40                  45

Met Ser Glu Asp Thr Gly Arg Arg Val Met Met Thr Ala His Arg Phe
    50                  55                  60

Gly Ser Ala Val Val Val Cys Glu Arg Asp Ile Ala Glu Thr Lys
65                  70                  75                  80

Ala Lys Glu Ala Thr Asp Leu Gly Lys Glu Ala Gly Phe Pro Leu Met
                85                  90                  95

Phe Thr Thr Glu Pro Glu Glu
                100

<210> SEQ ID NO 7
<211> LENGTH: 164
<212> TYPE: PRT
<213> ORGANISM: Homo sapiens
<220> FEATURE:
<221> NAME/KEY: MISC_FEATURE
<222> LOCATION: (1)..(164)
<223> OTHER INFORMATION: Scaffold for binder selection 2

<400> SEQUENCE: 7

Gln Val Ser Val Gln Pro Asn Phe Gln Gln Asp Lys Phe Leu Gly Arg
1               5                   10                  15

Trp Phe Ser Ala Gly Leu Ala Ser Asn Ser Ser Trp Leu Arg Glu Lys
            20                  25                  30

Lys Ala Ala Leu Ser Met Ala Lys Ser Val Val Ala Pro Ala Thr Asp
        35                  40                  45

Gly Gly Leu Asn Leu Thr Ser Thr Phe Leu Arg Lys Asn Gln Cys Glu
    50                  55                  60

Thr Arg Thr Met Leu Leu Gln Pro Ala Gly Ser Leu Gly Ser Tyr Ser
65                  70                  75                  80

Tyr Arg Ser Pro His Phe Gly Ser Thr Tyr Ser Val Ser Val Val Glu
                85                  90                  95

Thr Asp Tyr Asp Gln Tyr Ala Leu Leu Tyr Ser Gln Gly Ser Lys Gly
                100                 105                 110
```

```
Pro Gly Glu Asp Phe Arg Met Ala Thr Leu Tyr Ser Arg Thr Gln Thr
        115                 120                 125

Pro Arg Ala Glu Leu Lys Glu Lys Phe Thr Ala Phe Ser Lys Ala Gln
    130                 135                 140

Gly Phe Thr Glu Asp Thr Ile Val Phe Leu Pro Gln Thr Asp Lys Cys
145                 150                 155                 160

Met Thr Glu Gln

<210> SEQ ID NO 8
<211> LENGTH: 5
<212> TYPE: PRT
<213> ORGANISM: Artificial Sequence
<220> FEATURE:
<223> OTHER INFORMATION: Bait peptide for binder selection 1
<220> FEATURE:
<221> NAME/KEY: MISC_FEATURE
<222> LOCATION: (1)..(1)
<223> OTHER INFORMATION: N-terminal pyrazole methaniminated
<220> FEATURE:
<221> NAME/KEY: MISC_FEATURE
<222> LOCATION: (2)..(2)
<223> OTHER INFORMATION: Xaa is any natural amino acid
<220> FEATURE:
<221> NAME/KEY: MISC_FEATURE
<222> LOCATION: (4)..(5)
<223> OTHER INFORMATION: an internal nine atom polyethylene glycol
      spacer
<220> FEATURE:
<221> NAME/KEY: MISC_FEATURE
<222> LOCATION: (5)..(5)
<223> OTHER INFORMATION: C-terminal biotinylated

<400> SEQUENCE: 8

Phe Xaa Gly Gly Lys
1               5

<210> SEQ ID NO 9
<211> LENGTH: 174
<212> TYPE: PRT
<213> ORGANISM: Homo sapiens
<220> FEATURE:
<221> NAME/KEY: MISC_FEATURE
<222> LOCATION: (1)..(174)
<223> OTHER INFORMATION: Scaffold for binder selection 3

<400> SEQUENCE: 9

Gly Pro Val Pro Thr Pro Pro Asp Asn Ile Gln Val Gln Glu Asn Phe
1               5                   10                  15

Asn Ile Ser Arg Ile Tyr Gly Lys Trp Tyr Asn Leu Ala Ile Gly Ser
            20                  25                  30

Thr Ser Pro Trp Leu Lys Lys Ile Met Asp Arg Met Thr Val Ser Thr
        35                  40                  45

Leu Val Leu Gly Glu Gly Ala Thr Glu Ala Glu Ile Ser Met Thr Ser
    50                  55                  60

Thr Arg Trp Arg Lys Gly Val Cys Glu Glu Thr Ser Gly Ala Tyr Glu
65                  70                  75                  80

Lys Thr Asp Thr Asp Gly Lys Phe Leu Tyr His Lys Ser Lys Trp Asn
                85                  90                  95

Ile Thr Met Glu Ser Tyr Val Val His Thr Asn Tyr Asp Glu Tyr Ala
            100                 105                 110

Ile Phe Leu Thr Lys Lys Phe Ser Arg His His Gly Pro Thr Ile Thr
        115                 120                 125

Ala Lys Leu Tyr Gly Arg Ala Pro Gln Leu Arg Glu Thr Leu Leu Gln
    130                 135                 140
```

Asp Phe Arg Val Val Ala Gln Gly Val Gly Ile Pro Glu Asp Ser Ile
145                 150                 155                 160

Phe Thr Met Ala Asp Arg Gly Glu Cys Val Pro Gly Glu Gln
                165                 170

<210> SEQ ID NO 10
<211> LENGTH: 5
<212> TYPE: PRT
<213> ORGANISM: Artificial Sequence
<220> FEATURE:
<223> OTHER INFORMATION: Bait peptide for binder selection 2
<220> FEATURE:
<221> NAME/KEY: MISC_FEATURE
<222> LOCATION: (1)..(1)
<223> OTHER INFORMATION: N-terminal pyrazole methaniminated
<220> FEATURE:
<221> NAME/KEY: MISC_FEATURE
<222> LOCATION: (2)..(2)
<223> OTHER INFORMATION: Xaa is any natural amino acid
<220> FEATURE:
<221> NAME/KEY: MISC_FEATURE
<222> LOCATION: (4)..(5)
<223> OTHER INFORMATION: An internal nine atom polyethylene glycol
      spacer
<220> FEATURE:
<221> NAME/KEY: MISC_FEATURE
<222> LOCATION: (5)..(5)
<223> OTHER INFORMATION: C-terminal biotinylated

<400> SEQUENCE: 10

Leu Xaa Gly Gly Lys
1               5

<210> SEQ ID NO 11
<211> LENGTH: 46
<212> TYPE: DNA
<213> ORGANISM: Artificial Sequence
<220> FEATURE:
<223> OTHER INFORMATION: amRT_Cs2 oligonucleotide
<220> FEATURE:
<221> NAME/KEY: misc_feature
<222> LOCATION: (21)..(30)
<223> OTHER INFORMATION: n is a, c, g, or t

<400> SEQUENCE: 11
ttcgtagtcc gcgacactag nnnnnnnnnn gttaatggac tgagtg          46

<210> SEQ ID NO 12
<211> LENGTH: 46
<212> TYPE: DNA
<213> ORGANISM: Artificial Sequence
<220> FEATURE:
<223> OTHER INFORMATION: amRT_Cs4 oligonucleotide
<220> FEATURE:
<221> NAME/KEY: misc_feature
<222> LOCATION: (21)..(30)
<223> OTHER INFORMATION: n is a, c, g, or t

<400> SEQUENCE: 12
ttcgtagtcc gcgacactag nnnnnnnnnn cagtaccgac tgagtg          46

<210> SEQ ID NO 13
<211> LENGTH: 46
<212> TYPE: DNA
<213> ORGANISM: Artificial Sequence
<220> FEATURE:
<223> OTHER INFORMATION: amRT_Cs5 oligonucleotide
<220> FEATURE:
<221> NAME/KEY: misc_feature
<222> LOCATION: (21)..(30)

<223> OTHER INFORMATION: n is a, c, g, or t

<400> SEQUENCE: 13
ttcgtagtcc gcgacactag nnnnnnnnnn gttggttaac tgagtg                    46

<210> SEQ ID NO 14
<211> LENGTH: 46
<212> TYPE: DNA
<213> ORGANISM: Artificial Sequence
<220> FEATURE:
<223> OTHER INFORMATION: amRT_Cs1 oligonucleotide
<220> FEATURE:
<221> NAME/KEY: misc_feature
<222> LOCATION: (21)..(30)
<223> OTHER INFORMATION: n is a, c, g, or t

<400> SEQUENCE: 14
ttcgtagtcc gcgacactag nnnnnnnnnn ttaagtcgac tgagtg                    46

<210> SEQ ID NO 15
<211> LENGTH: 25
<212> TYPE: DNA
<213> ORGANISM: Artificial Sequence
<220> FEATURE:
<223> OTHER INFORMATION: coding tag oligonucleotide

<400> SEQUENCE: 15
cactcagtca gactattcac tcagt                                           25

<210> SEQ ID NO 16
<211> LENGTH: 20
<212> TYPE: DNA
<213> ORGANISM: Artificial Sequence
<220> FEATURE:
<223> OTHER INFORMATION: am-PL1 oligonucleotide

<400> SEQUENCE: 16
catagactag tagccggaac                                                 20

<210> SEQ ID NO 17
<211> LENGTH: 20
<212> TYPE: DNA
<213> ORGANISM: Artificial Sequence
<220> FEATURE:
<223> OTHER INFORMATION: am-PL2oligonucleotide

<400> SEQUENCE: 17
tcgacgtaat gacaccgctc                                                 20

<210> SEQ ID NO 18
<211> LENGTH: 45
<212> TYPE: DNA
<213> ORGANISM: Artificial Sequence
<220> FEATURE:
<223> OTHER INFORMATION: CT_PL1_S6 adaptor molecule
<220> FEATURE:
<221> NAME/KEY: misc_feature
<222> LOCATION: (20)..(21)
<223> OTHER INFORMATION: an internal six atom polyethylene glycol spacer

<400> SEQUENCE: 18
gttccggcta ctagtctatg cactcagttt tcctgtcac tcagt                      45

<210> SEQ ID NO 19
<211> LENGTH: 45
<212> TYPE: DNA
<213> ORGANISM: Artificial Sequence

```
<220> FEATURE:
<223> OTHER INFORMATION: CT_PL2_S6 adaptor molecule
<220> FEATURE:
<221> NAME/KEY: misc_feature
<222> LOCATION: (20)..(21)
<223> OTHER INFORMATION: an internal six atom polyethylene glycol spacer

<400> SEQUENCE: 19
gagcggtgtc attacgtcga cactcagttt ttcctgtcac tcagt            45

<210> SEQ ID NO 20
<211> LENGTH: 20
<212> TYPE: DNA
<213> ORGANISM: Artificial Sequence
<220> FEATURE:
<223> OTHER INFORMATION: coding tag barcode sequence 1

<400> SEQUENCE: 20
tggtagagcc acaaacagcc                                        20

<210> SEQ ID NO 21
<211> LENGTH: 20
<212> TYPE: DNA
<213> ORGANISM: Artificial Sequence
<220> FEATURE:
<223> OTHER INFORMATION: coding tag barcode sequence 2

<400> SEQUENCE: 21
ggtacaagca acgatctcca                                        20

<210> SEQ ID NO 22
<211> LENGTH: 20
<212> TYPE: DNA
<213> ORGANISM: Artificial Sequence
<220> FEATURE:
<223> OTHER INFORMATION: coding tag barcode sequence 3

<400> SEQUENCE: 22
ggaccatctg aatcatgcgc                                        20

<210> SEQ ID NO 23
<211> LENGTH: 20
<212> TYPE: DNA
<213> ORGANISM: Artificial Sequence
<220> FEATURE:
<223> OTHER INFORMATION: coding tag barcode sequence 4

<400> SEQUENCE: 23
ggatgacacg aactcacgac                                        20

<210> SEQ ID NO 24
<211> LENGTH: 20
<212> TYPE: DNA
<213> ORGANISM: Artificial Sequence
<220> FEATURE:
<223> OTHER INFORMATION: coding tag barcode sequence 5

<400> SEQUENCE: 24
ggcgatcaca gacattaacc                                        20

<210> SEQ ID NO 25
<211> LENGTH: 20
<212> TYPE: DNA
<213> ORGANISM: Artificial Sequence
<220> FEATURE:
<223> OTHER INFORMATION: coding tag barcode sequence 6
```

```
<400> SEQUENCE: 25
cacagccgat aattgcagac                                               20

<210> SEQ ID NO 26
<211> LENGTH: 20
<212> TYPE: DNA
<213> ORGANISM: Artificial Sequence
<220> FEATURE:
<223> OTHER INFORMATION: coding tag barcode sequence 7

<400> SEQUENCE: 26
ggtacagaca ctgcgacaac                                               20

<210> SEQ ID NO 27
<211> LENGTH: 20
<212> TYPE: DNA
<213> ORGANISM: Artificial Sequence
<220> FEATURE:
<223> OTHER INFORMATION: coding tag barcode sequence 8

<400> SEQUENCE: 27
gtggcaattc gtcgcaatac                                               20

<210> SEQ ID NO 28
<211> LENGTH: 20
<212> TYPE: DNA
<213> ORGANISM: Artificial Sequence
<220> FEATURE:
<223> OTHER INFORMATION: coding tag barcode sequence 9

<400> SEQUENCE: 28
gggtcatcac ggctcatcat                                               20

<210> SEQ ID NO 29
<211> LENGTH: 20
<212> TYPE: DNA
<213> ORGANISM: Artificial Sequence
<220> FEATURE:
<223> OTHER INFORMATION: coding tag barcode sequence 10

<400> SEQUENCE: 29
gccagatgtc aacacagcta                                               20

<210> SEQ ID NO 30
<211> LENGTH: 20
<212> TYPE: DNA
<213> ORGANISM: Artificial Sequence
<220> FEATURE:
<223> OTHER INFORMATION: coding tag barcode sequence 11

<400> SEQUENCE: 30
ccgccaaaca aatgtgtgca                                               20

<210> SEQ ID NO 31
<211> LENGTH: 20
<212> TYPE: DNA
<213> ORGANISM: Artificial Sequence
<220> FEATURE:
<223> OTHER INFORMATION: coding tag barcode sequence 12

<400> SEQUENCE: 31
atacacgctc ggaagactgc                                               20

<210> SEQ ID NO 32
<211> LENGTH: 20
```

```
<212> TYPE: DNA
<213> ORGANISM: Artificial Sequence
<220> FEATURE:
<223> OTHER INFORMATION: coding tag barcode sequence 13

<400> SEQUENCE: 32
atgatgaccg cactgactgg                                              20

<210> SEQ ID NO 33
<211> LENGTH: 20
<212> TYPE: DNA
<213> ORGANISM: Artificial Sequence
<220> FEATURE:
<223> OTHER INFORMATION: coding tag barcode sequence 14

<400> SEQUENCE: 33
ggacagcaga tccacctaag                                              20

<210> SEQ ID NO 34
<211> LENGTH: 20
<212> TYPE: DNA
<213> ORGANISM: Artificial Sequence
<220> FEATURE:
<223> OTHER INFORMATION: coding tag barcode sequence 15

<400> SEQUENCE: 34
cctgtgagag aagcagacac                                              20

<210> SEQ ID NO 35
<211> LENGTH: 20
<212> TYPE: DNA
<213> ORGANISM: Artificial Sequence
<220> FEATURE:
<223> OTHER INFORMATION: coding tag barcode sequence 16

<400> SEQUENCE: 35
ccgacagatc aaggcagtta                                              20

<210> SEQ ID NO 36
<211> LENGTH: 20
<212> TYPE: DNA
<213> ORGANISM: Artificial Sequence
<220> FEATURE:
<223> OTHER INFORMATION: coding tag barcode sequence 17

<400> SEQUENCE: 36
aatcgcagcc aagtgagtga                                              20

<210> SEQ ID NO 37
<211> LENGTH: 20
<212> TYPE: DNA
<213> ORGANISM: Artificial Sequence
<220> FEATURE:
<223> OTHER INFORMATION: coding tag barcode sequence 18

<400> SEQUENCE: 37
atagatgacg caccacggtc                                              20

<210> SEQ ID NO 38
<211> LENGTH: 20
<212> TYPE: DNA
<213> ORGANISM: Artificial Sequence
<220> FEATURE:
<223> OTHER INFORMATION: coding tag barcode sequence 19

<400> SEQUENCE: 38
```
agacacgaca cactggctta                                           20

<210> SEQ ID NO 39
<211> LENGTH: 20
<212> TYPE: DNA
<213> ORGANISM: Artificial Sequence
<220> FEATURE:
<223> OTHER INFORMATION: coding tag barcode sequence 20

<400> SEQUENCE: 39
aggagacgcc acatcgtatc                                           20

<210> SEQ ID NO 40
<211> LENGTH: 41
<212> TYPE: DNA
<213> ORGANISM: Artificial Sequence
<220> FEATURE:
<223> OTHER INFORMATION: adaptor molecule 1
<220> FEATURE:
<221> NAME/KEY: misc_feature
<222> LOCATION: (20)..(21)
<223> OTHER INFORMATION: an internal three carbon spacer
<220> FEATURE:
<221> NAME/KEY: misc_feature
<222> LOCATION: (41)..(40)
<223> OTHER INFORMATION: a 3'-terminal three carbon spacer

<400> SEQUENCE: 40
ggctgtttgt ggctctacca ggtaagagcg actgtagtgt g                   41

<210> SEQ ID NO 41
<211> LENGTH: 41
<212> TYPE: DNA
<213> ORGANISM: Artificial Sequence
<220> FEATURE:
<223> OTHER INFORMATION: adaptor molecule 2
<220> FEATURE:
<221> NAME/KEY: misc_feature
<222> LOCATION: (20)..(21)
<223> OTHER INFORMATION: an internal three-carbon spacer
<220> FEATURE:
<221> NAME/KEY: misc_feature
<222> LOCATION: (41)..(41)
<223> OTHER INFORMATION: a 3'-terminal three-carbon spacer

<400> SEQUENCE: 41
tggagatcgt tgcttgtacc ggtaagagcc gatgtagtgt g                   41

<210> SEQ ID NO 42
<211> LENGTH: 41
<212> TYPE: DNA
<213> ORGANISM: Artificial Sequence
<220> FEATURE:
<223> OTHER INFORMATION: adaptor molecule 3
<220> FEATURE:
<221> NAME/KEY: misc_feature
<222> LOCATION: (20)..(21)
<223> OTHER INFORMATION: an internal three-carbon spacer
<220> FEATURE:
<221> NAME/KEY: misc_feature
<222> LOCATION: (41)..(41)
<223> OTHER INFORMATION: a 3'-terminal three-carbon spacer

<400> SEQUENCE: 42
ggctgtttgt ggctctacca agagatggca cgtggtaaga g                   41

<210> SEQ ID NO 43
<211> LENGTH: 41
<212> TYPE: DNA
<213> ORGANISM: Artificial Sequence

```
<220> FEATURE:
<223> OTHER INFORMATION: adaptor molecule 4
<220> FEATURE:
<221> NAME/KEY: misc_feature
<222> LOCATION: (20)..(21)
<223> OTHER INFORMATION: an internal three-carbon spacer
<220> FEATURE:
<221> NAME/KEY: misc_feature
<222> LOCATION: (41)..(41)
<223> OTHER INFORMATION: a 3'-terminal three-carbon spacer

<400> SEQUENCE: 43
tggagatcgt tgcttgtacc agagatggtg cgtggtaaga g                           41

<210> SEQ ID NO 44
<211> LENGTH: 52
<212> TYPE: DNA
<213> ORGANISM: Artificial Sequence
<220> FEATURE:
<223> OTHER INFORMATION: Capping oligonucleotide
<220> FEATURE:
<221> NAME/KEY: misc_feature
<222> LOCATION: (52)..(52)
<223> OTHER INFORMATION: a 3'-terminal three-carbon spacer

<400> SEQUENCE: 44
gactggagtt cagacgtgtg ctcttccgat ctttctactc ttctcactca gt               52

<210> SEQ ID NO 45
<211> LENGTH: 13
<212> TYPE: PRT
<213> ORGANISM: Artificial Sequence
<220> FEATURE:
<223> OTHER INFORMATION: target peptide 1

<400> SEQUENCE: 45

Phe Ser Gly Val Ala Arg Gly Asp Val Arg Gly Gly Lys
 1               5                  10

<210> SEQ ID NO 46
<211> LENGTH: 13
<212> TYPE: PRT
<213> ORGANISM: Artificial Sequence
<220> FEATURE:
<223> OTHER INFORMATION: target peptide 2

<400> SEQUENCE: 46

Phe Leu Ala Glu Ile Arg Gly Asp Val Arg Gly Gly Lys
 1               5                  10

<210> SEQ ID NO 47
<211> LENGTH: 21
<212> TYPE: PRT
<213> ORGANISM: Artificial Sequence
<220> FEATURE:
<223> OTHER INFORMATION: target peptide 3

<400> SEQUENCE: 47

Leu Ala Gly Glu Leu Ala Gly Glu Leu Ala Gly Glu Ile Arg Gly Asp
 1               5                  10                  15

Val Arg Gly Gly Lys
            20

<210> SEQ ID NO 48
<211> LENGTH: 28
<212> TYPE: PRT
<213> ORGANISM: Artificial Sequence
<220> FEATURE:
```

```
<223> OTHER INFORMATION: target peptide 4
<220> FEATURE:
<221> NAME/KEY: MISC_FEATURE
<222> LOCATION: (1)..(1)
<223> OTHER INFORMATION: N-terminal dimethylated

<400> SEQUENCE: 48

Ala Glu Ser Ala Glu Ser Ala Ser Arg Phe Ser Gly Val Ala Met Pro
1               5                   10                  15

Gly Ala Glu Asp Asp Val Val Gly Ser Gly Ser Lys
            20                  25

<210> SEQ ID NO 49
<211> LENGTH: 18
<212> TYPE: PRT
<213> ORGANISM: Artificial Sequence
<220> FEATURE:
<223> OTHER INFORMATION: target peptide 5

<400> SEQUENCE: 49

Leu Ala Glu Ser Ala Phe Ser Gly Val Ala Arg Gly Asp Val Arg Gly
1               5                   10                  15

Gly Lys

<210> SEQ ID NO 50
<211> LENGTH: 12
<212> TYPE: PRT
<213> ORGANISM: Artificial Sequence
<220> FEATURE:
<223> OTHER INFORMATION: target peptide 6

<400> SEQUENCE: 50

Ser Gly Val Ala Arg Gly Asp Val Arg Gly Gly Lys
1               5                   10
```